United States Patent
Chan et al.

(10) Patent No.: US 10,590,163 B2
(45) Date of Patent: *Mar. 17, 2020

(54) NATURAL AND SYNTHETIC COMPOUNDS FOR TREATING CANCER AND OTHER DISEASES

(71) Applicant: PACIFIC ARROW LIMITED, Hong Kong (CN)

(72) Inventors: Pui-Kwong Chan, Sugarland, TX (US); May Sung Mak, Hong Kong (CN)

(73) Assignee: Pacific Arrow Limited (CN)

( * ) Notice: Subject to any disclaimer, the term of this patent is extended or adjusted under 35 U.S.C. 154(b) by 4 days.

This patent is subject to a terminal disclaimer.

(21) Appl. No.: 15/612,152

(22) Filed: Jun. 2, 2017

(65) Prior Publication Data
US 2017/0267714 A1  Sep. 21, 2017

Related U.S. Application Data

(63) Continuation-in-part of application No. 15/287,411, filed on Oct. 6, 2016, now Pat. No. 10,214,558, which is a continuation of application No. 14/313,080, filed on Jun. 24, 2014, now Pat. No. 9,499,577, which is a continuation-in-part of application No. 14/020,099, filed on Sep. 6, 2013, now Pat. No. 8,785,405, which is a continuation of application No. 13/259,480, filed as application No. PCT/US2011/044233 on Jul. 15, 2011, now abandoned, which is a continuation-in-part of application No. PCT/US2010/042240, filed on Jul. 16, 2010, which is a continuation-in-part of application No. 12/856,322, filed on Aug. 13, 2010, now Pat. No. 8,586,719, and a continuation-in-part of application No. 12/541,713, filed on Aug. 14, 2009, now Pat. No. 8,735,558, which is a continuation-in-part of application No. 14/233,031, filed as application No. PCT/US2012/046716 on Jul. 13, 2012, now Pat. No. 9,434,677, which is a continuation-in-part of application No. PCT/US2011/044233, filed on Jul. 15, 2011, which is a continuation-in-part of application No. PCT/US2010/042240, filed on Jul. 16, 2010.

(60) Provisional application No. 61/226,043, filed on Jul. 16, 2009, provisional application No. 62/345,743, filed on Jun. 3, 2016.

(51) Int. Cl.
*C07J 63/00* (2006.01)
*C07J 71/00* (2006.01)
*C07H 15/24* (2006.01)
*A61K 31/704* (2006.01)

(52) U.S. Cl.
CPC .......... *C07J 63/008* (2013.01); *A61K 31/704* (2013.01); *C07H 15/24* (2013.01); *C07J 71/0005* (2013.01); *Y02A 50/409* (2018.01)

(58) Field of Classification Search
None
See application file for complete search history.

(56) References Cited

PUBLICATIONS

Sheng-Xiang et al. Phytochemistry (1993), 34(5), 1385-1387. (Year: 1993).*

* cited by examiner

*Primary Examiner* — Jeffrey S Lundgren
*Assistant Examiner* — Michael J Schmitt
(74) *Attorney, Agent, or Firm* — Law Offices of Albert Wai-Kit Chan, PLLC

(57) ABSTRACT

This invention provides a method of synthesizing new active compounds for pharmaceutical uses including cancer treatment, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers. This invention is an anti-adhesion therapy which uses the compound as a mediator or inhibitor of adhesion proteins and angiopoietins. It inhibits excess adhesion and inhibits cell attachment. It modulates angiogenesis. The compounds also use as mediator of cell adhesion receptor, cell circulating, cell moving and inflammatory diseases. The compounds are attached with angeloyl, acetyl, tigloyl, senecioyl, Crotonoyl, 3,3-Dimethylartyloyl, Cinnamoyl, Pentenoyl, Hexanoyl, benzoyl, Ethylbutyryl, benzoyl, dibenzoyl, alkanoyl, alkenoyl, benzoyl alkyl substituted alkanoyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, O—C(2-18) Acyl.

20 Claims, 37 Drawing Sheets

Figure 12
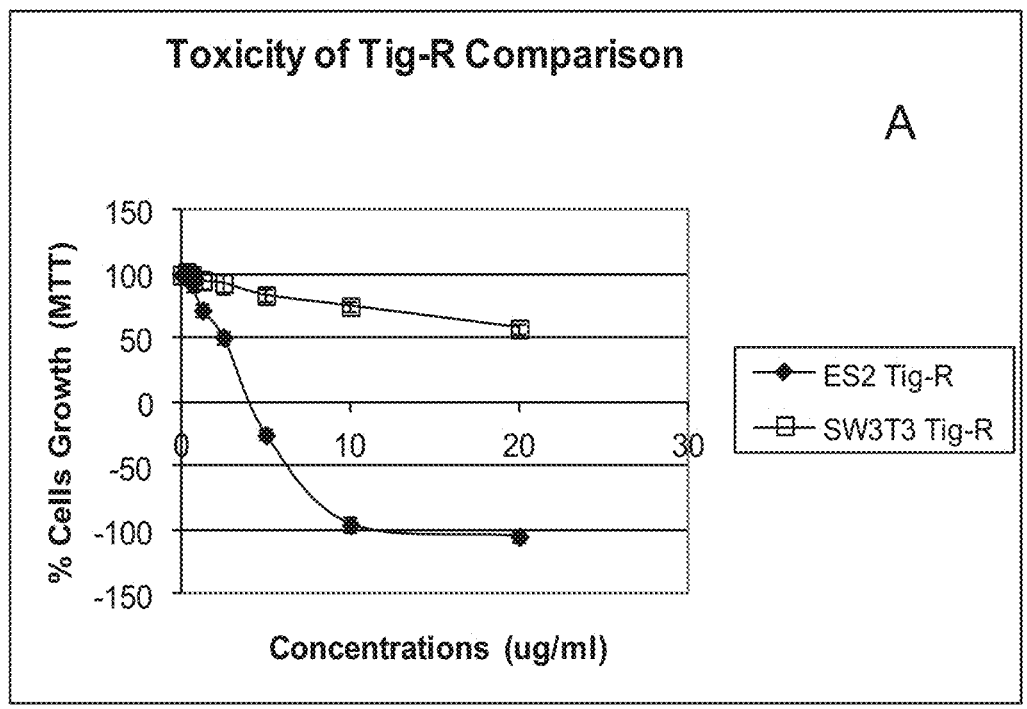
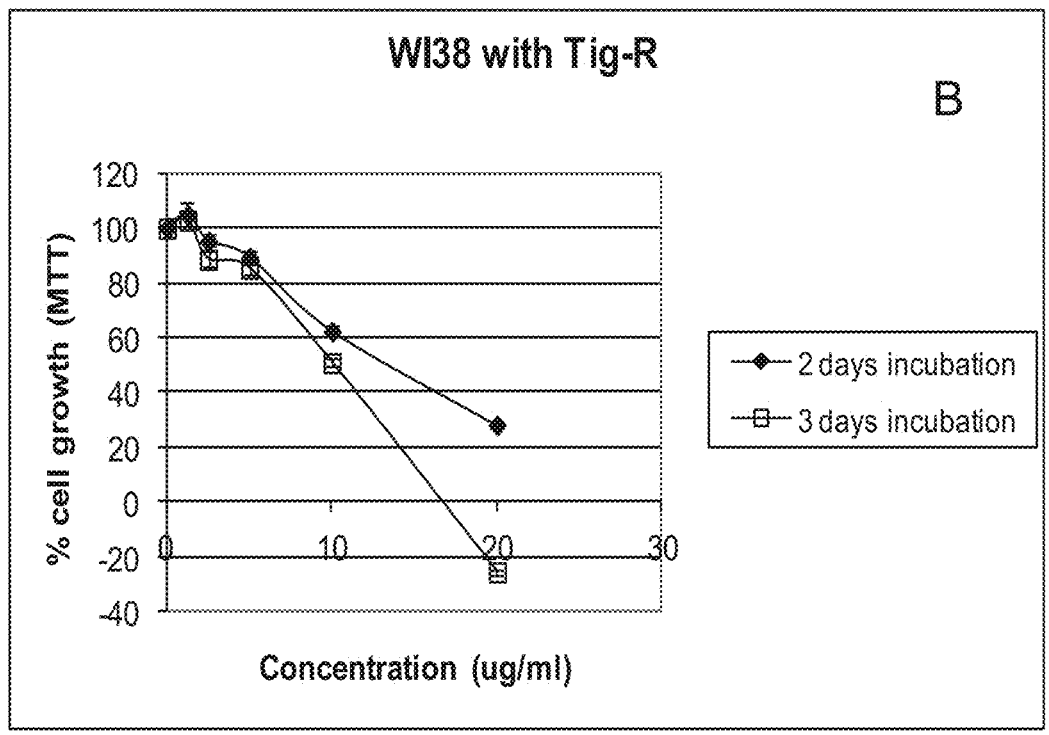

Figure 14
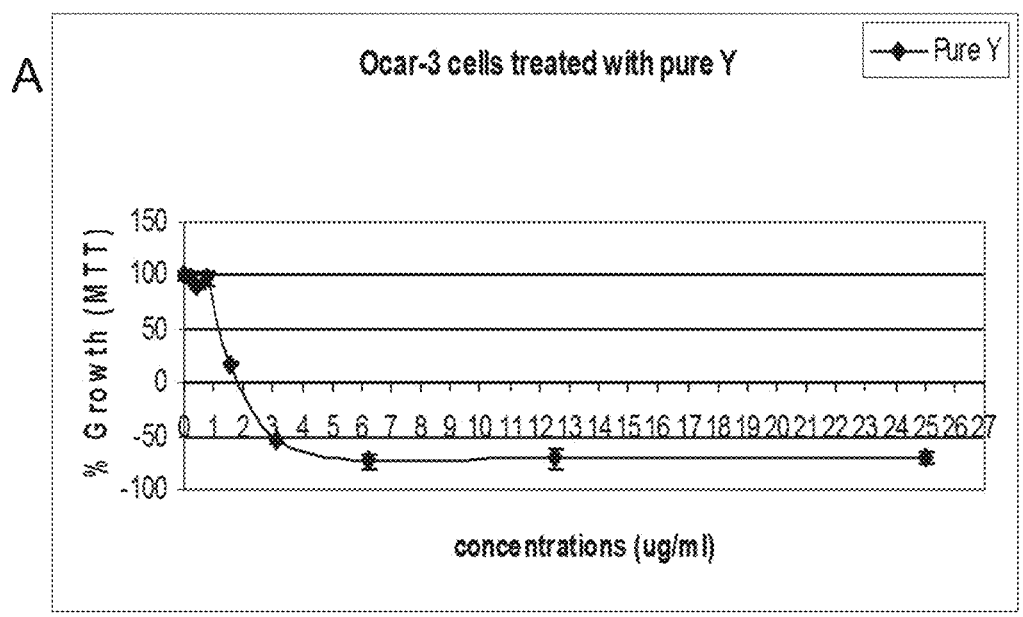
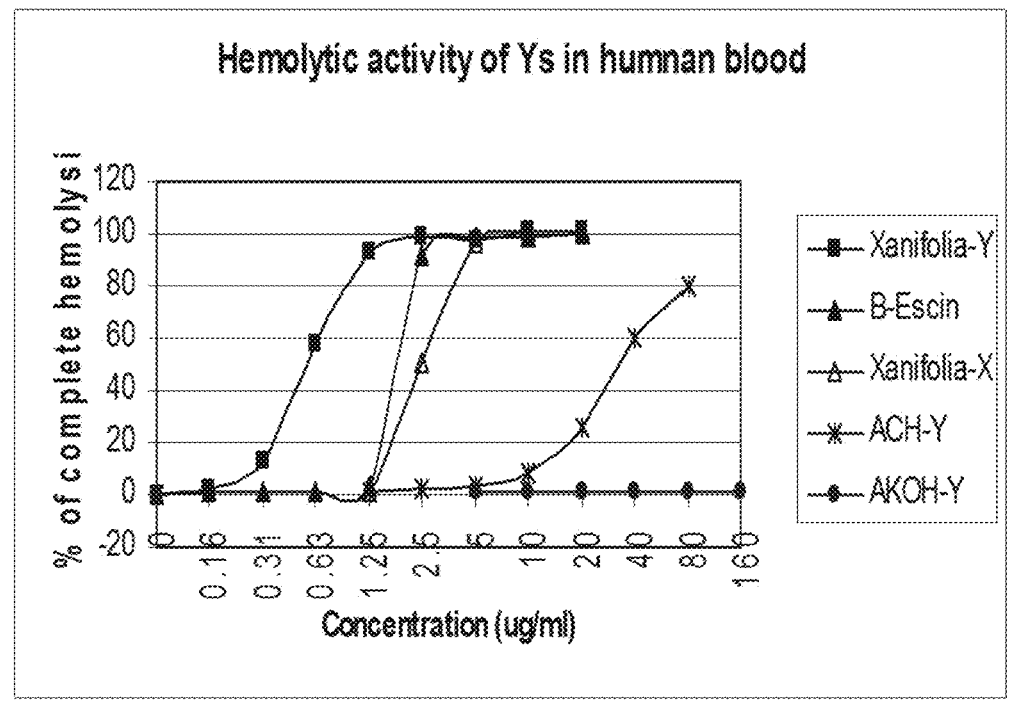

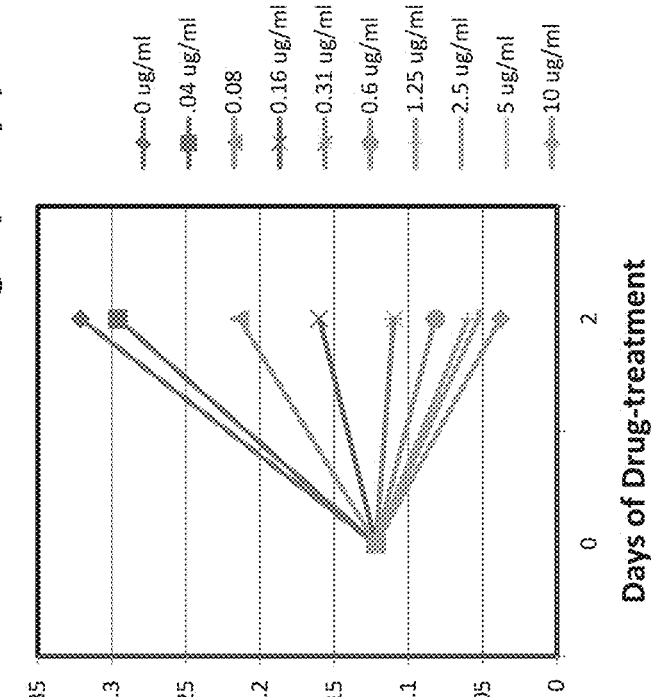
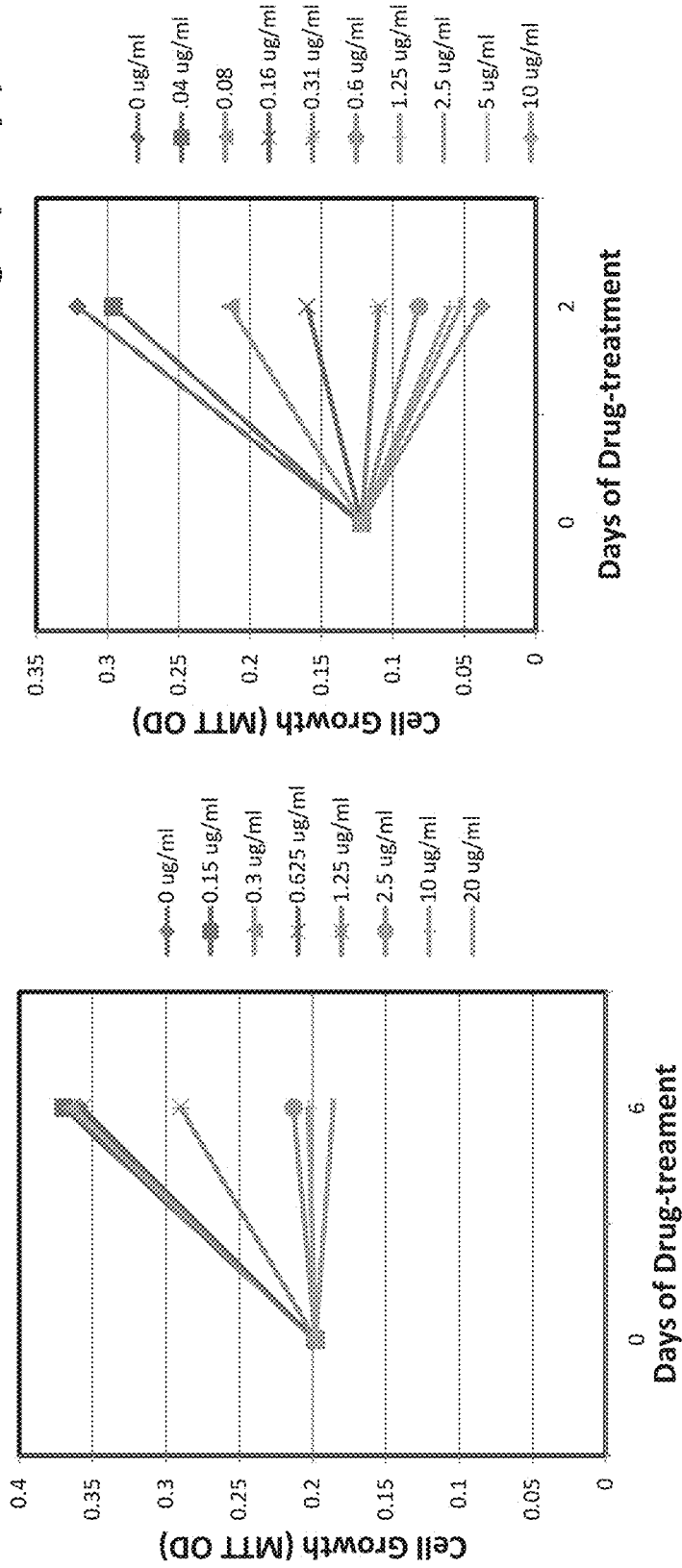
Figure 18

Activity of Ys

Figure 30
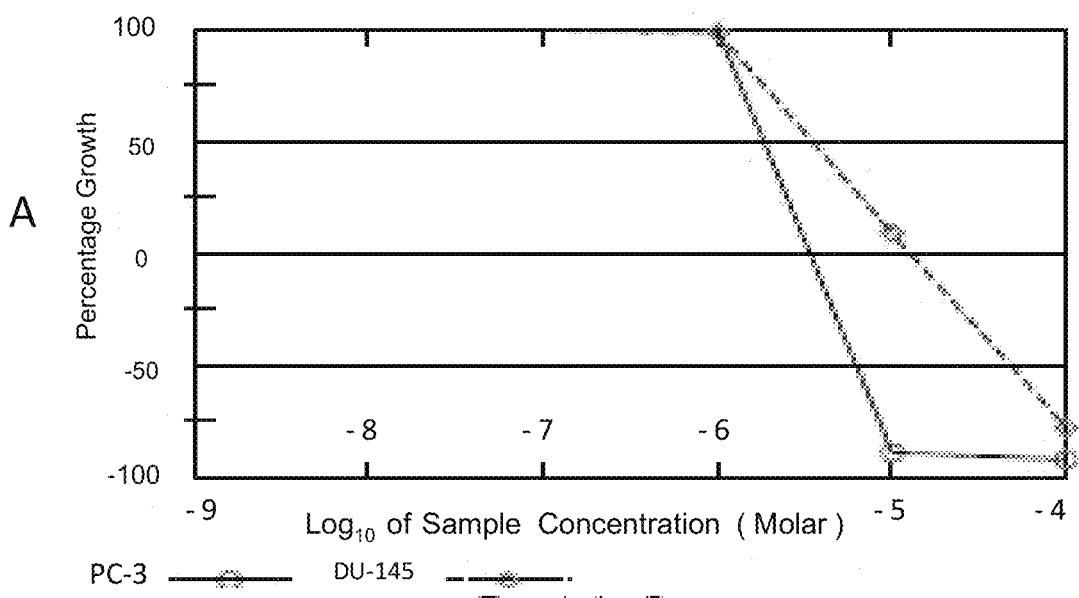
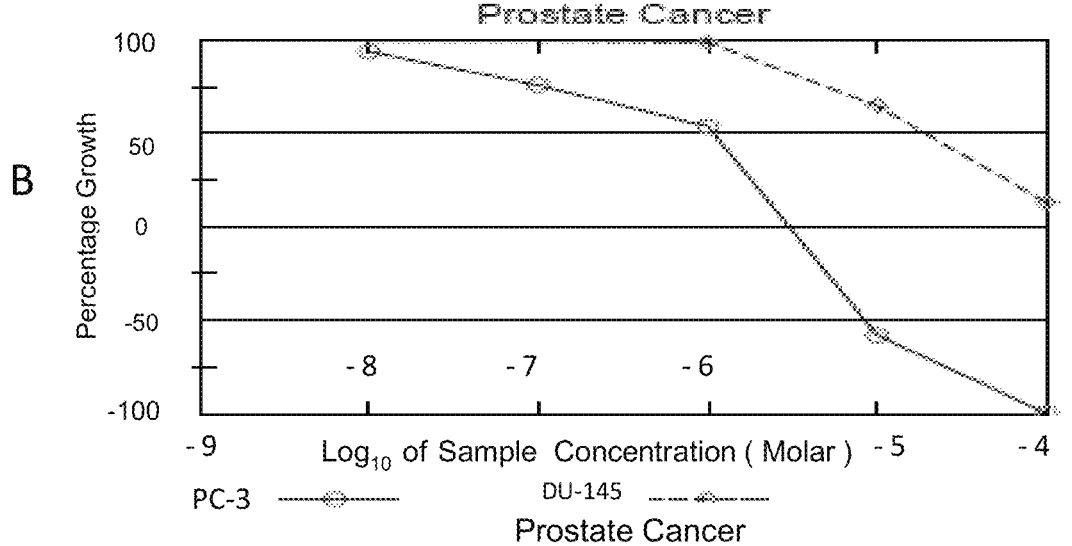
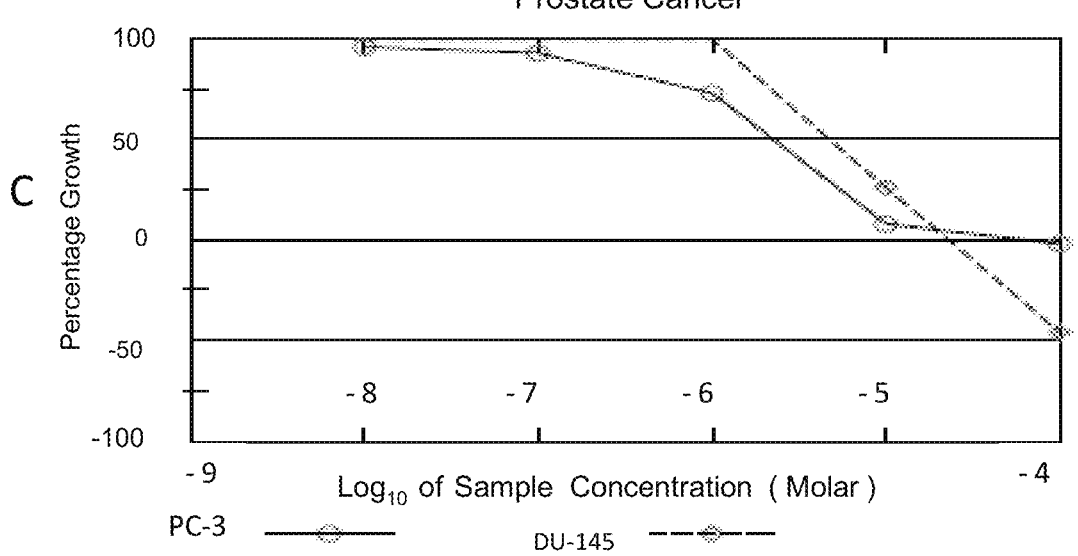

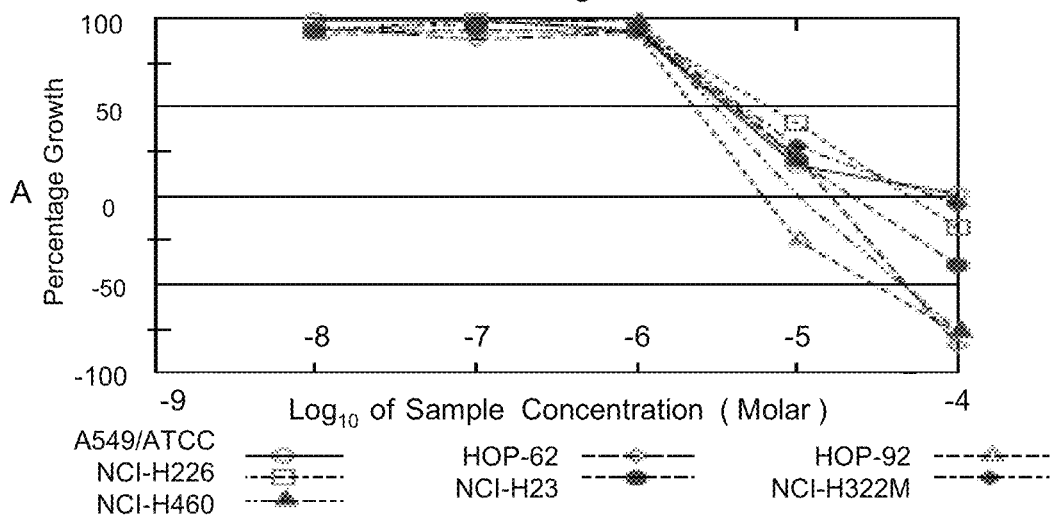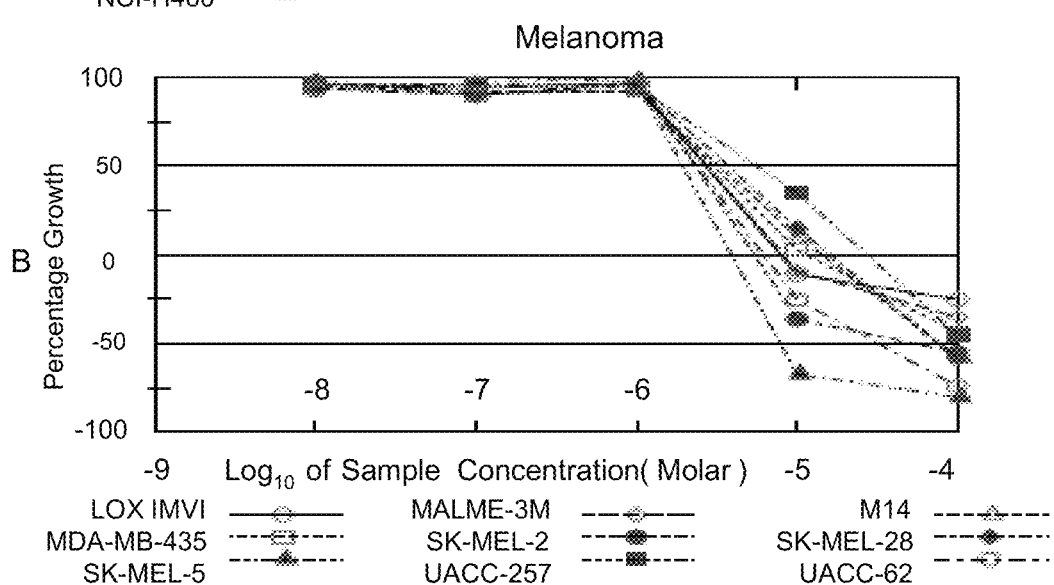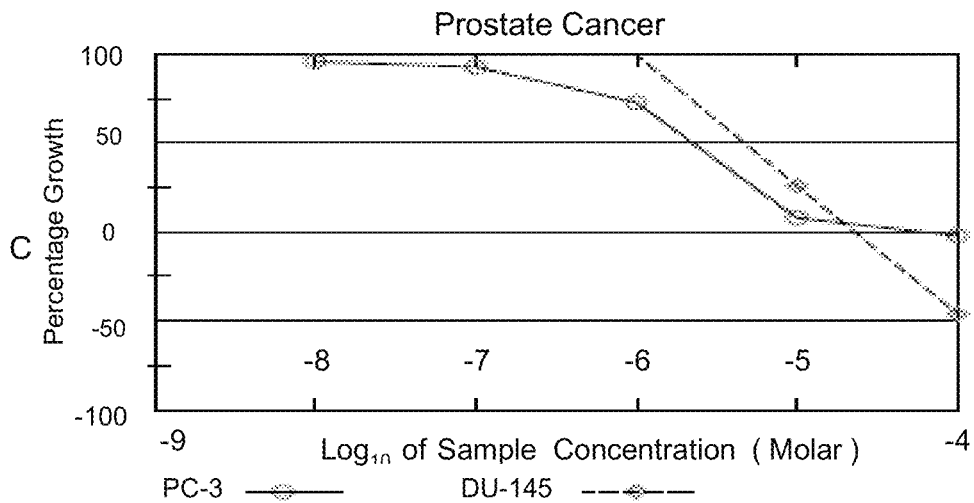
Figure 32

Figure 37
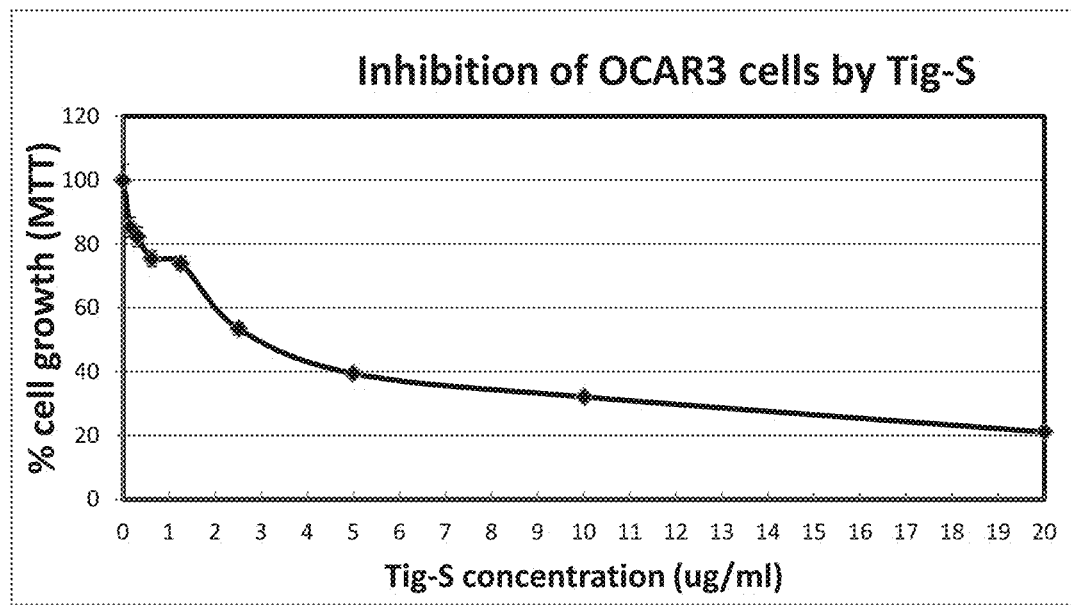
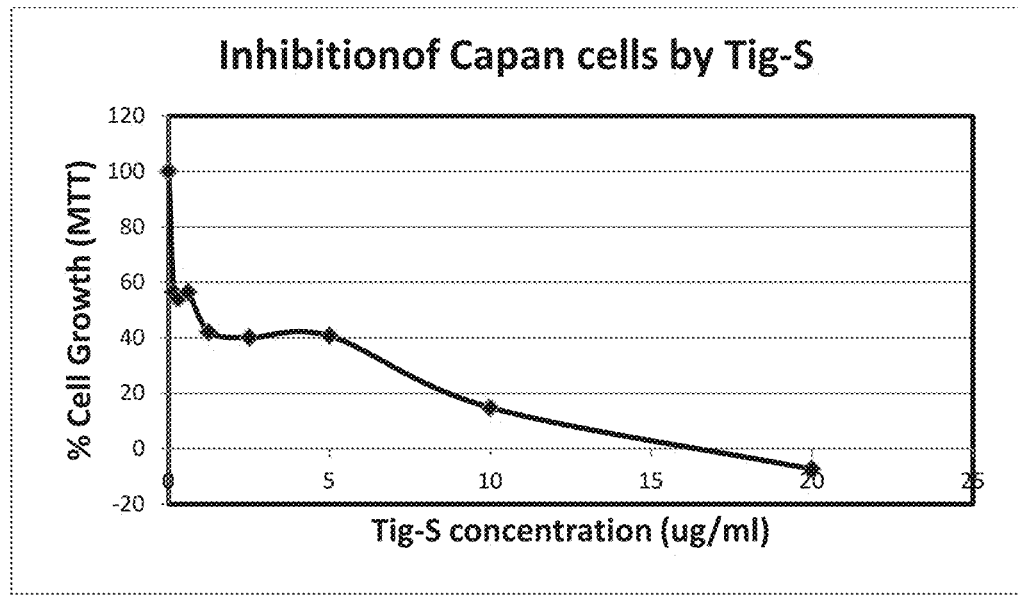

NATURAL AND SYNTHETIC COMPOUNDS FOR TREATING CANCER AND OTHER DISEASES

FIELD OF THE INVENTION

This invention provides methods of synthesing new compounds for pharmaceutical uses.

BACKGROUND OF THE INVENTION

This invention provides methods of synthesing new compounds for pharmaceutical uses. This invention provides methods, compounds and compositions for treating cancer, inhibiting cancer invasion, cell invasion, or cancer cell invasion, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers.

SUMMARY OF THE INVENTION

This invention provides methods of synthesizing new compounds for pharmaceutical uses. This invention provides compounds, compositions, and methods for treating cancer, inhibiting cancer invasion, cell invasion, macromolecular invasion, cancer cell invasion, and metastasis. This invention provides a use of compounds, compositions, for manufacturing medicament for treating cancer, inhibiting cancer invasion, macromolecular invasion, virus invasion and metastasis. This invention provides compounds for use as mediator or inhibitor of adhesion protein or angiopoietin, This invention provides compounds for use in a method of modulating attachment or adhesion of cells or angiogenesis, by modulating or inhibiting adhesion protein macromolecules, or angiopoietin, The compounds comprise the structures selected from the formulae in the present application, wherein the compounds are synthesized or isolated, wherein the compounds comprise the saponins, triterpenes, pentacyclic triterpenes, and compounds selected from formulae in the present application, wherein the cancers comprise breast, leukocytic, liver, ovarian, bladder, prostatic, skin, bone, brain, leukemia, lung, colon, CNS, melanoma, renal, cervical, esophageal, testicular, spleenic, kidney, lymphatic, pancreatic, stomach and thyroid cancers. This invention provides compounds for use as a mediator for cell circulating, cell moving cell homing and inflammatory diseases. This invention provides compounds for improving blood circulation; soothing stroke; preventing plaque formation and promote their dissipated; improve blood viscosity; reducing cardiovascular; reducing cerebrovascular; reducing thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, fluttering, Blood circulation, swelling, pain; Treating bronchiectasis, tuberculosis and lung abscess caused by too hemoptysis; reducing bleeding, antitussive, expectorant and analgesic effect, dilate blood vessels; reducing blood pressure and the treatment of cerebral arteriosclerosis; elevating blood lipids and reducing cholesterol.

BRIEF DESCRIPTION OF THE DRAWINGS

FIG. 18. A comparison of non-cancerous W138 with cancer cells: In these results, the MTT OD from cells before and after treated with different concentrations of drug was plotted. The result shows that: For W138 cells, the $IC_{100}$ value is about 10 ug/ml [$IC_{100}$ is defined as the MTT OD value after the drug-treatment equal to the original OD value before the drug-treatment. At this condition ($IC_{100}$), it indicates there is 100% inhibition of growth, but there is no cell lost]. At 20 ug/ml, the OD decrease to about 90% of the original value, indicating there is about 10% cell lost or dead. For ES2 cells, the $IC_{100}$ value is about 0.16-0.3 ug/ml. However, there is a big decrease of OD with higher drug concentrations indicating there are cell dead. At 10 ug/ml, the OD is 12% of the original value, indicating over 90% cells cell lost.

FIG. 30. Compare the activities of natural compound Y and synthetic compound Tig-S and Tig-R with prostate cancer. The synthetic compounds increase the potency and decrease the toxicity. A: Natural compound; B: synthetic compound Tig-S; C: synthetic compound Tig-R.

FIG. 31-33. Drug-effects of Tig-R

FIG. 37. Inhibition of overian cancer (OCAR3) by Tig-s, Tig-S inhibits OCAR3 cells' growth with an $IC_{50}$ value of 2.5 ug/ml; and inhibition of pancreas cancer (Capan), Tig-S inhibits Capan cells' growth with an $IC_{50}$ value of about 1 ug/ml.

DETAILED DESCRIPTION OF THE INVENTION

Figure 1:
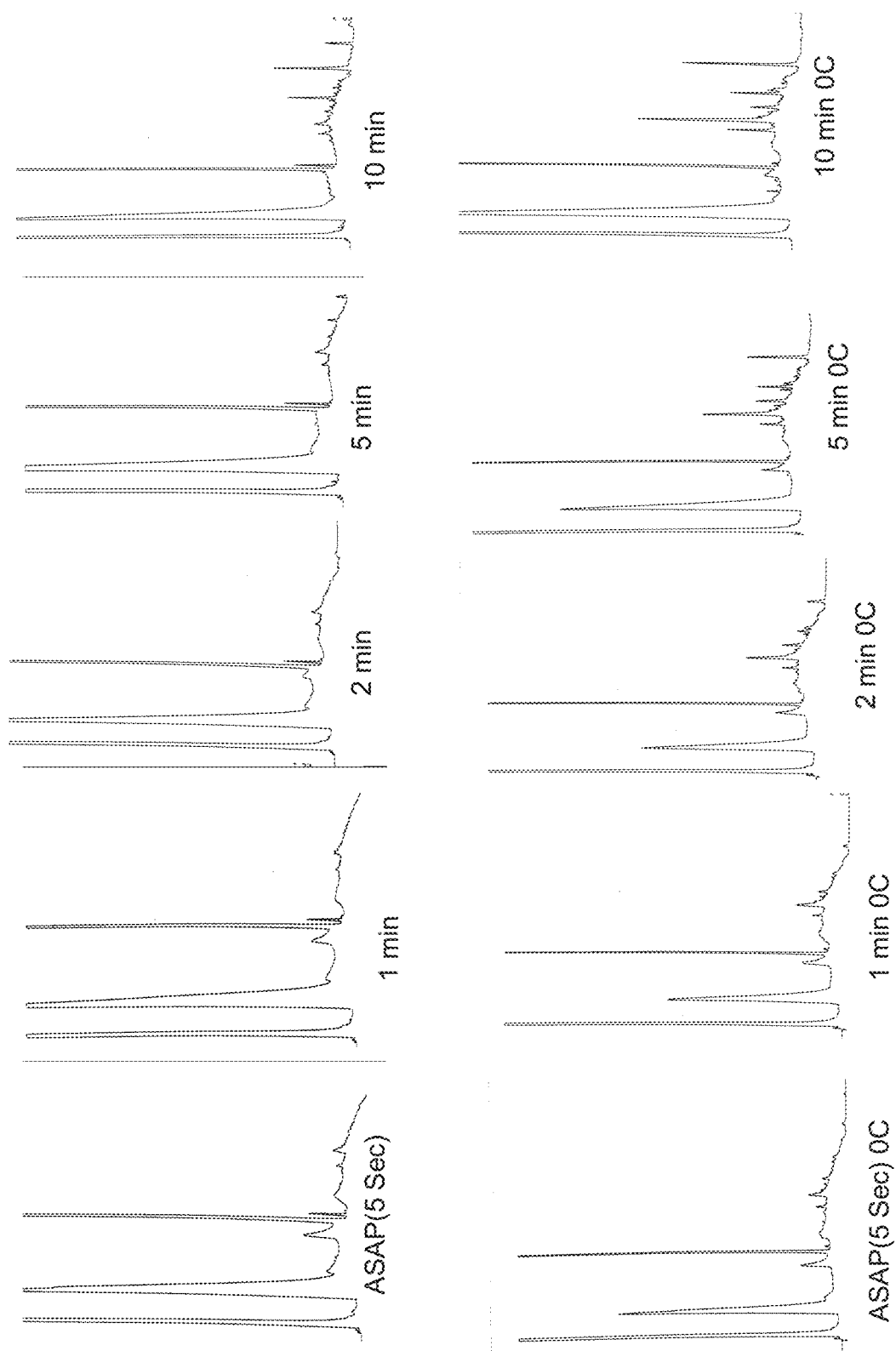
FIG. 1. HPLC profiles of esterification products of E4A with Tigloyl chloride (A) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature (Top row) and 0 C (bottom row).
Figure 2:
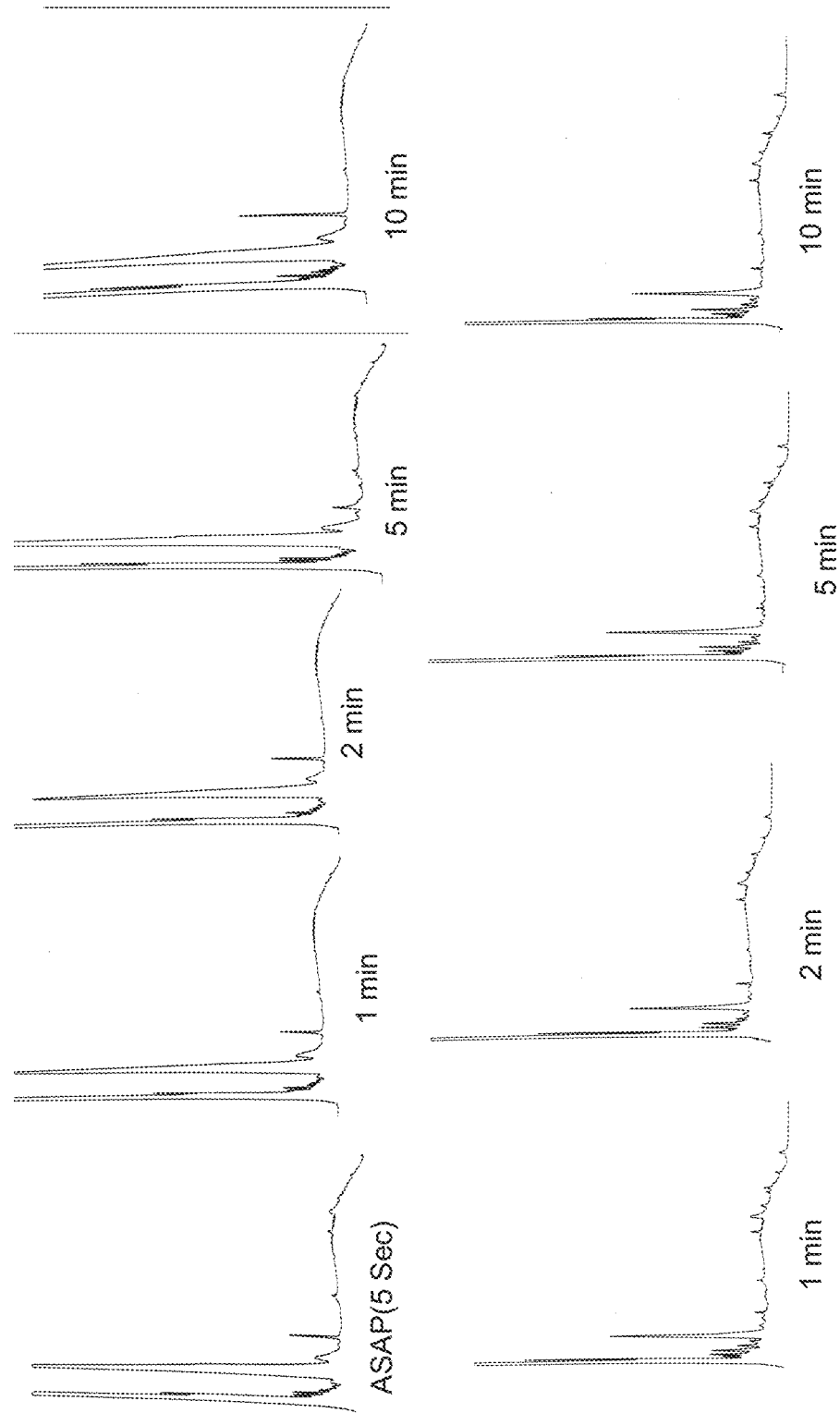
FIG. 2. HPLC profiles of esterification products of E4A with 3,3-dimethylacryloly chloride (B) from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature (Top row) and 0 C (bottom row).
Figure 3:
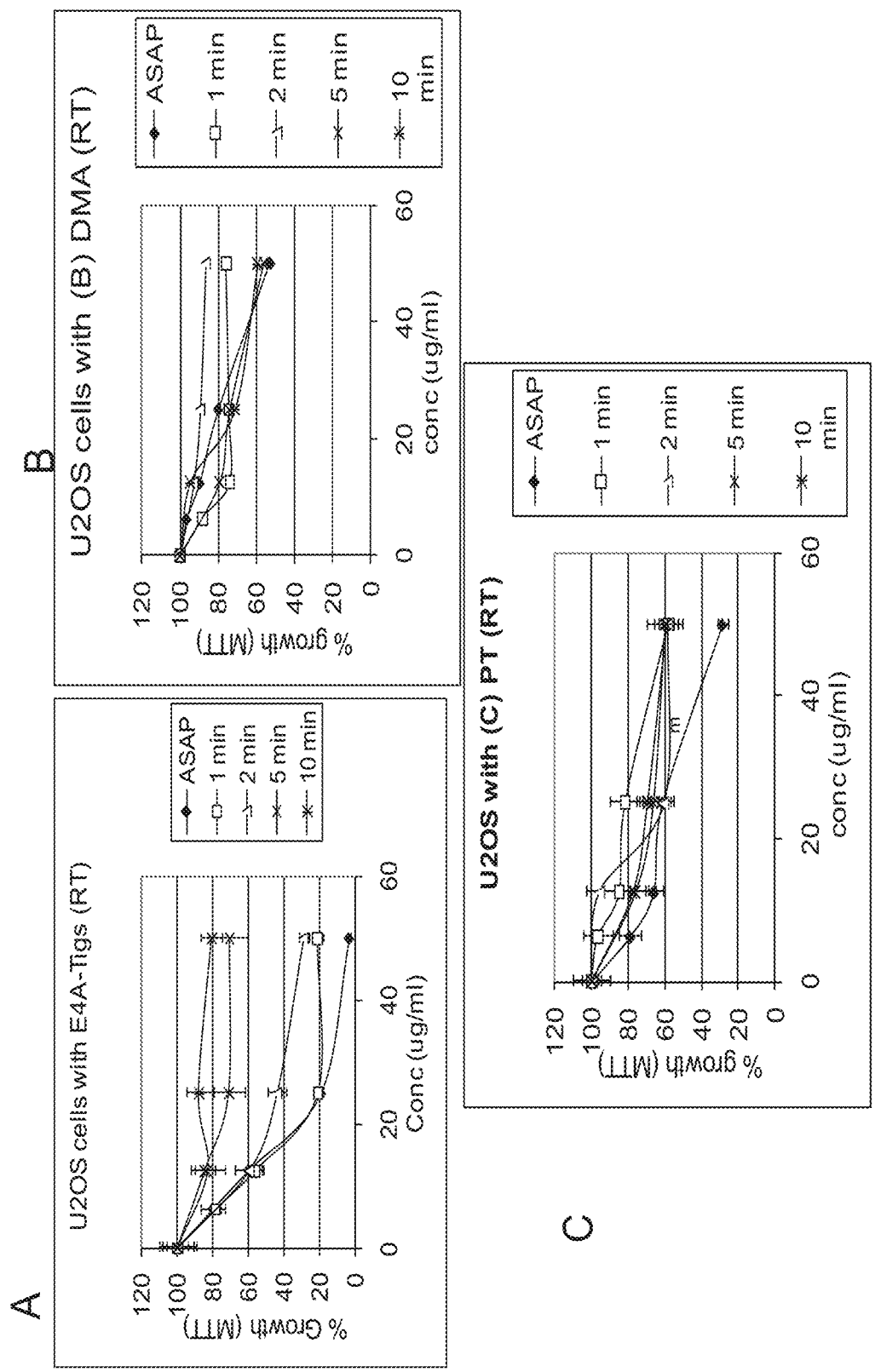
FIG. 3. MTT cytotoxic activity of times study at room temperature, A: E4A-Tigloyl(A); B: E4A-3,3-dimethylacryloly(B); C: E4A-4-pentenoyl(C).
Figure 4:
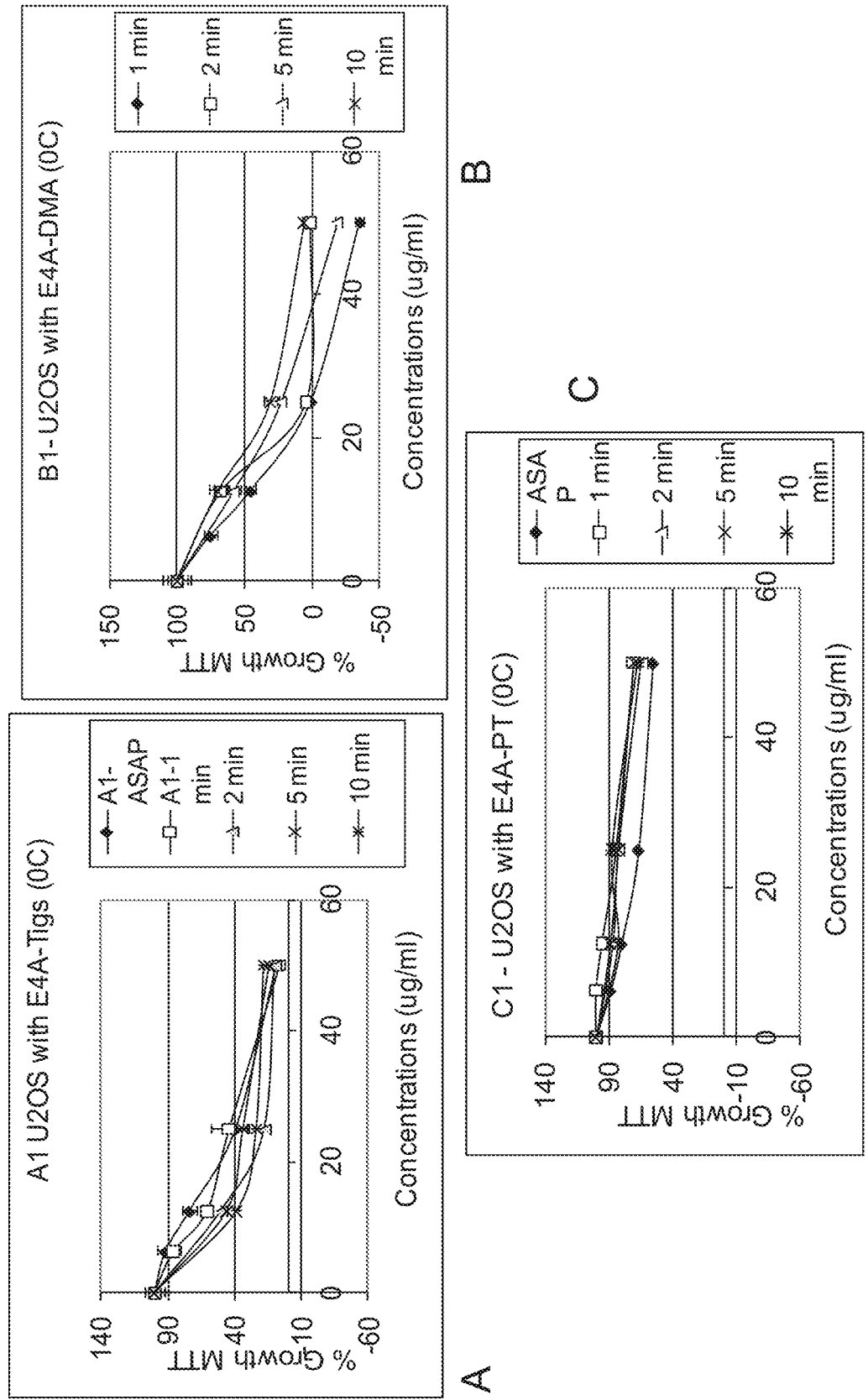
FIG. 4. MTT cytotoxic activity of times study at 0 C, A: E4A-Tigloyl(A); B: E4A-3,3-dimethylacryloly(B); C: E4A-4-pentenoyl(C).
Figure 5:
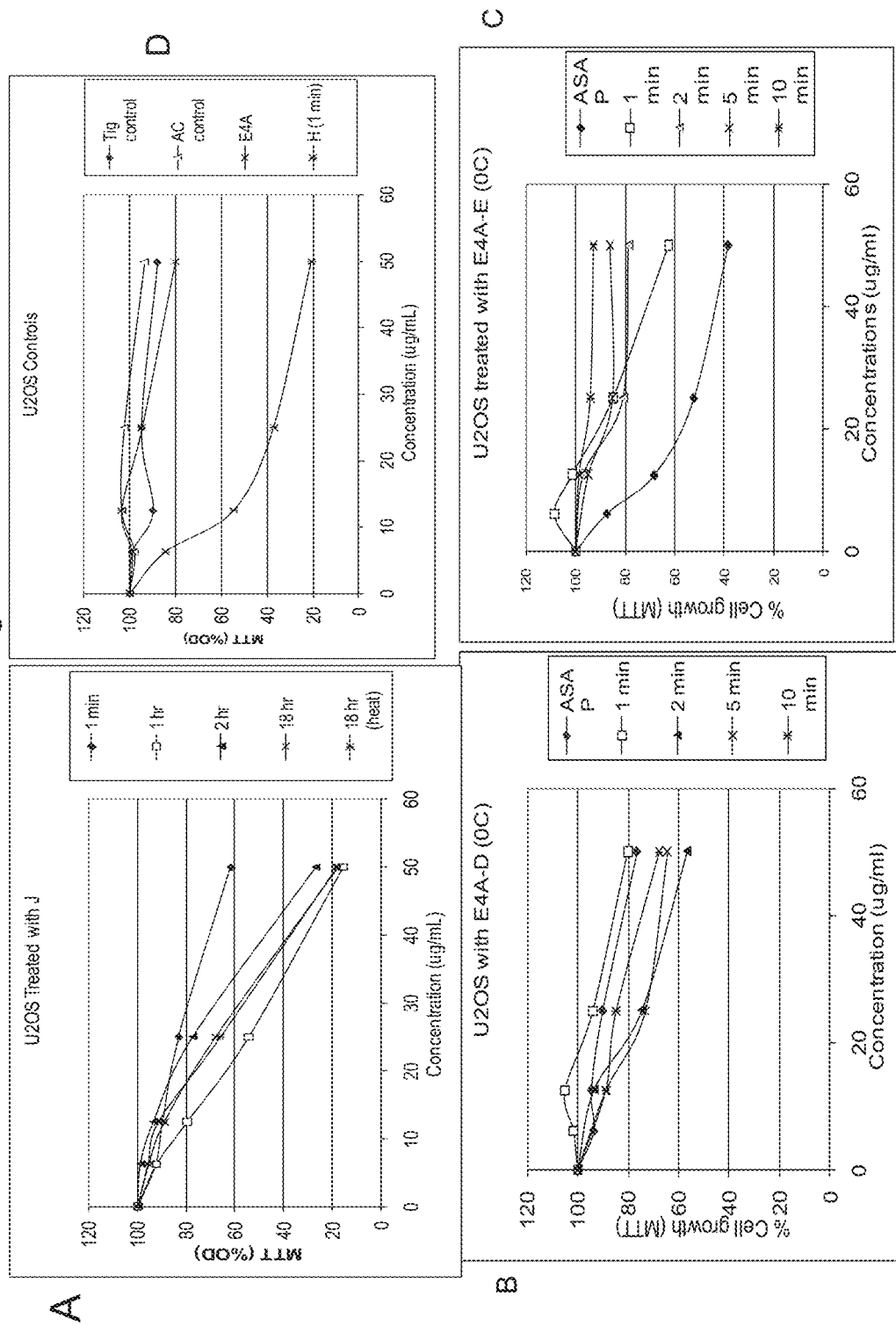
FIG. 5. MTT cytotoxic activity of times study, A: E4A-cinnamoyl(J); B: E4A-hexanoyl(D); C: E4A-2-ethylbutyryl (E); and D, controls: Tig control is tigloyl chloride without E4A; AC control is acetyl chloride without E4A; H is acetyl chloride with E4A reaction 1 min.
Figure 6:
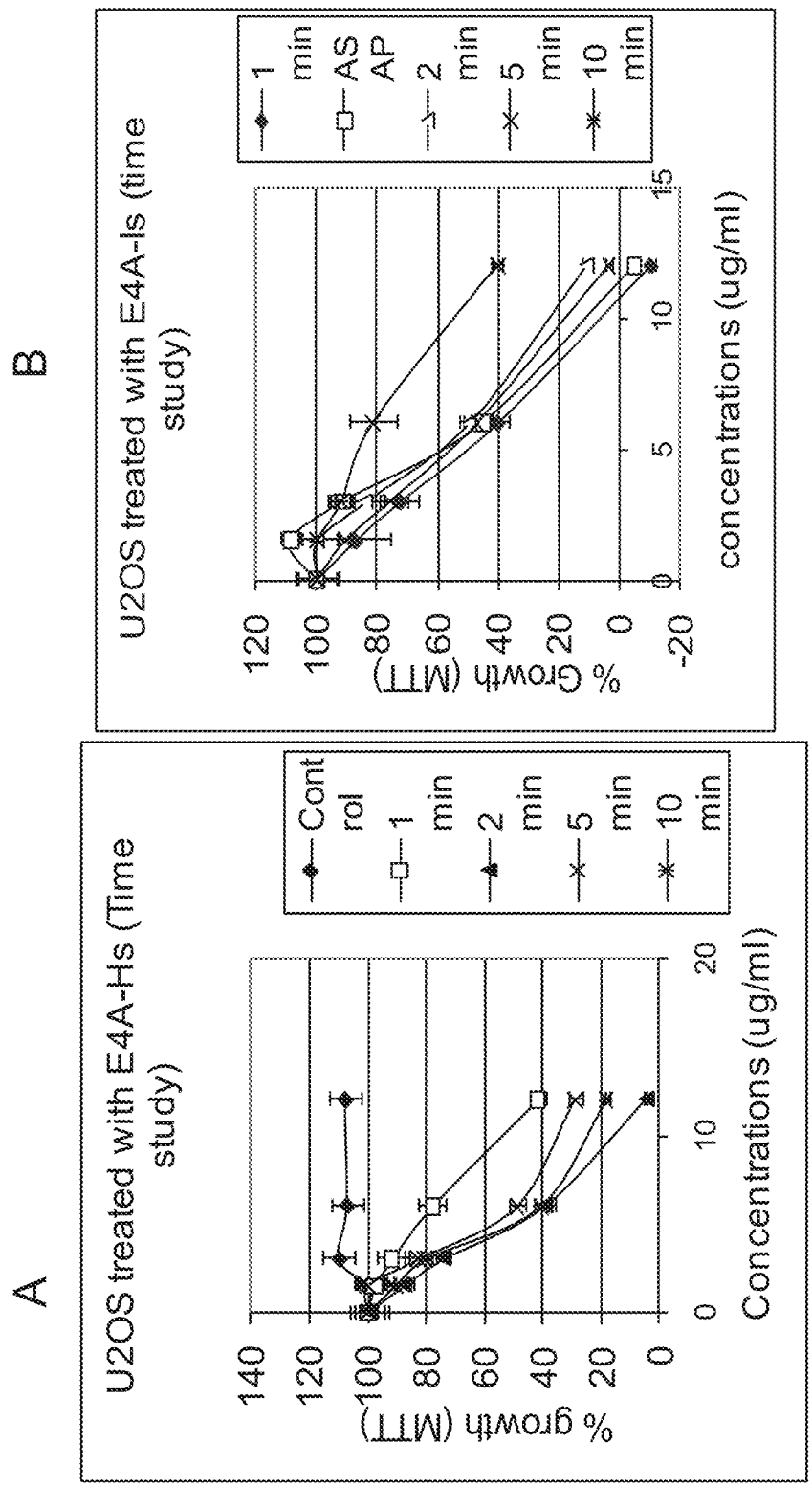
FIG. 6. MTT cytotoxic activity of times study, A: E4A-acetyl(H); B: E4A-crotonoyl(I)
Figure 7:
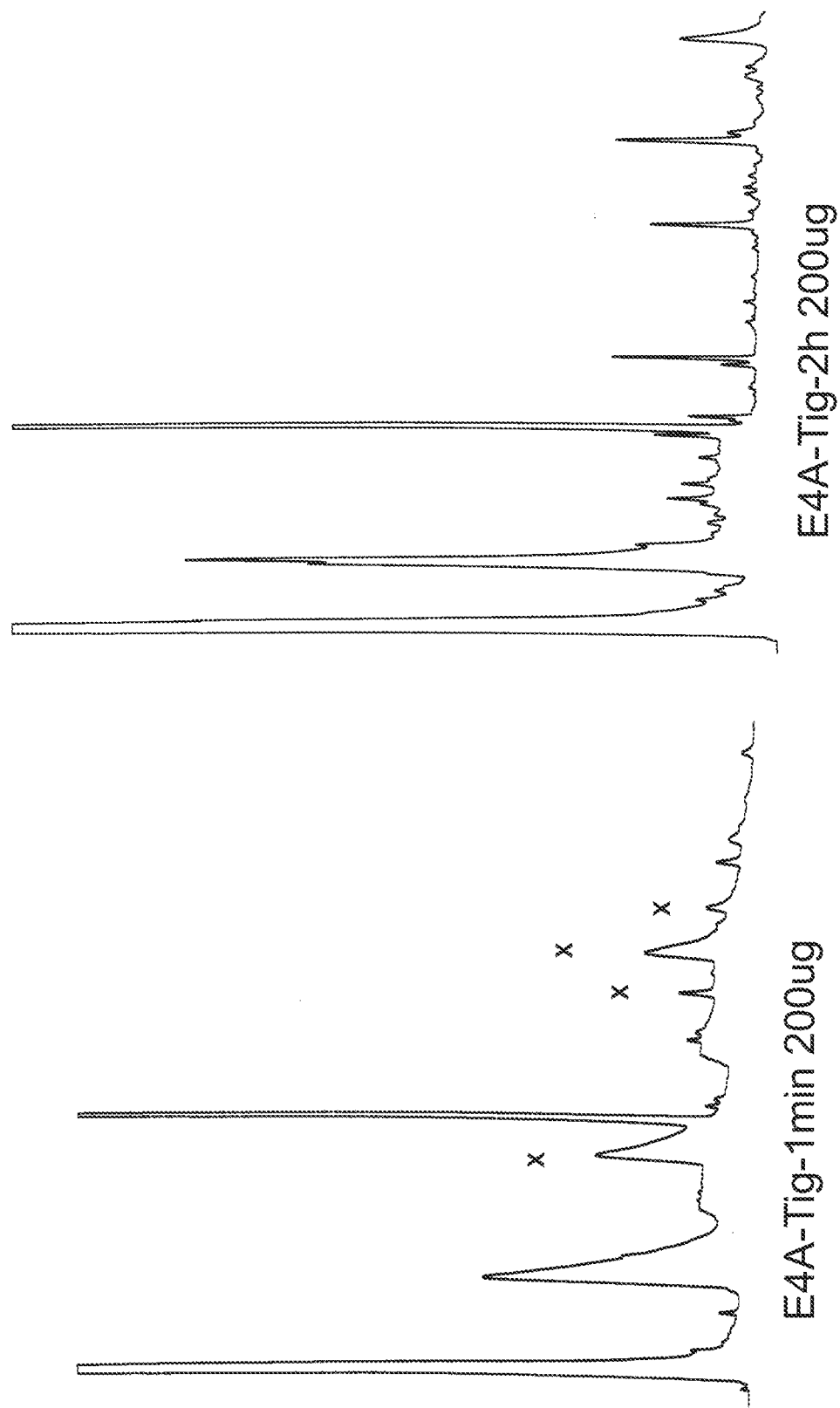
FIG. 7. HPLC profiles of E4A-Tig in 1 min and 2 hours
Figure 8:
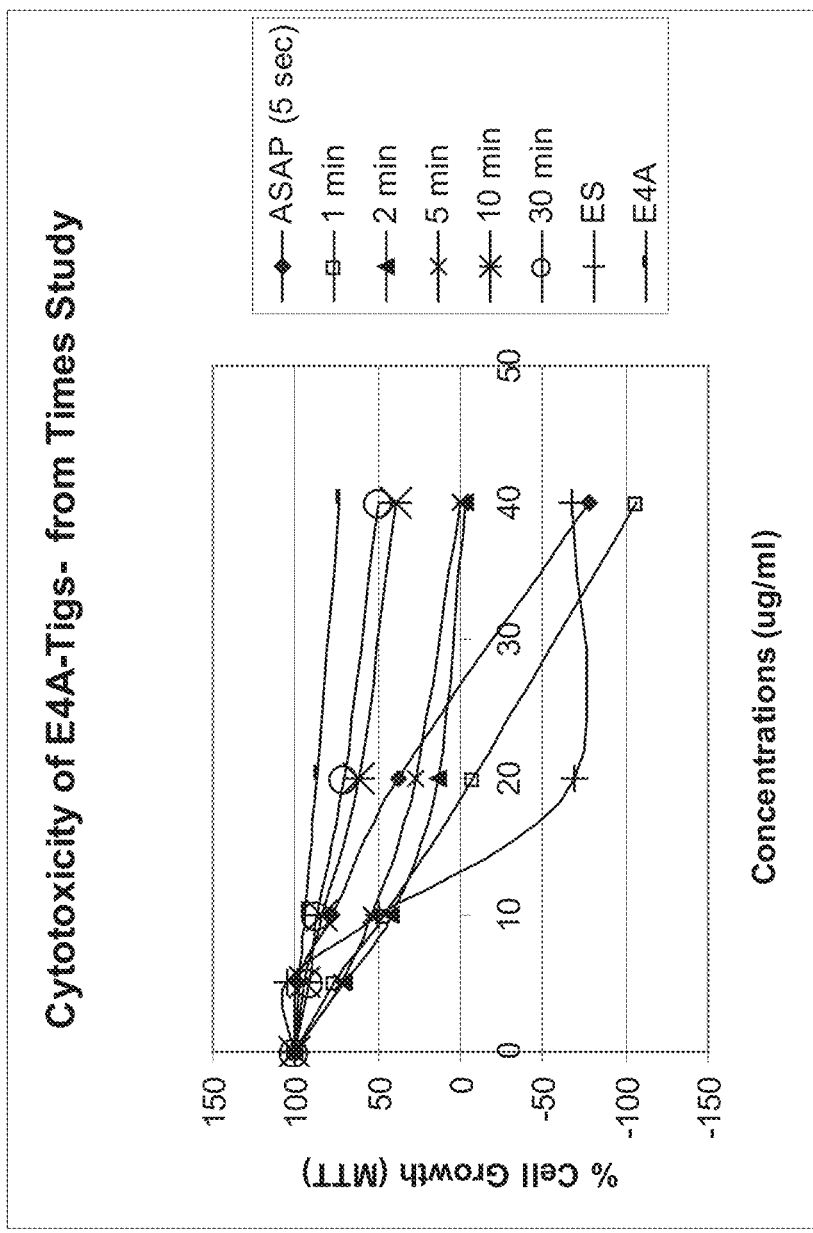
FIG. 8. MTT cytotoxic activity of times study for E4A-Tig. Results: E4A-Tigs from reaction of 5 sec to 1 min are most active. Activity decrease after 1 min of reaction. Minimum to no activity was obtained at 10 minutes or longer.
Figure 9:
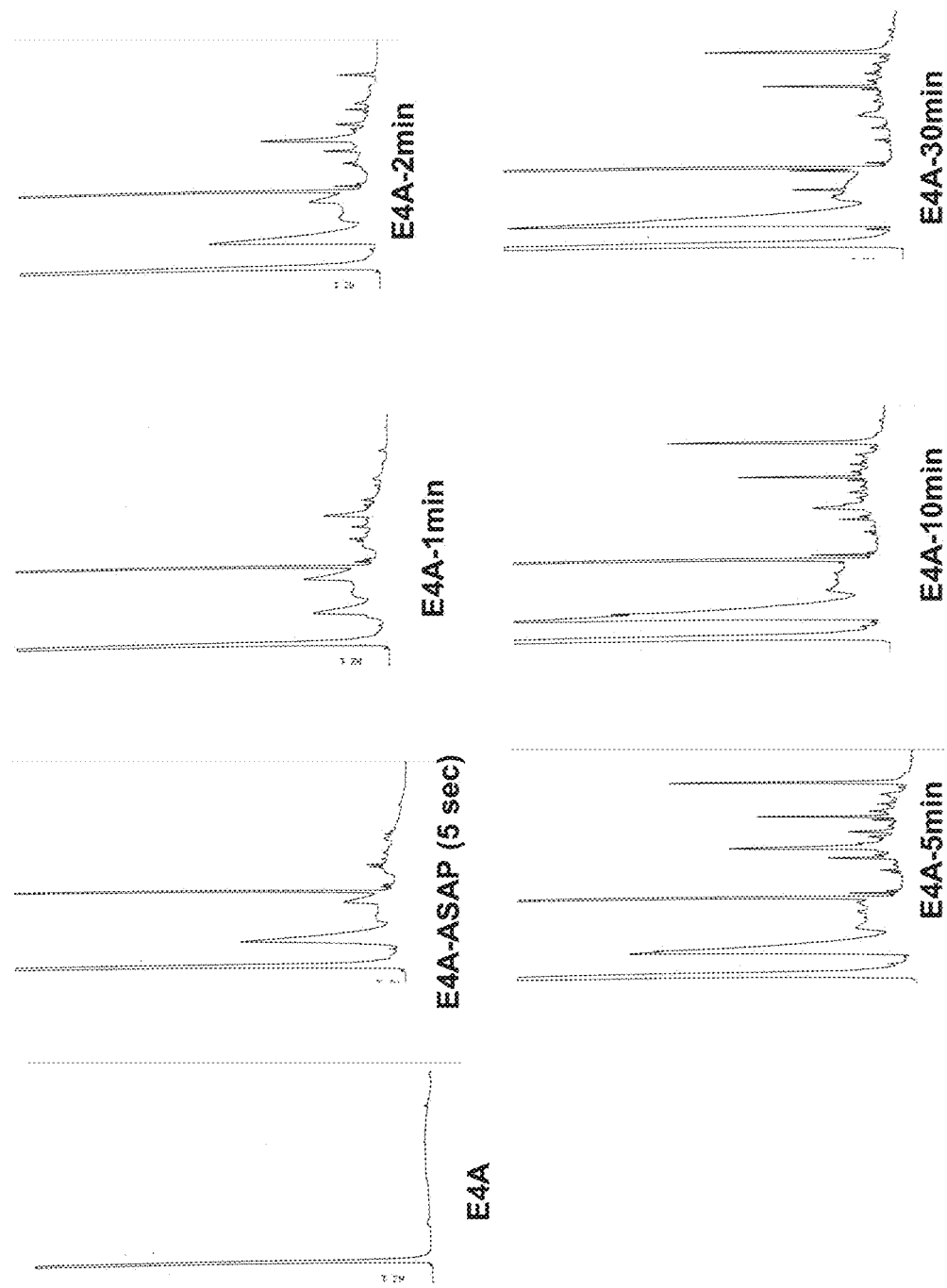
FIG. 9. Results of HPLC profiles of E4A-Tigs: E4A, E4A-ASAP (5 sec), E4A-1 min, E4A-2 min, E4A-5 min, E4A-10 min, E4A-30 min.
Figure 10:
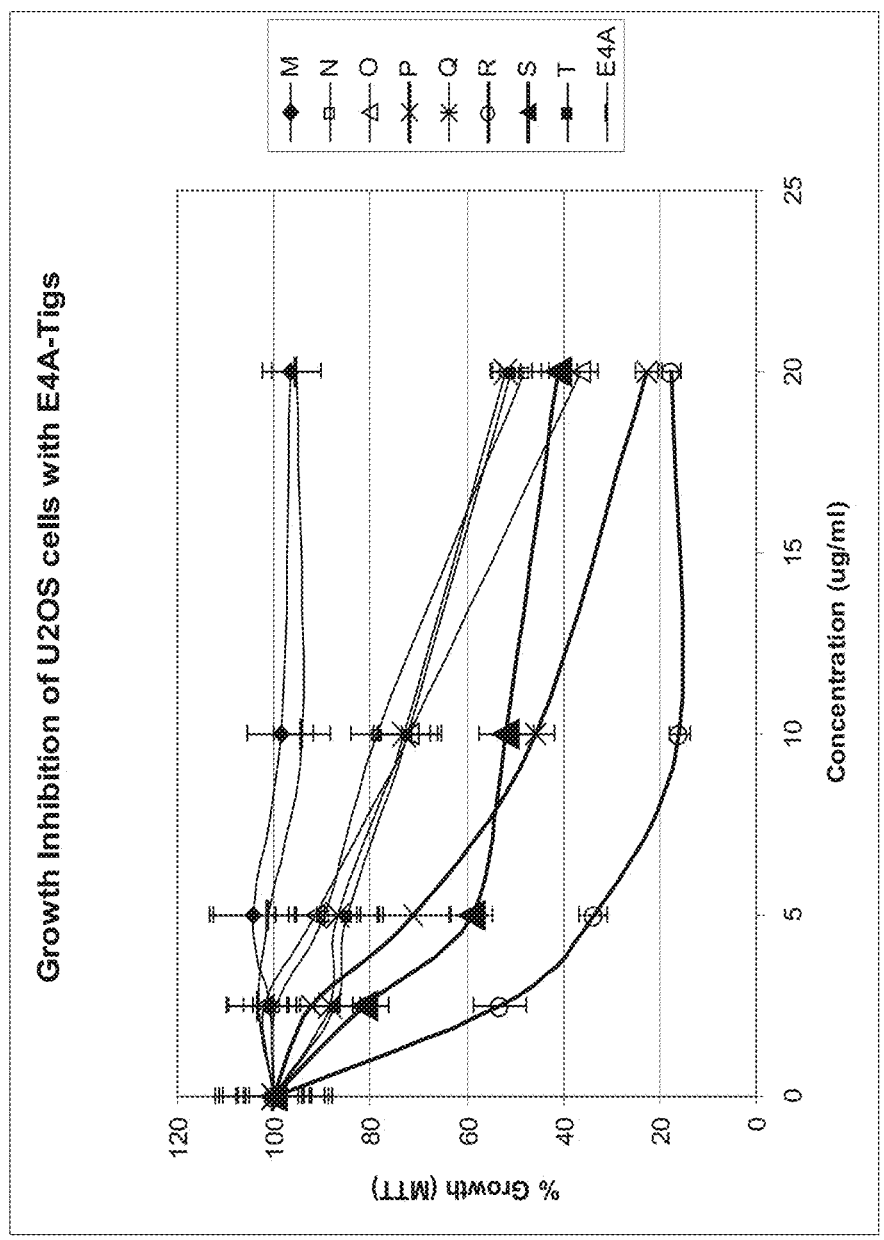
FIG. 10. Results of Activity order: M, N, O, P, Q, R, S, T, E4A; M=E4A has no activity.
Figure 11:
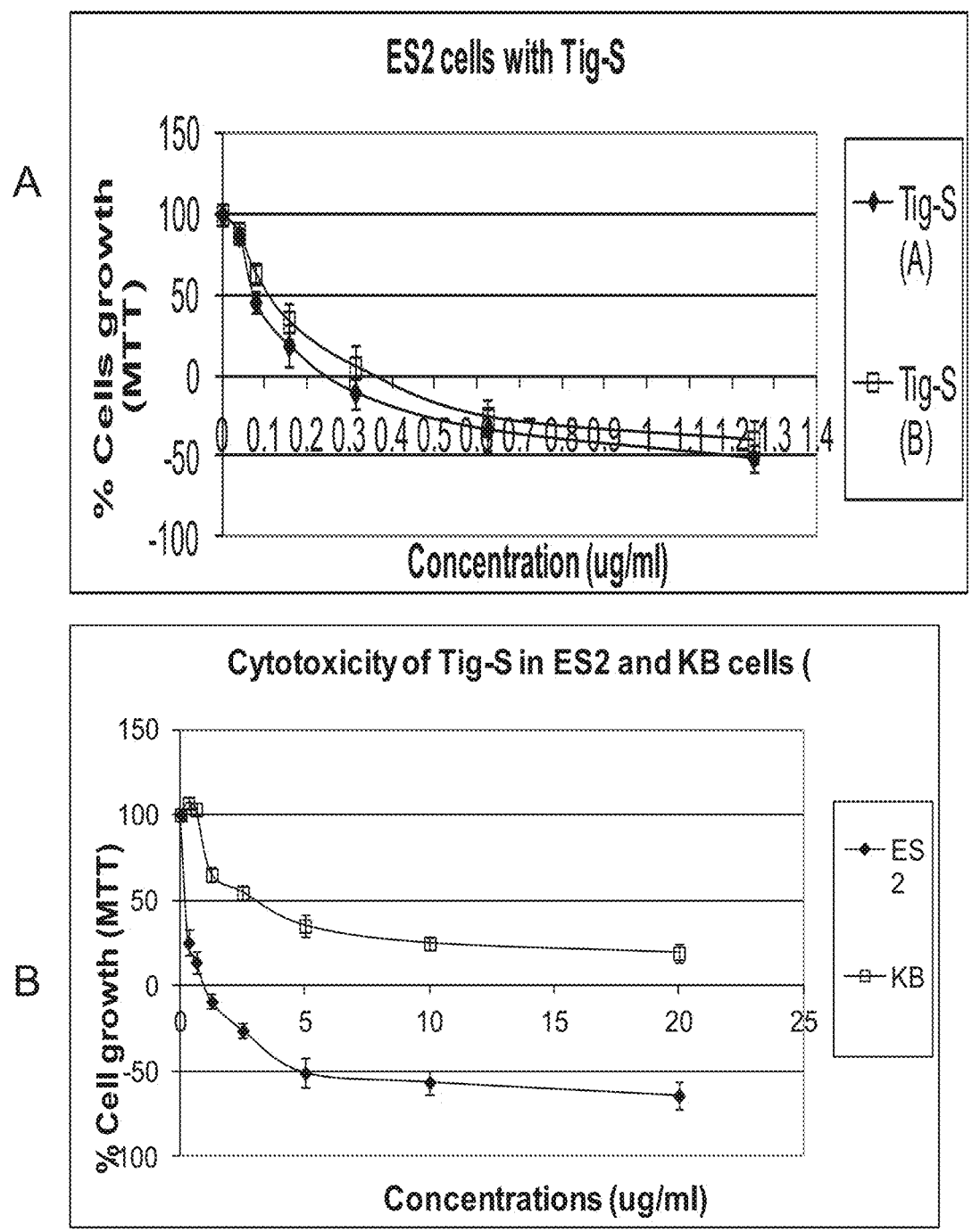
FIG. 11. (A) The IC50 of Tig-S in KB cells is about 4 ug/ml; and the corresponding IC50 in ES2 cells is less than 1 ug/ml; (B) The IC50 of Tig-S in ES2 cells, MTT assay with low doses of Tig-S, the IC50 of Tig-S in ES2 cells is approximately equal to 0.1 ug/ml FIG. 12. (A) Results: Swiss3T3 cells are mouse normal fibroblast which were used in this experiment to compare with ES2 (human ovarian cancer) in Tig-R cytotoxicity determination. The preliminary results indicate that the IC50 of Tig-R in SW3T3 cells is above 20 ug/ml while the corresponding IC50 in ES2 cells is about 2.8 ug/ml. (B) Effect of Tig-R on Normal human lung fibroblast (W138). Results: The IC50 of Tig-R in normal human fibroblast cells (W138) is about 10-15 ug/ml. This IC50 value is 3 times higher than those in ES2 (3 ug/ml).
Figure 13:
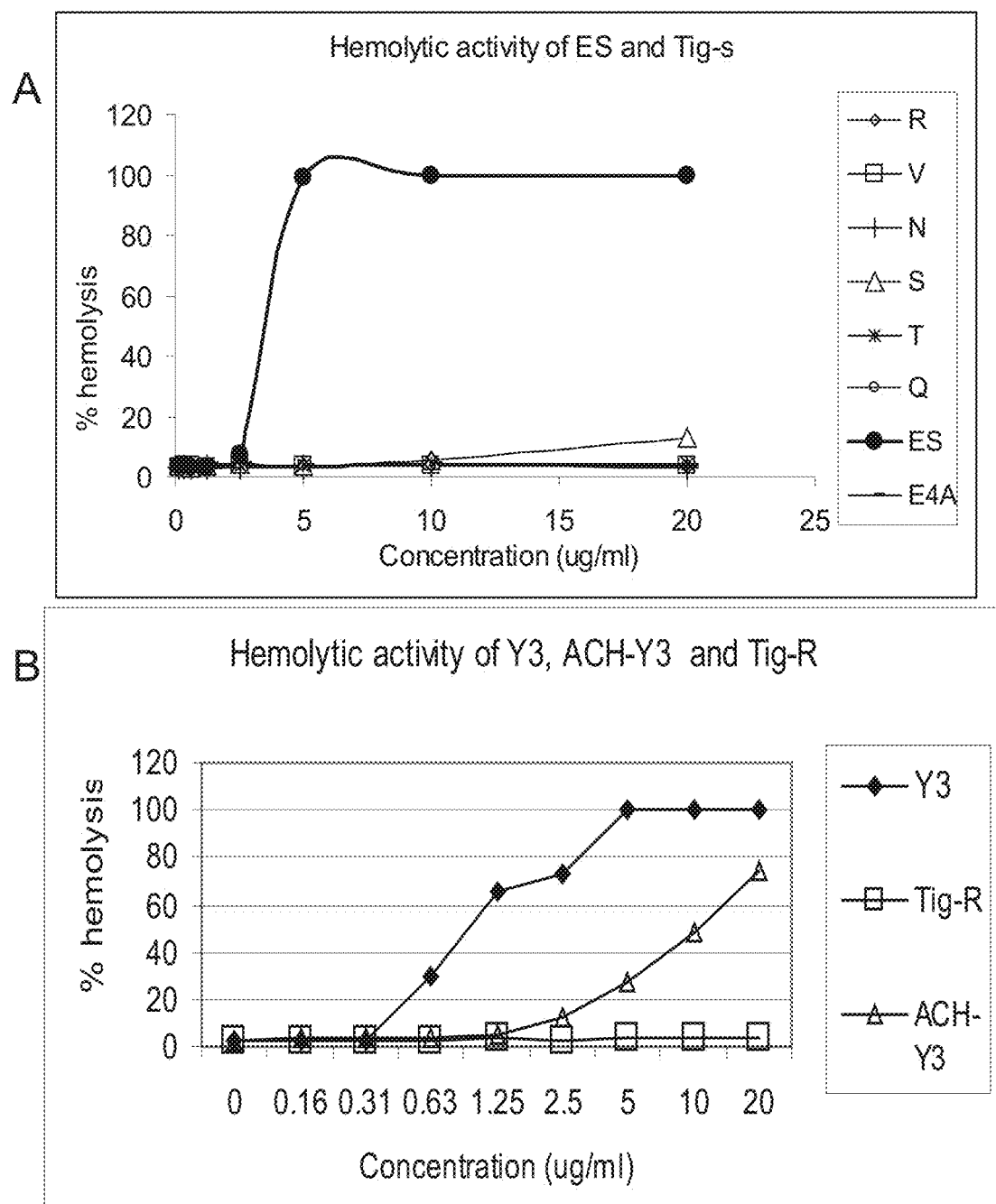
FIG. 13. (A) Results: Tig-N, -Q, -R, -T -S and -V do not have hemolytic activity up to 20 ug/ml. The graphs results are overlapped at the bottom of Figure. The original compound ES lyse 100% red blood cells (RBC) at 5 ug/ml. (B) Results: compare to Y3, the ACH-Y3 is less potent in hemolytic activity. Tig-R has no hemolytic activity FIG. 14. (A) Comparison of potency of compound Y in inhibiting growth of ovarian cancer cells. The IC50 for Compound Y is about 1.51 µg/ml. (B). Hemolytic activity of Xanifolia-Y, B-Escin, Xanifolia-X, ACH-Y and AKOH-Y FIG. 15. Inhibition of W138 cells with Tig-S (6 days); Result: IC50=1.5 ug/ml; At 10-20 ug/ml, about negative 10% cell growth.
Figure 15:
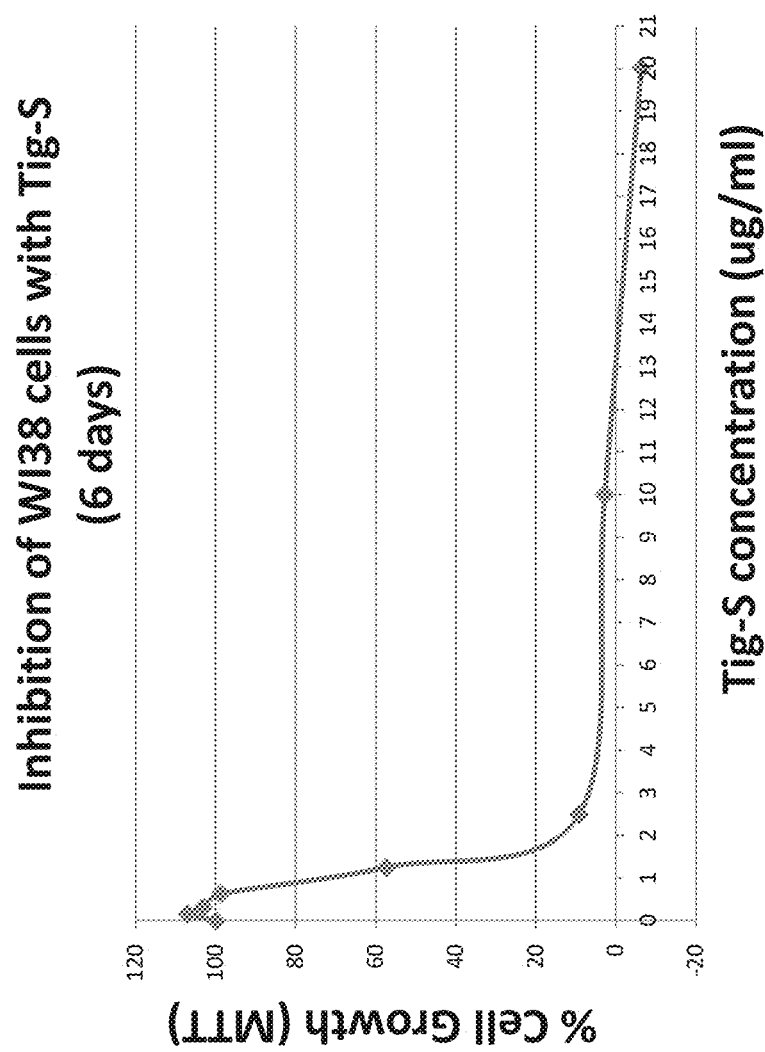
Figure 16:
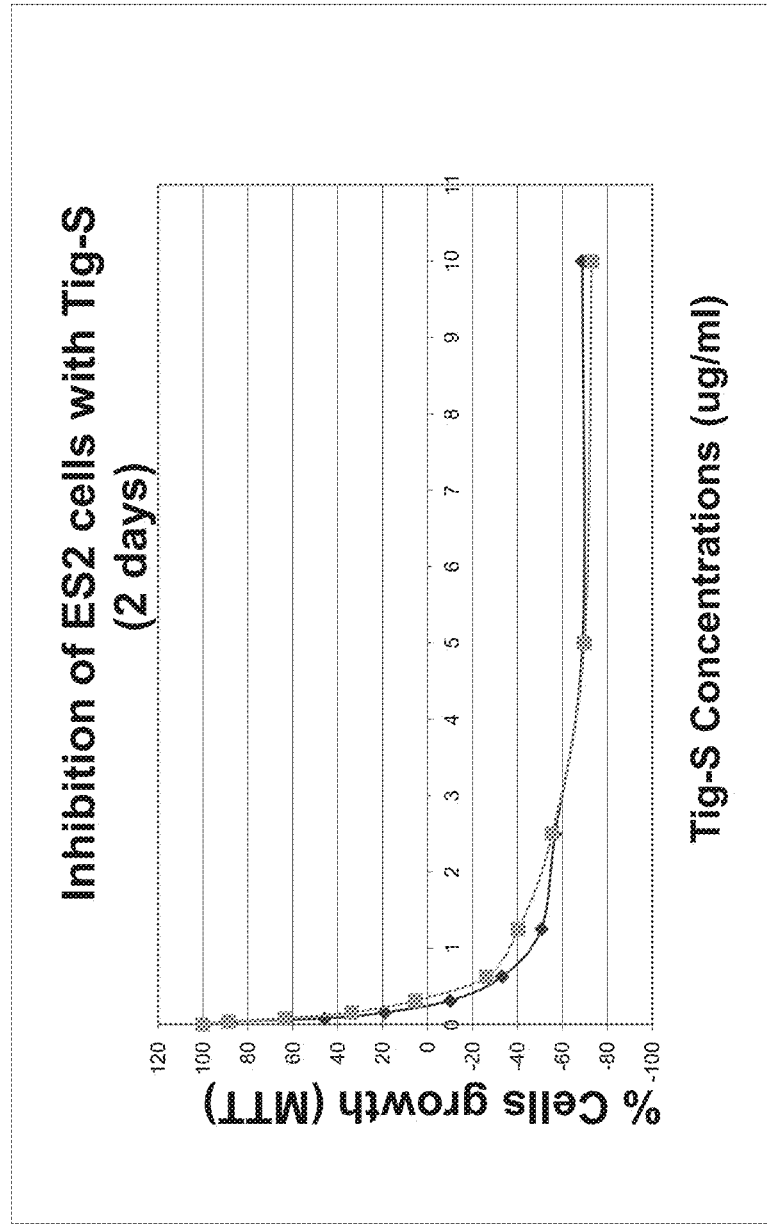
FIG. 16. Inhibition of ES2 cells with Tig-S (2 days); Results: IC50=0.3 ug/ml; At 5-10 ug/ml, negative 70% cells growth.
Figure 17:
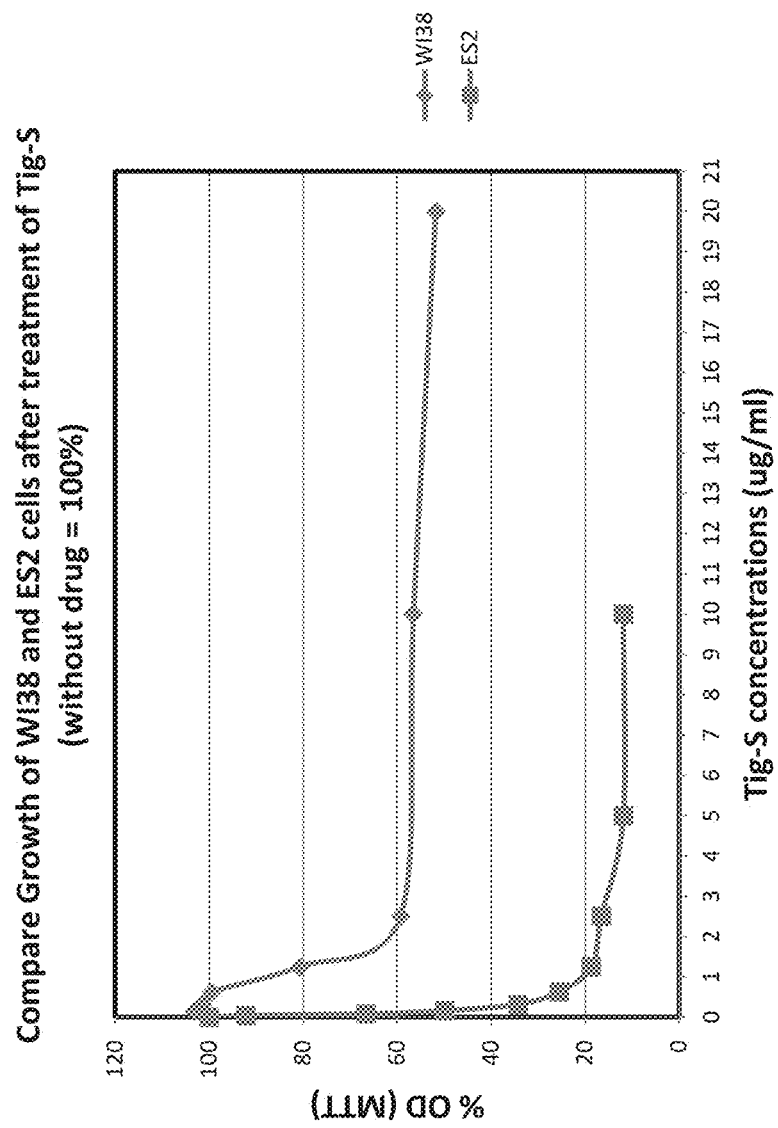
FIG. 17. A comparison of non-cancerous W138 with ES2 cancer cells. MTT OD is proportional to the amount of live cells. Here, the MTT OD in the no drug control represents 100% of cell growth. This study shows that at 10 ug/ml of Tig-S, W138 cells maintain about 55% of the control cell growth, while ES2 cells have only 10% of the control cell growth.

This invention provides a method of synthesising new active compounds for pharmaceutical uses. This invention provides an anti adhesion therapy which uses the compound as a mediator or inhibitor of adhesion proteins and angiopoietins. It inhibits excessive adhesion and inhibits cell viral and macromolecular attachment. It modulates angiogenesis. The compounds also use as mediator of cell viral and macromolecular adhesion receptor(s).

This invention provides compounds or a composition comprising the compounds provided in the invention for treating cancers; for inhibiting cancer growth, for inhibiting viruses; for preventing cerebral aging; for improving memory; improving cerebral functions; for curing enuresis, frequent micturition, urinary incontinence; neurodegenerative diseases, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment.

This invention provides compounds, compositions and methods for treating cancer diseases, inhibiting cancer invasion, for inhibiting cancer growth or for inhibiting cancer metastasis, wherein the compounds comprise the structures selected from the formulae of the present application, wherein the compounds can be synthesized or isolated, wherein the compounds comprise the triterpenes, pentacyclic triterpenes, saponins, and compounds selected from formulae in this application, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphatic cancer, pancreatic cancer, stomach cancer and thyroid cancer; wherein the cells comprise breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphhatic cell, pancreatic cell, stomach cell and thyroid cell.

This invention provides compounds for improving blood circulation; soothing stroke; preventing plaque formation and promote their dissipated; improve blood viscosity; reducing cardiovascular; reducing cerebrovascular; reducing thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, fluttering, Blood circulation, swelling, pain; Treating bronchiectasis, tuberculosis and lung abscess caused by too hemoptysis; reducing bleeding, antitussive, expectorant and analgesic effect, dilate blood vessels; reducing blood pressure and the treatment of cerebral arteriosclerosis; elevating blood lipids and reducing cholesterol.

This invention shows that the presence of group selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl, or sugar moiety substituted with acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl, at a pentacyclic triterpene, triterpene, triterpeniod, triterpeniod saponin, terpene, isoprene or compound selected from formulae of the present application, produces inhbition of cancer growth, cancer invasion, cells invasion, cancer cell invasion, cell adhesion, cell circulation or cell attachment, blocking the DNA synthesis of cancer cell, increase the potency and decrease the toxicity.

This invention shows that the presence of group selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl at carbon position 21, 22, 24 and/or 28 of a pentacyclic triterpene, triterpene, triterpeniod, triterpeniod saponin or compound selected from formulae of the present application, produces inhibition of cancer growth, cancer invasion, cells invasion, cancer cell invasion or macromolecular cell invasion. In an embodiment, the presence of group(s) selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl at carbon position 2, 3, 8, 15, 21, 22, 23, 24 and/or 28 of a pentacyclic triterpene, triterpeniod, triterpeniod saponin or compound selected from formulae of the present application produces activities including inhibition of cancer growth, cancer invasion, cells invasion, cancer cell invasion, cell adhesion, cell attachment or cell circulating wherein the group may attached with an O, S, NH, CH2O to the carbon of triterpene, triterpeniod, triterpeniod saponin or compound selected from formulae of the present application; wherein the group may be selected from group of CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, (CnH2n)O- angeloyl, (CnH2n)O-tigloyl, (CnH2n)O-senecioyl, (CnH2n)O-acetyl, (CnH2n)O-Crotonoyl, (CnH2n)O-3,3-Dimethylartyloyl, (CnH2n)O-Cinnamoyl, (CnH2n)O-Pentenoyl, (CnH2n)O-Hexanoyl, (CnH2n)O-benzoyl, (CnH2n)O-Ethylbutyryl, (CnH2n)O-alkyl, (CnH2n)O-dibenzoyl, (CnH2n)O-benzoyl, (CnH2n)O-alkanoyl, (CnH2n)O-alkenoyl, (CnH2n)O-benzoyl alkyl substituted O-alkanoyl, (CnH2n)O-alkanoyl substituted phenyl, (CnH2n)O-alkenoyl substituted phenyl, (CnH2n)O-aryl, (CnH2n)O-acyl, (CnH2n)O-heterocylic, (CnH2n)O-heteroaryl, (CnH2n)O-alkenylcarbonyl, (CnH2n)O-alkane, (CnH2n)O-alkene and (CnH2n)O-sugar moiety, wherein n is 1 or 2 or 3 or 4 or over 5. In an embodiment, the presence of group at carbon position 24, produces activities. In an embodiment, the presence of group at carbon position 24 and 28 produces activities. In an embodiment, the presence of group at carbon position 24 and 21 produces activities. In an embodiment, the presence of group at carbon position 24, 28 and 21, produces activities. In an embodiment, the presence of group at carbon position 24, 28 and 22 produces activities. In an embodiment, the presence of group at carbon position 24, 28 and 3 produces activities. In an embodiment, the presence of group at carbon position 24, and 3 produces activities. In an embodiment, the presence of group at carbon position 28 and 3 produces activities. In an embodiment, the presence of group at carbon position 3 produces activities. In an embodiment, the presence of group at carbon position 21 and 22 produces activities. In an embodiment, the hemolytic activity of the compound is reduced. In embodiment, the compound is attached a sugar moiety(ies), acid moiety(ies) or alduronic acid. In an embodiment, the presence of group at carbon position 1, produces activities. In an embodiment, the presence of group at carbon position 2, produces activities. In an embodiment, the presence of group at carbon position 3, produces activities. In an embodiment, the presence of group at carbon position 4, produces activities. In an embodiment, the presence of group at carbon position 5, produces activities. In an embodiment, the presence of group at carbon position 6, produces activities. In an embodiment, the presence of group at carbon position 7, produces activities. In an embodiment, the presence of group at carbon position 8, produces activities. In an embodiment, the presence of group at carbon position 9, produces activities. In an embodiment, the presence of group at carbon position 10, produces activities. In an embodiment, the presence of group at carbon position 11, produces activities. In an embodiment, the presence of group at carbon position 12, produces activities. In an embodiment, the presence of group at carbon position 13, produces activities. In an embodiment, the presence of group at carbon position 14, produces activities. In an embodiment, the presence of group at carbon position 15, produces activities. In an embodiment, the presence of group at carbon position 16, produces activities. In an embodiment, the presence of group at carbon position 17, produces activities. In an embodiment, the presence of group at carbon position 18, produces activities. In an embodiment, the presence of group at carbon position 19, produces activities. In an embodiment, the presence of group at carbon position 20, produces activities. In an embodiment, the presence of group at carbon position 21, produces activities. In an embodiment, the presence of group at carbon position 22, produces activities. In an embodiment, the presence of group at carbon position 23, produces activities. In an embodiment, the presence of group at carbon position 24, produces activities. In an embodiment, the presence of group at carbon position 25, produces activities. In an embodiment, the presence of group at carbon position 26, produces activities. In an embodiment, the presence of group at carbon position 27, produces activities. In an embodiment, the presence of group at carbon position 28, produces activities. In an embodiment, the presence of group at carbon position 29, produces activities. In an embodiment, the presence of group at carbon position 30, produces activities. In an embodiment, the activities are for treating cancers, inhibition of cancer growth, cancer invasion, cells invasion, cancer cell invasion; cell adhesion, cell attachment, cell circulating; for treating mad cow disease; treating prion diseases; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions or neurodegeneration; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment. In an embodiment, the compound is arresting cells in the S-phase and blocking their entering into the G2/M phase of cell cycle. The compound blocks the DNA synthesis of cancer cell.

This invention provides compounds for improving blood circulation; soothing stroke; preventing plaque formation and promote their dissipated; improve blood viscosity; reducing cardiovascular; reducing cerebrovascular; reducing thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, fluttering, Blood circulation, swelling, pain; Treating bronchiectasis, tuberculosis and lung abscess caused by too hemoptysis; reducing bleeding, antitussive, expectorant and analgesic effect, dilate blood vessels; reducing blood pressure and the treatment of cerebral arteriosclerosis; elevating blood lipids and reducing cholesterol.

In an embodiment, the compound is arresting cells in the S-phase and blocking their entering into the G2/M phase of cell cycle. The compound blocks the DNA synthesis of cancer cell. This application produce synthetic compounds increase the potency and decrease the toxicity.

In an embodiment, the presence of group at carbon position 1, reduces activities. In an embodiment, the presence of group at carbon position 2, reduces activities. In an embodiment, the presence of group at carbon position 3, reduces activities. In an embodiment, the presence of group at carbon position 4, reduces activities. In an embodiment, the presence of group at carbon position 5, reduces activities. In an embodiment, the presence of group at carbon position 6, reduces activities. In an embodiment, the presence of group at carbon position 7, reduces activities. In an embodiment, the presence of group at carbon position 8, reduces activities. In an embodiment, the presence of group at carbon position 9, reduces activities. In an embodiment, the presence of group at carbon position 10, reduces activities. In an embodiment, the presence of group at carbon position 11, reduces activities. In an embodiment, the presence of group at carbon position 12, reduces activities. In an embodiment, the presence of group at carbon position 13, reduces activities. In an embodiment, the presence of group at carbon position 14, reduces activities. In an embodiment, the presence of group at carbon position 15, reduces activities. In an embodiment, the presence of group at carbon position 16, reduces activities. In an embodiment, the presence of group at carbon position 17, reduces activities. In an embodiment, the presence of group at carbon position 18, reduces activities. In an embodiment, the presence of group at carbon position 19, reduces activities. In an embodiment, the presence of group at carbon position 20, reduces activities. In an embodiment, the presence of group at carbon position 21, reduces activities. In an embodiment, the presence of group at carbon position 22, reduces activities. In an embodiment, the presence of group at carbon position 23, reduces activities. In an embodiment, the presence of group at carbon position 24, reduces activities. In an embodiment, the presence of group at carbon position 25, reduces activities. In an embodiment, the presence of group at carbon position 26, reduces activities. In an embodiment, the presence of group at carbon position 27, reduces activities. In an embodiment, the presence of group at carbon position 28, reduces activities. In an embodiment, the presence of group at carbon position 29, reduces activities. In an embodiment, the presence of group at carbon position 30, reduces activities. In an embodiment the activities are included but not limited to hemolytic activity, cancer activity, arthritis, rheumatism, poor circulation, arteriosclerosis, Raynaud's syndrome, angina pectoris, cardiac disorder, coronary heart disease, headache, dizziness, kidney disorder; soothing stroke; plaque formation; cardiovascular; cerebrovascular; thrombosis, arteriosclerosis, coronary heart disease, hypertension, diabetes, thrombocytopenia purpura, hemoptysis, hematemesis; blood in the stool, uterine bleeding, traumatic bleeding, abdominal irritation, swelling, fluttering, swelling, pain; bronchiectasis, tuberculosis and lung abscess; bleeding, tussive, expectorant and analgesic effect, blood pressure and cerebral arteriosclerosis; blood lipids and cholesterol.

This invention shows a method of synthesizing active compound by attaching functional group to a core compound, wherein the functional group(s) comprises a group which is/are selected from ethanoyl, propanoyl, propenoyl, butanoyl, butenoyl, pentanoyl, pentenoyl, hexanoyl, hexenoyl, heptanoyl, heptenoyl, octanoyl, octenoyl, nonanoyl, nonenoyl, decanoyl, decenoyl, propionyl, 2-propenoyl, crotonoyl, 2-butenoyl, Isobutyryl, methylpropanoyl, 2-methyl-propanoyl, ethylbutyryl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, tigloyl, angeloyl, acetyl, crotonoyl, 3,3-Dimethylartyloyl, senecioyl, cinnamoyl, benzoyl, ethylbutyryl, dibenzoyl, alkanoyl, alkenoyl, benzoyl alkyl substituted alkanoyl, alkanoyl substituted phenyl, alkenoyl substituted phenyl, aryl, acyl, heterocylic, and heteroraryl, wherein the core compound is a triperpene or 5 ring triterpene. In embodiment, the core compound is a 4 ring terpene. In embodiment, the core compound is a 3 ring terpene. In embodiment, the core compound is a 2 ring terpene. In embodiment, the core compound is a 1 ring terpene. The compounds provided in the invention are for treating cancers, inhibition of cancer growth, cancer invasion, cells invasion, cancer cell invasion; cell adhesion, cell attachment, cell circulating; for treating mad cow disease; treating prion diseases; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions or neurodegeneration; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, antiparasitic; increase the expression of the genes: ANGPT2, DDIT3, LIF and NFKB1Z, and manufacturing an adjuvant composition and venotonic treatment. In an embodiment, the compound is arresting cells in the S-phase and blocking their entering into the G2/M phase of cell cycle. The compound blocks the DNA synthesis of cancer cell.

Experiments presented in this invention showed that the compound AKOH has no effect in inhibiting cancer growth, cancer invasion, cells invasion or cancer cell invasion. AKOH was obtained by removing the angeloyl groups from carbon positions 21 and 22 of the active Xanifolia Y(Y3). This invention shows that the ability for inhibiting cancer invasion, cells invasion or cancer cell invasion of Xanifolia Y(Y3) are lost by removing angeloyl groups from carbon positions 21 and 22.

Experiments presented in this invention showed that the core compound including E4A, E5A, Xanifolia Y-core have no effect in inhibiting cancer growth, cancer invasion, cells invasion or cancer cell invasion. Xanifolia Y-core was obtained by removing the angeloyl groups from carbon positions 21 and 22, and the sugar moieties from carbon 3 of the active Xanifolia Y(Y3). E4A (E IV A) was obtained by removing the groups from carbon positions 3, 21 and 22 of the active Escin. E5A (E V A) was obtained by removing the groups from carbon positions 3, 21 and 22 of the active Escin. This invention showed that the core compound including E4A, E4AY2, E5A, Xanifolia Y-core and AKOH have no hemolytic activity and no anti-cancer activity.

This invention showed that functional group attached at carbon position 24 of a pentacyclic triterpene did not produce hemolytic activity, which has bio-activities including inhibiting cancer growth, inhibiting cancer invasion, cells invasion or cancer cell invasion. This invention showed that functional group attached at carbon position 3 of a pentacyclic triterpene did not produce hemolytic activity, which has bio-activities including inhibiting cancer growth, inhibiting cancer invasion, cells invasion or cancer cell invasion. This invention showed that function group(s) attached at carbon position 3 and 1 or 2 or 3 of carbon position 28, 21, 22, 24 of a pentacyclic triterpene did not produce hemolytic activity, which has bio-activities including inhibiting cancer growth, inhibiting cancer invasion, cells invasion or cancer cell invasion.

This invention showed that functional group attached at carbon position 2 of a pentacyclic triterpene did not produce hemolytic activity, which has bio-activities including inhibiting cancer growth, inhibiting cancer invasion, cells invasion or cancer cell invasion. This invention showed that function group(s) attached at carbon position 2 and 1 or 2 or 3 of carbon position 28, 21, 22, 24 of a pentacyclic triterpene did not produce hemolytic activity, which has bio-activities including inhibiting cancer growth, inhibiting cancer invasion, cells invasion or cancer cell invasion.

This invention provides a pentacyclic triterpene with reduced hemolytic activity for treating diseases, wherein the triterpene comprising a group(s) attached at its core producing bio-activities. This invention provides a pentacyclic triterpene with reduced hemolytic activity comprising a group(s) attached at carbon position 3, or carbon position 24 and 1 or 2 or 3 of other position(s) of a pantacyclic triterpene, which has bio-activities. This invention provides a triterpene with reduced hemolytic activity comprising a group(s) attached at carbon position 15, 16, 21, 22, 23, 24, 28, 29, 30 and/or 3 of a pentacyclic triterpene, which has bio-activities. This invention provides a composition comprising a triterpene with reduced hemolytic activity comprising a group(s) attached at carbon position 3, or carbon position 24 and 1 or 2 or 3 of other position(s) of a pentacyclic triterpene, which has bio-activities. This invention provides a method for bio-ativities treatment including but not limited to treating cancers, comprising administering to said subject an effective amount of compound, wherein the compound is a pentacyclic triterpene with reduced hemolytic activity comprising a group(s) attached at carbon position 3, or carbon position 24 and 1 or 2 or 3 of other position(s) of a pentacyclic triterpene, which has bio-activities.

The compound of the present application can be obtained with the method:
1. Dissolving core compound or triterpenes, hydroxylated triterpenes core in pyridine,
2. Adding acyl chloride,
3. The mixture is stirred for length of time including 5 sec, 10 sec, 20 sec, 30 sec, 40 sec, 1 min, 2 min, 5 min, 10 min, 30 min, 1 hr, 2 hr, 18 hr, 2 days or 3 days at 0 C, 25 C, 50 C or 75 C,
4. At the end of reaction, an aqueous solution of acid or base, or water is added to the reaction mixture,
5. The solution is then extracted of ethyl acetate and ethyl acetate is removed by evaporation and lyophilization,
6. Dissolving the reaction product in acetonitrile with Trifluoroacetic acid or DMSO,
7. Testing the reaction product of mixtures and individual fractions with MTT cytotoxic assay,
8. Selecting the HPLC fractions for isolation is according to the cytotoxic activity of the reaction product obtained at a specific reaction time,
9. Purifiing the active esterification products with HPLC,
10. Collecting the products,
11. Testing the products.

The compound of present application, wherein the core compound is terpene, isoprene, or triterpene core; wherein the core compound is hydroxylated; wherein the core compound was dissolved in pyridine; wherein the acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride and Ethylbutyryl chloride; wherein the reaction time for the mixture is stirred for 5 sec, 1 min, 2 min, 5 min, 10 min, 30 min, 1 hr, 2 hr, 18 hr, 2 days or 3 days; wherein the temperature is 0 C, 25 C, 50 C or 75 C temperature; wherein the acid including HCl or the base is a weak base including NaHCO3 is added to the reaction mixture; wherein the solution is then extracted 3 times with ethyl acetate and lyophilization; wherein the reaction product is dissolved in 80% acetonitrile—0.005% Trifluoroacetic acid or DMSO; wherein selecting the HPLC fractions for isolation is according to the cytotoxic activity of the reaction product obtained at a reaction time of 5 sec, 1 min, 2 min, 5 min, 10 min, 30 min, 1 hr, 2 hr, 18 hr, 2 days or 3 days.

This invention showed that functional group attached at carbon position 23 of a pentacyclic triterpene did not produce hemolytic activity, which has bio-activities including inhibiting cancer growth, inhibiting cancer invasion, cells invasion or cancer cell invasion. This invention showed that function group(s) attached at carbon position 24 and 1 or 2 or 3 of carbon position 28, 21, 22 of a pentacyclic triterpene did not produce hemolytic activity, which has bio-activities including inhibiting cancer growth, inhibiting cancer invasion, cells invasion or cancer cell invasion.

This invention showed that functional group attached at carbon position 24 of a pentacyclic triterpene did not produce hemolytic activity, which has bio-activities including inhibiting cancer growth, inhibiting cancer invasion, cells invasion or cancer cell invasion. This invention showed that function group(s) attached at carbon position 24 and 1 or 2 or 3 of carbon position 28, 21, 22 of a pentacyclic triterpene did not produce hemolytic activity, which has bio-activities including inhibiting cancer growth, inhibiting cancer invasion, cells invasion or cancer cell invasion.

This invention provides a triterpene with reduced hemolytic activity for treating diseases, wherein the triterpene comprising a group(s) attached at its core producing bio-activities. This invention provides a pentacyclic triterpene with reduced hemolytic activity comprising a group(s) attached at carbon position 24, or carbon position 24 and 1 or 2 or 3 of other position(s) of a pentacyclic triterpene, which has bio-activities. This invention provides a composition comprising a pentacyclic triterpene with reduced hemolytic activity comprising a group(s) attached at carbon position 24, or carbon position 24 and 1 or 2 or 3 of other position(s) of a pentacyclic triterpene, which has bio-activities. This invention provides a method for bio-ativities treatment including but not limited to treating cancers, comprising administering to said subject an effective amount of compound, wherein the compound is a triterpene with reduced hemolytic activity comprising a group(s) attached at carbon position 24, or carbon position 24 and 1 or 2 or 3 of other position(s) of a pentacyclic triterpene, which has bio-activities.

This invention showed that Tig-N, Tig-Q, Tig-R, Tig-T Tig-S and Tig-V do not have hemolytic activity up to 20 ug/ml. The original compound ES lyse 100% red blood cells (RBC) at 5 ug/ml. Compare to Y3, the ACH-Y3 is less potent in hemolytic activity. Tig-R has no hemolytic activity. This invention showed that Tig-N, Tig-Q, Tig-R, Tig-T Tig-S and Tig-V have anti cancer activities.

Many saponins and triterpenes have hemolytic characteristic that damage red blood cells. This severe side effect make people hesitate to use saponins or triterpenes in medicines. This invention produces sythesised saponins and triterpenes with reduced hemolytic characteristic for use as medicament. This invention produces compounds with reduced hemolytic characteristic for use as medicament. The medicament can be used for treating cancer, inhibiting cancer growth, cancer invasion, cells invasion or cancer cell invasion. This application produce synthetic compounds increase the potency and decrease the toxicity.

This invention shows that the ability for inhibiting cancer growth, cancer invasion, cells invasion or cancer cell invasion are maintained when the sugar moieties are removed from carbon position 3 of an active compound, triterpene, triterpeniod, or triterpeniod saponin. Experiments presented in this invention showed that the compound ACH-Y3 has the ability to inhibit cancer invasion, cells invasion or cancer cell invasion. The compound ACH-Y3 was obtained by removing the sugar moieties from carbon position 3 of a active Xanifolia Y(Y3). This invention shows that the ability for inhibiting cancer invasion, cells invasion or cancer cell invasion are maintained when the sugar moieties are removed from the carbon position 3 of active Xanifolia Y(Y3).

A compound which has bio-activities including inhibiting cancer growth, inhibiting cancer invasion, cells invasion or cancer cell invasion is called active compound.

This invention provides a use for compounds, compositions, and methods for manufacturing medicament for treating cancers, inhibition of cancer growth, cancer invasion, cells invasion, cancer cell invasion; cell adhesion, cell attachment, cell circulating, or for inhibiting cancer metastasis, wherein the compounds comprise the structures selected from the formulae of the present application, wherein the compounds can be synthesized or isolated, wherein the compounds comprise the pentacyclic triterpenes, wherein the compounds with reduced hemolytic, wherein the cells comprise cancer cells, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer. The method of inhibiting cancer invasion, cells invasion or cancer cell invasion activities uses non-cytotoxic drug concentrations. The method of inhibiting metastasis uses non-cytotoxic drug concentrations. There is no noticeable change in cell morphology.

This invention provides triterpene(s) with reduced hemolytic activity for treating diseases, wherein the triterpene can be a pentacyclic triterpene comprising a group(s) attached at its core producing bio-activities. This invention provides a pentacyclic triterpene with reduced hemolytic effect, comprising a group(s) attached at carbon position 24, or carbon position 24 and 1 or 2 or 3 of other position(s) of a pentacyclic triterpene, which has bio-activities. This invention provides a composition comprising a triterpene with reduced hemolytic activity comprising a group(s) attached at carbon position 24, or carbon position 24 and 1 or 2 or 3 of other position(s) of a pentacyclic triterpene, which has bio-activities. This invention provides a method for bio-ativities treatment including but not limited to treating cancers, comprising administering to said subject an effective amount of compound, wherein the compound is a triterpene with reduced hemolytic activity, comprising a group(s) attached at carbon position 24, or carbon position 24 and 1 or 2 or 3 of other position(s) of a triterpene, which has bio-activities, wherein a compound selected from A1-18, A20-32, B1-18, B20-32, C1-18, C20-32, D1-18, D20-32, D1-18, D20-32, D1-18, D20-32, D1-18, D20-32, D1-18, D20-32, E1-18, E20-32, G1-18, G20-32, H1-18, H20-32, 11-18, 120-32, J1-18, J20-32, K1-18, K20-32, Tig-Sen-n, Tig-Cro-n, Tig-Acy-n, Tig-Pen-n, Tig-Hex-n, Tig-Cin-n, Tig-Ang-n, Tig-Eth-n, Tig-R-Sen-n, Tig-R-Cro-n, Tig-R-Acy-n, Tig-R-Pen-n, Tig-R-Hex-n, Tig-R-Cin-n, Tig-R-Ang-n, Tig-R-Eth-n, wherein n=1 to 6, and a salt, ester, metabolite thereof, and the compounds selected from formulae 2A, and K; wherein the compound is selected from Tig-N, Tig-Q, Tig-R, Tig-T Tig-S and Tig-V.

This invention provides methods for treating cancers, inhibition of cancer growth, cancer invasion, cells invasion, cancer cell invasion; cell adhesion, cell attachment, cell circulating, migration, metastasis or growth of cancers, wherein the methods comprise affecting gene expression, wherein the methods comprise stimulating gene expression, or wherein the methods comprise inhibiting the gene expression, or wherein the methods comprise administering to a subject an effective amount of compounds, compositions in this application. In an embodiment, the method comprises contacting said cell with a compound selected from A1-18, A20-32, B1-18, B20-32, C1-18, C20-32, D1-18, D20-32, D1-18, D20-32, D1-18, D20-32, D1-18, D20-32, D1-18, D20-32, E1-18, E20-32, G1-18, G20-32, H1-18, H20-32, 11-18, 120-32, J1-18, J20-32, K1-18, K20-32, Xanifolia Y0, Y1, Y2, Y(Y3), Y5, Y7, Y8, Y9, Y10, Xanifolia (x), M10, Escin(bES), Aescin, ACH-Y(Y3), ACH-Y10, ACH-Y2, ACH-Y8, ACH-Y7, ACH-Y0, ACH-X, ACH-Z4, ACH-Z1, ACH-Escin(bES), ACH-M10, Tig-Sen-n, Tig-Cro-n, Tig-Acy-n, Tig-Pen-n, Tig-Hex-n, Tig-Cin-n, Tig-Ang-n, Tig-Eth-n, Tig-R-Sen-n, Tig-R-Cro-n, Tig-R-Acy-n, Tig-R-Pen-n, Tig-R-Hex-n, Tig-R-Cin-n, Tig-R-Ang-n, Tig-R-Eth-n, wherein n=1 to 6, and a salt, ester, metabolite thereof, and the compounds selected from formulae 2A, and K. In vitro studies show that a compound selected from structure (2A) or (K) inhibits cell adhesion to culture flasks. The compound blocks the function of these adhesive molecules on cells. In an embodiment, the selected compound blocks the function of these adhesive molecules on cells. In an embodiment, the selected compound blocks the function of these adhesive molecules on carcinoma cells. In an embodiment, the selected compound blocks the function of these adhesive molecules on the mesothelial cells. This invention provides an anti adhesion therapy which uses the compound as a mediator or inhibitor of adhesion proteins and angiopoietins. It inhibits excess adhesion and inhibits cell attachment. This invention provides compounds for use as a mediator for cell circulating, cell moving and inflammatory diseases. In an embodiment, the selected compound binds to the adhesive proteins (by masking) on the membrane and inhibits the interaction of adhesion proteins with their receptors. In an embodiment, the selected compound's action on the membrane affects adhesion proteins' function in the membrane. The lost of adhesion activity of cancer cells is result from direct or indirect action of the selected compound on membrane proteins. (Our purification methods and biological assays include the MTT assay in International Application No. PCT/US05/31900, filed Sep. 7, 2005, U.S. Ser. No. 11/289,142, filed Nov. 28, 2005, and U.S. Ser. No. 11/131, 551, filed May 17, 2005, and PCT/US2008/002086, 1188-ALA-PCT, filed Feb. 15, 2008, the cell invasion experiments methods in International Application PCT/US2010/0042240, filed Jul. 16, 2010)

This invention provides a use of compounds or methods for inhibiting cancer invasion, cell invasion, cancer cell invasion, macromolecular cell invasion, migration, metastasis or growth of cancers, wherein this invention comprises a process and method for administration of the composition, wherein administration is by intravenous injection, intravenous drip, intraperitoneal injection or oral administration; wherein administration is by intravenous drip: 0.003-0.03 mg/kg body weight of compound dissolved in 250 ml of 10% glucose solution or in 250 ml of 0.9% NaCl solution, or by intravenous injection: 0.003-0.03 mg/kg body weight per day of compound dissolved in 10-20 ml of 10% glucose solution or of 0.9% NaCl solution, or 0.01-0.03 mg/kg body weight of compound dissolved in 250 ml of 10% glucose solution or in 250 ml of 0.9% NaCl solution, or by intravenous injection: 0.01-0.03 mg/kg body weight per day of compound dissolved in 10-20 ml of 10% glucose solution or of 0.9% NaCl solution, or 0.01-0.05 mg/kg body weight of compound dissolved in 250 ml of 10% glucose solution or in 250 ml of 0.9% NaCl solution, or by intravenous injection: 0.01-0.05 mg/kg body weight per day of compound dissolved in 10-20 ml of 10% glucose solution or of 0.9% NaCl solution, or 0.05-0.2 mg/kg body weight of compound dissolved in 250 ml of 10% glucose solution or in 250 ml of 0.9% NaCl solution, or by intravenous injection: 0.05-0.2 mg/kg body weight per day of compound dissolved in 10-20 ml of 10% glucose solution or of 0.9% NaCl solution, or by intravenous drip: 0.1-0.2 mg/kg body weight per day of compound dissolved in 250 ml of 10% glucose solution or in 250 ml of 0.9% NaCl solution, or by intravenous injection: 0.1-0.2 mg/kg body weight per day compound dissolved in 10-20 ml of 10% glucose solution or of 0.9% NaCl solution, or by intraperitoneal injection (I.P.): 2.5 mg/kg body weight per day compound dissolved in 10% glucose solution or of 0.9% NaCl solution, or by oral administration wherein the dosage of mammal is 1-10 mg/kg, 10-30 mg/kg, 30-60 mg/kg, or 60-90 mg/kg body weight of compound, or by intravenous injection or intravenous drip wherein the dosage of mammal is 0.01-0.1 mg/kg body weight, 0.1-0.2 mg/kg, 0.2-0.4 mg/kg body weight, or 0.4-0.6 mg/kg body weight of compound, or by intraperitoneal injection (I.P.) wherein the dosage of mammal is 1-3 mg/kg, 3-5 mg/kg, 4-6 mg/kg, or 6-10 mg/kg body weight of compound, or 10-50 mg/kg body weight of compound, or 50-100 mg/kg body weight of compound, or 30-70 mg/kg body weight of compound or 100-150 mg/kg body weight of compound.

This invention provides a use of compounds or methods for treating cancers, inhibition of cancer growth, cancer invasion, cells invasion, cancer cell invasion; macromolecular cell invasion, cell adhesion, cell attachment, cell circulating, migration, metastasis or growth of cancers, infection or re-infection of virus or infectious macromolecules, and cancer cell fusion, wherein the invention comprises a pharmaceutical composition comprising the compound of this invention or a pharmaceutically acceptable salt thereof, and a pharmaceutically acceptable carrier or diluent, wherein said compound is present in a concentration of 0.01 ug/ml to 65 ug/ml, or wherein said compound is present in a concentration of 0.01 ug/ml to 40 ug/ml, or wherein said compound is present in a concentration of 0.01 ug/ml to 30 ug/ml, or wherein said compound is present in a concentration of 0.01 ug/ml to 10 ug/ml, or wherein said compound is present in a concentration of 0.01 ug/ml to 5 ug/ml, or wherein said compound is present in a concentration of 5 ug/ml to 10 ug/ml, or wherein said compound is present in a concentration of 0.1 ug/ml to 5 ug/ml, or wherein said compound is present in a concentration of 0.1 ug/ml to 7.5 ug/ml, or wherein said compound is present in a concentration of 0.1 ug/ml to 10 ug/ml, or wherein said compound is present in a concentration of 0.1 ug/ml to 15 ug/ml, or wherein said compound is present in a concentration of 0.1 ug/ml to 20 ug/ml, or wherein said compound is present in a concentration of 0.1 ug/ml to 30 ug/ml, or wherein said compound is present in a concentration of 1 ug/ml to 5 ug/ml, or wherein said compound is present in a concentration of 1 ug/ml to 7.5 ug/ml, or wherein said compound is present in a concentration of 1 ug/ml to 10 ug/ml, or wherein said compound is present in a concentration of 1 ug/ml to 15 ug/ml, or wherein said compound is present in a concentration of 1 ug/ml to 20 ug/ml, or wherein said compound is present in a concentration of 1 ug/ml to 30 ug/ml, or wherein said compound is present in a concentration of 3 ug/ml to 5 ug/ml, or wherein said compound is present in a concentration of 3 ug/ml to 7.5 ug/ml, or wherein said compound is present in a concentration of 3 ug/ml to 10 ug/ml, or wherein said compound is present in a concentration of 3 ug/ml to 15 ug/ml, or wherein said compound is present in a concentration of 3 ug/ml to 20 ug/ml, or wherein said compound is present in a concentration of 3 ug/ml to 30 ug/ml, or wherein said compound is present in a concentration of 4 ug/ml to 5 ug/ml, or wherein said compound is present in a concentration of 4 ug/ml to 7.5 ug/ml, or wherein said compound is present in a concentration of 4 ug/ml to 10 ug/ml, or wherein said compound is present in a concentration of 4 ug/ml to 15 ug/ml, or wherein said compound is present in a concentration of 4 ug/ml to 20 ug/ml, or wherein said compound is present in a concentration of 4 ug/ml to 30 ug/ml, or wherein said compound is present in a concentration of 5 ug/ml to 8 ug/ml, or wherein said compound is present in a concentration of 5 ug/ml to 9 ug/ml, or wherein said compound is present in a concentration of 5 ug/ml to 10 ug/ml, or wherein said compound is present in a concentration of 5 ug/ml to 15 ug/ml, or wherein said compound is present in a concentration of 5 ug/ml to 20 ug/ml, or wherein said compound is present in a concentration of 5 ug/ml to 30 ug/ml, or wherein said compound is present in a concentration of 7 ug/ml to 8 ug/ml, or wherein said compound is present in a concentration of 7 ug/ml to 9 ug/ml, or wherein said compound is present in a concentration of 7 ug/ml to 10 ug/ml, or wherein said compound is present in a concentration of 7 ug/ml to 15 ug/ml, or wherein said compound is present in a concentration of 7 ug/ml to 20 ug/ml, or wherein said compound is present in a concentration of 7 ug/ml to 30 ug/ml, or wherein said compound is present in a concentration of 30 ug/ml to 70 ug/ml or wherein said compound is present in a concentration of 70 ug/ml to 100 ug/ml or wherein said compound is present in a concentration of 100 ug/ml to 150 ug/ml.

This invention provides a use of compounds or methods for treating cancers, inhibition of cancer growth, cancer invasion, cells invasion, cancer cell invasion; macromolecular cell invasion, cell adhesion, cell attachment, cell circulating, migration, metastasis or growth of cancers, infection or re-infection of virus or infectious macromolecules, and cancer cell fusion, wherein the invention comprises a pharmaceutical composition comprising the compound of this invention or a pharmaceutically acceptable salt thereof, and a pharmaceutically acceptable carrier or diluent, wherein said compound is present in a concentration of 0.008 uM to 80 uM, or wherein said compound is present in a concentration of 0.01 uM to 60 uM, or wherein said compound is present in a concentration of 0.01 uM to 50 uM, or wherein said compound is present in a concentration of 0.01 uM to 40 uM, or wherein said compound is present in a concentration of 0.01 uM to 30 uM, or wherein said compound is present in a concentration of 0.01 uM to 20 uM, or wherein said compound is present in a concentration of 0.01 uM to 10 uM, or wherein said compound is present in a concentration of 5 uM to 10 uM, or wherein said compound is present in a concentration of 0.1 uM to 5 uM, or wherein said compound is present in a concentration of 0.1 uM to 7.5 uM, or wherein said compound is present in a concentration of 0.1 uM to 10 uM, or wherein said compound is present in a concentration of 0.1 uM to 15 uM, or wherein said compound is present in a concentration of 0.1 uM to 20 uM, or wherein said compound is present in a concentration of 0.1 uM to 30 uM or wherein said compound is present in a concentration of 0.1 uM to 40 uM, or wherein said compound is present in a concentration of 0.1 uM to 50 uM or wherein said compound is present in a concentration of 0.1 uM to 60 uM, or wherein said compound is present in a concentration of 0.1 uM to 80 uM, or wherein said compound is present in a concentration of 1 uM to 5 uM, or wherein said compound is present in a concentration of 1 uM to 7.5 uM, or wherein said compound is present in a concentration of 1 uM to 10 uM, or wherein said compound is present in a concentration of 1 uM to 15 uM, or wherein said compound is present in a concentration of 1 uM to 20 uM, or wherein said compound is present in a concentration of 1 uM to 30 uM or wherein said compound is present in a concentration of 1 uM to 40 uM, or wherein said compound is present in a concentration of 1 uM to 50 uM or wherein said compound is present in a concentration of 1 uM to 60 uM, or wherein said compound is present in a concentration of 1 uM to 80 uM, or wherein said compound is present in a concentration of 3 uM to 5 uM, or wherein said compound is present in a concentration of 3 uM to 7.5 uM, or wherein said compound is present in a concentration of 3 uM to 10 uM, or wherein said compound is present in a concentration of 3 uM to 15 uM, or wherein said compound is present in a concentration of 3 uM to 20 uM, or wherein said compound is present in a concentration of 3 uM to 30 uM or wherein said compound is present in a concentration of 3 uM to 40 uM, or wherein said compound is present in a concentration of 3 uM to 50 uM or wherein said compound is present in a concentration of 3 uM to 60 uM, or wherein said compound is present in a concentration of 3 uM to 80 uM, or wherein said compound is present in a concentration of 5 uM to 8 uM, or wherein said compound is present in a concentration of 5 uM to 10 uM, or wherein said compound is present in a concentration of 5 uM to 15 uM, or wherein said compound is present in a concentration of 5 uM to 20 uM, or wherein said compound is present in a concentration of 5 uM to 30 uM or wherein said compound is present in a concentration of 5 uM to 40 uM, or wherein said compound is present in a concentration of 5 uM to 50 uM or wherein said compound is present in a concentration of 5 uM to 60 uM, or wherein said compound is present in a concentration of 5 uM to 80 uM. or wherein said compound is present in a concentration of 7 uM to 8 uM, or wherein said compound is present in a concentration of 7 uM to 10 uM, or wherein said compound is present in a concentration of 7 uM to 15 uM, or wherein said compound is present in a concentration of 7 uM to 20 uM, or wherein said compound is present in a concentration of 7 uM to 30 uM or wherein said compound is present in a concentration of 7 uM to 40 uM, or wherein said compound is present in a concentration of 7 uM to 50 uM or wherein said compound is present in a concentration of 7 uM to 60 uM, or wherein said compound is present in a concentration of 7 uM to 80 uM or wherein said compound is present in a concentration of 70 uM to 100 uM, or wherein said compound is present in a concentration of 90 uM to 120 uM.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains.

It is to be noted that the transitional term "comprising", which is synonymous with "including", "containing" or "characterized by", is inclusive or open-ended and does not exclude additional, un-recited elements or method steps.

Example 1

Tablet for Dose Containing 10 mg, 20 mg 30 mg of Active Compound

| | | | | | |
|---|---|---|---|---|---|
| Active compound | 1 mg | 5 mg | 10 mg | 20 mg | 30 mg |
| Microcrystalline cellulose | 20 mg | 20 mg | 19.75 mg | 60 mg | 100 mg |
| Corn starch | 29 mg | 24.5 mg | 19.75 mg | 19.25 mg | 18.5 mg |
| Magnesium stearate | 0 mg | 0.5 mg | 0.5 mg | 0.75 mg | 1.5 mg |

The active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1, 5, 10, 20, 30 mg, respectively of active ingredient per tablet.

Example 2

Intravenous Solution Preparation

An intravenous dosage form of the active compound is prepared as follows:
Active compound 1-10 ug
Sodium citrate 5-50 mg
Citric acid 1-15 mg
Sodium chloride 1-8 mg
Water for injection (USP) q.s. to 1 mL
Utilizing the above quantities, the active compound is dissolved at room temperature in a prepared solution of sodium chloride, citric acid, and sodium citrate in water for injection.

Example 3

Intravenous Drip Preparation 0.25-2.5 mg compound dissolved in 250 ml of 10% glucose solution or in 250 ml of 0.9% NaCl solution.

Intravenous drip preparation: 1-2 mg compound dissolved in 250 ml of 10% glucose solution or in 250 ml of 0.9% NaCl solution Treatment of angelic acid with one of the many standard chlorinating reagents including phosphorus ocychloride, phosphorus trichloride and thionyl chloride produces tigloyl chloride. Oxalyl chloride produces a 2:1 ratio of angeloyl chloride to tigloyl chloride. Treatment of potassium salt in diethyl ether with oxalyl chloride and catalytic DMF for 2 hr at 0 C produces pure angeloyl chloride.

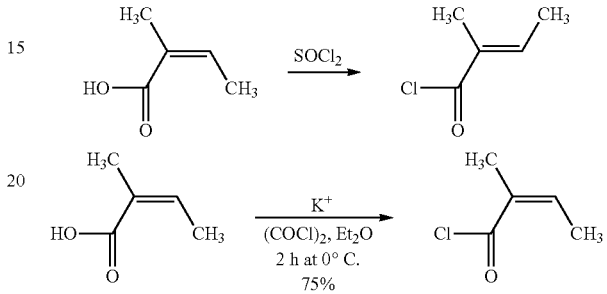

Acid Hydrolysis of the Following Compounds:
a) Xanifolia(Y),

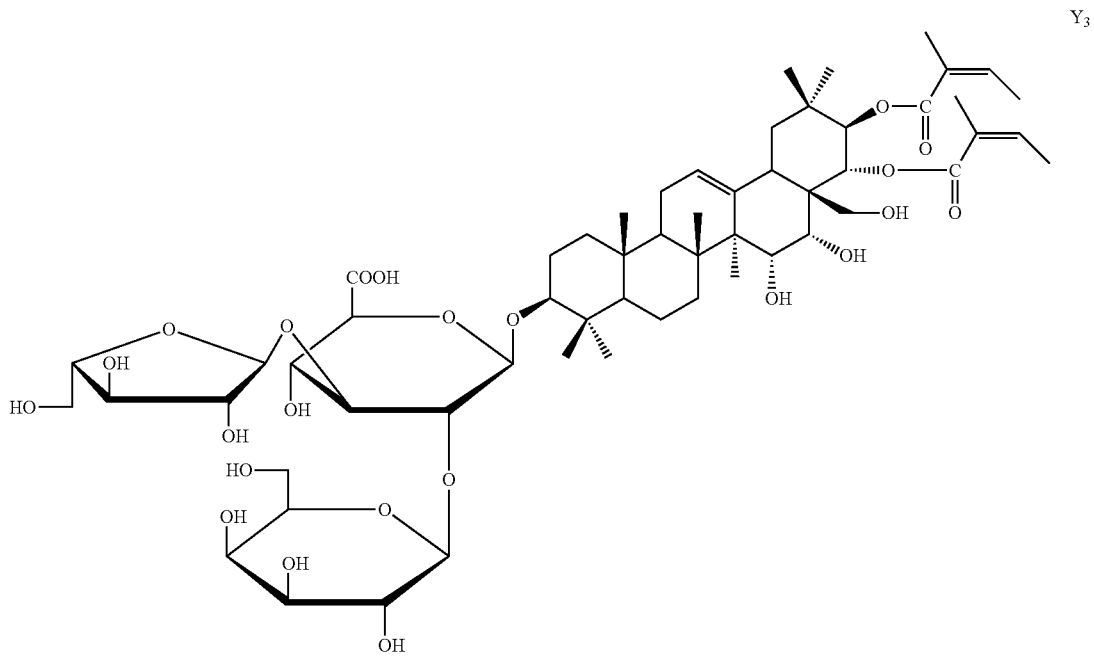

or chemical name: 3-O-[β-D-galactopyranosyl (1→2)]-α-L-arabinofuranosy (1→3)-β-D-glucuronopyranosyl-21,22-O-diangeloyl-3β, 15α, 16α, 21β, 22α, 28-hexahydroxyolean-12-ene;

c) Xanifolia (Y2),
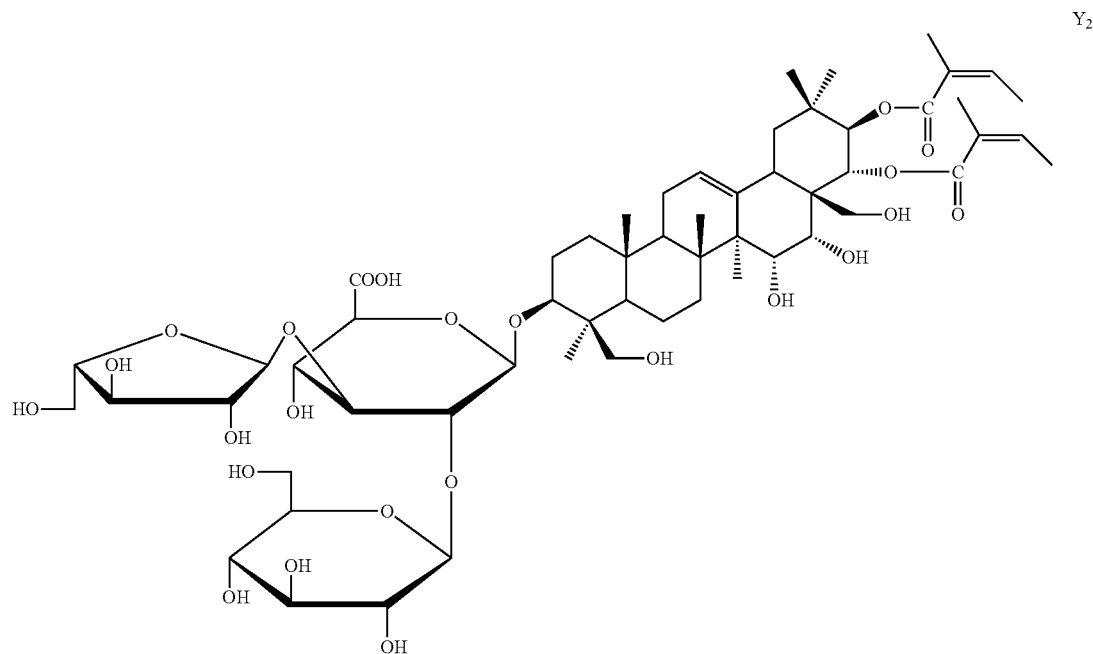
or chemical name: 3-O-[β-D-glucopyranosyl-(1→2)]-α-L-arabinofuranosy (1→3)-β-D-glucuronopyranosyl-21,22-O-diangeloyl-3β, 15α, 16α, 21β, 22α, 24β, 28-heptahydroxy-olean-12-ene;
d) Xanifolia (Y8),
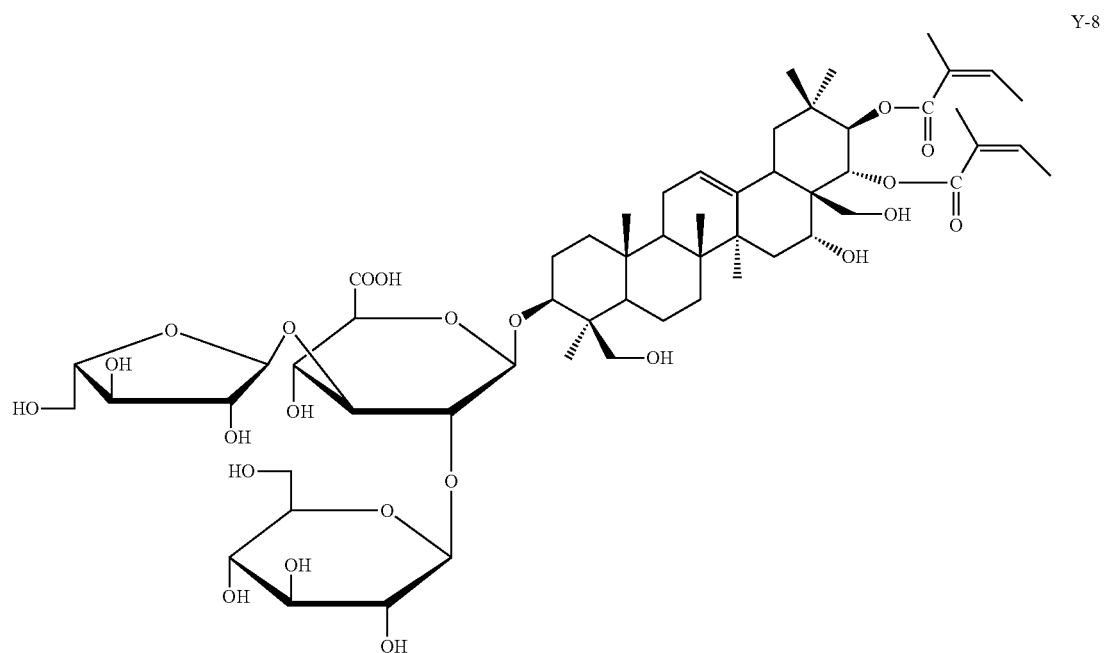
or chemical name: 3-O-[β-glucopyranosyl (1→2)]-α-arabinofuranosyl (1→3)-β-glucuronopyranosyl-21, 22-O-diangeloyl-3β, 16α, 21β, 22α, 24β, 28-hexahydroxyolean-12-ene;

f) Xanifolia (Y10),
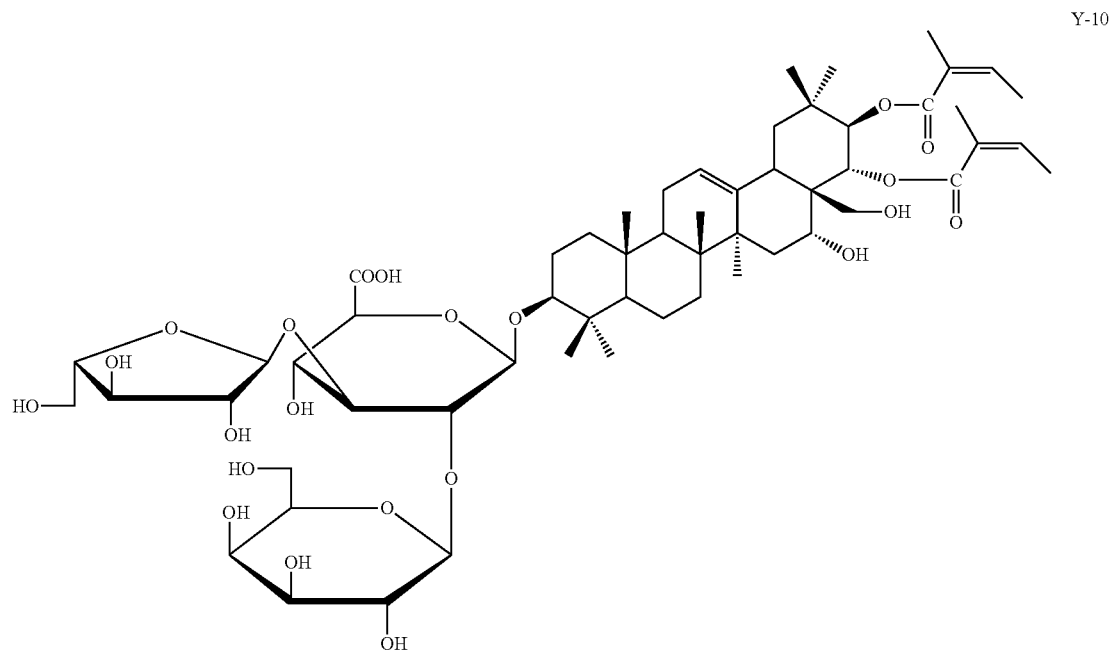
or chemical name: 3-O-[β-galactopyranosyl (1→2)]-α-arabinofuranosyl (1→3)-β-glucuronopyranosyl-21, 22-O-diangeloyl-3β, 16α, 21β, 22α, 28-pentahydroxyolean-12-ene.
j) structure (M10)
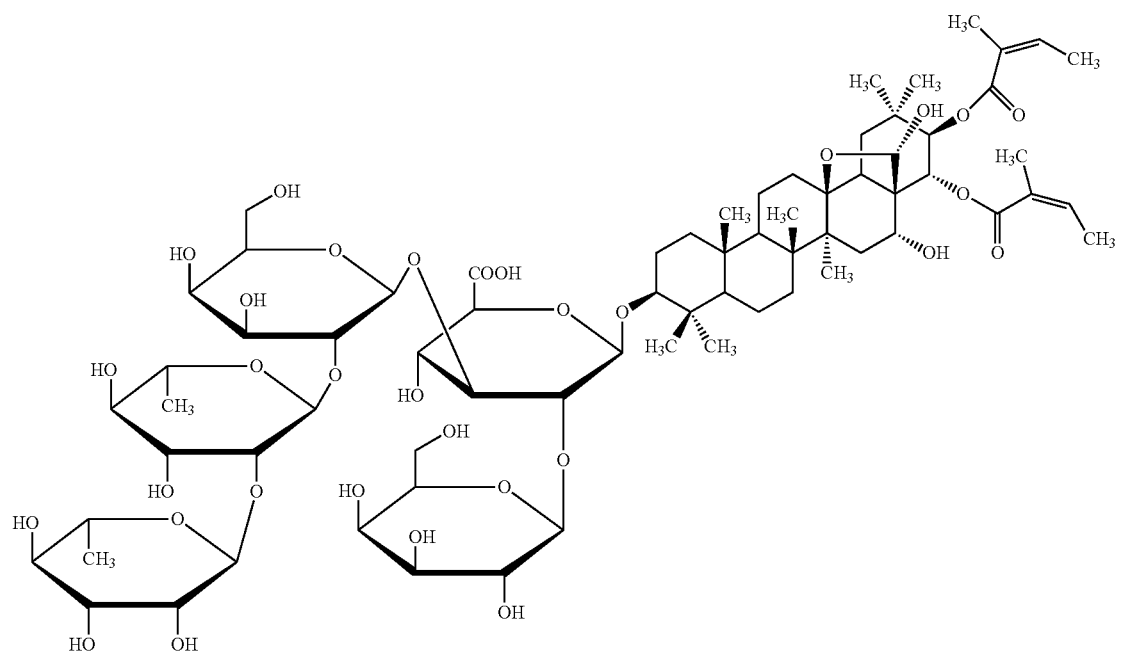

m) structure (bES):
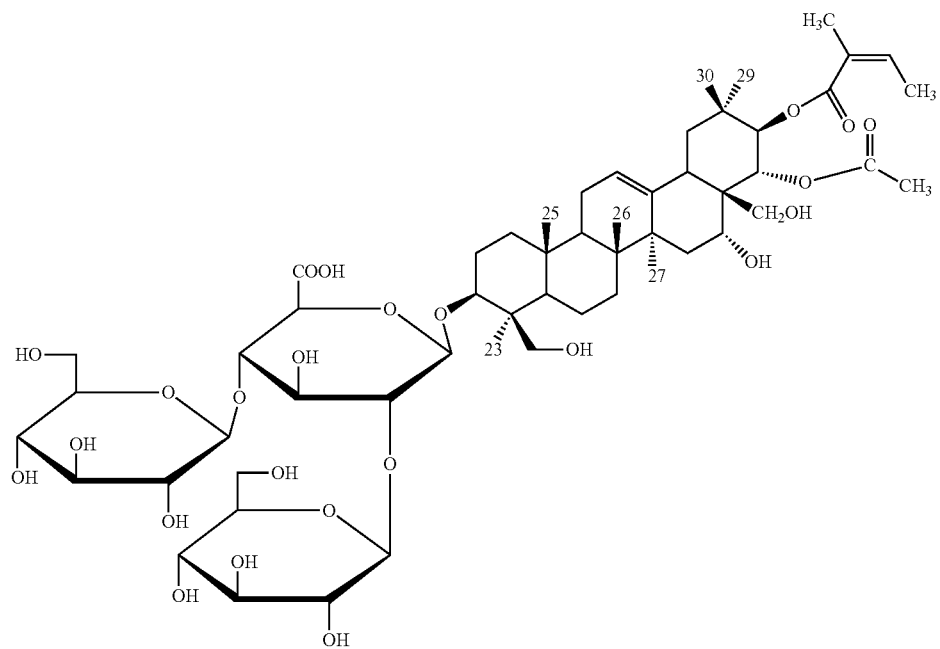
n)
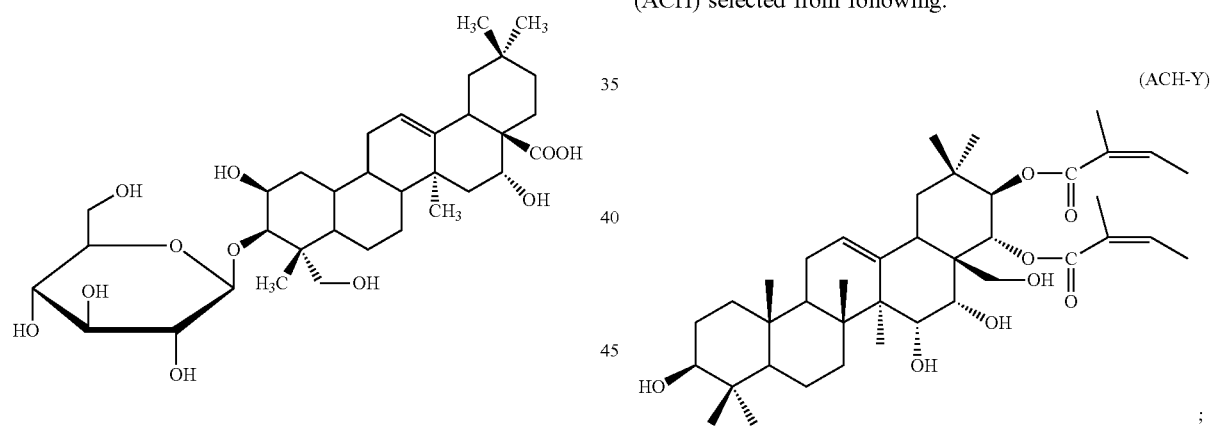
p)
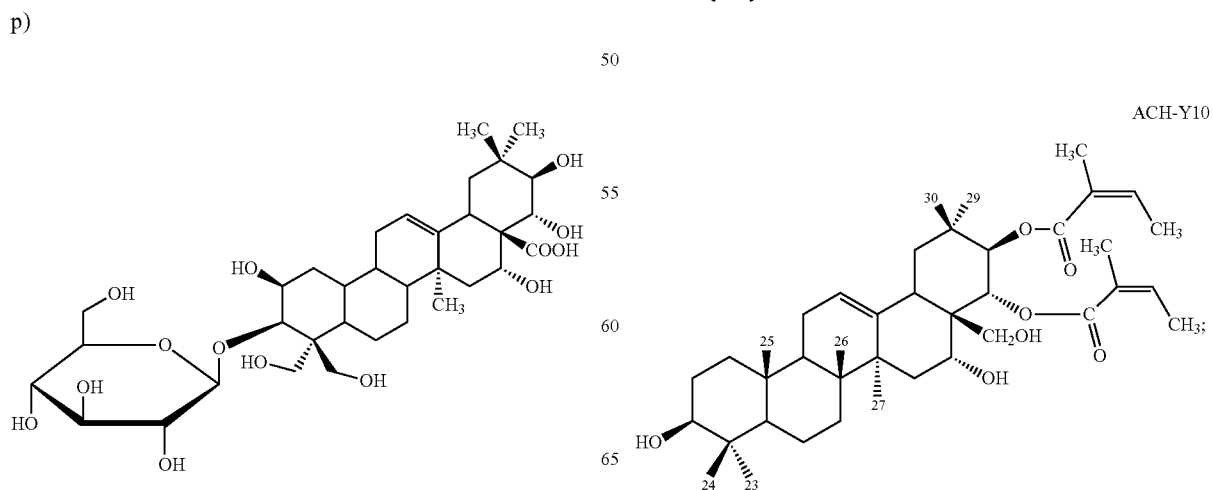
After acid hydrolysis of the above, an isolated, purified or synthesized compound is produced having a structure (ACH) selected from following:

-continued

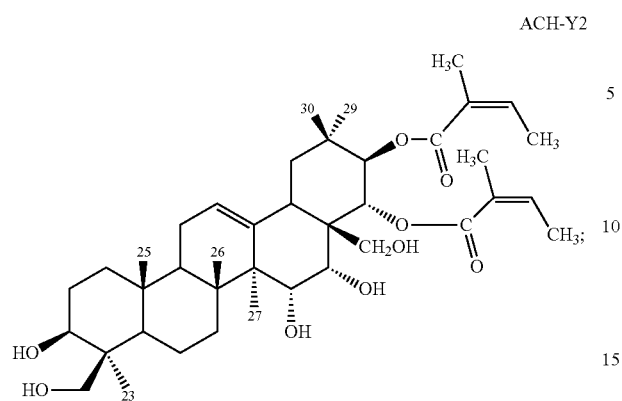
ACH-Y2

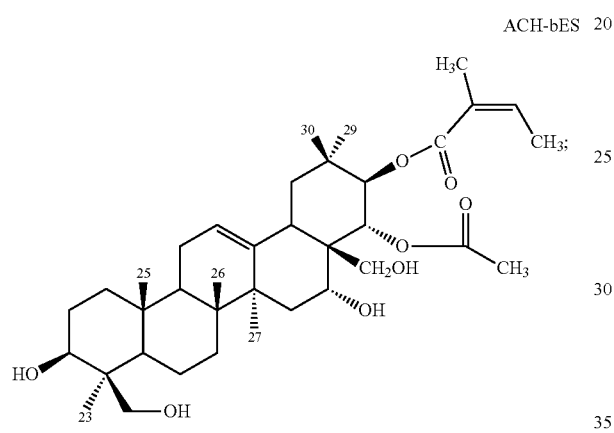
ACH-bES

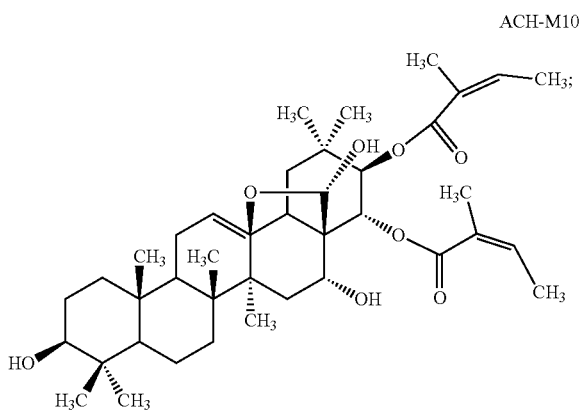
ACH-M10

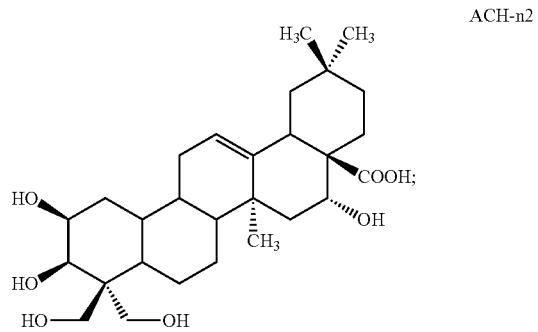
ACH-n2

-continued

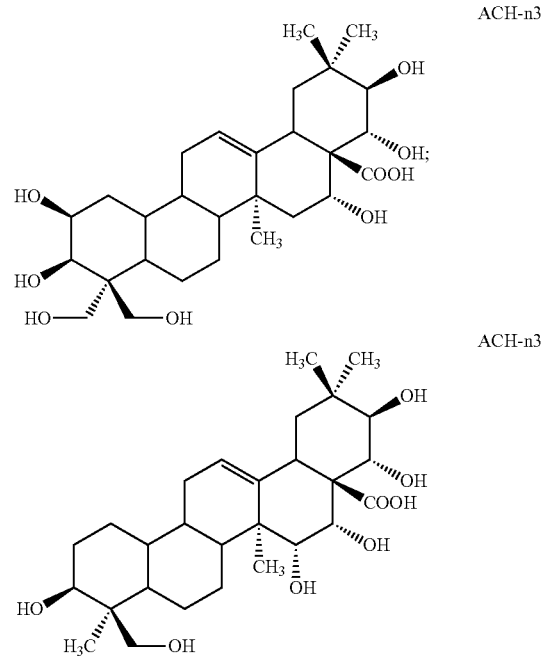
ACH-n3

ACH-n3

The composition comprises bioactive compounds from natural plants or synthesis.

The program is based on our purification methods and biological assays including the MTT assay. See International Application No. PCT/US05/31900, filed Sep. 7, 2005, U.S. Ser. No. 11/289,142, filed Nov. 28, 2005, and U.S. Ser. No. 11/131,551, filed May 17, 2005, and PCT/US2008/002086, 1188-ALA-PCT, filed Feb. 15, 2008, Ser. No. 12/344,682, 1020-B1-US, filed Dec. 29, 2008. The details of Analysis of gene expression of ES2 cells after Y-treatment by Microarray, Data Analysis Methods and Western blot in PCT/US2008/002086, 1188-ALA-PCT, filed Feb. 15, 2008, and the cell invasion experiments methods in International Application PCT/US2010/0042240, filed Jul. 16, 2010.

The Haemolytic Assay

Erythrocytes (RBC) were isolated from human blood (EDTA whole blood, collected randomly). 50 ul of the 10% RBC suspension (in PBS) was added to 2 ml of sample solutions (concentration range from 0.1 ug/ml to 400 ug/ml) in PBS. The mixture was vortexed briefly and sat for 60 min at room temperature. The mixture was spun at 3K for 10 min and the relative amounts of lysed hemoglobin in the supernatant were measured at 540 nm. The synthetic compounds of present application were tested with this method.

Acid Hydrolysis of Saponin 15 mg Xanifolia-Y was dissolved in 1 ml of methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (ACH-Y) was achieved by HPLC with isocratic elution of 80-100% acetonitrile. Repeating the experiment with compounds Z4, Y10, Y2, Y8, Y7, Y0, X, M10 and ESCIN (bES) gives the following compounds respectively: ACH-Z4, ACH-Y10, ACH-Y2, ACH-Y8, ACH-Y7, ACH-Y0, ACH-X, ACH-E, ACH-Z5, ACH-M10 and ACH-bES.

Removal of the Acyl Group by Alkaline Hydrolysis 20 mg of Xanifolia-Y was dissolved in 0.5 ml of 1N NaOH. The solution was incubated in 80 C water bath for 4 hours. It was cooled to room temperature before being neutralized with 0.5 ml 1N HCl (adjust pH to about 3). The mixture was extracted with 2 ml 1-butanol 3 times. The butanol fractions were collected and lyophilized. The hydrolyzed saponin was further purified with HPLC in a C-18 column eluted with 25% acetonitrile.

also be obtained by synthetic methods. A method for synthesizing the core compound is as follows:

Beta-Escin, compound Y, Y10, Y2, Y8, Y7, Y0, X, or M10 dissolved in 1M NaOH (20 mg/ml) was incubated at 70 C for 5 hours. The hydrolyzed solution was neutralized with HCl and the water was evaporated by lyophilization. The product was dissolved in 50% methanol and 1N HCl. The mixture was incubated at 70 C for 5 hours. The solution was neutralized with NaOH. The hydrolyzed product was

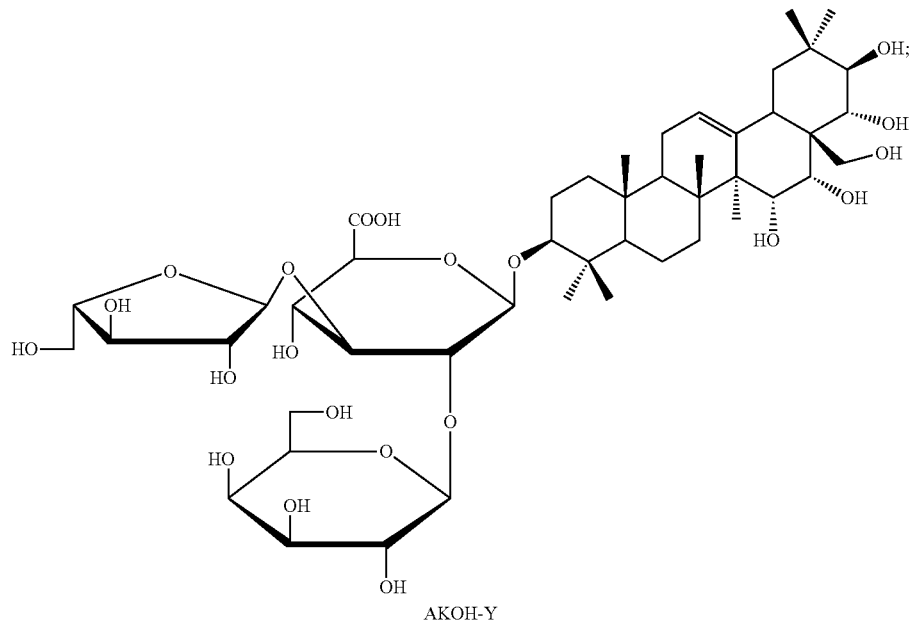

AKOH-Y

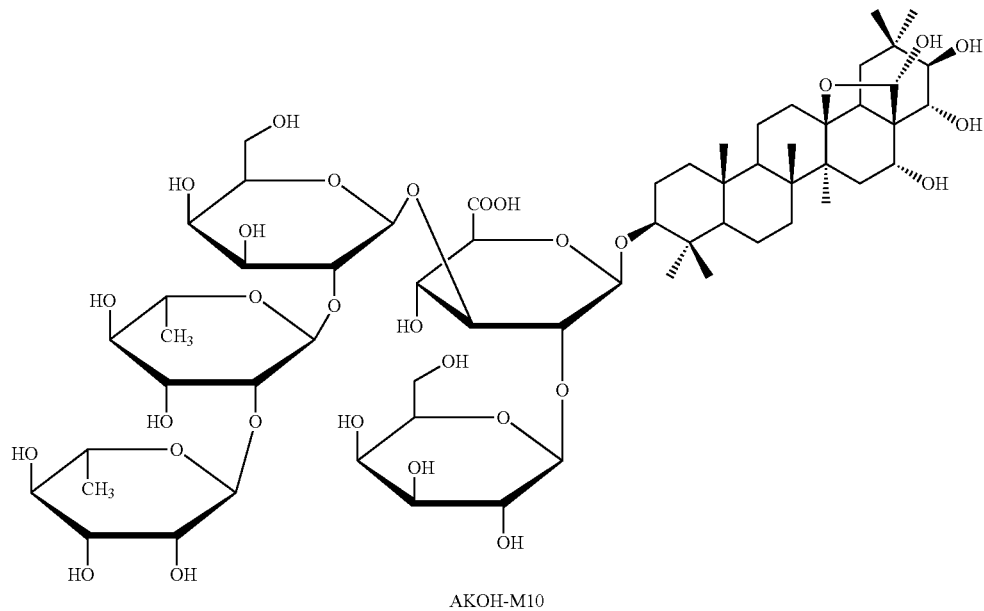

AKOH-M10

Compounds AKOH-Y and AKOH-M10 do not show the ability to inhibit cancer growth, cancer invasion, cells invasion or cancer cell invasion.

Core Compound

A core compound or pentacyclic triterpenes, hydroxylated triterpenes is obtained by acid and alkaline hydroysis of saponin from natural sources. A pentacyclic triterpene can extracted with ethylacetate, which was subsequently removed by evaporation. Further purification of the hydrolyzed product of core compounds including (E4A) were archived with FPLC chromatography in a C18 column equilibrated with 70% acetonitrile/TFA at the flow rate of 1 ml/min. The core compounds are obtained.

The core compounds do not show the ability to inhibit cancer growth, cancer invasion, or cell adhesion. The structures of core compounds:
(A)
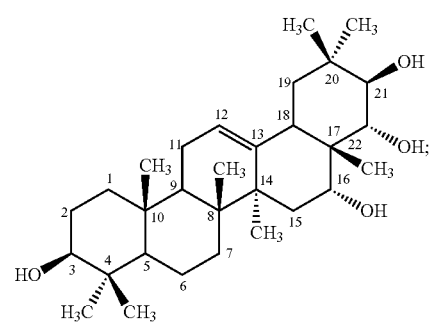
(B)
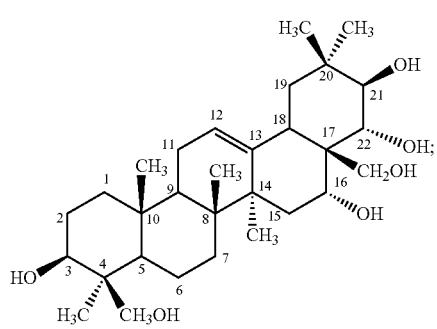
(C)
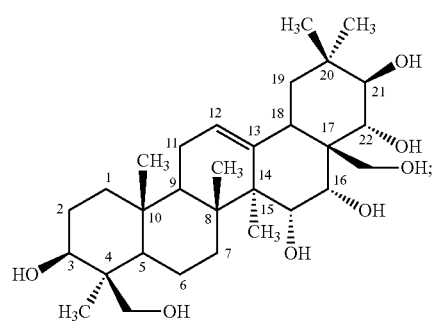
(D1)
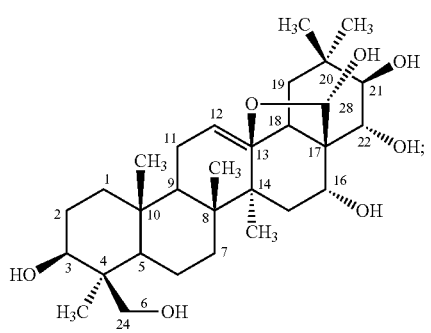
(D2)
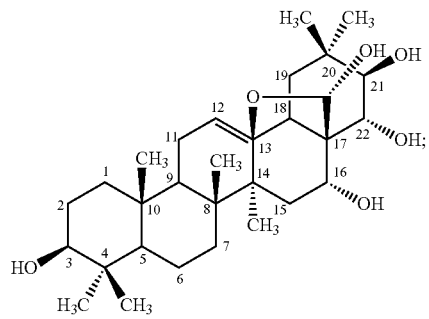
(E)
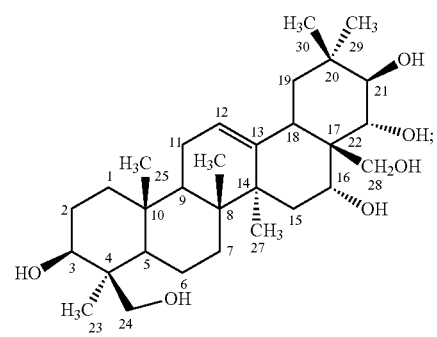
also named as bES-core, E IV A, ES4A, E4A or E4AY2
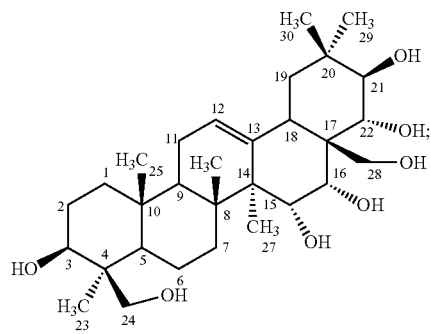
E6A
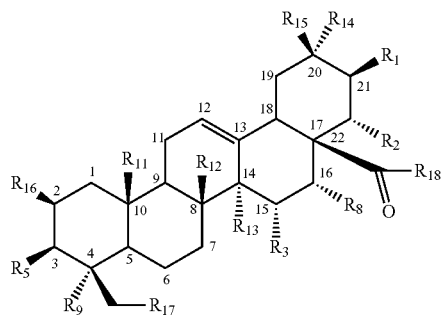

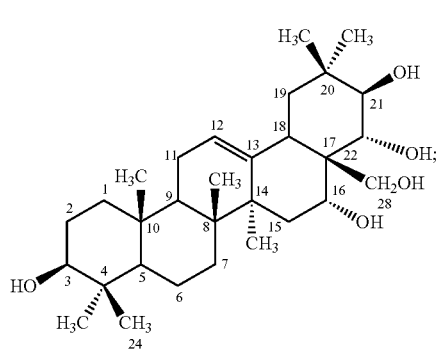

(F)

as names as ES V, E5A or

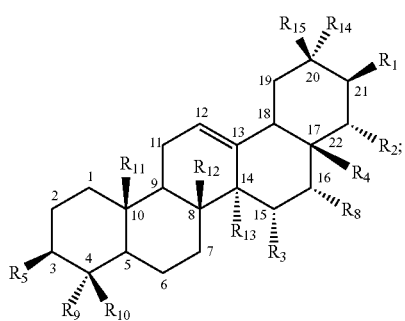

(G)

wherein R1, R2, R5, R8 represent OH; R3 represents OH, H or absent; R4, R10 represent CH3 or CH2OH; R9, R11, R12, R13, R14, R15 represent CH3;

(H1)

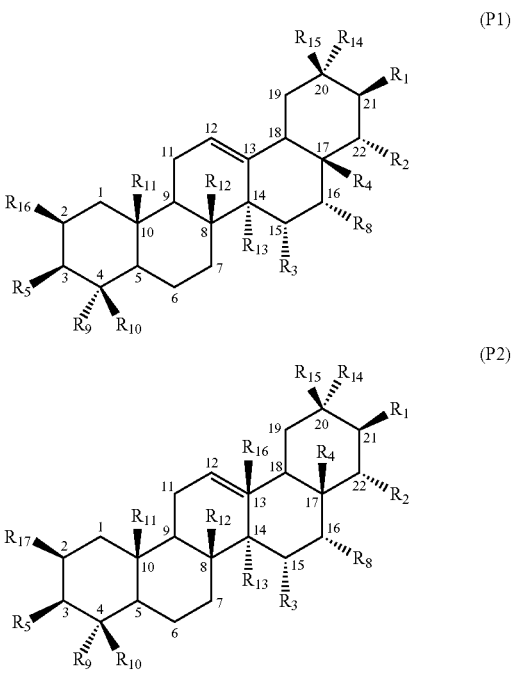

(H2)

wherein R1, R2, R5, R8, R17, R18 represent OH; R3 represents OH, H or absent; R9, R11, R12, R13, R14, R15 represent CH3.

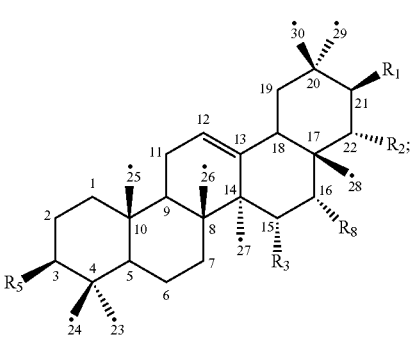

(J)

A typical numbering 1 to 30 of carbon positions of a pentacyclic triterpene.

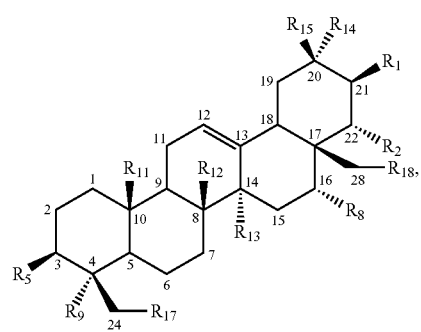

wherein R1, R2, R5, R8, R17, R18 represent OH; R9, R11, R12, R13, R14, R15 represent CH3, also named E4A or (E).

(P1)

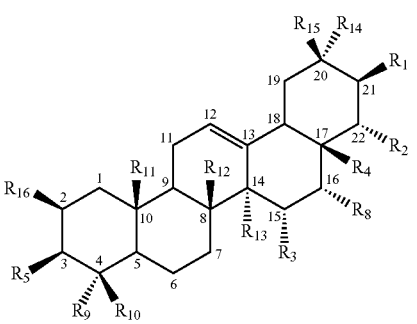

(P2)

wherein R1, R2, R3, R4, R5, R8, R9, R10, R11, R12, R13, R14, R15, R16 R17 represent H, OH, CH2OH, COOH, OR CH3, named as (P1), (P2).

This invention provides a method of synthesizing new active compounds. A method of attaching functional groups to the core compounds including but not limited to (A), (B), (C), (D1), (D2), (E), (F), (G), (H1), (H2), (J), E4A, E4A2Y, E6A, (P1), P(2),] involves esterification of core compounds with acyl halide, wherein the halide including chloride, bromide, fluoride and iodide, wherein the acyl halide comprises acyl chloride, wherein acyl chloride including but not limited to Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, Propionyl chloride, 2-Propenoyl chloride, Isobutyryl chloride, Butyryl chloride, (2E)-2-pentenoyl chloride, 4-Pentenoyl chloride, 5-Hexenoyl chloride, Heptanoyl chloride, Octanoyl chloride, Nonanoyl chloride, Decanoyl chloride, Lauroyl chloride, Myristoyl chloride, Oleoyl chloride for 5 sec, 1 min, 2 min, 5 min, 10 min, 30 min, 1 hr, 2 hr, 18 hr, 2 days or 3 days at 0 C, 25 C or 75 C temperature. At the end of reaction, 5 ml of 2N HCl or 1M NaHCO3 is added to the reaction mixture. The solution is then extracted 3 times with 10 ml of ethyl acetate which is then evaporated under vacuum and at 45 C and lyophilization. The reaction product is dissolved in 80% acetonitrile—0.005% Trifluoroacetic acid. The active esterification products are purified with HPLC. MTT activity was performed to test the activity of acyl chloride, solution after the reaction, individual fractions, and individual compounds. The core compounds are synthetic, semi synthetic or from natural source. The core compounds are including terpene, isoprene, triterpenes, and hydroxylated triterpenes.

MTT activity of acylation of core compounds in different reaction time period of (ASAP)5 sec, 1 min, 2 min, 5 min, 10 min, 30 min, 1 hr, 2 hr, 18 hr, 2 days or 3 days at 0 C, 25 C or 75 C temperature were studied. HPLC profiles of esterification products of core compound E4A with acyl halide, wherein the halide comprise chloride, bromide, fluoride and iodide, wherein the acyl halide comprise acyl chloride, wherein acyl chloride comprise tigloyl chloride, angeloyl chloride, acetyl chloride, crotonoyl chloride, 3,3-dimethylartyloyl chloride, senecioyl chloride, cinnamoyl chloride, pentenoyl chloride, hexanoyl chloride, benzoyl chloride, ethylbutyryl chloride, propionyl chloride, 2-propenoyl chloride, isobutyryl chloride, butyryl chloride, (2E)-2-pentenoyl chloride, 4-Pentenoyl chloride, 5-hexenoyl chloride, heptanoyl chloride, octanoyl chloride, nonanoyl chloride, decanoyl chloride, Lauroyl chloride, myristoyl chloride, oleoyl chloride show that the compounds vary in composition when the time or temperature of the reaction is changed. See example in FIGS. 1-12 (U.S. Ser. No. 14/313, 080) and Experiments 1-29

The peaks, fractions and compounds are selected according to the activities of times studies and the changes of peaks. Selecting the HPLC fractions for isolation is according to the cytotoxic activity of the reaction product obtained at a specific time. The compounds having strong to weak activities are selected and isolated. Selecting the HPLC fractions for isolation may be according to the cytotoxic activity of times studies and the change of peaks. The anti cancer activities are the MTT studies of bone (U2OS), lung (H460), bladder (HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), luekemia (K562), cervix (HeLa).

Esterification of core compound E4A with Tigloyl chloride and isolation of the compounds with HPLC give the following compounds: wherein Tig=Tigloyl

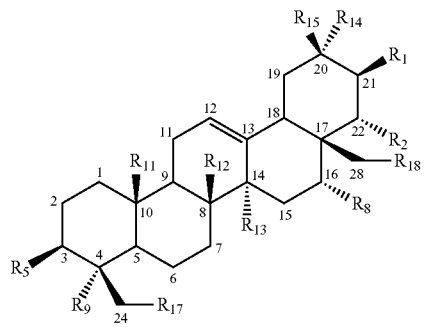

|  | R1 | R2 | R5 | R8 | R17 | R18 | Cytotoxicity activity |
|---|---|---|---|---|---|---|---|
| E4A | OH | OH | OH | OH | OH | OH | none |
| A1 | OH | OH | OH | OH | O-Tig | OH | moderate |
| A2 | OH | OH | OH | OH | OH | O-Tig | moderate |
| A3 | OH | OH | OH | OH | O-Tig | O-Tig | strong |
| A4 | O-Tig | OH | OH | OH | O-Tig | O-Tig | moderate |
| A5 | OH | O-Tig | OH | OH | O-Tig | O-Tig | moderate |
| A6 | OH | OH | O-Tig | OH | O-Tig | O-Tig | moderate |
| A7 | OH | OH | OH | O-Tig | O-Tig | O-Tig | moderate |
| A8 | O-Tig | O-Tig | OH | OH | O-Tig | O-Tig | weak |
| A9 | OH | O-Tig | O-Tig | OH | O-Tig | O-Tig | weak |
| A10 | OH | OH | O-Tig | O-Tig | O-Tig | O-Tig | weak |
| A11 | O-Tig | OH | O-Tig | OH | O-Tig | O-Tig | weak |
| A12 | OH | O-Tig | OH | O-Tig | O-Tig | O-Tig | weak |
| A13 | O-Tig | OH | OH | O-Tig | O-Tig | O-Tig | weak |
| A14 | OH | O-Tig | O-Tig | OH | O-Tig | O-Tig | weak |
| A15 | O-Tig | O-Tig | O-Tig | OH | O-Tig | O-Tig | weak |
| A16 | O-Tig | O-Tig | OH | O-Tig | O-Tig | O-Tig | weak |
| A17 | O-Tig | OH | O-Tig | O-Tig | O-Tig | O-Tig | weak |
| A18 | OH | O-Tig | O-Tig | O-Tig | O-Tig | O-Tig | weak |
| A19 | O-Tig | O-Tig | O-Tig | O-Tig | O-Tig | O-Tig | none |
| A20 | O-Tig | O-Tig | OH | OH | OH | O-Tig | moderate |
| A21 | O-Tig | O-Tig | OH | OH | O-Tig | OH | moderate |
| A22 | O-Tig | O-Tig | OH | O-Tig | OH | OH | moderate |
| A23 | O-Tig | O-Tig | O-Tig | OH | OH | OH | moderate |
| A24 | O-Tig | O-Tig | OH | OH | OH | OH | moderate |

-continued

|     | R1    | R2    | R5    | R8    | R17   | R18   | Cytotoxicity activity |
|-----|-------|-------|-------|-------|-------|-------|-----------------------|
| A25 | O-Tig | OH    | OH    | OH    | OH    | O-Tig | moderate |
| A26 | OH    | O-Tig | OH    | OH    | OH    | O-Tig | moderate |
| A27 | OH    | OH    | O-Tig | OH    | OH    | O-Tig | moderate |
| A28 | OH    | OH    | OH    | O-Tig | OH    | O-Tig | moderate |
| A29 | O-Tig | OH    | OH    | OH    | O-Tig | OH    | moderate |
| A30 | OH    | O-Tig | OH    | OH    | O-Tig | OH    | moderate |
| A31 | OH    | OH    | O-Tig | OH    | O-Tig | OH    | moderate |
| A32 | OH    | OH    | OH    | O-Tig | O-Tig | OH    | moderate |

Esterification of core compound E4A with Angeloyl chloride and isolation of the compounds with HPLC give the following compounds: wherein Ang=Angeloyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none |
| G1  | OH    | OH    | OH    | OH    | O-Ang | OH    | moderate |
| G2  | OH    | OH    | OH    | OH    | OH    | O-Ang | moderate |
| G3  | OH    | OH    | OH    | OH    | O-Ang | O-Ang | strong |
| G4  | O-Ang | OH    | OH    | OH    | O-Ang | O-Ang | moderate |
| G5  | OH    | O-Ang | OH    | OH    | O-Ang | O-Ang | moderate |
| G6  | OH    | OH    | O-Ang | OH    | O-Ang | O-Ang | moderate |
| G7  | OH    | OH    | OH    | O-Ang | O-Ang | O-Ang | moderate |
| G8  | O-Ang | O-Ang | OH    | OH    | O-Ang | O-Ang | weak |
| G9  | OH    | O-Ang | O-Ang | OH    | O-Ang | O-Ang | weak |
| G10 | OH    | OH    | O-Ang | O-Ang | O-Ang | O-Ang | weak |
| G11 | O-Ang | OH    | O-Ang | OH    | O-Ang | O-Ang | weak |
| G12 | OH    | O-Ang | OH    | O-Ang | O-Ang | O-Ang | weak |
| G13 | O-Ang | OH    | OH    | O-Ang | O-Ang | O-Ang | weak |
| G14 | OH    | O-Ang | O-Ang | OH    | O-Ang | O-Ang | weak |
| G15 | O-Ang | O-Ang | O-Ang | OH    | O-Ang | O-Ang | weak |
| G16 | O-Ang | O-Ang | OH    | O-Ang | O-Ang | O-Ang | weak |
| G17 | O-Ang | OH    | O-Ang | O-Ang | O-Ang | O-Ang | weak |
| G18 | OH    | O-Ang | O-Ang | O-Ang | O-Ang | O-Ang | weak |
| G19 | O-Ang | O-Ang | O-Ang | O-Ang | O-Ang | O-Ang | none |
| G20 | O-Ang | O-Ang | OH    | OH    | OH    | O-Ang | moderate |
| G21 | O-Ang | O-Ang | OH    | OH    | O-Ang | OH    | moderate |
| G22 | O-Ang | O-Ang | OH    | O-Ang | OH    | OH    | moderate |
| G23 | O-Ang | O-Ang | O-Ang | OH    | OH    | OH    | moderate |
| G24 | O-Ang | O-Ang | OH    | OH    | OH    | OH    | moderate |
| G25 | O-Ang | OH    | OH    | OH    | OH    | O-Ang | moderate |
| G26 | OH    | O-Ang | OH    | OH    | OH    | O-Ang | moderate |
| G27 | OH    | OH    | O-Ang | OH    | OH    | O-Ang | moderate |
| G28 | OH    | OH    | OH    | O-Ang | OH    | O-Ang | moderate |
| G29 | O-Ang | OH    | OH    | OH    | O-Ang | OH    | moderate |
| G30 | OH    | O-Ang | OH    | OH    | O-Ang | OH    | moderate |
| G31 | OH    | OH    | O-Ang | OH    | O-Ang | OH    | moderate |
| G32 | OH    | OH    | OH    | O-Ang | O-Ang | OH    | moderate |

Esterification of core compound E4A with (3,3-Dimethylartyloyl chloride) senecioyl chloride and isolation of the compounds with HPLC give the following compounds: Wherein Sen=senecioyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none |
| B1  | OH    | OH    | OH    | OH    | O-Sen | OH    | moderate |
| B2  | OH    | OH    | OH    | OH    | OH    | O-Sen | moderate |
| B3  | OH    | OH    | OH    | OH    | O-Sen | O-Sen | strong |
| B4  | O-Sen | OH    | OH    | OH    | O-Sen | O-Sen | moderate |
| B5  | OH    | O-Sen | OH    | OH    | O-Sen | O-Sen | moderate |
| B6  | OH    | OH    | O-Sen | OH    | O-Sen | O-Sen | moderate |
| B7  | OH    | OH    | OH    | O-Sen | O-Sen | O-Sen | moderate |
| B8  | O-Sen | O-Sen | OH    | OH    | O-Sen | O-Sen | weak |
| B9  | OH    | O-Sen | O-Sen | OH    | O-Sen | O-Sen | weak |
| B10 | OH    | OH    | O-Sen | O-Sen | O-Sen | O-Sen | weak |
| B11 | O-Sen | OH    | O-Sen | OH    | O-Sen | O-Sen | weak |
| B12 | OH    | O-Sen | OH    | O-Sen | O-Sen | O-Sen | weak |
| B13 | O-Sen | OH    | OH    | O-Sen | O-Sen | O-Sen | weak |

-continued

|     | R1    | R2    | R5    | R8    | R17   | R18   | Cytotoxicity activity |
|-----|-------|-------|-------|-------|-------|-------|-----------------------|
| B14 | OH    | O-Sen | O-Sen | OH    | O-Sen | O-Sen | weak                  |
| B15 | O-Sen | O-Sen | O-Sen | OH    | O-Sen | O-Sen | weak                  |
| B16 | O-Sen | O-Sen | OH    | O-Sen | O-Sen | O-Sen | weak                  |
| B17 | O-Sen | OH    | O-Sen | O-Sen | O-Sen | O-Sen | weak                  |
| B18 | OH    | O-Sen | O-Sen | O-Sen | O-Sen | O-Sen | weak                  |
| B19 | O-Sen | O-Sen | O-Sen | O-Sen | O-Sen | O-Sen | none                  |
| B20 | O-Sen | O-Sen | OH    | OH    | OH    | O-Sen | moderate              |
| B21 | O-Sen | O-Sen | OH    | OH    | O-Sen | OH    | moderate              |
| B22 | O-Sen | O-Sen | OH    | O-Sen | OH    | OH    | moderate              |
| B23 | O-Sen | O-Sen | O-Sen | OH    | OH    | OH    | moderate              |
| B24 | O-Sen | O-Sen | OH    | OH    | OH    | OH    | moderate              |
| B25 | O-Sen | OH    | OH    | OH    | OH    | O-Sen | moderate              |
| B26 | OH    | O-Sen | OH    | OH    | OH    | O-Sen | moderate              |
| B27 | OH    | OH    | O-Sen | OH    | OH    | O-Sen | moderate              |
| B28 | OH    | OH    | OH    | O-Sen | OH    | O-Sen | moderate              |
| B29 | O-Sen | OH    | OH    | OH    | O-Sen | OH    | moderate              |
| B30 | OH    | O-Sen | OH    | OH    | O-Sen | OH    | moderate              |
| B31 | OH    | OH    | O-Sen | OH    | O-Sen | OH    | moderate              |
| B32 | OH    | OH    | OH    | O-Sen | O-Sen | OH    | moderate              |

Esterification of core compound E4A with 4-Pentenoyl chloride and isolation of the compounds with HPLC give the following compounds: wherein Pen=4-Pentenoyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| C1  | OH    | OH    | OH    | OH    | O—Pen | OH    | moderate              |
| C2  | OH    | OH    | OH    | OH    | OH    | O—Pen | moderate              |
| C3  | OH    | OH    | OH    | OH    | O—Pen | O—Pen | strong                |
| C4  | O—Pen | OH    | OH    | OH    | O—Pen | O—Pen | moderate              |
| C5  | OH    | O—Pen | OH    | OH    | O—Pen | O—Pen | moderate              |
| C6  | OH    | OH    | O—Pen | OH    | O—Pen | O—Pen | moderate              |
| C7  | OH    | OH    | OH    | O—Pen | O—Pen | O—Pen | moderate              |
| C8  | O—Pen | O—Pen | OH    | OH    | O—Pen | O—Pen | weak                  |
| C9  | OH    | O—Pen | O—Pen | OH    | O—Pen | O—Pen | weak                  |
| C10 | OH    | OH    | O—Pen | O—Pen | O—Pen | O—Pen | weak                  |
| C11 | O—Pen | OH    | O—Pen | OH    | O—Pen | O—Pen | weak                  |
| C12 | OH    | O—Pen | OH    | O—Pen | O—Pen | O—Pen | weak                  |
| C13 | O—Pen | OH    | OH    | O—Pen | O—Pen | O—Pen | weak                  |
| C14 | OH    | O—Pen | O—Pen | OH    | O—Pen | O—Pen | weak                  |
| C15 | O—Pen | O—Pen | O—Pen | OH    | O—Pen | O—Pen | weak                  |
| C16 | O—Pen | O—Pen | OH    | O—Pen | O—Pen | O—Pen | weak                  |
| C17 | O—Pen | OH    | O—Pen | O—Pen | O—Pen | O—Pen | weak                  |
| C18 | OH    | O—Pen | O—Pen | O—Pen | O—Pen | O—Pen | weak                  |
| C19 | O—Pen | O—Pen | O—Pen | O—Pen | O—Pen | O—Pen | none                  |
| C20 | O—Pen | O—Pen | OH    | OH    | OH    | O—Pen | moderate              |
| C21 | O—Pen | O—Pen | OH    | OH    | O—Pen | OH    | moderate              |
| C22 | O—Pen | O—Pen | OH    | O—Pen | OH    | OH    | moderate              |
| C23 | O—Pen | O—Pen | O—Pen | OH    | OH    | OH    | moderate              |
| C24 | O—Pen | O—Pen | OH    | OH    | OH    | OH    | moderate              |
| C25 | O—Pen | OH    | OH    | OH    | OH    | O—Pen | moderate              |
| C26 | OH    | O—Pen | OH    | OH    | OH    | O—Pen | moderate              |
| C27 | OH    | OH    | O—Pen | OH    | OH    | O—Pen | moderate              |
| C28 | OH    | OH    | OH    | O—Pen | OH    | O—Pen | moderate              |
| C29 | O—Pen | OH    | OH    | OH    | O—Pen | OH    | moderate              |
| C30 | OH    | O—Pen | OH    | OH    | O—Pen | OH    | moderate              |
| C31 | OH    | OH    | O—Pen | OH    | O—Pen | OH    | moderate              |
| C32 | OH    | OH    | OH    | O—Pen | O—Pen | OH    | moderate              |

Esterification of core compound E4A with Hexanoyl chloride and isolation of the compounds with HPLC give the following compounds: wherein Hex=Hexanoyl

|     | R1    | R2    | R5    | R8    | R17   | R18   | Cytotoxicity activity |
|-----|-------|-------|-------|-------|-------|-------|-----------------------|
| E4A | OH    | OH    | OH    | OH    | OH    | OH    | none                  |
| D1  | OH    | OH    | OH    | OH    | O-Hex | OH    | moderate              |
| D2  | OH    | OH    | OH    | OH    | OH    | O-Hex | moderate              |
| D3  | OH    | OH    | OH    | OH    | O-Hex | O-Hex | strong                |
| D4  | O-Hex | OH    | OH    | OH    | O-Hex | O-Hex | moderate              |
| D5  | OH    | O-Hex | OH    | OH    | O-Hex | O-Hex | moderate              |
| D6  | OH    | OH    | O-Hex | OH    | O-Hex | O-Hex | moderate              |

-continued

| | R1 | R2 | R5 | R8 | R17 | R18 | Cytotoxicity activity |
|---|---|---|---|---|---|---|---|
| D7 | OH | OH | OH | O-Hex | O-Hex | O-Hex | moderate |
| D8 | O-Hex | O-Hex | OH | OH | O-Hex | O-Hex | weak |
| D9 | OH | O-Hex | O-Hex | OH | O-Hex | O-Hex | weak |
| D10 | OH | OH | O-Hex | O-Hex | O-Hex | O-Hex | weak |
| D11 | O-Hex | OH | O-Hex | OH | O-Hex | O-Hex | weak |
| D12 | OH | O-Hex | OH | O-Hex | O-Hex | O-Hex | weak |
| D13 | O-Hex | OH | OH | O-Hex | O-Hex | O-Hex | weak |
| D14 | OH | O-Hex | O-Hex | OH | O-Hex | O-Hex | weak |
| D15 | O-Hex | O-Hex | O-Hex | OH | O-Hex | O-Hex | weak |
| D16 | O-Hex | O-Hex | OH | O-Hex | O-Hex | O-Hex | weak |
| D17 | O-Hex | OH | O-Hex | O-Hex | O-Hex | O-Hex | weak |
| D18 | OH | O-Hex | O-Hex | O-Hex | O-Hex | O-Hex | weak |
| D19 | O-Hex | O-Hex | O-Hex | O-Hex | O-Hex | O-Hex | none |
| D20 | O-Hex | O-Hex | OH | OH | OH | O-Hex | moderate |
| D21 | O-Hex | O-Hex | OH | OH | O-Hex | OH | moderate |
| D22 | O-Hex | O-Hex | OH | O-Hex | OH | OH | moderate |
| D23 | O-Hex | O-Hex | O-Hex | OH | OH | OH | moderate |
| D24 | O-Hex | O-Hex | OH | OH | OH | OH | moderate |
| D25 | O-Hex | OH | OH | OH | OH | O-Hex | moderate |
| D26 | OH | O-Hex | OH | OH | OH | O-Hex | moderate |
| D27 | OH | OH | O-Hex | OH | OH | O-Hex | moderate |
| D28 | OH | OH | OH | O-Hex | OH | O-Hex | moderate |
| D29 | O-Hex | OH | OH | OH | O-Hex | OH | moderate |
| D30 | OH | O-Hex | OH | OH | O-Hex | OH | moderate |
| D31 | OH | OH | O-Hex | OH | O-Hex | OH | moderate |
| D32 | OH | OH | OH | O-Hex | O-Hex | OH | moderate |

Esterification of core compound E4A with 2-Ethylbutyryl chloride and isolation of the compounds with HPLC give the following compounds: wherein Eth=2-Ethylbutyryl

| | R1 | R2 | R5 | R8 | R17 | R18 | Cytotoxicity activity |
|---|---|---|---|---|---|---|---|
| E4A | OH | OH | OH | OH | OH | OH | none |
| E1 | OH | OH | OH | OH | O-Eth | OH | moderate |
| E2 | OH | OH | OH | OH | OH | O-Eth | moderate |
| E3 | OH | OH | OH | OH | O-Eth | O-Eth | strong |
| E4 | O-Eth | OH | OH | OH | O-Eth | O-Eth | moderate |
| E5 | OH | O-Eth | OH | OH | O-Eth | O-Eth | moderate |
| E6 | OH | OH | O-Eth | OH | O-Eth | O-Eth | moderate |
| E7 | OH | OH | OH | O-Eth | O-Eth | O-Eth | moderate |
| E8 | O-Eth | O-Eth | OH | OH | O-Eth | O-Eth | weak |
| E9 | OH | O-Eth | O-Eth | OH | O-Eth | O-Eth | weak |
| E10 | OH | OH | O-Eth | O-Eth | O-Eth | O-Eth | weak |
| E11 | O-Eth | OH | O-Eth | OH | O-Eth | O-Eth | weak |
| E12 | OH | O-Eth | OH | O-Eth | O-Eth | O-Eth | weak |
| E13 | O-Eth | OH | OH | O-Eth | O-Eth | O-Eth | weak |
| E14 | OH | O-Eth | O-Eth | OH | O-Eth | O-Eth | weak |
| E15 | O-Eth | O-Eth | O-Eth | OH | O-Eth | O-Eth | weak |
| E16 | O-Eth | O-Eth | OH | O-Eth | O-Eth | O-Eth | weak |
| E17 | O-Eth | OH | O-Eth | O-Eth | O-Eth | O-Eth | weak |
| E18 | OH | O-Eth | O-Eth | O-Eth | O-Eth | O-Eth | weak |
| E19 | O-Eth | O-Eth | O-Eth | O-Eth | O-Eth | O-Eth | none |
| E20 | O-Eth | O-Eth | OH | OH | OH | O-Eth | moderate |
| E21 | O-Eth | O-Eth | OH | OH | O-Eth | OH | moderate |
| E22 | O-Eth | O-Eth | OH | O-Eth | OH | OH | moderate |
| E23 | O-Eth | O-Eth | O-Eth | OH | OH | OH | moderate |
| E24 | O-Eth | O-Eth | OH | OH | OH | OH | moderate |
| E25 | O-Eth | OH | OH | OH | OH | O-Eth | moderate |
| E26 | OH | O-Eth | OH | OH | OH | O-Eth | moderate |
| E27 | OH | OH | O-Eth | OH | OH | O-Eth | moderate |
| E28 | OH | OH | OH | O-Eth | OH | O-Eth | moderate |
| E29 | O-Eth | OH | OH | OH | O-Eth | OH | moderate |
| E30 | OH | O-Eth | OH | OH | O-Eth | OH | moderate |
| E31 | OH | OH | O-Eth | OH | O-Eth | OH | moderate |
| E32 | OH | OH | OH | O-Eth | O-Eth | OH | moderate |

Esterification of core compound E4A with Acetyl chloride (H) and isolation of the compounds with HPLC give the following compounds: wherein Acy=Acetyl

| | R1 | R2 | R5 | R8 | R17 | R18 | Cytotoxicity activity |
|---|---|---|---|---|---|---|---|
| E4A | OH | OH | OH | OH | OH | OH | none |
| H1 | OH | OH | OH | OH | O-Acy | OH | moderate |
| H2 | OH | OH | OH | OH | OH | O-Acy | moderate |
| H3 | OH | OH | OH | OH | O-Acy | O-Acy | strong |
| H4 | O-Acy | OH | OH | OH | O-Acy | O-Acy | moderate |
| H5 | OH | O-Acy | OH | OH | O-Acy | O-Acy | moderate |
| H6 | OH | OH | O-Acy | OH | O-Acy | O-Acy | moderate |
| H7 | OH | OH | OH | O-Acy | O-Acy | O-Acy | moderate |
| H8 | O-Acy | O-Acy | OH | OH | O-Acy | O-Acy | weak |
| H9 | OH | O-Acy | O-Acy | OH | O-Acy | O-Acy | weak |
| H10 | OH | OH | O-Acy | O-Acy | O-Acy | O-Acy | weak |
| H11 | O-Acy | OH | O-Acy | OH | O-Acy | O-Acy | weak |
| H12 | OH | O-Acy | OH | O-Acy | O-Acy | O-Acy | weak |
| H13 | O-Acy | OH | OH | O-Acy | O-Acy | O-Acy | weak |
| H14 | OH | O-Acy | O-Acy | OH | O-Acy | O-Acy | weak |
| H15 | O-Acy | O-Acy | O-Acy | OH | O-Acy | O-Acy | weak |
| H16 | O-Acy | O-Acy | OH | O-Acy | O-Acy | O-Acy | weak |
| H17 | O-Acy | OH | O-Acy | O-Acy | O-Acy | O-Acy | weak |
| H18 | OH | O-Acy | O-Acy | O-Acy | O-Acy | O-Acy | weak |
| H19 | O-Acy | O-Acy | O-Acy | O-Acy | O-Acy | O-Acy | none |
| H20 | O-Acy | O-Acy | OH | OH | OH | O-Acy | moderate |
| H21 | O-Acy | O-Acy | OH | OH | O-Acy | OH | moderate |
| H22 | O-Acy | O-Acy | OH | O-Acy | OH | OH | moderate |
| H23 | O-Acy | O-Acy | O-Acy | OH | OH | OH | moderate |
| H24 | O-Acy | O-Acy | OH | OH | OH | OH | moderate |
| H25 | O-Acy | OH | OH | OH | OH | O-Acy | moderate |
| H26 | OH | O-Acy | OH | OH | OH | O-Acy | moderate |
| H27 | OH | OH | O-Acy | OH | OH | O-Acy | moderate |
| H28 | OH | OH | OH | O-Acy | OH | O-Acy | moderate |
| H29 | O-Acy | OH | OH | OH | O-Acy | OH | moderate |
| H30 | OH | O-Acy | OH | OH | O-Acy | OH | moderate |
| H31 | OH | OH | O-Acy | OH | O-Acy | OH | moderate |
| H32 | OH | OH | OH | O-Acy | O-Acy | OH | moderate |

Esterification of core compound E4A with Crotonoyl chloride and isolation of the compounds with HPLC give the following compounds: wherein Cro=Crotonoyl

| | R1 | R2 | R5 | R8 | R17 | R18 | Cytotoxicity activity |
|---|---|---|---|---|---|---|---|
| E4A | OH | OH | OH | OH | OH | OH | none |
| I 1 | OH | OH | OH | OH | O-Cro | OH | moderate |
| I 2 | OH | OH | OH | OH | OH | O-Cro | moderate |
| I 3 | OH | OH | OH | OH | O-Cro | O-Cro | strong |
| I 4 | O-Cro | OH | OH | OH | O-Cro | O-Cro | moderate |
| I 5 | OH | O-Cro | OH | OH | O-Cro | O-Cro | moderate |
| I 6 | OH | OH | O-Cro | OH | O-Cro | O-Cro | moderate |
| I 7 | OH | OH | OH | O-Cro | O-Cro | O-Cro | moderate |
| I 8 | O-Cro | O-Cro | OH | OH | O-Cro | O-Cro | weak |
| I 9 | OH | O-Cro | O-Cro | OH | O-Cro | O-Cro | weak |
| I 10 | OH | OH | O-Cro | O-Cro | O-Cro | O-Cro | weak |
| I 11 | O-Cro | OH | O-Cro | OH | O-Cro | O-Cro | weak |
| I 12 | OH | O-Cro | OH | O-Cro | O-Cro | O-Cro | weak |
| I 13 | O-Cro | OH | OH | O-Cro | O-Cro | O-Cro | weak |
| I 14 | OH | O-Cro | O-Cro | OH | O-Cro | O-Cro | weak |
| I 15 | O-Cro | O-Cro | O-Cro | OH | O-Cro | O-Cro | weak |
| I 16 | O-Cro | O-Cro | OH | O-Cro | O-Cro | O-Cro | weak |
| I 17 | O-Cro | OH | O-Cro | O-Cro | O-Cro | O-Cro | weak |
| I 18 | OH | O-Cro | O-Cro | O-Cro | O-Cro | O-Cro | weak |
| I 19 | O-Cro | O-Cro | O-Cro | O-Cro | O-Cro | O-Cro | none |
| I 20 | O-Cro | O-Cro | OH | OH | OH | O-Cro | moderate |
| I 21 | O-Cro | O-Cro | OH | OH | O-Cro | OH | moderate |
| I 22 | O-Cro | O-Cro | OH | O-Cro | OH | OH | moderate |
| I 23 | O-Cro | O-Cro | O-Cro | OH | OH | OH | moderate |
| I 24 | O-Cro | O-Cro | OH | OH | OH | OH | moderate |
| I 25 | O-Cro | OH | OH | OH | OH | O-Cro | moderate |
| I 26 | OH | O-Cro | OH | OH | OH | O-Cro | moderate |
| I 27 | OH | OH | O-Cro | OH | OH | O-Cro | moderate |
| I 28 | OH | OH | OH | O-Cro | OH | O-Cro | moderate |
| I 29 | O-Cro | OH | OH | OH | O-Cro | OH | moderate |
| I 30 | OH | O-Cro | OH | OH | O-Cro | OH | moderate |

-continued

| | R1 | R2 | R5 | R8 | R17 | R18 | Cytotoxicity activity |
|---|---|---|---|---|---|---|---|
| I 31 | OH | OH | O-Cro | OH | O-Cro | OH | moderate |
| I 32 | OH | OH | OH | O-Cro | O-Cro | OH | moderate |

Esterification of core compound E4A with Cinnamoyl chloride and isolation of the compounds with HPLC give the following compounds: wherein Cin=Cinnamoyl

| | R1 | R2 | R5 | R8 | R17 | R18 | Cytotoxicity activity |
|---|---|---|---|---|---|---|---|
| E4A | OH | OH | OH | OH | OH | OH | none |
| J1 | OH | OH | OH | OH | O-Cin | OH | moderate |
| J2 | OH | OH | OH | OH | OH | O-Cin | moderate |
| J3 | OH | OH | OH | OH | O-Cin | O-Cin | strong |
| J4 | O-Cin | OH | OH | OH | O-Cin | O-Cin | moderate |
| J5 | OH | O-Cin | OH | OH | O-Cin | O-Cin | moderate |
| J6 | OH | OH | O-Cin | OH | O-Cin | O-Cin | moderate |
| J7 | OH | OH | OH | O-Cin | O-Cin | O-Cin | moderate |
| J8 | O-Cin | O-Cin | OH | OH | O-Cin | O-Cin | weak |
| J9 | OH | O-Cin | O-Cin | OH | O-Cin | O-Cin | weak |
| J10 | OH | O-Cin | OH | O-Cin | O-Cin | O-Cin | weak |
| J11 | O-Cin | OH | O-Cin | OH | O-Cin | O-Cin | weak |
| J12 | OH | O-Cin | OH | O-Cin | O-Cin | O-Cin | weak |
| J13 | O-Cin | OH | OH | O-Cin | O-Cin | O-Cin | weak |
| J14 | OH | OH | O-Cin | OH | O-Cin | O-Cin | weak |
| J15 | O-Cin | O-Cin | O-Cin | OH | O-Cin | O-Cin | weak |
| J16 | O-Cin | O-Cin | OH | O-Cin | O-Cin | O-Cin | weak |
| J17 | O-Cin | OH | O-Cin | O-Cin | O-Cin | O-Cin | weak |
| J18 | OH | O-Cin | O-Cin | O-Cin | O-Cin | O-Cin | weak |
| J19 | O-Cin | O-Cin | O-Cin | O-Cin | O-Cin | O-Cin | none |
| J20 | O-Cin | O-Cin | OH | OH | OH | O-Cin | moderate |
| J21 | O-Cin | O-Cin | OH | OH | O-Cin | OH | moderate |
| J22 | O-Cin | O-Cin | OH | O-Cin | OH | OH | moderate |
| J23 | O-Cin | O-Cin | O-Cin | OH | OH | OH | moderate |
| J24 | O-Cin | O-Cin | OH | OH | OH | OH | moderate |
| J25 | O-Cin | OH | OH | OH | OH | O-Cin | moderate |
| J26 | OH | O-Cin | OH | OH | OH | O-Cin | moderate |
| J27 | OH | OH | O-Cin | OH | OH | O-Cin | moderate |
| J28 | OH | OH | OH | O-Cin | OH | O-Cin | moderate |
| J29 | O-Cin | OH | OH | OH | O-Cin | OH | moderate |
| J30 | OH | O-Cin | OH | OH | O-Cin | OH | moderate |
| J31 | OH | OH | O-Cin | OH | O-Cin | OH | moderate |
| J32 | OH | OH | OH | O-Cin | O-Cin | OH | moderate |

Esterification of core compound E4A with benzoyl chloride and isolation of the compounds with HPLC give the following compounds: wherein Ben=benzoyl

| | R1 | R2 | R5 | R8 | R17 | R18 | Cytotoxicity activity |
|---|---|---|---|---|---|---|---|
| E4A | OH | OH | OH | OH | OH | OH | None |
| K1 | OH | OH | OH | OH | O-Ben | OH | moderate |
| K2 | OH | OH | OH | OH | OH | O-Ben | moderate |
| K3 | OH | OH | OH | OH | O-Ben | O-Ben | strong |
| K4 | O-Ben | OH | OH | OH | O-Ben | O-Ben | moderate |
| K5 | OH | O-Ben | OH | OH | O-Ben | O-Ben | moderate |
| K6 | OH | OH | O-Ben | OH | O-Ben | O-Ben | moderate |
| K7 | OH | OH | OH | O-Ben | O-Ben | O-Ben | moderate |
| K8 | O-Ben | O-Ben | OH | OH | O-Ben | O-Ben | weak |
| K9 | OH | O-Ben | O-Ben | OH | O-Ben | O-Ben | weak |
| K10 | OH | OH | O-Ben | O-Ben | O-Ben | O-Ben | weak |
| K11 | O-Ben | OH | O-Ben | OH | O-Ben | O-Ben | weak |
| K12 | OH | O-Ben | OH | O-Ben | O-Ben | O-Ben | weak |
| K13 | O-Ben | OH | OH | O-Ben | O-Ben | O-Ben | weak |
| K14 | OH | OH | O-Ben | OH | O-Ben | O-Ben | weak |
| K15 | O-Ben | O-Ben | O-Ben | OH | O-Ben | O-Ben | weak |
| K16 | O-Ben | O-Ben | OH | O-Ben | O-Ben | O-Ben | weak |
| K17 | O-Ben | OH | O-Ben | O-Ben | O-Ben | O-Ben | weak |
| K18 | OH | O-Ben | O-Ben | O-Ben | O-Ben | O-Ben | weak |
| K19 | O-Ben | O-Ben | O-Ben | O-Ben | O-Ben | O-Ben | none |
| K20 | O-Ben | O-Ben | OH | OH | OH | O-Ben | moderate |
| K21 | O-Ben | O-Ben | OH | OH | O-Ben | OH | moderate |
| K22 | O-Ben | O-Ben | OH | O-Ben | OH | OH | moderate |
| K23 | O-Ben | O-Ben | O-Ben | OH | OH | OH | moderate |
| K24 | O-Ben | O-Ben | OH | OH | OH | OH | moderate |
| K25 | O-Ben | OH | OH | OH | OH | O-Ben | moderate |
| K26 | OH | O-Ben | OH | OH | OH | O-Ben | moderate |
| K27 | OH | OH | O-Ben | OH | OH | O-Ben | moderate |
| K28 | OH | OH | OH | O-Ben | OH | O-Ben | moderate |
| K29 | O-Ben | OH | OH | OH | O-Ben | OH | moderate |
| K30 | OH | O-Ben | OH | OH | O-Ben | OH | moderate |
| K31 | OH | OH | O-Ben | OH | O-Ben | OH | moderate |
| K32 | OH | OH | OH | O-Ben | O-Ben | OH | moderate |

Esterification of core compound E4A with Propionyl chloride and isolation of the compounds with HPLC give the following compounds: wherein Ppi=Propionyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Ppi | OH | moderate |
| K2 | OH | OH | OH | OH | OH | O-Ppi | moderate |
| K3 | OH | OH | OH | OH | O-Ppi | O-Ppi | strong |
| K4 | O-Ppi | OH | OH | OH | O-Ppi | O-Ppi | moderate |
| K5 | OH | O-Ppi | OH | OH | O-Ppi | O-Ppi | moderate |
| K6 | OH | OH | O-Ppi | OH | O-Ppi | O-Ppi | moderate |
| K7 | OH | OH | OH | O-Ppi | O-Ppi | O-Ppi | moderate |
| K8 | O-Ppi | O-Ppi | OH | OH | O-Ppi | O-Ppi | weak |
| K9 | OH | O-Ppi | O-Ppi | OH | O-Ppi | O-Ppi | weak |
| K10 | OH | OH | O-Ppi | O-Ppi | O-Ppi | O-Ppi | weak |
| K11 | O-Ppi | OH | O-Ppi | OH | O-Ppi | O-Ppi | weak |
| K12 | OH | O-Ppi | OH | O-Ppi | O-Ppi | O-Ppi | weak |
| K13 | O-Ppi | OH | OH | O-Ppi | O-Ppi | O-Ppi | weak |
| K14 | OH | O-Ppi | O-Ppi | OH | O-Ppi | O-Ppi | weak |
| K15 | O-Ppi | O-Ppi | O-Ppi | OH | O-Ppi | O-Ppi | weak |
| K16 | O-Ppi | O-Ppi | OH | O-Ppi | O-Ppi | O-Ppi | weak |
| K17 | O-Ppi | OH | O-Ppi | O-Ppi | O-Ppi | O-Ppi | weak |
| K18 | OH | O-Ppi | O-Ppi | O-Ppi | O-Ppi | O-Ppi | weak |
| K19 | O-Ppi | O-Ppi | O-Ppi | O-Ppi | O-Ppi | O-Ppi | none |
| K20 | O-Ppi | O-Ppi | OH | OH | OH | O-Ppi | moderate |
| K21 | O-Ppi | O-Ppi | OH | OH | O-Ppi | OH | moderate |
| K22 | O-Ppi | O-Ppi | OH | O-Ppi | OH | OH | moderate |
| K23 | O-Ppi | O-Ppi | O-Ppi | OH | OH | OH | moderate |
| K24 | O-Ppi | O-Ppi | OH | OH | OH | OH | moderate |
| K25 | O-Ppi | OH | OH | OH | OH | O-Ppi | moderate |
| K26 | OH | O-Ppi | OH | OH | OH | O-Ppi | moderate |
| K27 | OH | OH | O-Ppi | OH | OH | O-Ppi | moderate |
| K28 | OH | OH | OH | O-Ppi | OH | O-Ppi | moderate |
| K29 | O-Ppi | OH | OH | OH | O-Ppi | OH | moderate |
| K30 | OH | O-Ppi | OH | OH | O-Ppi | OH | moderate |
| K31 | OH | OH | O-Ppi | OH | O-Ppi | OH | moderate |
| K32 | OH | OH | OH | O-Ppi | O-Ppi | OH | moderate |

Esterification of core compound E4A with 2-propenoyl chloride and isolation of the compounds with HPLC give the following compounds: wherein Ppe=Propenoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Ppe | OH | moderate |
| K2 | OH | OH | OH | OH | OH | O-Ppe | moderate |

-continued

| | R1 | R2 | R5 | R8 | R17 | R18 | Cytotoxicity activity |
|---|---|---|---|---|---|---|---|
| K3 | OH | OH | OH | OH | O-Ppe | O-Ppe | strong |
| K4 | O-Ppe | OH | OH | OH | O-Ppe | O-Ppe | moderate |
| K5 | OH | O-Ppe | OH | OH | O-Ppe | O-Ppe | moderate |
| K6 | OH | OH | O-Ppe | OH | O-Ppe | O-Ppe | moderate |
| K7 | OH | OH | OH | O-Ppe | O-Ppe | O-Ppe | moderate |
| K8 | O-Ppe | O-Ppe | OH | OH | O-Ppe | O-Ppe | weak |
| K9 | OH | O-Ppe | O-Ppe | OH | O-Ppe | O-Ppe | weak |
| K10 | OH | OH | O-Ppe | O-Ppe | O-Ppe | O-Ppe | weak |
| K11 | O-Ppe | OH | O-Ppe | OH | O-Ppe | O-Ppe | weak |
| K12 | OH | O-Ppe | OH | O-Ppe | O-Ppe | O-Ppe | weak |
| K13 | O-Ppe | OH | OH | O-Ppe | O-Ppe | O-Ppe | weak |
| K14 | OH | O-Ppe | O-Ppe | OH | O-Ppe | O-Ppe | weak |
| K15 | O-Ppe | O-Ppe | O-Ppe | OH | O-Ppe | O-Ppe | weak |
| K16 | O-Ppe | O-Ppe | OH | O-Ppe | O-Ppe | O-Ppe | weak |
| K17 | O-Ppe | OH | O-Ppe | O-Ppe | O-Ppe | O-Ppe | weak |
| K18 | OH | O-Ppe | O-Ppe | O-Ppe | O-Ppe | O-Ppe | weak |
| K19 | O-Ppe | O-Ppe | O-Ppe | O-Ppe | O-Ppe | O-Ppe | none |
| K20 | O-Ppe | O-Ppe | OH | OH | OH | O-Ppe | moderate |
| K21 | O-Ppe | O-Ppe | OH | OH | O-Ppe | OH | moderate |
| K22 | O-Ppe | O-Ppe | OH | O-Ppe | OH | OH | moderate |
| K23 | O-Ppe | O-Ppe | O-Ppe | OH | OH | OH | moderate |
| K24 | O-Ppe | O-Ppe | OH | OH | OH | OH | moderate |
| K25 | O-Ppe | OH | OH | OH | OH | O-Ppe | moderate |
| K26 | OH | O-Ppe | OH | OH | OH | O-Ppe | moderate |
| K27 | OH | OH | O-Ppe | OH | OH | O-Ppe | moderate |
| K28 | OH | OH | OH | O-Ppe | OH | O-Ppe | moderate |
| K29 | O-Ppe | OH | OH | OH | O-Ppe | OH | moderate |
| K30 | OH | O-Ppe | OH | OH | O-Ppe | OH | moderate |
| K31 | OH | OH | O-Ppe | OH | O-Ppe | OH | moderate |
| K32 | OH | OH | OH | O-Ppe | O-Ppe | OH | moderate |

Esterification of core compound E4A with Isobutyryl chloride and isolation of the compounds with HPLC give the following compounds: wherein Iso=Isobutyryl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Iso | OH | moderate |
| K2 | OH | OH | OH | OH | OH | O-Iso | moderate |
| K3 | OH | OH | OH | OH | O-Iso | O-Iso | strong |
| K4 | O-Iso | OH | OH | OH | O-Iso | O-Iso | moderate |
| K5 | OH | O-Iso | OH | OH | O-Iso | O-Iso | moderate |
| K6 | OH | OH | O-Iso | OH | O-Iso | O-Iso | moderate |
| K7 | OH | OH | OH | O-Iso | O-Iso | O-Iso | moderate |
| K8 | O-Iso | O-Iso | OH | OH | O-Iso | O-Iso | weak |
| K9 | OH | O-Iso | O-Iso | OH | O-Iso | O-Iso | weak |
| K10 | OH | OH | O-Iso | O-Iso | O-Iso | O-Iso | weak |
| K11 | O-Iso | OH | O-Iso | OH | O-Iso | O-Iso | weak |
| K12 | OH | O-Iso | OH | O-Iso | O-Iso | O-Iso | weak |
| K13 | O-Iso | OH | OH | O-Iso | O-Iso | O-Iso | weak |
| K14 | OH | O-Iso | O-Iso | OH | O-Iso | O-Iso | weak |
| K15 | O-Iso | O-Iso | O-Iso | OH | O-Iso | O-Iso | weak |
| K16 | O-Iso | O-Iso | OH | O-Iso | O-Iso | O-Iso | weak |
| K17 | O-Iso | OH | O-Iso | O-Iso | O-Iso | O-Iso | weak |
| K18 | OH | O-Iso | O-Iso | O-Iso | O-Iso | O-Iso | weak |
| K19 | O-Iso | O-Iso | O-Iso | O-Iso | O-Iso | O-Iso | none |
| K20 | O-Iso | O-Iso | OH | OH | OH | O-Iso | moderate |
| K21 | O-Iso | O-Iso | OH | OH | O-Iso | OH | moderate |
| K22 | O-Iso | O-Iso | OH | O-Iso | OH | OH | moderate |
| K23 | O-Iso | O-Iso | O-Iso | OH | OH | OH | moderate |
| K24 | O-Iso | O-Iso | OH | OH | OH | OH | moderate |
| K25 | O-Iso | OH | OH | OH | OH | O-Iso | moderate |
| K26 | OH | O-Iso | OH | OH | OH | O-Iso | moderate |
| K27 | OH | OH | O-Iso | OH | OH | O-Iso | moderate |
| K28 | OH | OH | OH | O-Iso | OH | O-Iso | moderate |
| K29 | O-Iso | OH | OH | OH | O-Iso | OH | moderate |
| K30 | OH | O-Iso | OH | OH | O-Iso | OH | moderate |
| K31 | OH | OH | O-Iso | OH | O-Iso | OH | moderate |
| K32 | OH | OH | OH | O-Iso | O-Iso | OH | moderate |

Esterification of core compound E4A with Butyryl chloride and isolation of the compounds with HPLC give the following compounds: wherein But=Butyryl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-But | OH | moderate |
| K2 | OH | OH | OH | OH | OH | O-But | moderate |
| K3 | OH | OH | OH | OH | O-But | O-But | strong |
| K4 | O-But | OH | OH | OH | O-But | O-But | moderate |
| K5 | OH | O-But | OH | OH | O-But | O-But | moderate |
| K6 | OH | OH | O-But | OH | O-But | O-But | moderate |
| K7 | OH | OH | OH | O-But | O-But | O-But | moderate |
| K8 | O-But | O-But | OH | OH | O-But | O-But | weak |
| K9 | OH | O-But | O-But | OH | O-But | O-But | weak |
| K10 | OH | OH | O-But | O-But | O-But | O-But | weak |
| K11 | O-But | OH | O-But | OH | O-But | O-But | weak |
| K12 | OH | O-But | OH | O-But | O-But | O-But | weak |
| K13 | O-But | OH | OH | O-But | O-But | O-But | weak |
| K14 | OH | O-But | O-But | OH | O-But | O-But | weak |
| K15 | O-But | O-But | O-But | OH | O-But | O-But | weak |
| K16 | O-But | O-But | OH | O-But | O-But | O-But | weak |
| K17 | O-But | OH | O-But | O-But | O-But | O-But | weak |
| K18 | OH | O-But | O-But | O-But | O-But | O-But | weak |
| K19 | O-But | O-But | O-But | O-But | O-But | O-But | none |
| K20 | O-But | O-But | OH | OH | OH | O-But | moderate |
| K21 | O-But | O-But | OH | OH | O-But | OH | moderate |
| K22 | O-But | O-But | OH | O-But | OH | OH | moderate |
| K23 | O-But | O-But | O-But | OH | OH | OH | moderate |
| K24 | O-But | O-But | OH | OH | OH | OH | moderate |
| K25 | O-But | OH | OH | OH | OH | O-But | moderate |
| K26 | OH | O-But | OH | OH | OH | O-But | moderate |
| K27 | OH | OH | O-But | OH | OH | O-But | moderate |
| K28 | OH | OH | OH | O-But | OH | O-But | moderate |
| K29 | O-But | OH | OH | OH | O-But | OH | moderate |
| K30 | OH | O-But | OH | OH | O-But | OH | moderate |
| K31 | OH | OH | O-But | OH | O-But | OH | moderate |
| K32 | OH | OH | OH | O-But | O-But | OH | moderate |

Esterification of core compound E4A with (2E)-2-pentenoyl chloride and isolation of the compounds with HPLC give the following compounds: wherein 2pe=2-pentenoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-2pe | OH | moderate |
| K2 | OH | OH | OH | OH | OH | O-2pe | moderate |
| K3 | OH | OH | OH | OH | O-2pe | O-2pe | strong |
| K4 | O-2pe | OH | OH | OH | O-2pe | O-2pe | moderate |
| K5 | OH | O-2pe | OH | OH | O-2pe | O-2pe | moderate |
| K6 | OH | OH | O-2pe | OH | O-2pe | O-2pe | moderate |
| K7 | OH | OH | OH | O-2pe | O-2pe | O-2pe | moderate |
| K8 | O-2pe | O-2pe | OH | OH | O-2pe | O-2pe | weak |
| K9 | OH | O-2pe | O-2pe | OH | O-2pe | O-2pe | weak |
| K10 | OH | OH | O-2pe | O-2pe | O-2pe | O-2pe | weak |
| K11 | O-2pe | OH | O-2pe | OH | O-2pe | O-2pe | weak |
| K12 | OH | O-2pe | OH | O-2pe | O-2pe | O-2pe | weak |
| K13 | O-2pe | OH | OH | O-2pe | O-2pe | O-2pe | weak |
| K14 | OH | O-2pe | O-2pe | OH | O-2pe | O-2pe | weak |
| K15 | O-2pe | O-2pe | O-2pe | OH | O-2pe | O-2pe | weak |
| K16 | O-2pe | O-2pe | OH | O-2pe | O-2pe | O-2pe | weak |
| K17 | O-2pe | OH | O-2pe | O-2pe | O-2pe | O-2pe | weak |
| K18 | OH | O-2pe | O-2pe | O-2pe | O-2pe | O-2pe | weak |
| K19 | O-2pe | O-2pe | O-2pe | O-2pe | O-2pe | O-2pe | none |
| K20 | O-2pe | O-2pe | OH | OH | OH | O-2pe | moderate |
| K21 | O-2pe | O-2pe | OH | OH | O-2pe | OH | moderate |
| K22 | O-2pe | O-2pe | OH | O-2pe | OH | OH | moderate |
| K23 | O-2pe | O-2pe | O-2pe | OH | OH | OH | moderate |
| K24 | O-2pe | O-2pe | OH | OH | OH | OH | moderate |
| K25 | O-2pe | OH | OH | OH | OH | O-2pe | moderate |
| K26 | OH | O-2pe | OH | OH | OH | O-2pe | moderate |

-continued

| | R1 | R2 | R5 | R8 | R17 | R18 | Cytotoxicity activity |
|---|---|---|---|---|---|---|---|
| K27 | OH | OH | O-2pe | OH | OH | O-2pe | moderate |
| K28 | OH | OH | OH | O-2pe | OH | O-2pe | moderate |
| K29 | O-2pe | OH | OH | OH | O-2pe | OH | moderate |
| K30 | OH | O-2pe | OH | OH | O-2pe | OH | moderate |
| K31 | OH | OH | O-2pe | OH | O-2pe | OH | moderate |
| K32 | OH | OH | OH | O-2pe | O-2pe | OH | moderate |

Esterification of core compound E4A with Octanoyl chloride and isolation of the compounds with HPLC give the following compounds: wherein Oct=Octanoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Oct | OH | moderate |
| K2 | OH | OH | OH | OH | OH | O-Oct | moderate |
| K3 | OH | OH | OH | OH | O-Oct | O-Oct | strong |
| K4 | O-Oct | OH | OH | OH | O-Oct | O-Oct | moderate |
| K5 | OH | O-Oct | OH | OH | O-Oct | O-Oct | moderate |
| K6 | OH | OH | O-Oct | OH | O-Oct | O-Oct | moderate |
| K7 | OH | OH | OH | O-Oct | O-Oct | O-Oct | moderate |
| K8 | O-Oct | O-Oct | OH | OH | O-Oct | O-Oct | weak |
| K9 | OH | O-Oct | O-Oct | OH | O-Oct | O-Oct | weak |
| K10 | OH | OH | O-Oct | O-Oct | O-Oct | O-Oct | weak |
| K11 | O-Oct | OH | O-Oct | OH | O-Oct | O-Oct | weak |
| K12 | OH | O-Oct | OH | O-Oct | O-Oct | O-Oct | weak |
| K13 | O-Oct | OH | OH | O-Oct | O-Oct | O-Oct | weak |
| K14 | OH | O-Oct | O-Oct | OH | O-Oct | O-Oct | weak |
| K15 | O-Oct | O-Oct | O-Oct | OH | O-Oct | O-Oct | weak |
| K16 | O-Oct | O-Oct | OH | O-Oct | O-Oct | O-Oct | weak |
| K17 | O-Oct | OH | O-Oct | O-Oct | O-Oct | O-Oct | weak |
| K18 | OH | O-Oct | O-Oct | O-Oct | O-Oct | O-Oct | weak |
| K19 | O-Oct | O-Oct | O-Oct | O-Oct | O-Oct | O-Oct | none |
| K20 | O-Oct | O-Oct | OH | OH | OH | O-Oct | moderate |
| K21 | O-Oct | O-Oct | OH | OH | O-Oct | OH | moderate |
| K22 | O-Oct | O-Oct | OH | O-Oct | OH | OH | moderate |
| K23 | O-Oct | O-Oct | O-Oct | OH | OH | OH | moderate |
| K24 | O-Oct | O-Oct | OH | OH | OH | OH | moderate |
| K25 | O-Oct | OH | OH | OH | OH | O-Oct | moderate |
| K26 | OH | O-Oct | OH | OH | OH | O-Oct | moderate |
| K27 | OH | OH | O-Oct | OH | OH | O-Oct | moderate |
| K28 | OH | OH | OH | O-Oct | OH | O-Oct | moderate |
| K29 | O-Oct | OH | OH | OH | O-Oct | OH | moderate |
| K30 | OH | O-Oct | OH | OH | O-Oct | OH | moderate |
| K31 | OH | OH | O-Oct | OH | O-Oct | OH | moderate |
| K32 | OH | OH | OH | O-Oct | O-Oct | OH | moderate |

Esterification of core compound E4A with Decanoyl chloride and isolation of the compounds with HPLC give the following compounds: wherein Dec=Decanoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Dec | OH | moderate |
| K2 | OH | OH | OH | OH | OH | O-Dec | moderate |
| K3 | OH | OH | OH | OH | O-Dec | O-Dec | strong |
| K4 | O-Dec | OH | OH | OH | O-Dec | O-Dec | moderate |
| K5 | OH | O-Dec | OH | OH | O-Dec | O-Dec | moderate |
| K6 | OH | OH | O-Dec | OH | O-Dec | O-Dec | moderate |
| K7 | OH | OH | OH | O-Dec | O-Dec | O-Dec | moderate |
| K8 | O-Dec | O-Dec | OH | OH | O-Dec | O-Dec | weak |
| K9 | OH | O-Dec | O-Dec | OH | O-Dec | O-Dec | weak |
| K10 | OH | OH | O-Dec | O-Dec | O-Dec | O-Dec | weak |
| K11 | O-Dec | OH | O-Dec | OH | O-Dec | O-Dec | weak |
| K12 | OH | O-Dec | OH | O-Dec | O-Dec | O-Dec | weak |
| K13 | O-Dec | OH | OH | O-Dec | O-Dec | O-Dec | weak |
| K14 | OH | O-Dec | O-Dec | OH | O-Dec | O-Dec | weak |
| K15 | O-Dec | O-Dec | O-Dec | OH | O-Dec | O-Dec | weak |
| K16 | O-Dec | O-Dec | OH | O-Dec | O-Dec | O-Dec | weak |
| K17 | O-Dec | OH | O-Dec | O-Dec | O-Dec | O-Dec | weak |
| K18 | OH | O-Dec | O-Dec | O-Dec | O-Dec | O-Dec | weak |
| K19 | O-Dec | O-Dec | O-Dec | O-Dec | O-Dec | O-Dec | none |
| K20 | O-Dec | O-Dec | OH | OH | OH | O-Dec | moderate |
| K21 | O-Dec | O-Dec | OH | OH | O-Dec | OH | moderate |
| K22 | O-Dec | O-Dec | OH | O-Dec | OH | OH | moderate |
| K23 | O-Dec | O-Dec | O-Dec | OH | OH | OH | moderate |
| K24 | O-Dec | O-Dec | OH | OH | OH | OH | moderate |
| K25 | O-Dec | OH | OH | OH | OH | O-Dec | moderate |
| K26 | OH | O-Dec | OH | OH | OH | O-Dec | moderate |
| K27 | OH | OH | O-Dec | OH | OH | O-Dec | moderate |
| K28 | OH | OH | OH | O-Dec | OH | O-Dec | moderate |
| K29 | O-Dec | OH | OH | OH | O-Dec | OH | moderate |
| K30 | OH | O-Dec | OH | OH | O-Dec | OH | moderate |
| K31 | OH | OH | O-Dec | OH | O-Dec | OH | moderate |
| K32 | OH | OH | OH | O-Dec | O-Dec | OH | moderate |

Esterification of core compound E4A with Myristoyl chloride and isolation of the compounds with HPLC give the following compounds: wherein Myr=Myristoyl

| | R1 | R2 | R5 | R8 | R17 | R18 | Cytotoxicity activity |
|---|---|---|---|---|---|---|---|
| E4A | OH | OH | OH | OH | OH | OH | none |
| K1 | OH | OH | OH | OH | O-Myr | OH | moderate |
| K2 | OH | OH | OH | OH | OH | O-Myr | moderate |
| K3 | OH | OH | OH | OH | O-Myr | O-Myr | strong |
| K4 | O-Myr | OH | OH | OH | O-Myr | O-Myr | moderate |
| K5 | OH | O-Myr | OH | OH | O-Myr | O-Myr | moderate |
| K6 | OH | OH | O-Myr | OH | O-Myr | O-Myr | moderate |
| K7 | OH | OH | OH | O-Myr | O-Myr | O-Myr | moderate |
| K8 | O-Myr | O-Myr | OH | OH | O-Myr | O-Myr | weak |
| K9 | OH | O-Myr | O-Myr | OH | O-Myr | O-Myr | weak |
| K10 | OH | OH | O-Myr | O-Myr | O-Myr | O-Myr | weak |
| K11 | O-Myr | OH | O-Myr | OH | O-Myr | O-Myr | weak |
| K12 | OH | O-Myr | OH | O-Myr | O-Myr | O-Myr | weak |
| K13 | O-Myr | OH | OH | O-Myr | O-Myr | O-Myr | weak |
| K14 | OH | O-Myr | O-Myr | OH | O-Myr | O-Myr | weak |
| K15 | O-Myr | O-Myr | O-Myr | OH | O-Myr | O-Myr | weak |
| K16 | O-Myr | O-Myr | OH | O-Myr | O-Myr | O-Myr | weak |
| K17 | O-Myr | OH | O-Myr | O-Myr | O-Myr | O-Myr | weak |
| K18 | OH | O-Myr | O-Myr | O-Myr | O-Myr | O-Myr | weak |
| K19 | O-Myr | O-Myr | O-Myr | O-Myr | O-Myr | O-Myr | none |
| K20 | O-Myr | O-Myr | OH | OH | OH | O-Myr | moderate |
| K21 | O-Myr | O-Myr | OH | OH | O-Myr | OH | moderate |
| K22 | O-Myr | O-Myr | OH | O-Myr | OH | OH | moderate |
| K23 | O-Myr | O-Myr | O-Myr | OH | OH | OH | moderate |
| K24 | O-Myr | O-Myr | OH | OH | OH | OH | moderate |
| K25 | O-Myr | OH | OH | OH | OH | O-Myr | moderate |
| K26 | OH | O-Myr | OH | OH | OH | O-Myr | moderate |
| K27 | OH | OH | O-Myr | OH | OH | O-Myr | moderate |
| K28 | OH | OH | OH | O-Myr | OH | O-Myr | moderate |
| K29 | O-Myr | OH | OH | OH | O-Myr | OH | moderate |
| K30 | OH | O-Myr | OH | OH | O-Myr | OH | moderate |
| K31 | OH | OH | O-Myr | OH | O-Myr | OH | moderate |
| K32 | OH | OH | OH | O-Myr | O-Myr | OH | moderate |

Esterification of E4A-Tig-N with senecioyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Sen-1 | OH | OH | OH | OH | O-Tig | O-Sen | strong |
| Tig-Sen-2 | O-Sen | OH | OH | OH | O-Tig | O-Sen | moderate |
| Tig-Sen-3 | OH | O-Sen | OH | OH | O-Tig | O-Sen | moderate |
| Tig-Sen-4 | OH | OH | O-Sen | OH | O-Tig | O-Sen | moderate |

-continued

|  | R1 | R2 | R5 | R8 | R17 | R18 | Cytotoxicity activity |
|---|---|---|---|---|---|---|---|
| Tig-Sen-5 | O-Sen | OH | OH | OH | O-Tig | OH | moderate |
| Tig-Sen-6 | OH | O-Sen | OH | OH | O-Tig | OH | moderate |

Esterification of E4A-Tig-N with Crotonoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Cro-1 | OH | OH | OH | OH | O-Tig | O-Cro | strong |
| Tig-Cro-2 | O-Cro | OH | OH | OH | O-Tig | O-Cro | moderate |
| Tig-Cro-3 | OH | O-Cro | OH | OH | O-Tig | O-Cro | moderate |
| Tig-Cro-4 | OH | OH | O-Cro | OH | O-Tig | O-Cro | moderate |
| Tig-Cro-5 | O-Cro | OH | OH | OH | O-Tig | OH | moderate |
| Tig-Cro-6 | OH | O-Cro | OH | OH | O-Tig | OH | moderate |

Esterification of E4A-Tig-N with Acetyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Acy-1 | OH | OH | OH | OH | O-Tig | O-Acy | strong |
| Tig-Acy-2 | O-Acy | OH | OH | OH | O-Tig | O-Acy | moderate |
| Tig-Acy-3 | OH | O-Acy | OH | OH | O-Tig | O-Acy | moderate |
| Tig-Acy-4 | OH | OH | O-Acy | OH | O-Tig | O-Acy | moderate |
| Tig-Acy-5 | O-Acy | OH | OH | OH | O-Tig | OH | moderate |
| Tig-Acy-6 | OH | O-Acy | OH | OH | O-Tig | OH | moderate |

Esterification of E4A-Tig-N with 4-Pentenoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Pen-1 | OH | OH | OH | OH | O-Tig | O-Pen | strong |
| Tig-Pen-2 | O-Pen | OH | OH | OH | O-Tig | O-Pen | moderate |
| Tig-Pen-3 | OH | O-Pen | OH | OH | O-Tig | O-Pen | moderate |
| Tig-Pen-4 | OH | OH | O-Pen | OH | O-Tig | O-Pen | moderate |
| Tig-Pen-5 | O-Pen | OH | OH | OH | O-Tig | OH | moderate |
| Tig-Pen-6 | OH | O-Pen | OH | OH | O-Tig | OH | moderate |

Esterification of E4A-Tig-N with Hexanoly chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Hex-1 | OH | OH | OH | OH | O-Tig | O-Hex | strong |
| Tig-Hex-2 | O-Hex | OH | OH | OH | O-Tig | O-Hex | moderate |
| Tig-Hex-3 | OH | O-Hex | OH | OH | O-Tig | O-Hex | moderate |
| Tig-Hex-4 | OH | OH | O-Hex | OH | O-Tig | O-Hex | moderate |
| Tig-Hex-5 | O-Hex | OH | OH | OH | O-Tig | OH | moderate |
| Tig-Hex-6 | OH | O-Hex | OH | OH | O-Tig | OH | moderate |

Esterification of E4A-Tig-N with Cinnamoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Cin-1 | OH | OH | OH | OH | O-Tig | O-Cin | strong |
| Tig-Cin-2 | O-Cin | OH | OH | OH | O-Tig | O-Cin | moderate |
| Tig-Cin-3 | OH | O-Cin | OH | OH | O-Tig | O-Cin | moderate |
| Tig-Cin-4 | OH | OH | O-Cin | OH | O-Tig | O-Cin | moderate |
| Tig-Cin-5 | O-Cin | OH | OH | OH | O-Tig | OH | moderate |
| Tig-Cin-6 | OH | O-Cin | OH | OH | O-Tig | OH | moderate |

Esterification of E4A-Tig-N with Angeloyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Ang-1 | OH | OH | OH | OH | O-Tig | O-Ang | strong |
| Tig-Ang-2 | O-Ang | OH | OH | OH | O-Tig | O-Ang | moderate |
| Tig-Ang-3 | OH | O-Ang | OH | OH | O-Tig | O-Ang | moderate |
| Tig-Ang-4 | OH | OH | O-Ang | OH | O-Tig | O-Ang | moderate |
| Tig-Ang-5 | O-Ang | OH | OH | OH | O-Tig | OH | moderate |
| Tig-Ang-6 | OH | O-Ang | OH | OH | O-Tig | OH | moderate |

Esterification of E4A-Tig-N with 2-Ethylbutyryl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-N | OH | OH | OH | OH | O-Tig | OH | moderate |
| Tig-Eth-1 | OH | OH | OH | OH | O-Tig | O-Eth | strong |
| Tig-Eth-2 | O-Eth | OH | OH | OH | O-Tig | O-Eth | moderate |
| Tig-Eth-3 | OH | O-Eth | OH | OH | O-Tig | O-Eth | moderate |
| Tig-Eth-4 | OH | OH | O-Eth | OH | O-Tig | O-Eth | moderate |
| Tig-Eth-5 | O-Eth | OH | OH | OH | O-Tig | OH | moderate |
| Tig-Eth-6 | OH | O-Eth | OH | OH | O-Tig | OH | moderate |

Esterification of E4A-Tig-R with senecioyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Sen-1 | O-Sen | O-Sen | OH | OH | O-Tig | O-Tig | weak |
| Tig-R-Sen-2 | O-Sen | OH | OH | OH | O-Tig | O-Tig | moderate |
| Tig-R-Sen-3 | OH | O-Sen | OH | OH | O-Tig | O-Tig | moderate |
| Tig-R-Sen-4 | OH | OH | O-Sen | OH | O-Tig | O-Tig | moderate |
| Tig-R-Sen-5 | O-Sen | OH | O-Sen | OH | O-Tig | O-Tig | weak |
| Tig-R-Sen-6 | OH | O-Sen | O-Sen | OH | O-Tig | O-Tig | weak |

Esterification of E4A-Tig-R with Crotonoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Cro-1 | O-Cro | O-Cro | OH | OH | O-Tig | O-Tig | weak |
| Tig-R-Cro-2 | O-Cro | OH | OH | OH | O-Tig | O-Tig | moderate |
| Tig-R-Cro-3 | OH | O-Cro | OH | OH | O-Tig | O-Tig | moderate |
| Tig-R-Cro-4 | OH | OH | O-Cro | OH | O-Tig | O-Tig | moderate |
| Tig-R-Cro-5 | O-Cro | OH | O-Cro | OH | O-Tig | O-Tig | weak |
| Tig-R-Cro-6 | OH | O-Cro | O-Cro | OH | O-Tig | O-Tig | weak |

Esterification of E4A-Tig-R with Acetyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Acy-1 | O-Acy | O-Acy | OH | OH | O-Tig | O-Tig | weak |
| Tig-R-Acy-2 | O-Acy | OH | OH | OH | O-Tig | O-Tig | moderate |
| Tig-R-Acy-3 | OH | O-Acy | OH | OH | O-Tig | O-Tig | moderate |
| Tig-R-Acy-4 | OH | OH | O-Acy | OH | O-Tig | O-Tig | moderate |
| Tig-R-Acy-5 | O-Acy | OH | O-Acy | OH | O-Tig | O-Tig | weak |
| Tig-R-Acy-6 | OH | O-Acy | O-Acy | OH | O-Tig | O-Tig | weak |

Esterification of E4A-Tig-R with 4-Pentenoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Pen-1 | O-Pen | O-Pen | OH | OH | O-Tig | O-Tig | weak |
| Tig-R-Pen-2 | O-Pen | OH | OH | OH | O-Tig | O-Tig | moderate |
| Tig-R-Pen-3 | OH | O-Pen | OH | OH | O-Tig | O-Tig | moderate |
| Tig-R-Pen-4 | OH | OH | O-Pen | OH | O-Tig | O-Tig | moderate |
| Tig-R-Pen-5 | O-Pen | OH | O-Pen | OH | O-Tig | O-Tig | weak |
| Tig-R-Pen-6 | OH | O-Pen | O-Pen | OH | O-Tig | OH | weak |

Esterification of E4A-Tig-R with Hexanoly chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Hex-1 | O-Hex | O-Hex | OH | OH | O-Tig | O-Tig | weak |
| Tig-R-Hex-2 | O-Hex | OH | OH | OH | O-Tig | O-Tig | moderate |
| Tig-R-Hex-3 | OH | O-Hex | OH | OH | O-Tig | O-Tig | moderate |
| Tig-R-Hex-4 | OH | OH | O-Hex | OH | O-Tig | O-Tig | moderate |
| Tig-R-Hex-5 | O-Hex | OH | O-Hex | OH | O-Tig | O-Tig | weak |
| Tig-R-Hex-6 | OH | O-Hex | O-Hex | OH | O-Tig | O-Tig | weak |

Esterification of E4A-Tig-R with Cinnamoyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Cin-1 | O-Cin | O-Cin | OH | OH | O-Tig | O-Tig | weak |
| Tig-R-Cin-2 | O-Cin | OH | OH | OH | O-Tig | O-Tig | moderate |
| Tig-R-Cin-3 | OH | O-Cin | OH | OH | O-Tig | O-Tig | moderate |
| Tig-R-Cin-4 | OH | OH | O-Cin | OH | O-Tig | O-Tig | moderate |
| Tig-R-Cin-5 | O-Cin | OH | O-Cin | OH | O-Tig | O-Tig | weak |
| Tig-R-Cin-6 | OH | O-Cin | O-Cin | OH | O-Tig | O-Tig | weak |

Esterification of E4A-Tig-R with Angeloyl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Ang-1 | O-Ang | O-Ang | OH | OH | O-Tig | O-Tig | weak |
| Tig-R-Ang-2 | O-Ang | OH | OH | OH | O-Tig | O-Tig | moderate |
| Tig-R-Ang-3 | OH | O-Ang | OH | OH | O-Tig | O-Tig | moderate |

-continued

|  | R1 | R2 | R5 | R8 | R17 | R18 | Cytotoxicity activity |
|---|---|---|---|---|---|---|---|
| Tig-R-Ang-4 | OH | OH | O-Ang | OH | O-Tig | O-Tig | moderate |
| Tig-R-Ang-5 | O-Ang | OH | O-Ang | OH | O-Tig | O-Tig | weak |
| Tig-R-Ang-6 | OH | O-Ang | O-Ang | OH | O-Tig | O-Tig | weak |

Esterification of E4A-Tig-R with 2-Ethylbutyryl chloride and isolation of the compounds with HPLC give the following compounds:

|  | R1 | R2 | R5 | R8 | R17 | R18 | Cytotoxicity activity |
|---|---|---|---|---|---|---|---|
| E4A-Tig-R | OH | OH | OH | OH | O-Tig | O-Tig | strong |
| Tig-R-Eth-1 | O-Eth | O-Eth | OH | OH | O-Tig | O-Tig | weak |
| Tig-R-Eth-2 | O-Eth | OH | OH | OH | O-Tig | O-Tig | moderate |
| Tig-R-Eth-3 | OH | O-Eth | OH | OH | O-Tig | O-Tig | moderate |
| Tig-R-Eth-4 | OH | OH | O-Eth | OH | O-Tig | O-Tig | moderate |
| Tig-R-Eth-5 | O-Eth | OH | O-Eth | OH | O-Tig | O-Tig | weak |
| Tig-R-Eth-6 | OH | O-Eth | O-Eth | OH | O-Tig | O-Tig | weak |

Esterification of compound (A), (B), (C), (D1), (D2), (E), (F), (G), (H1), (H2), E4A, E4A2Y, (P1), P(2), terpene, isoprene, triterpenes, hydroxylated triterpenes, with acyl halide, wherein the halide comprise chloride, bromide, fluoride and iodide, wherein the acyl halide comprise acyl chloride, wherein acyl chloride comprise tigloyl chloride, angeloyl chloride, acetyl chloride, crotonoyl chloride, 3,3-dimethylartyloyl chloride, senecioyl chloride, cinnamoyl chloride, pentenoyl chloride, hexanoyl chloride, benzoyl chloride, ethylbutyryl chloride, propionyl chloride, 2-propenoyl chloride, isobutyryl chloride, butyryl chloride, (2E)-2-pentenoyl chloride, 4-Pentenoyl chloride, 5-hexenoyl chloride, heptanoyl chloride, octanoyl chloride, nonanoyl chloride, decanoyl chloride, Lauroyl chloride, myristoyl chloride, oleoyl chloride. The compounds vary in composition when the time or temperature of the reaction is changed. The peaks, fractions and compounds are selected according to the activities of times studies and the changes of peaks. The compounds having strong to weak activities are selected and isolated. The anti cancer activities (Cytotoxic Assay) are the MTT studies of bone (U2OS), lung (H460), bladder (HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), luekemia (K562), cervix (HeLa). The active esterification products are purified with HPLC. The reaction product of mixtures and individual compounds are tested with MTT Cytotoxic Assay. Details of method are in Experiment 3 of the present application. A second esterification of compound can be selected from the above experiment results to produce new active compounds. A partial esterification compound is selected from the above experiments to perform a second or repeated with a third esterification with different acyl chloride in order to produce new active compounds with the experiments in the present application.

A method is 1) Dissolving core compound or triterpenes core, hydroxylated triterpenes core, in pyridine; 2) Adding acyl halide or acyl chloride; 3, The mixture is stirred for length of time including 5 sec, 10 sec, 20 sec, 30 sec, 40 sec, 1 min, 2 min, 5 min, 10 min, 30 min, 1 hr, 2 hr, 18 hr, 2 days or 3 days at different temperature; 4) At the end of reaction, aqueous solution of acid or weak base, or water is added to the reaction mixture; 5) The solution is then extracted of ethyl acetate and ethyl acetate is removed by evaporation and lyophilization; 6) Dissolving the reaction product in acetonitrile with Trifluoroacetic acid or DMSO; 7) Testing the reaction product of mixtures and individual fractions with MTT cytotoxic assay; 8) Selecting the HPLC fractions for isolation is according to the cytotoxic activity of the reaction product obtained at a specific reaction time; 10) Purifiing the active esterification products with HPLC; 11) Collecting the products; 12) Testing the products; wherein the core compound is terpene, isoprene, or triterpene core or hydroxylated triterpenes core; wherein the core compound was dissolved in pyridine; wherein the acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, Propionyl chloride, 2-Propenoyl chloride, Isobutyryl chloride, Butyryl chloride, (2E)-2-pentenoyl chloride, 4-Pentenoyl chloride, 5-Hexenoyl chloride, Heptanoyl chloride, Octanoyl chloride, Nonanoyl chloride, Decanoyl chloride, Lauroyl chloride, Myristoyl chloride, and Oleoyl chloride; wherein the reaction time for the mixture is stirred for 5 sec, 10 sec, 20 sec, 30 sec, 40 sec, 1 min, 2 min, 5 min, 10 min, 30 min, 1 hr, 2 hr, 18 hr, 2 days or 3 days; wherein the temperature is 0 C, 25 C, 50 C or 75 C temperature; wherein the acid including HCl or the base including NaHCO3 is added to the reaction mixture; wherein the solution is then extracted 3 times with ethyl acetate and lyophilization; wherein the reaction product is dissolved in 80% acetonitrile—0.005% Trifluoroacetic acid or DMSO; wherein selecting the HPLC fractions for isolation is according to the cytotoxic activity of the reaction product obtained at a reaction time of 5 sec, 10 sec, 20 sec, 30 sec, 40 sec, 1 min, 2 min, 5 min, 10 min, 30 min, 1 hr, 2 hr, 18 hr, 2 days or 3 days. In an embodiment, the reaction time may be ove 3 days. In an embodiment, the experiment may be performed under 0 C. In an embodiment, the experiment may be performed over 75 C.

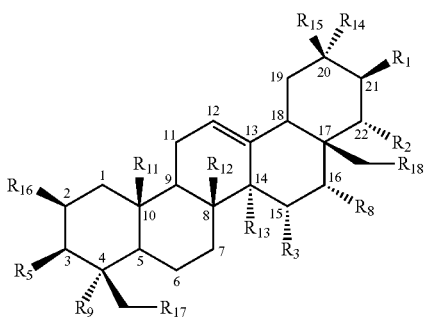

wherein (R1, R2, or R18) and (R17, R5 or R16) are independently selected from the group of O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Caryloyl, O-Lauroyl, O-Dodecanoyl, O-Myristoyl, O-Tetradecanoyl, O-Oleoyl; wherein wherein R1, R2, R3, R4, R5, R8, R9, R10, R11, R12, R13, R14, R15, R16, R17 are independently selected from the group of H, OH, CH2OH, COOH, OR CH3, The anti-cancer activities of Tig-R compound: IC50 of bone (U2OS) is 4.5 ug/ml, lung (H460) is 4.8 ug/ml, bladder (HTB-9) is 2.5 ug/ml, ovary (ES2) is 2.8 ug/ml, colon (HCT116) is 5.2 ug/ml, pancreas (Capan) 2.4 ug/ml, ovary (OVCAR3) is 5.8, prostate (DU145) is 3.6 ug/ml, skin (SK-Mel-5) is 5.1 ug/ml, mouth (KB) is 3 ug/ml, kidney (A498) 10 is 3.5 ug/ml, breast (MCF-7) is 4.5 ug/ml, liver (HepG2) is 6 ug/ml, brain (T98G) is 8 ug/ml), leukemia (K562) is 2 ug/ml, cervix (HeLa) is 5 ug/ml.

The anti-cancer activities of Tig-V compound: IC50 of bone (U2OS) is 7 ug/ml, lung (H460) is 6.8 ug/ml, bladder (HTB-9) is 4 ug/ml, ovary (ES2) is 2 ug/ml, colon (HCT116) is 8 ug/ml, pancreas (Capan) 5 ug/ml, ovary (OVCAR3) is 9, prostate (DU145) is 4 ug/ml, skin (SK-Mel-5) is 6 ug/ml, mouth (KB) is 4.5 ug/ml, kidney (A498) is 4.8 ug/ml, breast (MCF-7) is 9 ug/ml, liver (HepG2) is 12 ug/ml, brain (T98G) is 14 ug/ml), leukemia (K562) is 4 ug/ml, cervix (HeLa) is 7 ug/ml.

The anti-cancer activities of Tig-N compound: IC50 of bone (U2OS) is 15 ug/ml, lung (H460) is 13 ug/ml, bladder (HTB-9) is 7.5 ug/ml, ovary (ES2) is 9 ug/ml, colon (HCT116) is 15 ug/ml, pancreas (Capan) 8 ug/ml, ovary (OVCAR3) is 18, prostate (DU145) is 4.8 ug/ml, skin (SK-Mel-5) is 15 ug/ml, mouth (KB) is 9 ug/ml, kidney (A498) is 11 ug/ml, breast (MCF-7) is 13 ug/ml, liver (HepG2) is 18 ug/ml, brain (T98G) is 19 ug/ml), leukemia (K562) is 6 ug/ml, cervix (HeLa) is 15 ug/ml.

The anti-cancer activities of Tig-Q compound: IC50 of bone (U2OS) is 20 ug/ml, lung (H460) is 18 ug/ml, bladder (HTB-9) is 10 ug/ml, ovary (ES2) is 12 ug/ml, colon (HCT116) is 22 ug/ml, pancreas (Capan) 9 ug/ml, ovary (OVCAR3) is 23, prostate (DU145) is 15 ug/ml, skin (SK-Mel-5) is 20 ug/ml, mouth (KB) is 12 ug/ml, kidney (A498) is 13 ug/ml, breast (MCF-7) is 18 ug/ml, liver (HepG2) is 24 ug/ml, brain (T98G) is 29 ug/ml), leukemia (K562) is 6 ug/ml, cervix (HeLa) is 20 ug/ml.

The anti-cancer activities of Tig-T compound: IC50 of bone (U2OS) is 20 ug/ml, lung (H460) is 21 ug/ml, bladder (HTB-9) is 12 ug/ml, ovary (ES2) is 14 ug/ml, colon (HCT116) is 23 ug/ml, pancreas (Capan) 10 ug/ml, ovary (OVCAR3) is 25, prostate (DU145) is 16 ug/ml, skin (SK-Mel-5) is 22 ug/ml, mouth (KB) is 13 ug/ml, kidney (A498) is 15 ug/ml, breast (MCF-7) is 20 ug/ml, liver (HepG2) is 26 ug/ml, brain (T98G) is 26 ug/ml), leukemia (K562) is 9 ug/ml, cervix (HeLa) is 18 ug/ml.

The anti-cancer activities of Tig-S compound: IC50 of bone (U2OS) is 5.2 ug/ml, lung (H460) is 5.6 ug/ml, bladder (HTB-9) is 3.5 ug/ml, ovary (ES2) is 0.1 ug/ml, colon (HCT116) is 6.6 ug/ml, pancreas (Capan) 2.9 ug/ml, ovary (OVCAR3) is 6.5, prostate (DU145) is 4.3 ug/ml, skin (SK-Mel-5) is 5.8 ug/ml, mouth (KB) is 4 ug/ml, kidney (A498) is 4.8 ug/ml, breast (MCF-7) is 6.3 ug/ml, liver (HepG2) is 8.5 ug/ml, brain (T98G) is 9 ug/ml), leukemia (K562) is 4.3 ug/ml, cervix (HeLa) is 7 ug/ml.

The anti-cancer activities of Tig-U compound: IC50 of bone (U2OS) is 23 ug/ml, lung (H460) is 19 ug/ml, bladder (HTB-9) is 15 ug/ml, ovary (ES2) is 17 ug/ml, colon (HCT116) is 26 ug/ml, pancreas (Capan) 9 ug/ml, ovary (OVCAR3) is 27, prostate (DU145) is 15 ug/ml, skin (SK-Mel-5) is 24 ug/ml, mouth (KB) is 16 ug/ml, kidney (A498) is 18 ug/ml, breast (MCF-7) is 25 ug/ml, liver (HepG2) is 23 ug/ml, brain (T98G) is 22 ug/ml), leukemia (K562) is 10 ug/ml, cervix (HeLa) is 17 ug/ml.

The IC50 of Tig-R in normal human fibroblast cells (W138) is about 10-15 ug/ml. This IC50 value is 3 times higher than those in ovary ES2 (2.8 ug/ml) and lung (H460) is 4.8 ug/ml.

Swiss3T3 cells are mouse normal fibroblast which were used in this experiment to compare with ES2 (human ovarian cancer) in Tig-R cytotoxicity determination. The preliminary results indicate that the IC50 of Tig-R in SW3T3 cells is above 20 ug/ml while the corresponding IC50 in ES2 cells is about 2.8 ug/ml.

This invention provides compounds, methods, or uses of a compound for the manufacture of a medicament, or uses of a compound for medicament selected from formula (2A), for treating cancers, inhibition of cancer growth, cancer invasion, cells invasion, cancer cell invasion; cell adhesion, cell attachment, cell circulating; for treating mad cow disease; treating prion diseases; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions or neurodegeneration; for treating arthritis, rheumatism, poor blood circulation, arteriosclerosis, Raynaud's syndrome, angina pectoris, cardiac disorder, coronary heart disease, headache, dizziness, kidney disorder; cerebrovascular diseases; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and post-operative swelling; for inhibiting blood clots, for inhibiting ethanol absorption; for lowering blood sugar; for regulating adrenocorticotropin and corticosterone levels; for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; for improving blood circulation; soothing stroke; preventing plaque formation and promote their dissipated; improve blood viscosity; reducing cardiovascular; reducing cerebrovascular; reducing thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, fluttering, Blood circulation, swelling, pain; treating bronchiectasis, tuberculosis and lung abscess caused by too hemoptysis; reducing bleeding; antitussive; reducing expectorant; reducing analgesic effect; dilate blood vessels; reducing blood pressure; treatment of cerebral arteriosclerosis; elevating blood lipids; reducing cholesterol; manufacturing an adjuvant composition for treatment, using compounds selected from the following:

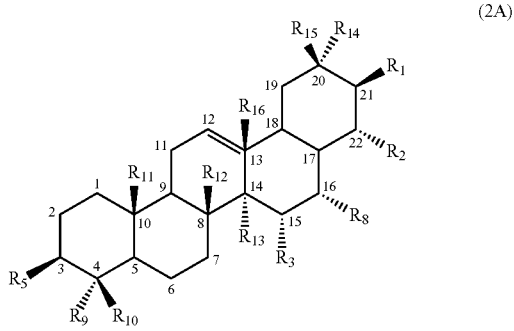

(2A)

$R_1$, $R_2$, $R_3$, $R_4$, $R_5$, $R_8$, $R_9$, $R_{10}$, $R_{11}$, $R_{12}$, $R_{13}$, $R_{14}$, $R_{15}$, $R_{16}$ are independently selected from the group of O, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, alkane, alkene and sugar moiety or derivatives thereof; or wherein the structure (2A) comprises at least 2 groups selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; or wherein $R_1$ and $R_2$ are selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; or wherein $R_4$ and $R_{10}$ are selected from CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroaryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C (2-18) Acyl. In an embodiment, R1 and R2 are attached OH. In an embodiment, R4 and R10 are attached a CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, or CH2O-Ethylbutyryl. In an embodiment, R3 and R8 is hydrogen or hydroxyl, In an embodiment, R9, R11, R12, R13, R14 and R15 are independently attached with a methyl. In an embodiment, R4 represents CH3, CHO, $CH_2R6$ or COR6, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroaryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl and derivatives thereof. In an embodiment, R3 is H or OH; In an embodiment, wherein R8 is H or OH; In an embodiment, R16 is H, CH3, OH, or R4 and R16 may together form —CH2-X—, CH(OH)—X— or C(=O)—X—, wherein the —X— may be O or NH or S; wherein when the C12-13 of ring 3 of the triterpene has a double bond then R16 is H or absent. In an embodiment, R10 represents CH3, CHO, or $CH_2R6$, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroaryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl and derivatives thereof; In an embodiment, R5 is a hydrogen, hydroxyl, heterocyclic or O-sugar moiety(ies), wherein the sugar moiety(ies) is/are selected from a group but not limited of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof; In embodiment, the above structures were attached an 0 with double bond; wherein R9, R10, R11, R12, R13, R14, R15, R16 are independently attached a group selecting from $CH_3$, $CH_2OH$, CHO, COOH, COO-alkyl, COO-aryl, COO-heterocyclic, COO-heteroaryl, $CH_2Oaryl$, $CH_2O$— heterocyclic, $CH_2O$— heteroaryl, alkyls group, hydroxyl, acetyl group; wherein R4 and R16 form a divalent radical of formula CH2O, CH(OR7)O, or COOR7, wherein R7 is hydrogen, alkyl, angeloyl, tigloyl, senecioyl, dibenzoyl, benzoyl, alkanoyl, alkenoyl, benzoyl alkyl substituted alkanoyl, aryl, acyl, heterocylic, heteroaryl, and derivatives thereof; wherein at least two of R1, R2 and R6 are attached a group selected from O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-dibenzoyl, O-benzoyl, O-alkanoyl, O-alkenoyl, O-benzoyl alkyl substituted O-alkanoyl, O-aryl, O-acyl, O-heterocylic, O-heteroaryl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl and derivatives thereof; or at least one of R1, R2, and R4 is a sugar moiety having at least two groups selected from a group consisting of angeloyl, acetyl, tigloyl, senecioyl, Crotonoyl, 3,3-Dimethylartyloyl, Cinnamoyl, Pentenoyl, Hexanoyl, benzoyl, Ethylbutyryl, benzoyl, dibenzoyl, alkanoyl, alkenoyl, benzoyl alkyl substituted alkanoyl, aryl, acyl, heterocylic, heteroaryl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, O—C(2-18) Acyl and their derivatives thereof; or wherein R4 represents $CH_2R6$, wherein R6 is selected from hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroaryl, O-alkenylcarbonyl and derivatives thereof; wherein R5 is/are the sugar moiety(ies) selected from the following sugars and alduronic acids: glucose, galactose, rhamnose, arabinose, xylose, fucose, allose, altrose, gulose, idose, lyxose, mannose, psicose, ribose, sorbose, tagatose, talose, fructose, glucuronic acid, galacturonic acid; or their derivatives thereof, In an embodiment, R5 is a hydroxyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl and derivatives thereof. In an embodiment, R1, R2, R3, R4, R5, R8, R9, R10, R11, R12, R13, R14 or R15 comprise of one or more sugar moieties. In an embodiment, R1, R2, R3, R4, R5, R8, R9, R10, R11, R12, R13, R14 or R15 comprise of one or more acids. In an embodiment, at least 1, or 2, or 3, or 4 of R1, R2, R3, R4, R5, R8, R9, R10, R11, R12, R13, R14 and R15 is hydroxyl. In an embodiment, at least 2, or 3, or 4, or 5, or 6, or 7 of R1, R2, R3, R4, R5, R8, R9, R10, R11, R12, R13, R14 and R15 are independently attached a group selected from the group of O-acetyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, alkane, alkene and derivatives thereof, wherein the group is attached to the triterpene directly or by connecting moiety(ies); In an embodiment, at least 1 or 2, or 3, or 4, or 5, or 6, or 7 of R1, R2, R3, R4, R5, R8 and R10 are independently attached a group selected from the group of O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl and derivatives thereof, wherein the group is attached to the triterpene directly or by connecting moiety(ies). In embodiment, the compound is attached a sugar moiety(ies), acid moiety(ies) or alduronic acid.

In an embodiment, the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer; wherein the cells comprise breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphhatic cell, pancreatic cell, stomach cell and thyroid cell. In an embodiment, the compound is selected from the structure:

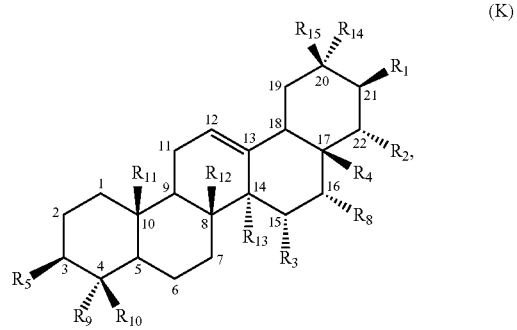

(K)

R1, R2, R3, R4, R5, R8, R9, R10, R11, R12, R13, R14, R15 are independently selected from the group of CH3, CH2OH, COOH, O, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-alkane, O-alkene, O-sugar moiety, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-alkane, CH2O-alkene and CH2O-sugar moiety, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, (CnH2n)O-angeloyl, (CnH2n)O-tigloyl, (CnH2n)O-senecioyl, (CnH2n)O-acetyl, (CnH2n)O-Crotonoyl, (CnH2n)O-3,3-Dimethylartyloyl, (CnH2n)O-Cinnamoyl, (CnH2n)O-Pentenoyl, (CnH2n)O-Hexanoyl, (CnH2n)O-benzoyl, (CnH2n)O-Ethylbutyryl, (CnH2n)O-alkyl, (CnH2n)O-dibenzoyl, (CnH2n)O-benzoyl, (CnH2n)O-alkanoyl, (CnH2n)O-alkenoyl, (CnH2n)O-benzoyl alkyl substituted O-alkanoyl, (CnH2n)O-alkanoyl substituted phenyl, (CnH2n)O-alkenoyl substituted phenyl, (CnH2n)O-aryl, (CnH2n)O-acyl, (CnH2n)O-heterocylic, (CnH2n)O-heteroraryl, (CnH2n)O-alkenylcarbonyl, (CnH2n)O-alkane, (CnH2n)O-alkene and (CnH2n)O-sugar moiety, wherein n is 1 or 2 or 3 or 4 or over 5 or derivatives thereof; or wherein any 1 or 2 or 3 or 4 of R1, R2, R3, R4, R5, R8 and R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethyl butyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R9, R11, R12, R13, R14, R15 are independently attached a CH3; or wherein R10 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R4 and/or R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; wherein R3 is OH or H or absent; wherein R1, R2, R3, R5, R8 are OH or H or absent; wherein R9, R11, R12, R13, R14, and R15 are CH3; or wherein R1, R2, R5, R8 represent OH; R3 represents OH, H or absent; or wherein R4, R10 represent CH2Oangeloyl; R9, R11, R12, R13, R14, R15 represent CH3; or wherein R1, R2, R5, R8 represent OH or O-tigloyl; R3 represents OH, H, or absent; or wherein R4, R10 represent CH2O tigloyl; R9, R11, R12, R13, R14, R15 represent CH3; wherein the group attaching to the core compound selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C (2-18) Acyl are interchangeable; wherein the attached group can be the same group or in combination thereof; wherein the connecting group between the core compound and attached group may be O, S,S(O), S (0)2, C(O), C(O)O, NH, N-alkyl, CH2 or CH2O. In an embodiment, R4 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl. In embodiment, the above structures were attached an O with double bond. In an embodiment, the connecting group between the functional group of angeloyl, tigloyl, senecioyl, acetyl, Crotonoyl, 3,3-Dimethylartyloyl, Cinnamoyl, Pentenoyl, Hexanoyl, benzoyl, Ethylbutyryl, alkyl, dibenzoyl, benzoyl, alkanoyl, alkenoyl, benzoyl alkyl substituted alkanoyl, alkanoyl substituted phenyl, alkenoyl substituted phenyl, aryl, acyl, heterocylic, heteroraryl, and alkenylcarbonyl ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl can be O, S, S(O), S(O)2, C(O), C(O)O, NH, N-alkyl, CH2 or CH2O. In an embodiment, wherein any 1 or 2 or 3 or 4 or 5 or 6 of R1, R2, R3, R4, R5, R8, R9, R10, R11, R12, R13, R14, R15 are independently selected from the group of A-B, wherein A can be O, S, S(O), S(O)2, C(O), C(O)O, NH, N-alkyl, CH2 or CH2O; wherein B is selected from the group of acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heterorary, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methylmethacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl and C(2-18) Acyl. In an enbodiment, R1 is A-B. In an enbodiment, R2 is A-B. In an enbodiment, R3 is A-B. In an enbodiment, R4 is A-B. In an enbodiment, R5 is A-B. In an enbodiment, R6 is A-B. In an enbodiment, R7 is A-B. In an enbodiment, R8 is A-B. In an enbodiment, R9 is A-B. In an enbodiment, R10 is A-B. In an enbodiment, R11 is A-B. In an enbodiment, R12 is A-B.

In an enbodiment, R13 is A-B. In an enbodiment, R14 is A-B. In an enbodiment, R15 is A-B. In embodiment, the compound is attached a sugar moiety(ies), acid moiety(ies) or alduronic acid. In an embodiment, the compound is selected from the structure:

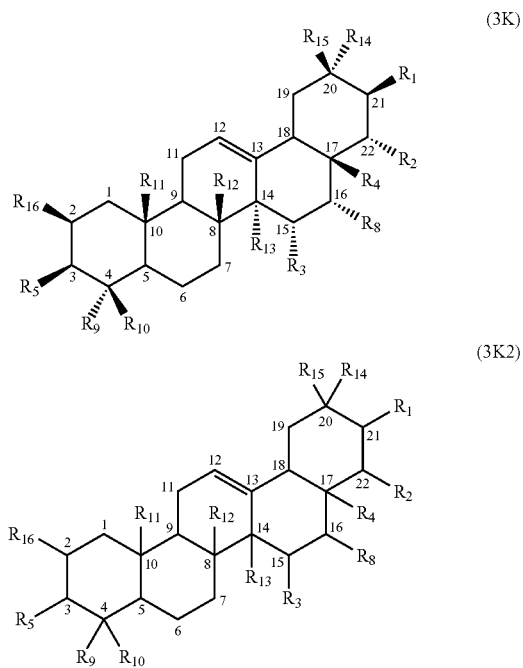

R1, R2, R3, R4, R5, R8, R9, R10, R11, R12, R13, R14, R15, R16 are independently selected from the group of H, O, OH, CH3, CH2OH, COOH, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-alkane, O-alkene, O-sugar moiety, O-acid moiety, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, COO-angeloyl, COO-tigloyl, COO-senecioyl, COO-acetyl, COO-Crotonoyl, COO-3,3-Dimethylartyloyl, COO-Cinnamoyl, COO-Pentenoyl, COO-Hexanoyl, COO-benzoyl, COO-Ethylbutyryl, COO-alkyl, COO-dibenzoyl, COO-benzoyl, COO-alkanoyl, CH2O-alkenoyl, COO-benzoyl alkyl substituted O-alkanoyl, COO-alkanoyl substituted phenyl, COO-alkenoyl substituted phenyl, COO-aryl, COO-acyl, COO-heterocylic, COO-heteroraryl, COO-alkenylcarbonyl, COO-alkane, COO-alkene, COO-sugar moiety, COO-acid moiety, COO-ethanoyl, COO-propanoyl, COO-propenoyl, COO-butanoyl, COO-butenoyl, COO-pentanoyl, COO-hexenoyl, COO-heptanoyl, COO-heptenoyl, COO-octanoyl, COO-octenoyl, COO-nonanoyl, COO-nonenoyl, COO-decanoyl, COO-decenoyl, COO-propionyl, COO-2-propenoyl, COO-2-butenoyl, COO-Isobutyryl, COO-2-methylpropanoyl, COO-2-ethylbutyryl, COO-ethylbutanoyl, COO-2-ethylbutanoyl, COO-butyryl, COO-(E)-2,3-Dimethylacryloyl, COO-(E)-2-Methylcrotonoyl, COO-3-cis-Methyl-methacryloyl, COO-3-Methyl-2-butenoyl, COO-3-Methylcrotonoyl, COO-4-Pentenoyl, COO-(2E)-2-pentenoyl, COO-Caproyl, COO-5-Hexenoyl, COO-Capryloyl, COO-Lauroyl, COO-Dodecanoyl, COO-Myristoyl, COO-Tetradecanoyl, COO-Oleoyl, COO—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-alkane, CH2O-alkene and CH2O-sugar moiety, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-

Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, (CnH2n)O-angeloyl, (CnH2n)O-tigloyl, (CnH2n)O-senecioyl, (CnH2n)O-acetyl, (CnH2n)O-Crotonoyl, (CnH2n)O-3,3-Dimethylartyloyl, (CnH2n)O-Cinnamoyl, (CnH2n)O-Pentenoyl, (CnH2n)O-Hexanoyl, (CnH2n)O-benzoyl, (CnH2n)O-Ethylbutyryl, (CnH2n)O-alkyl, (CnH2n)O-dibenzoyl, (CnH2n)O-benzoyl, (CnH2n)O-alkanoyl, (CnH2n)O-alkenoyl, (CnH2n)O-benzoyl alkyl substituted O-alkanoyl, (CnH2n)O-alkanoyl substituted phenyl, (CnH2n)O-alkenoyl substituted phenyl, (CnH2n)O-aryl, (CnH2n)O-acyl, (CnH2n)O-heterocylic, (CnH2n)O-heteroraryl, (CnH2n)O-alkenylcarbonyl, (CnH2n)O-alkane, (CnH2n)O-alkene and (CnH2n)O-sugar moiety and (CnH2n)O-acid moiety, wherein n is 1 or 2 or 3 or 4 or over 5 or derivatives thereof; wherein the sugar moiety(ies) is/are selected from a group of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof; or wherein any 1 or 2 or 3 or 4 of R1, R2, R3, R4, R5, R8, R16 and R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R9, R11, R12, R13, R14, R15, are independently attached a CH3; or wherein R10 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; or wherein R4 and/or R10 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; wherein R3 is OH or H or absent; wherein R1, R2, R3, R5, R8, R16 are OH or H or absent; or wherein an O were attached to the above structures with double bond; wherein R9, R11, R12, R13, R14, and R15 are CH3; or wherein R1, R2, R5, R8 represent OH; R3 represents OH, H or absent; or wherein R4, R10 represent CH2Oangeloyl; R9, R11, R12, R13, R14, R15 represent CH3; or wherein R1, R2, R5, R8 represent OH or O-tigloyl; R3 represents OH, H, or absent; or wherein R4, R10 represent CH2O tigloyl; R9, R11, R12, R13, R14, R15 represent CH3; wherein the group attaching to the core compound selected from acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocyclic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methyl propanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl are interchangeable; wherein the attached group can be the same group or in combination thereof; wherein the connecting group between the core compound and attached group may be O, S, S(O), S(O)2, C(O), C(O)O, NH, N-alkyl, CH2 or CH2O. In an embodiment, R4 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl, In an embodiment, the connecting group between the functional group of angeloyl, tigloyl, senecioyl, acetyl, Crotonoyl, 3,3-Dimethylartyloyl, Cinnamoyl, Pentenoyl, Hexanoyl, benzoyl, Ethylbutyryl, alkyl, dibenzoyl, benzoyl, alkanoyl, alkenoyl, benzoyl alkyl substituted alkanoyl, alkanoyl substituted phenyl, alkenoyl substituted phenyl, aryl, acyl, heterocylic, heteroraryl, and alkenylcarbonyl ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl, C(2-18) Acyl can be O, S, S(O), S(O)2, C(O), C(O)O, NH, N-alkyl, CH2 or CH2O. In an embodiment, any 1 or 2 or 3 or 4 or 5 or 6 of R1, R2, R3, R4, R5, R8, R9, R10, R11, R12, R13, R14, R15, R16 are independently selected from the group of A-B, wherein A can be O, S, S(O), S(O)2, C(O), C(O)O, NH, N-alkyl, CH2 or CH2O; wherein B is selected from the group of acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl and C(2-18) Acyl. In an embodiment, R1 is A-B. In an embodiment, R2 is A-B. In an embodiment, R3 is A-B. In an embodiment, R4 is A-B. In an embodiment, R5 is A-B. In an embodiment, R6 is A-B. In an embodiment, R7 is A-B. In an embodiment, R8 is A-B. In an embodiment, R9 is A-B. In an embodiment, R10 is A-B. In an embodiment, R11 is A-B. In an embodiment, R12 is A-B. In an embodiment, R13 is A-B. In an embodiment, R14 is A-B. In an embodiment, R15 is A-B. In an embodiment, this invention provides compounds of the above to improve blood circulation; soothing stroke; Prevent plaque formation and promote their dissipated; improve blood viscosity; reduce cardiovascular; reduce cerebrovascular; reduce thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, flutter, Blood circulation, swelling, pain; Treating bronchiectasis, tuberculosis and lung abscess caused by too hemoptysis; reducing bleeding, antitussive, expectorant and analgesic effect, dilate blood vessels; reducing blood pressure and the treatment of cerebral arteriosclerosis; elevated blood lipids and reduced cholesterol. The R1, R2, R3, R4, R5, R8, R9, R10, R11, R12, R13, R14, R15, R16 bonds of (3K2) can be alpha or beta.

R1, R2, R3, R4, R5, R8, R9, R10, R11, R12, R13, R14, R15, R16 are independently selected from the group of 0, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, In embodiment the core having structures:

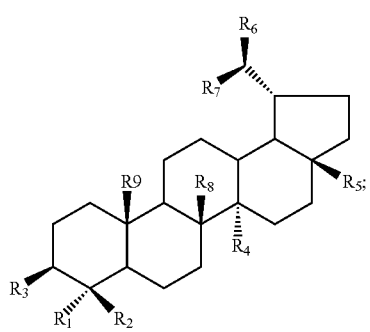
T1

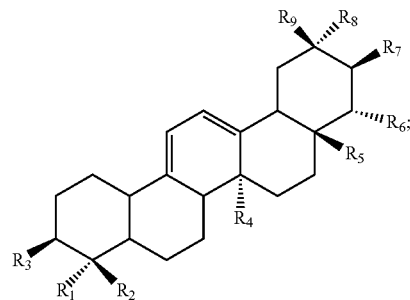
T2

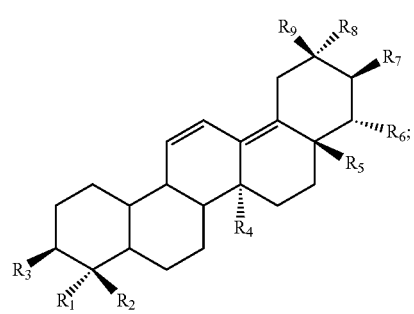
T3

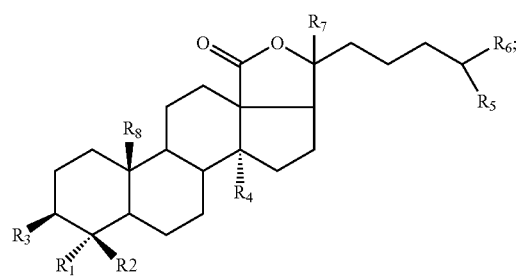
T4

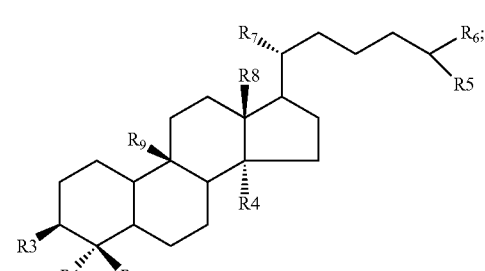
T5

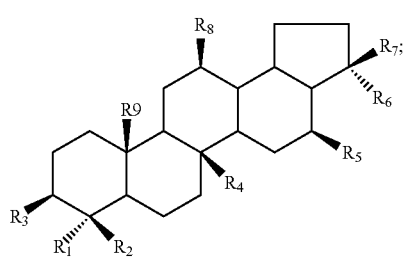
T6

T7
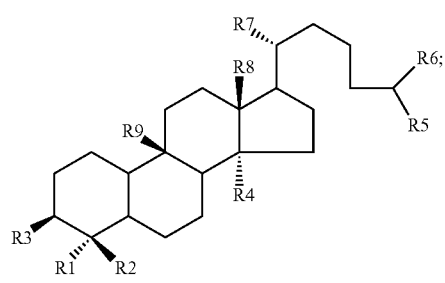
T8
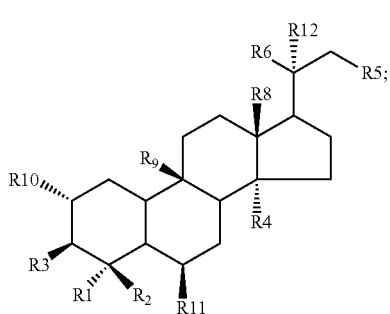
T9
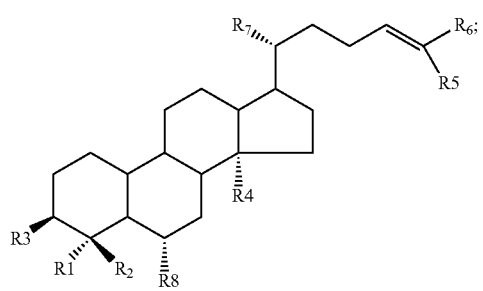
T10
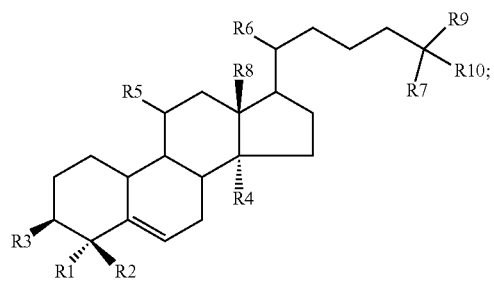
T11
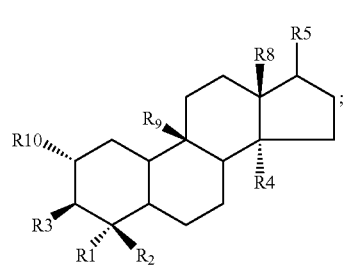
T12
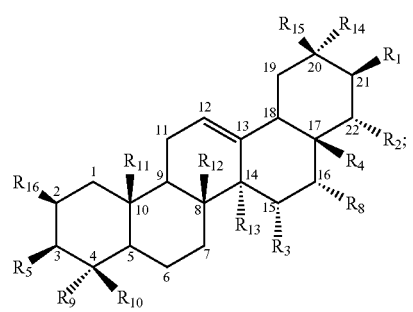
T13
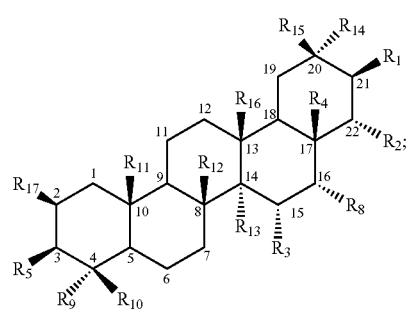
T14
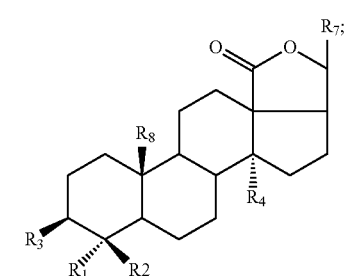
T15
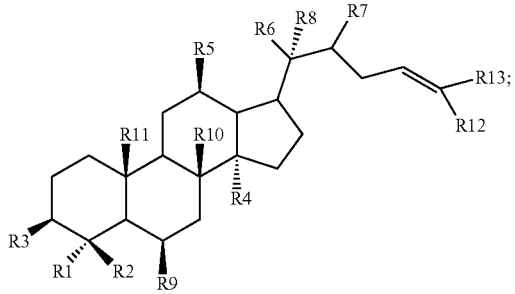
T16
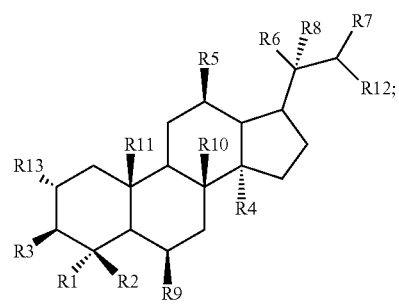

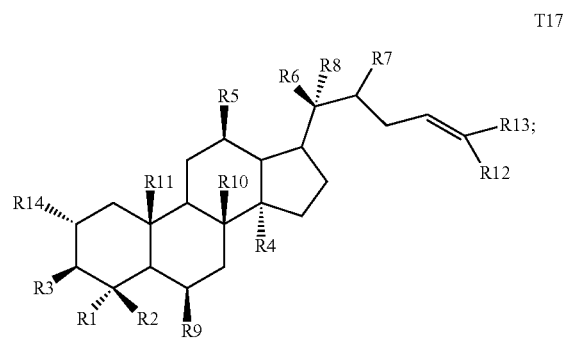
T17
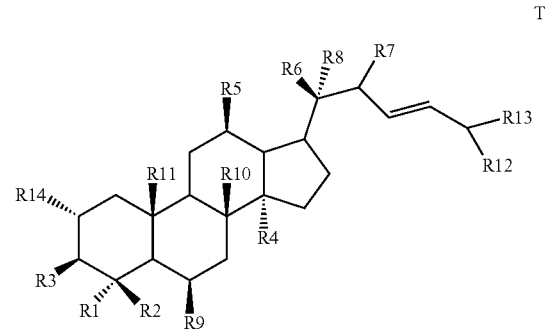
T18
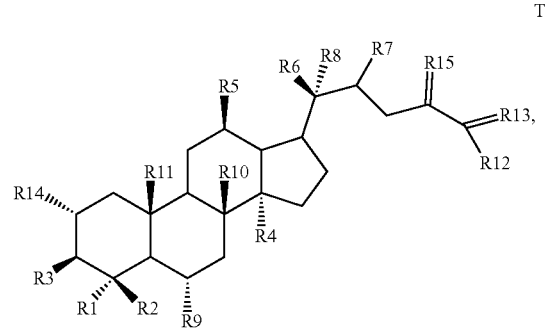
T19
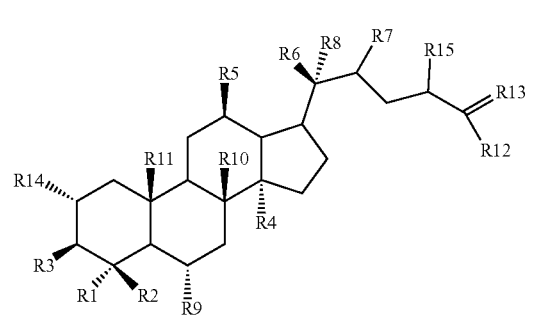
T
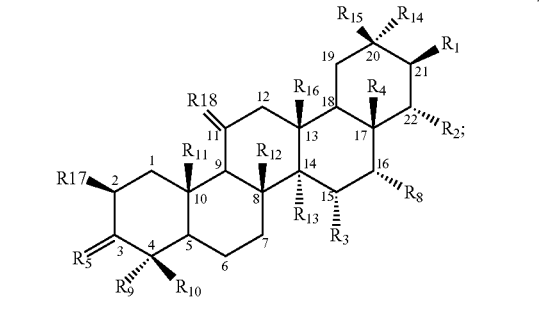
T21
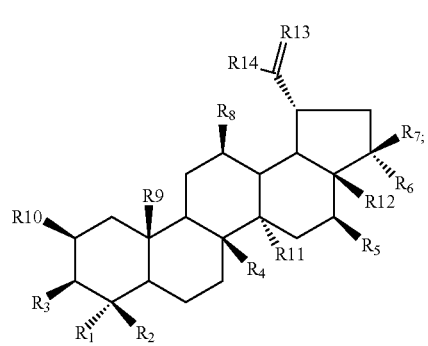
T22
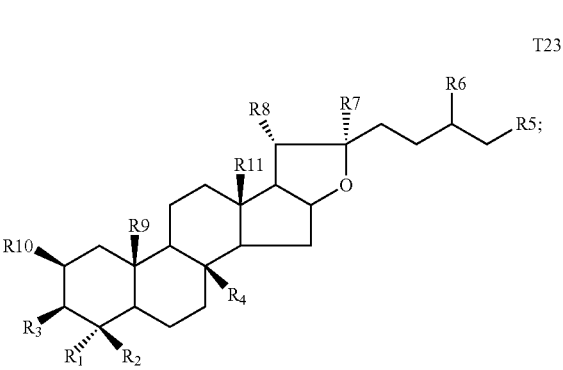
T23
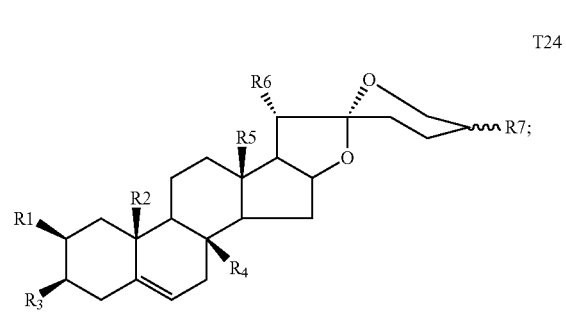
T24
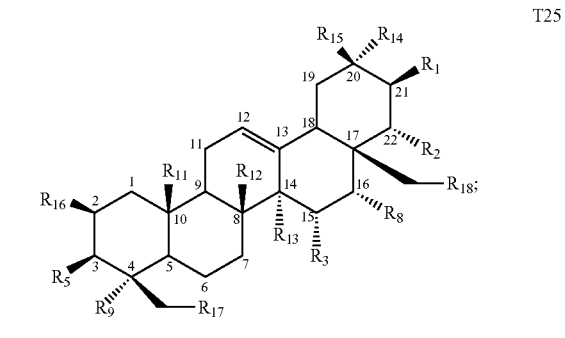
T25
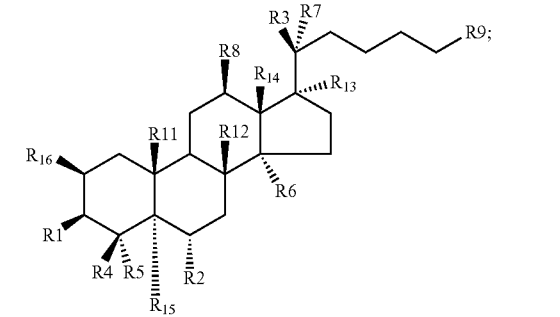
T26

-continued

T27

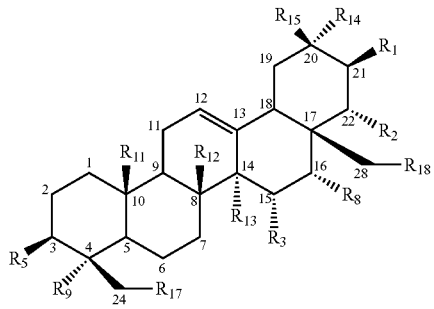

wherein R1, R2, R3, R4, R5, R8, R9, R10, R11, R12, R13, R14, R15, R16, R17, R18, of T19, T20, T21, T22, T23, T24, T25, T26, T27 represent H, OH, O, CH2OH, COOH or CH3. The bonds can be in forms of alpha or beta or in combinations.

Esterification the above core compound with acyl halide, wherein the halide comprise chloride, bromide, fluoride and iodide, wherein the acyl halide comprise acyl chloride, wherein acyl chloride comprise tigloyl chloride, angeloyl chloride, acetyl chloride, crotonoyl chloride, 3,3-dimethylartyloyl chloride, senecioyl chloride, cinnamoyl chloride, pentenoyl chloride, hexanoyl chloride, benzoyl chloride, ethylbutyryl chloride, propionyl chloride, 2-propenoyl chloride, isobutyryl chloride, butyryl chloride, (2E)-2-pentenoyl chloride, 4-Pentenoyl chloride, 5-hexenoyl chloride, heptanoyl chloride, octanoyl chloride, nonanoyl chloride, decanoyl chloride, Lauroyl chloride, myristoyl chloride, oleoyl chloride. The compounds vary in composition when the time or temperature of the reaction is changed. The peaks, fractions and compounds are selected according to the activities of times studies and the changes of peaks. The compounds having strong to weak activities are selected and isolated. The anti cancer activities (Cytotoxic Assay) are the MTT studies of bone (U2OS), lung (H460), bladder(HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), luekemia (K562), cervix (HeLa). The active esterification products are purified with HPLC. The reaction product of mixtures and individual compounds are tested with MTT Cytotoxic Assay. Details of method are in Experiment 3 of the present application. A second esterification of compound can be selected from the above experiment results to produce new active compounds. A partial esterification compound is selected from the above experiments to perform a second or repeated with a third esterification with different acyl chloride in order to produce new active compounds with the experiments in the present application.

A method is 1) Dissolving core compound or triterpenes core, hydroxylated triterpenes core, in pyridine; 2) Adding acyl halide or acyl chloride; 3, The mixture is stirred for length of time including 5 sec, 10 sec, 20 sec, 30 sec, 40 sec, 1 min, 2 min, 5 min, 10 min, 30 min, 1 hr, 2 hr, 18 hr, 2 days or 3 days at different temperature; 4) At the end of reaction, aqueous solution of acid or weak base, or water is added to the reaction mixture; 5) The solution is then extracted of ethyl acetate and ethyl acetate is removed by evaporation and lyophilization; 6) Dissolving the reaction product in acetonitrile with Trifluoroacetic acid or DMSO; 7) Testing the reaction product of mixtures and individual fractions with MTT cytotoxic assay; 8) Selecting the HPLC fractions for isolation is according to the cytotoxic activity of the reaction product obtained at a specific reaction time; 10) Purifiing the active esterification products with HPLC; 11) Collecting the products; 12) Testing the products; wherein the core compound is terpene, isoprene, or triterpene core or hydroxylated triterpenes core; wherein the core compound was dissolved in pyridine; wherein the acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, Propionyl chloride, 2-Propenoyl chloride, Isobutyryl chloride, Butyryl chloride, (2E)-2-pentenoyl chloride, 4-Pentenoyl chloride, 5-Hexenoyl chloride, Heptanoyl chloride, Octanoyl chloride, Nonanoyl chloride, Decanoyl chloride, Lauroyl chloride, Myristoyl chloride, and Oleoyl chloride; wherein the reaction time for the mixture is stirred for 5 sec, 10 sec, 20 sec, 30 sec, 40 sec, 1 min, 2 min, 5 min, 10 min, 30 min, 1 hr, 2 hr, 18 hr, 2 days or 3 days; wherein the temperature is 0 C, 25 C, 50 C or 75 C temperature; wherein the acid including HCl or the base including NaHCO3 is added to the reaction mixture; wherein the solution is then extracted 3 times with ethyl acetate and lyophilization; wherein the reaction product is dissolved in 80% acetonitrile—0.005% Trifluoroacetic acid or DMSO; wherein selecting the HPLC fractions for isolation is according to the cytotoxic activity of the reaction product obtained at a reaction time of 5 sec, 10 sec, 20 sec, 30 sec, 40 sec, 1 min, 2 min, 5 min, 10 min, 30 min, 1 hr, 2 hr, 18 hr, 2 days or 3 days. In an embodiment, the reaction time may be ove 3 days. In an embodiment, the experiment may be performed under 0 C. In an embodiment, the experiment may be performed over 750 C. In embodiment, the attachment of sugar moiety(ies) can be biosynthesized.

This invention provide the compound having structures of T1, T2, T3, T4, T5, T6, T7, T8, T9, T10, T11, T12, T13, T14, T15, T16, T17; T18, T19, T20, T21, T22, T23, T24, T25, T26, T27 wherein the R1, R2, R3, R4, R5, R8, R9, R10, R11, R12, R13, R14, R15, R16, R17, R18 are independently selected from the group of hydrogen, hydroxyl, methyl, O, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methyl-crotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, O-4-(dimethylamino)-2-methylbut-2-enoyl, O-4-[(2-methoxyethyl)amino]-2-methyl-4oxobut-2-enoyl, O-sugar moiety(ies), O-acid moiety(ies), CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O- aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methylmethacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C (2-18) Acyl, CH2O-4-(dimethylamino)-2-methylbut-2-enoyl, CH2O-4-[(2-methoxyethyl)amino]-2-methyl-4oxobut-2-enoyl, alkane, alkene and derivatives thereof. In an embodiment, the compound is attached a sugar moiety(ies), acid moiety(ies) or alduronic acid, wherein the sugar moiety(ies) is/are selected from a group of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof. In an embodiment, the compound is attached a group selected from (CnH2n)O-angeloyl, (CnH2n)O-tigloyl, (CnH2n)O-senecioyl, (CnH2n)O-acetyl, (CnH2n)O-Crotonoyl, (CnH2n)O-3,3-Dimethylartyloyl, (CnH2n)O-Cinnamoyl, (CnH2n)O-Pentenoyl, (CnH2n)O-Hexanoyl, (CnH2n)O-benzoyl, (CnH2n)O-Ethylbutyryl, (CnH2n)O-alkyl, (CnH2n)O-dibenzoyl, (CnH2n)O-benzoyl, (CnH2n)O-alkanoyl, (CnH2n)O-alkenoyl, (CnH2n)O-benzoyl alkyl substituted O-alkanoyl, (CnH2n)O-alkanoyl substituted phenyl, (CnH2n)O-alkenoyl substituted phenyl, (CnH2n)O-aryl, (CnH2n)O-acyl, (CnH2n)O-heterocylic, (CnH2n)O-heteroraryl, (CnH2n)O-alkenylcarbonyl, (CnH2n)O-alkane, (CnH2n)O-alkene and (CnH2n)O-sugar moiety and (CnH2n)O-acid moiety; wherein the sugar moiety(ies) is/are included but not limited to a group of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof; wherein n is 1 or 2 or 3 or 4 or over 5.

This invention provide the compound having structures of T1, T2, T3, T4, T5, T6, T7, T8, T9, T10, T11, T12, T13, T14, T15, T16, T17; T18, T19, T20, T21, T22, T23, T24, T25. T26 provided for treating cancers, inhibition of cancer growth, cancer invasion, cells invasion, cancer cell invasion; cell adhesion, cell attachment, cell circulating; for treating mad cow disease; treating prion diseases; for treating diabetes; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions or neurodegeneration; for treating arthritis, rheumatism, poor circulation, arteriosclerosis, Raynaud's syndrome, angina pectoris, cardiac disorder, coronary heart disease, headache, dizziness, kidney disorder; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment. The compound blocks the DNA synthesis of cancer cell; wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer. This invention provides compounds to improve blood circulation; soothing stroke; Prevent plaque formation and promote their dissipated; improve blood viscosity; reduce cardiovascular; reduce cerebrovascular; reduce thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, flutter, Blood circulation, swelling, pain; Treating bronchiectasis, tuberculosis and lung abscess caused by too hemoptysis; reducing bleeding, antitussive, expectorant and analgesic effect, dilate blood vessels; reducing blood pressure and the treatment of cerebral arteriosclerosis; elevated blood lipids and reduced cholesterol.

Liposome is artificially prepared vesicles which made up of a lipid bilayer. Certain sizes of liposome can enter tumour sites from blood due to the enhanced permeability and retention effect. While human blood vessels are all surrounded by endothelial cells bound by tight junctions, those tight junctions binding tumour vessels are leakier than those binding other vessels and thus liposomes are able to enter these vessels to enhance the delivery, efficacy, bioavailability and absorption of liposome enclosed drug. This invention provides methods to use liposomes or nanoparticles capsules as a carrier delivering the compound as medicament, wherein the size of liposomes or nanoparticles capsules is less than 200 nm or 100-200 nm or 50-100 nm or 5-50 nm or less than 50 nm, wherein the medicament is included but not limited for treating cancer, inhibiting cancer growth, inhibiting cancer invasion, inhibiting cancer metastasis, modulating cell adhesion, modulating cell attachment, wherein the compound is selected from formula (2A) or formula (K) at the above.

Substitution, deletion and/or addition of any group in the above-described compounds by other group(s) will be apparent to one of ordinary skill in the art based on the teachings of this application. In a further embodiment, the substitution, deletion and/or addition of the group(s) in the compound of the invention does not substantially affect the biological function of the compound is included in the invention.

In an embodiment, the compound is selected from the structures:
Compound E4A-Tig-R
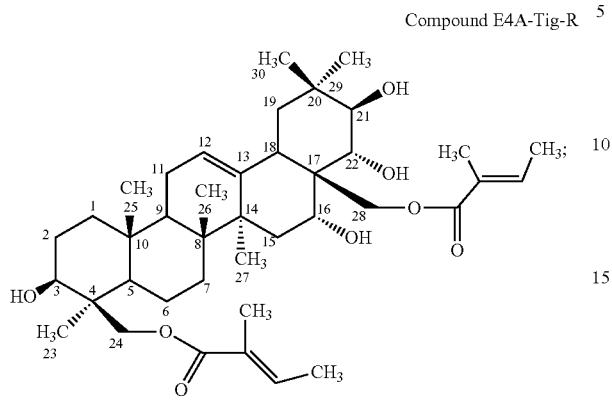
Compound E4A-Tig-N
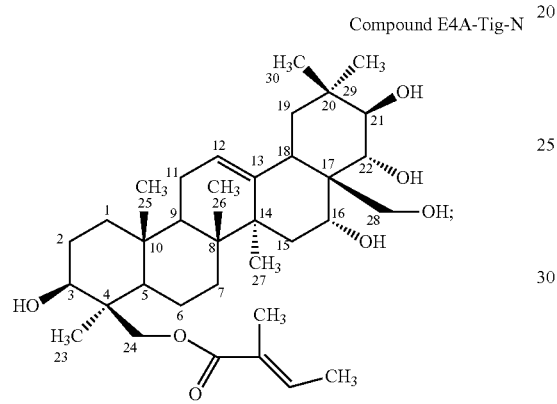
Compound E4A-Tig-Q
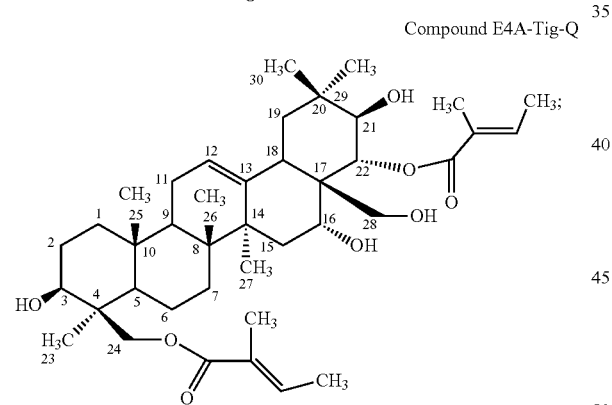
Compound E4A-Tig-V
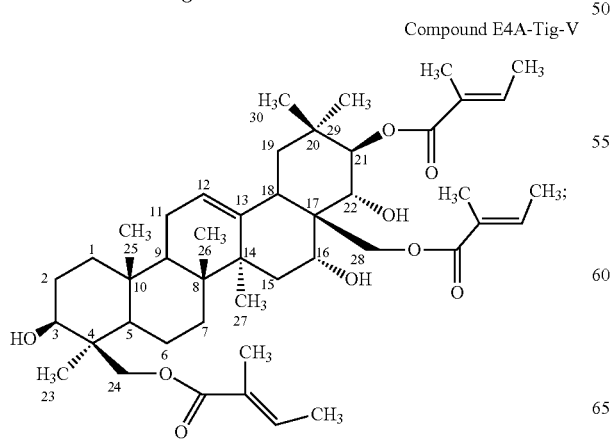
Compound E4A-Tig-T
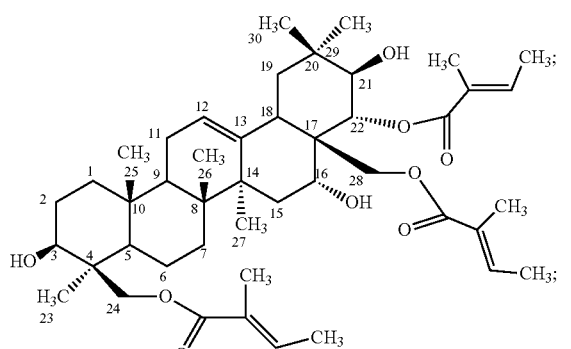
Compound E4A-Tig-U
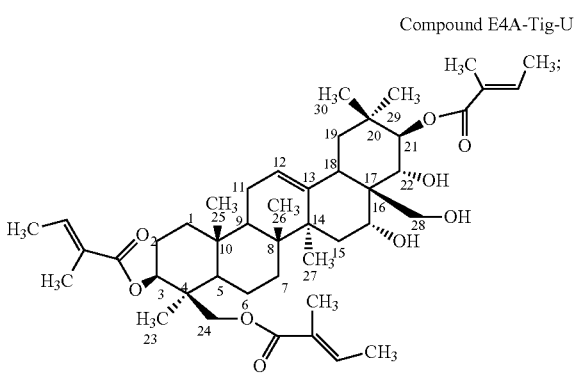
Compound E4A-Tig-S
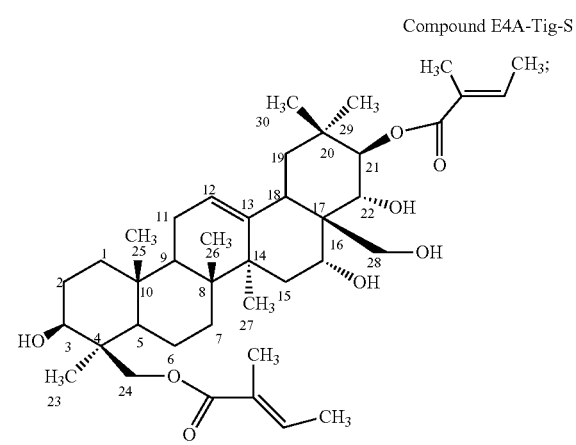
Compound E4A-Ang-R
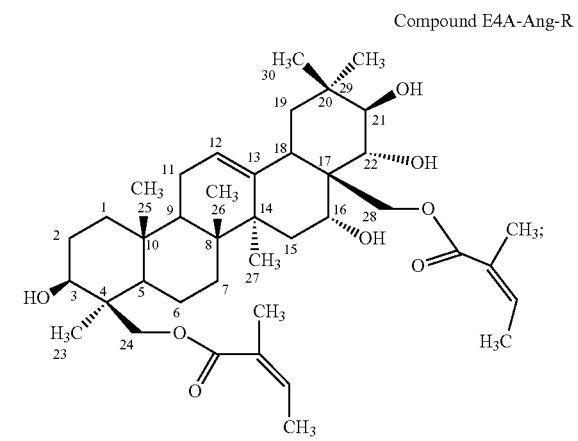

-continued
Compound E4A-Ang-V
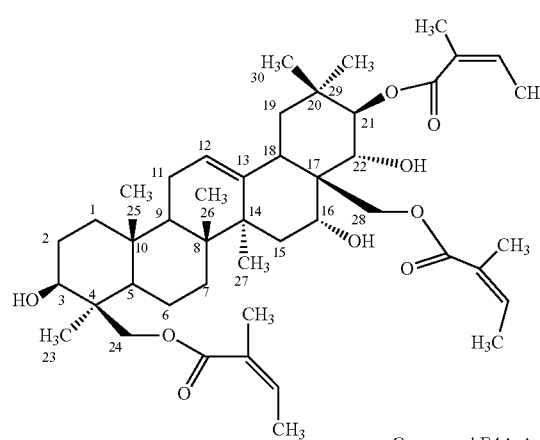
Compound E4A-Ang-Q
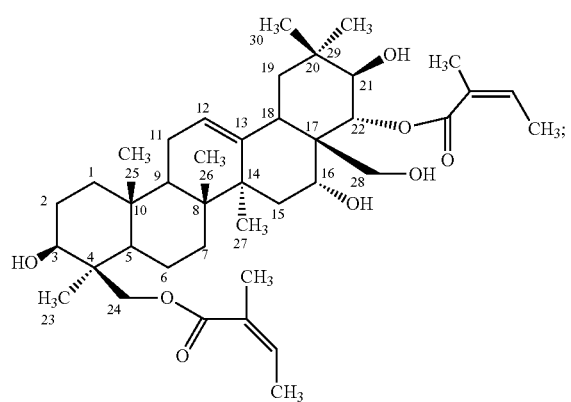
Compound E4A-Ang-N
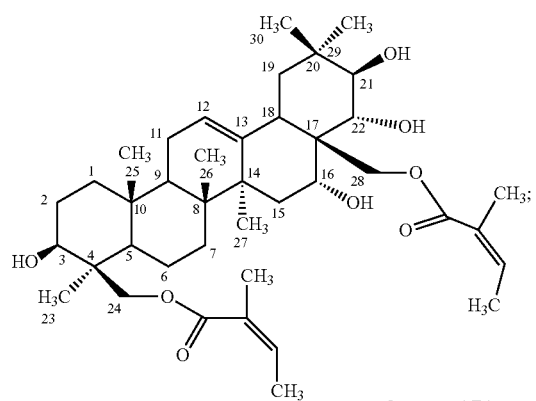
Compound E4A-Ang-T
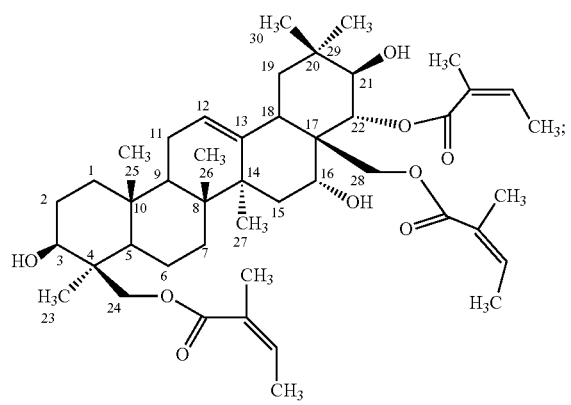
-continued
Compound E4A-Ang-U
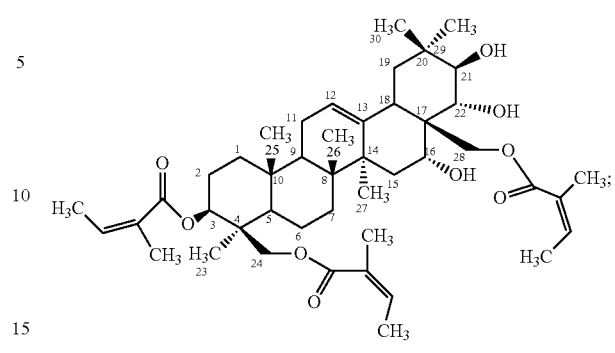
Compound E4A-Ang-S
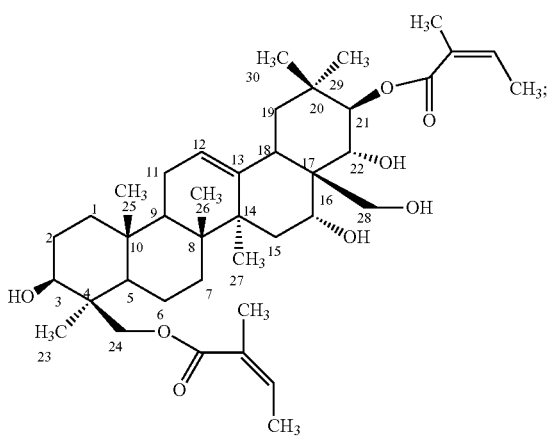
Compound E4A-Sen-R
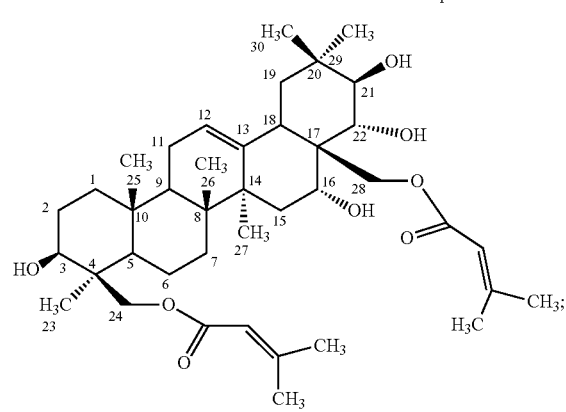
Compound E4A-Sen-V
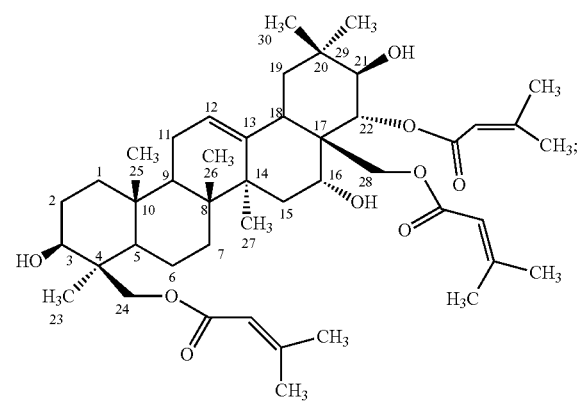

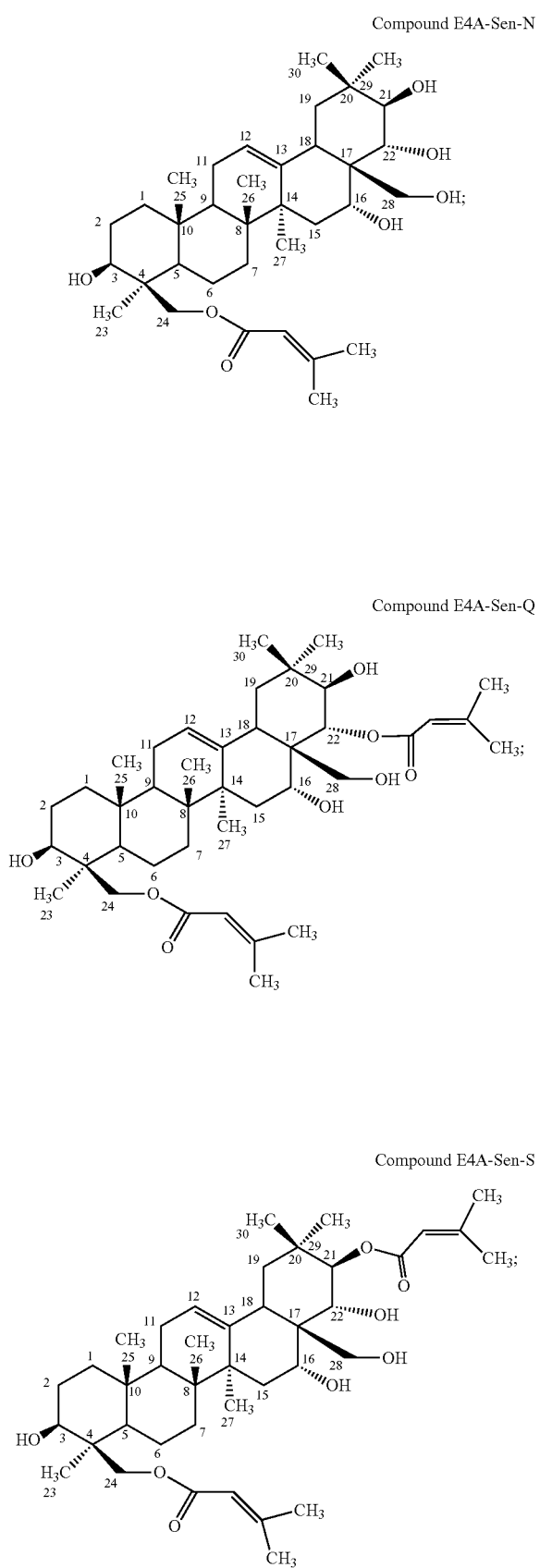
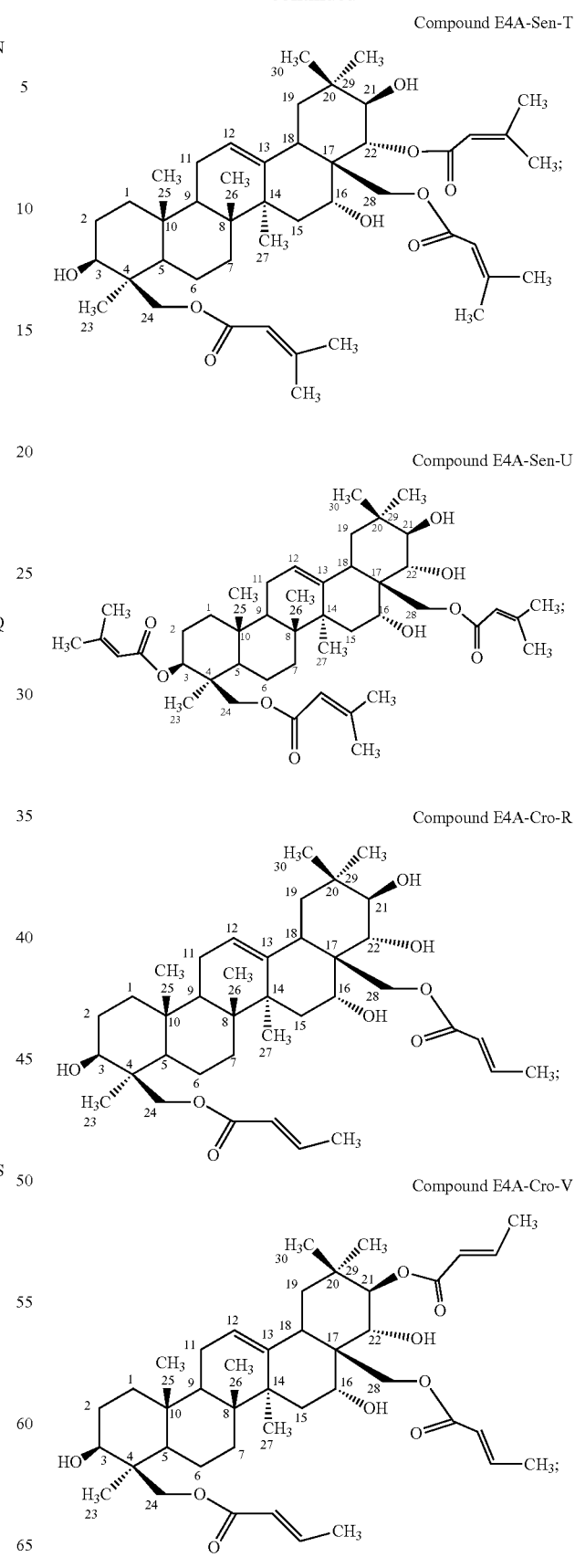

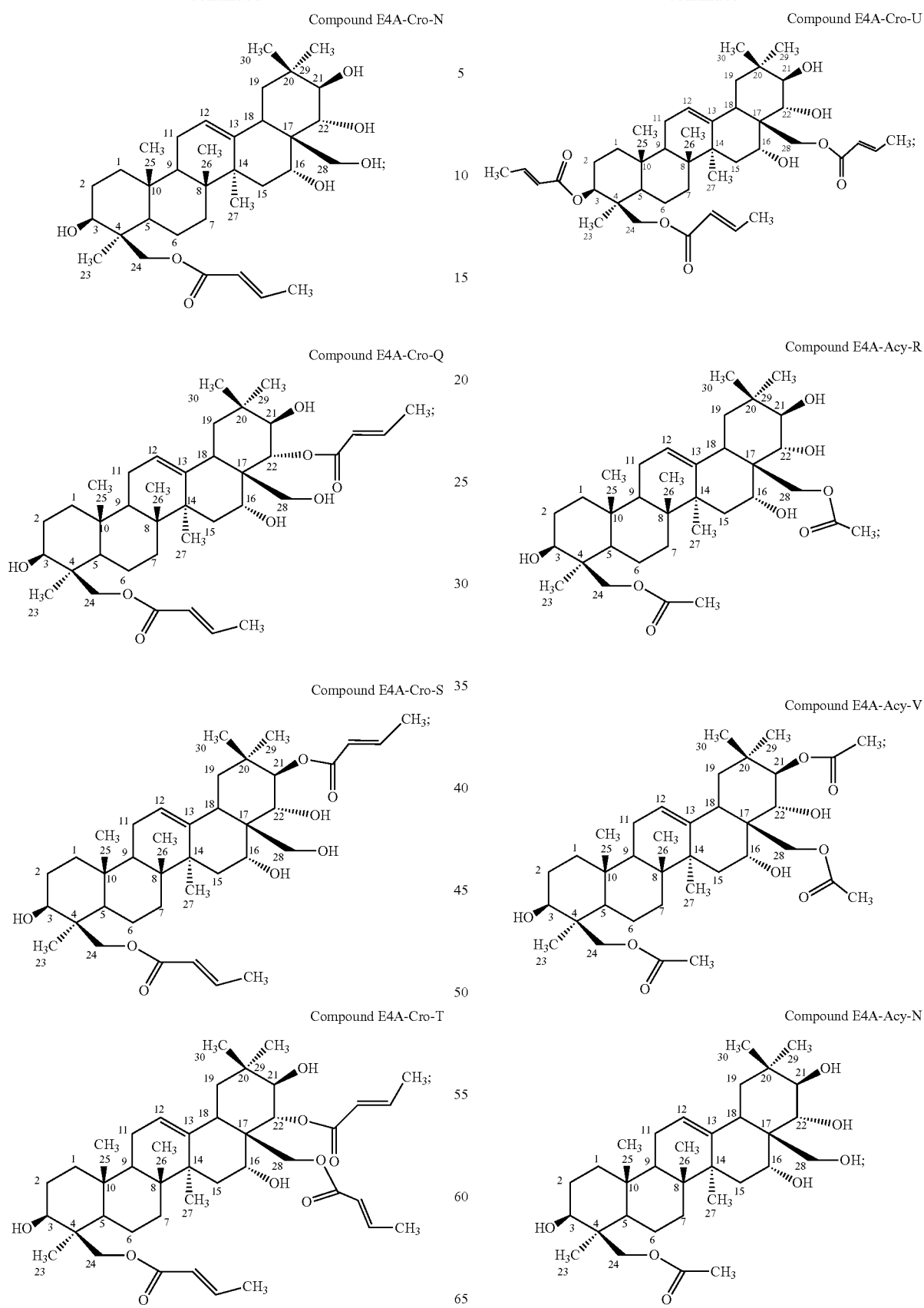

-continued
Compound E4A-Acy-Q
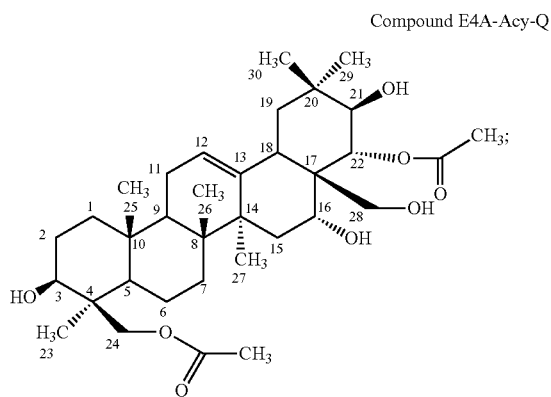
Compound E4A-Acy-S
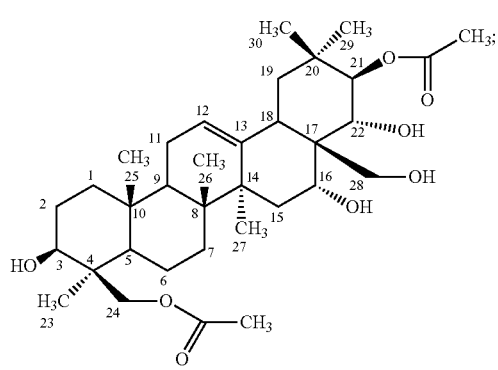
Compound E4A-Acy-T
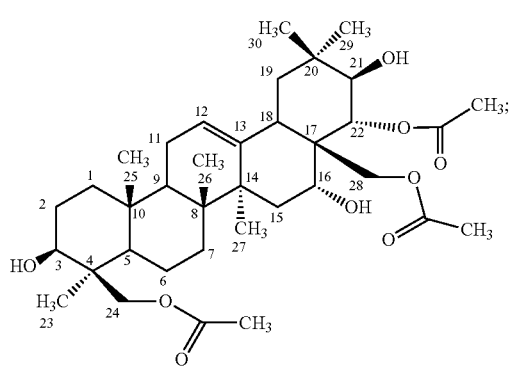
Compound E4A-Acy-U
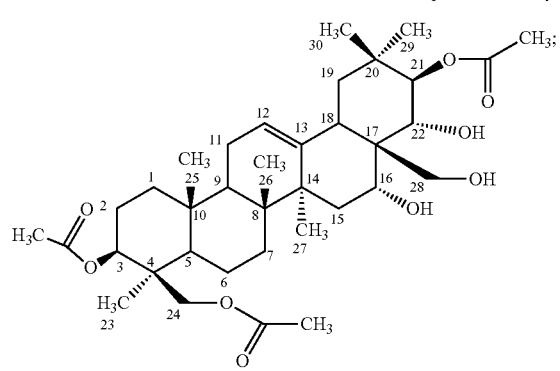
-continued
Compound E4A-Pen-R
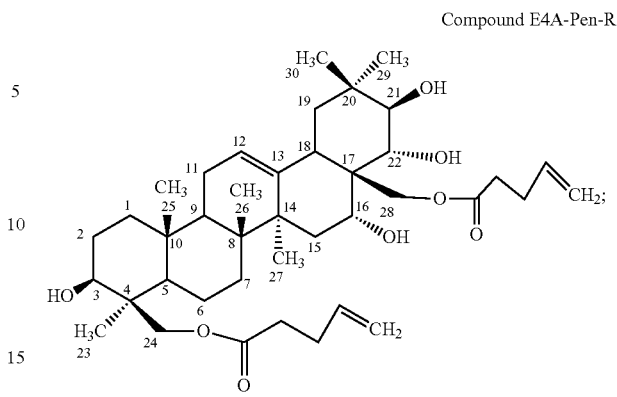
Compound E4A-Pen-V
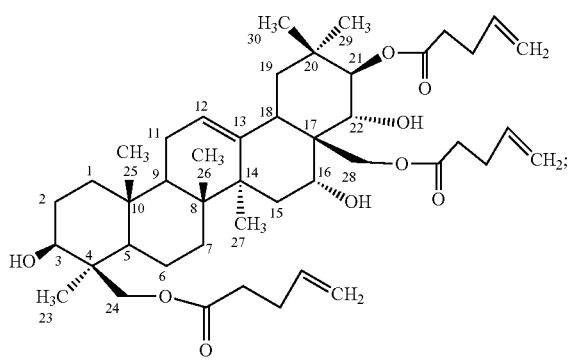
Compound E4A-Pen-N
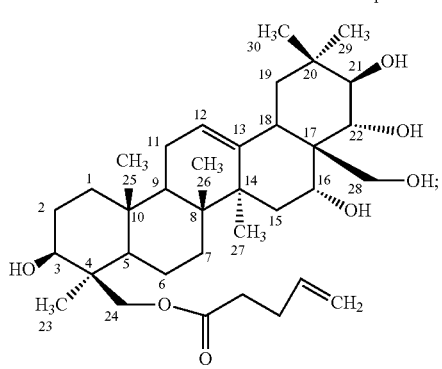
Compound E4A-Pen-Q
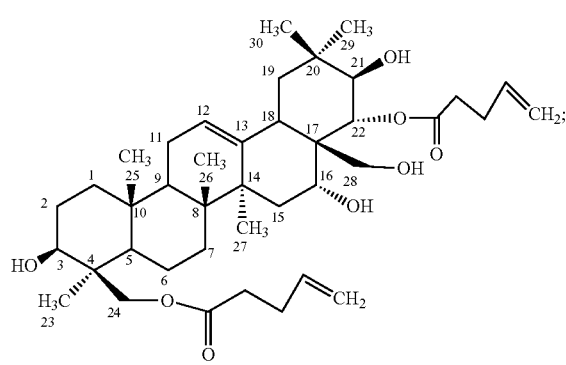

Compound E4A-Pen-S
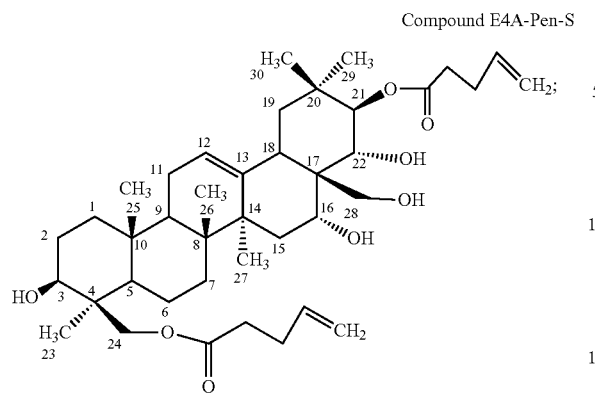
Compound E4A-Pen-T
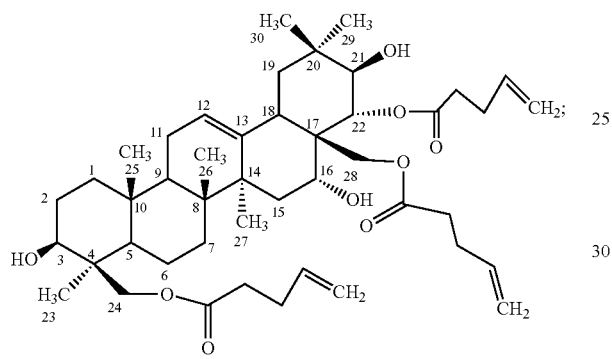
Compound E4A-Pen-U
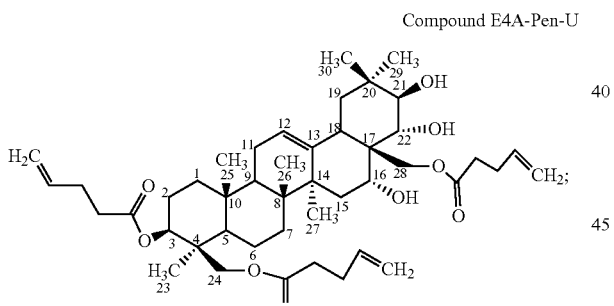
Compound E4A-Cin-R
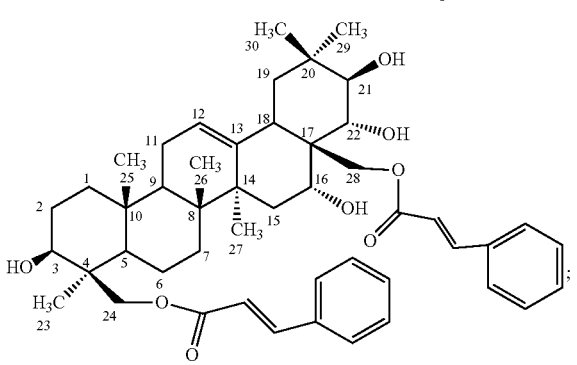
Compound E4A-Cin-V
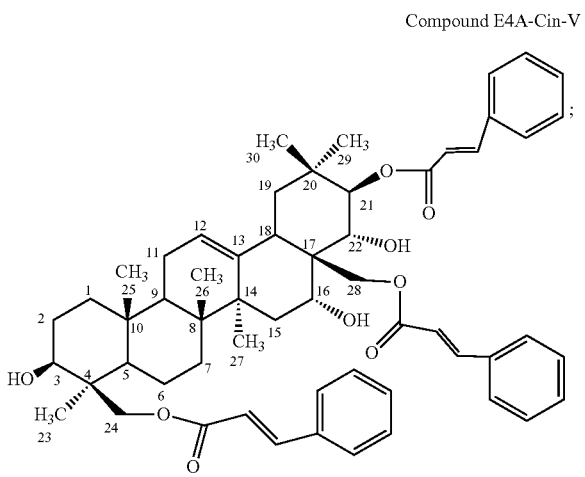
Compound E4A-Cin-N
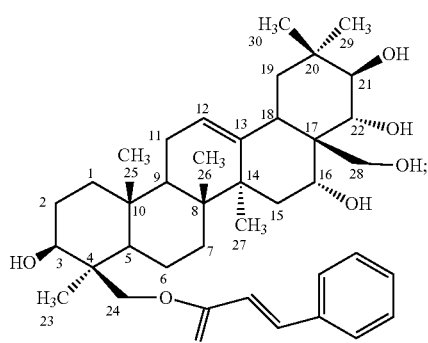
Compound E4A-Cin-Q Compound E4A-Cin-S
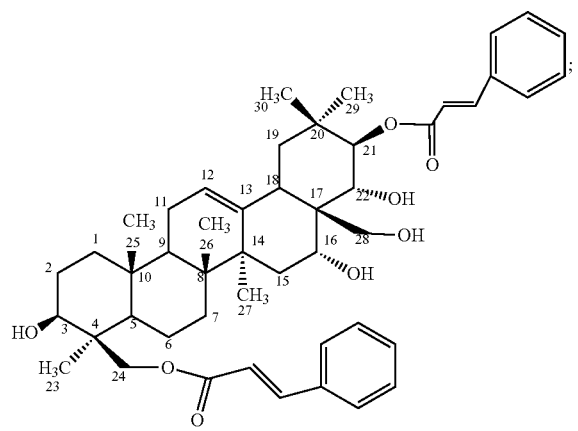
Compound E4A-Cin-T
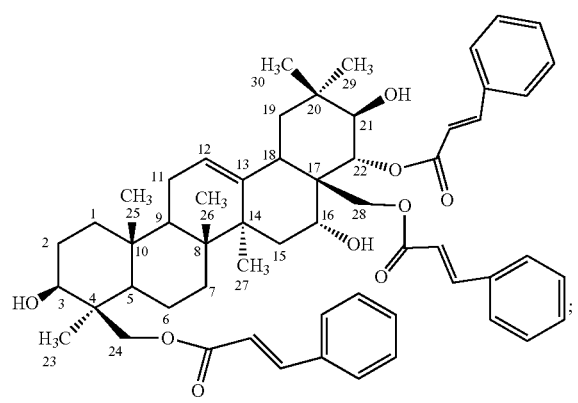
Compound E4A-Cin-U
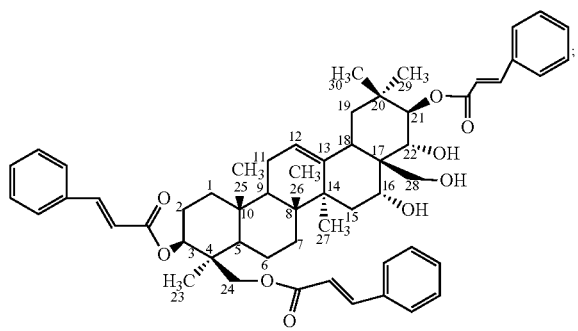
Tig-Cro-1
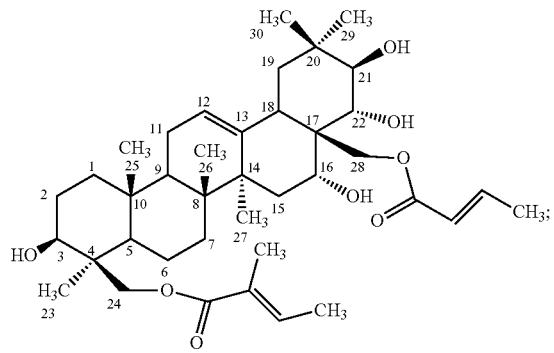
Tig-Ang-1
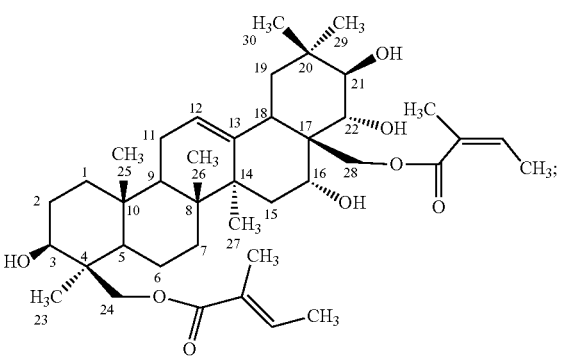
Tig-Pen-1
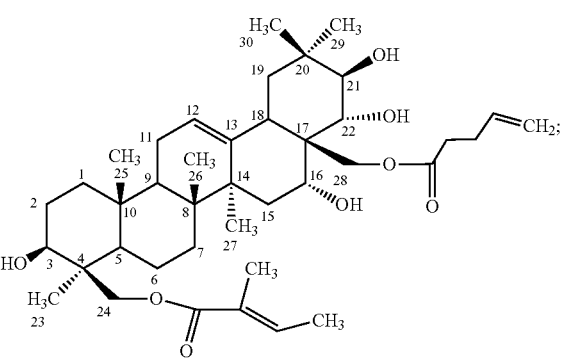
Tig-Sen-1
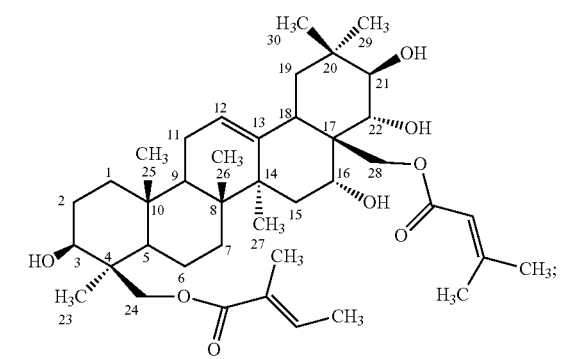
Tig-Acy-1
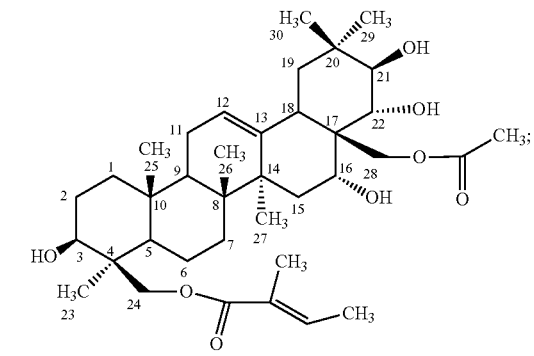

-continued

Tig-Hex-1

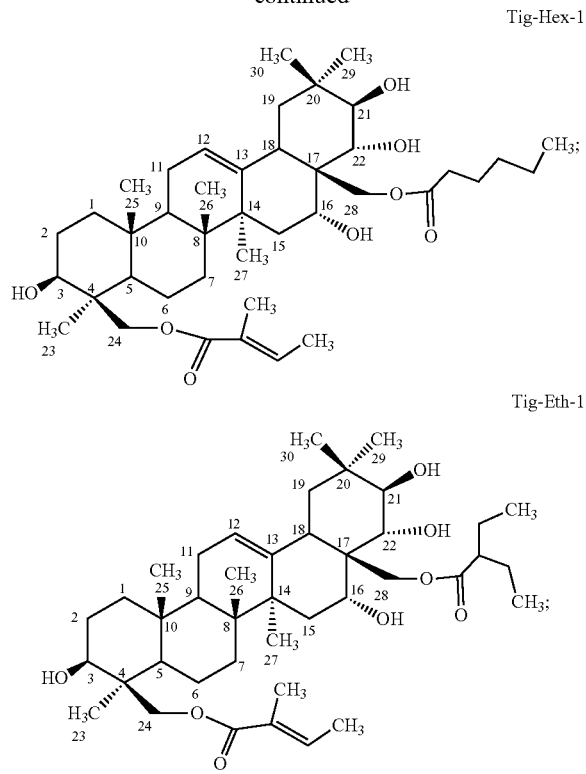

Tig-Eth-1

In embodiment, sugar moiety(ies) or acid moiety(ies) can be attached to the above compounds. In embodiment, the attachment of sugar moiety(ies) can be biosynthesized; In embodiment, the attachment of acid moiety can be biosynthesized; wherein the sugar moiety(ies) or acid moiety(ies) is/are included but not limited to a group of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof;

This invention provides compounds by esterification of core compound (C) or (D1) with acetyl chloride, angeloyl chloride, tigloyl chloride, senecioyl chloride, Crotonoyl chloride, O-3,3-Dimethylartyloyl chloride, Cinnamoyl chloride, Pentenoyl chloride, Hexanoyl chloride, benzoyl chloride, Ethylbutyryl chloride, and isolation of the compounds with HPLC, for treating cancer, inhibiting cancer growth, inhibiting cancer invasion, inhibiting cancer metastasis, modulating cell adhesion, modulating cell attachment, wherein the core compound selected from the following:

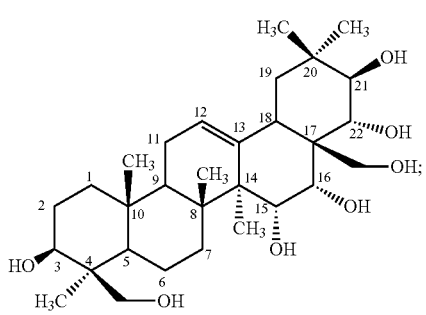

-continued

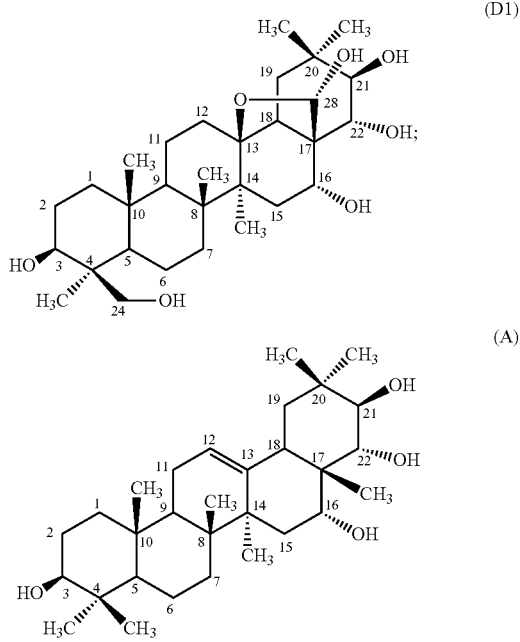

Esterification of compounds (A), (C), or (D1) with acyl chloride including Tigloyl chloride, angeloyl chloride, Acetyl chloride, Crotonoyl chloride, 3,3-Dimethylartyloyl chloride, senecioyl chloride, Cinnamoyl chloride, Pentenoyl chloride, Hexanoyl chloride, benzoyl chloride, Ethylbutyryl chloride, ethanoyl chloride, propanoyl chloride, propenoyl chloride, butanoyl chloride, butenoyl chloride, pentanoyl chloride, hexenoyl chloride, heptanoyl chloride, heptenoyl chloride, octanoyl chloride, octenoyl chloride, nonanoyl chloride, nonenoyl chloride, decanoyl chloride, decenoyl chloride, propionyl chloride, 2-propenoyl chloride, 2-butenoyl chloride, Isobutyryl chloride, 2-methylpropanoyl chloride, 2-ethylbutyryl chloride, ethylbutanoyl chloride, 2-ethylbutanoyl chloride, butyryl chloride, (E)-2,3-Dimethylacryloyl chloride, (E)-2-Methylcrotonoyl chloride, 3-cis-Methyl-methacryloyl chloride, 3-Methyl-2-butenoyl chloride, 3-Methylcrotonoyl chloride, 4-Pentenoyl chloride, (2E)-2-pentenoyl chloride, Caproyl chloride, 5-Hexenoyl chloride, Capryloyl chloride, Lauroyl chloride, Dodecanoyl chloride, Myristoyl chloride, Tetradecanoyl chloride, Oleoyl chloride, C (2-18) Acyl chloride, The compounds vary in composition when the time or temperature of the reaction is changed. The peaks, fractions and compounds are selected according to the activities of times studies and the changes of peaks. The compounds having strong to weak activities are selected and isolated. The anti cancer activities are the MTT studies of bone (U2OS), lung (H460), bladder (HTB-9), ovary (ES2), colon (HCT116), pancreas (Capan), ovary (OVCAR3), prostate (DU145), skin (SK-Mel-5), mouth (KB), kidney (A498), breast (MCF-7), liver (HepG2), brain (T98G), luekemia (K562), cervix (HeLa). The active esterification products are purified with HPLC. The reaction product of mixtures and individual compounds are tested with MTT Cytotoxic Assay. Details of method are in Experiment 3 of the present application. A second esterification of compound can be selected from the above experiment results to produce new active compounds. A partial esterification compound is selected from the above experiments to perform a second or repeated with a third esterification with different acyl chloride in order to produce new active compounds with the experiments in the present application, wherein the compound can be selected from K, (H1) or (H2):

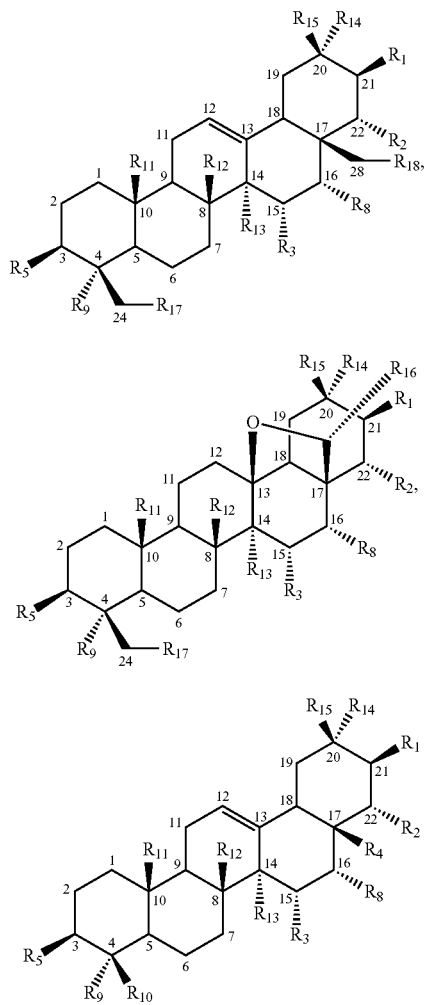

(H1)

(H2)

(K)

R1, R2, R3, R4, R5, R8, R9, R10, R11, R12, R13, R14, R15, R16, R17, R18 are independently selected from the group of CH3, CH2OH, COOH, hydrogen, hydroxyl, methyl, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-alkane, O-alkene, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; CH2O-angeloyl, CH2O-ti-gloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; CH2O-4-(dimethylamino)-2-methylbut-2-enoyl, CH2O-4-[(2-methoxyethyl)amino]-2-methyl-4oxobut-2-enoyl or wherein any 1 or 2 or 3 or 4 of R1, R2, R3, R4, R5, R8, R10, R16, R17, R18 is/are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-

Lauroyl, CH2O-Dodecanoyl, CH2O-Myristoyl, CH2O-Tetradecanoyl, CH2O-Oleoyl, CH2O—C(2-18) Acyl, CH2O-4-(dimethylamino)-2-methylbut-2-enoyl, CH2O-4-[(2-methoxyethyl)amino]-2-methyl-4oxobut-2-enoyl; R9, R1, R12, R13, R14, R15 are independently attached a CH3; or wherein R10 is attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl, O-4-(dimethylamino)-2-methylbut-2-enoyl, and O-4-[(2-methoxyethyl)amino]-2-methyl-4oxobut-2-enoyl, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; CH2O-4-(dimethylamino)-2-methylbut-2-enoyl, CH2O-4-[(2-methoxyethyl)amino]-2-methyl-4oxobut-2-enoyl or wherein R4 and R10 are independently attached an CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O—C(2-18) Acyl; CH2O-4-(dimethylamino)-2-methylbut-2-enoyl, CH2O-4-[(2-methoxyethyl)amino]-2-methyl-4oxobut-2-enoyl or wherein R17 and R18 are independently attached an O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O—C(2-18) Acyl; wherein R3 is OH or H or absent; wherein R1, R2, R3, R5, R8 are OH or H or absent; wherein R9, R11, R12, R13, R14, and R15 are CH3; or wherein R1, R2, R5, R8 represent OH; R3 represents OH, H or absent; R4, R10 represent CH2Oangeloyl; R9, R11, R12, R13, R14, R15 represent CH3; or wherein R1, R2, R5, R8 represent OH or O-tigloyl; R3 represents OH, H, or absent; R4, R10 represent CH2O tigloyl; R9, R11, R12, R13, R14, R15 represent CH3; wherein the group attaching to the core compound selected from acetyl, angeloyl, tigloyl, senecioyl, Crotonoyl, O-3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, O-4-(dimethylamino)-2-methylbut-2-enoyl, and O-4-[(2-methoxyethyl)amino]-2-methyl-4oxobut-2-enoyl are interchangeable or replaceable thereof. They can be the same group or in combination thereof. The compounds of present application on cells is arresting cells in the S-phase and blocking their entering into the G2/M phase of cell cycle. The compounds block the DNA synthesis of cancer cell. This invention provides compounds and method for improving blood circulation; soothing stroke; Prevent plaque formation and promote their dissipated; improve blood viscosity; reducing cardiovascular; reducing cerebrovascular; reducing thrombosis, arteriosclerosis, coronary heart disease, hypertension, diabetes, thrombocytopenia purpura, hemoptysis, hematemesis; treating blood in the stool, uterine bleeding, traumatic bleeding, abdominal irritation, swelling, flutter, Blood circulation, swelling, pain; Treating bronchiectasis, tuberculosis and lung abscess caused by too hemoptysis; reducing bleeding, antitussive, expectorant and analgesic effect, dilate blood vessels; reducing blood pressure and the treatment of cerebral arteriosclerosis; elevated blood lipids and reduced cholesterol.

A composition comprising an effective amount of compound selected from the above formula or a salt, ester, metabolite or derivative thereof can be used as a medicament for blocking the invasion, migration, metastasis of cancer cells, inhibiting tumor or cancer cell growth and for treating cancer, wherein the cancers comprise breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer.

This invention provides a composition comprising the compounds provided in the invention for treating cancers; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; diabetes; cerebrovascular diseasea; inhibiting NF-kappa B activation; for treating brain edema, severe acute respiratory syndrome, respiratory viral diseases, chronic venous insufficiency, hypertension, chronic venous disease, oedema, inflammation, hemonhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels. This invention provides a composition for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-eclamptic, anti-edemic, anti-encaphalitic, anti-epiglottitic, anti-exudative, anti-flu, anti-fracture, anti-gingivitic, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, anti-parasitic; increase the expression of the genes: ANGPT2, DDIT3, LIF and NFKB1Z, and manufacturing an adjuvant composition and venotonic treatment. The composition block the DNA synthesis of cancer cell.

Alkenyl means unsaturated linear or branched structures and combinations thereof, having formula R2 C═CR2, one or more double bonds therein. Examples of alkenyl groups include vinyl, propenyl, isopropenyl, butenyl, s- and t-butenyl, pentenyl, hexenyl, butadienyl, pentadienyl, and hexadienyl. An aryl is a functional group of organic molecule derived from an aromatic compound such as benzene, a 6-14 membered carbocyclic aromatic ring system comprising 1-3 benzene rings. If two or more aromatic rings are present, then the rings are fused together, so that adjacent rings share a common bond. Examples include phenyl and naphthyl. The aryl group may be substituted with one or more substitutes independently selected from halogen, alkyl or alkoxy. Acyl is a functional group which can be obtained from an organic acid by the removal of the carboxyl. Acyl groups can be written using the general formula —COR, where there is a double bond between the carbon and oxygen. The names of acyl groups typically end in -yl, such as formyl, acetyl, propionyl, butyryl and benzoyl. Benzoyl is one of the acyls, $C_6H_5COR$, obtained from benzoic acid by the removal of the carboxyl. A heterocyclic compound is a compound containing a heterocyclic ring which refers to a non-aromatic ring having 1-4 heteroatoms, said ring being isolated or fused to a second ring selected from 3- to 7-membered alicyclic ring containing O-4 heteroatoms, aryl and heteroaryl, wherein heterocyclic compounds include pyrrolidinyl, pipyrazinyl, morpholinyl, trahydrofuranyl, imidazolinyl, thiomorpholinyl, and the like. Heterocyclyl groups are derived from heteroarenes by removal of a hydrogen atom from any ring atom. Alkanoyl is the general name for an organic functional group RCO—, where R represents hydrogen or an alkyl group. Examples of alkanoyls are acetyl, propionoyl, butyryl, isobutyryl, pentanoyl and hexanoyl. Alkenoyl is an alkenylcarbonyl in which the alkenyl is defined above. Examples are pentenoyl (tigloyl) and pentenoyl (angeloyl). Alkyl is a radical containing only carbon and hydrogen atoms arranged in a chain, branched, cyclic or bicyclic structure or their combinations, having 1-18 carbon atoms. Examples include but are not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl and cyclohexyl. Benzoyl alkyl substituted alkanoyl refers to straight or branched alkanoyl substituted with at least one benzoyl and at least one alkyl, wherein the benzoyl is attached to a straight or branched alkyl. An example of a benzoyl alkyl substituted alkanoyl is benzoyl methyl isobutanoyl. A sugar moiety is a segment of molecule comprising one or more sugars or derivatives thereof or alduronic acid thereof.

(Y)Y3, Y and Y3 represent the same compound. YM and (ACH-Y) represent the same compound. Connecting moiety is a substructure or a group of atoms which connect the functional group to a core compound. Example: angeloyl group is connected by a sugar moiety to a triterpene core.

Acetyl=ethanoyl; Propionyl=methylpropanoyl; Crotonoyl=2-butenoyl; Isobutyryl=2-methylpropanoyl; 2-Ethylbutyryl=2-Ethylbutanoyl; Butyryl=n-Butyryl=butanoyl=C-4 Acyl; trans-2-Methyl-2-butenoyl=(E)-2,3-Dimethylacryloyl chloride=(E)-2-Methylcrotonoyl=3-cis-Methyl-methacryloyl=Tigloyl; 3,3-Dimethylacryloyl=3-Methyl-2-butenoyl=3-Methylcrotonoyl=Senecioyl; Propionyl chloride=methylpropanoyl; Hexanoyl=Caproyl; Heptanoyl=Enanthic=Oenanthic; Octanoyl=Capryloyl; Dodecanoyl=Lauroyl; Tetradecanoyl=Myristoyl; C (2-18) Acyl is an acyl group having 2 to 18 carbons. ethanoyl is a C-2 Acyl, propanoyl is a C-3 Acyl, propenoyl is a C-3 Acyl, propionyl is a C-3 Acyl, butanoyl is a C-4 Acyl, butenoyl is a C-4 Acyl, crotonoyl is a C-4 Acyl, pentanoyl is a C-5 Acyl, pentenoyl is a C-5 Acyl, angeloyl is C-5 Acyl, tigloyl is C-5 Acyl, senecioyl is C-5 Acyl, hexanoyl is a C-6 Acyl, hexenoyl is a C-6 Acyl, heptanoyl is a C-7 Acyl, heptenoyl is a C-7 Acyl, octanoyl is a C-8 Acyl, octenoyl is a C-8 Acyl, nonanoyl is a C-9 Acyl, nonenoyl is a C-9 Acyl, decanoyl is a C-10 Acyl, decenoyl is a C-10 Acyl, lauroyl is a C-12 Acyl, dodecanoyl is a C-12 Acyl, myristoyl is a C-14 Acyl, oleoyl is a C-18 Acyl.

The building blocks used in the invention including triterpenes, hydroxylated triterpenes, acetyl, angeloyl, tigloyl, senecioyl, Crotonoyl, 3,3-Dimethylartyloyl, Cinnamoyl, Pentenoyl, Hexanoyl, benzoyl, Ethylbutyryl, alkyl, dibenzoyl, benzoyl, methylbutanoyl, methylpropanoyl, alkanoyl, alkenoyl, benzoyl alkyl substituted alkanoyl, alkanoyl substituted phenyl, alkenoyl substituted phenyl, aryl, acyl, heterocylic, heteroraryl, alkenylcarbonyl, ethanoyl, propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl and Oleoyl, 4-(dimethylamino)-2-methylbut-2-enoyl, 4-[(2-methoxyethyl)amino]-2-methyl-4oxobut-2-enoyl or halides thereof, or chloride. thereof.

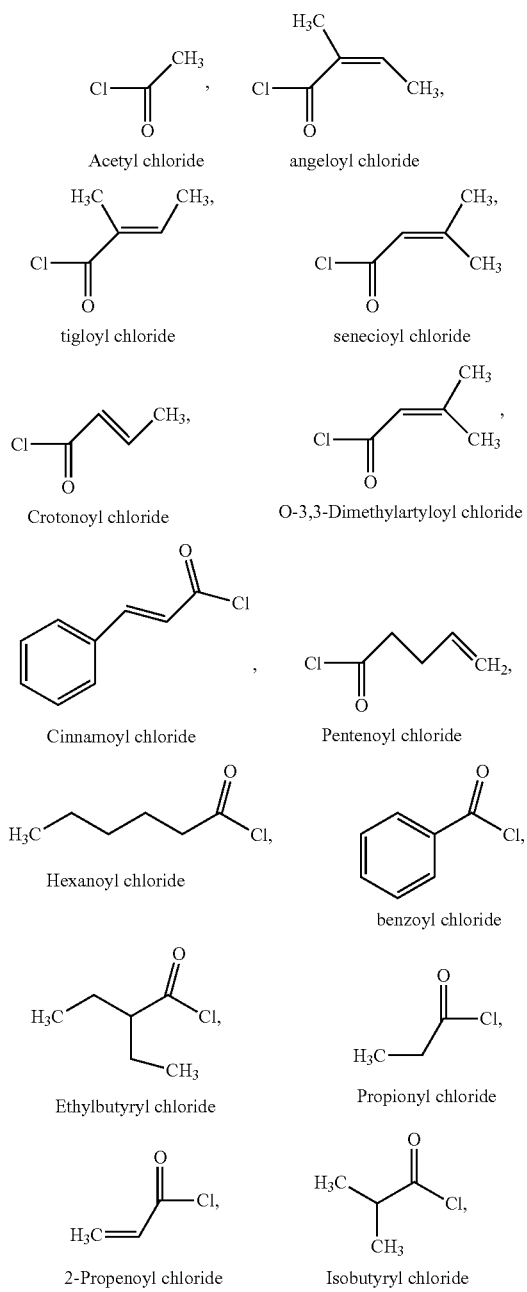
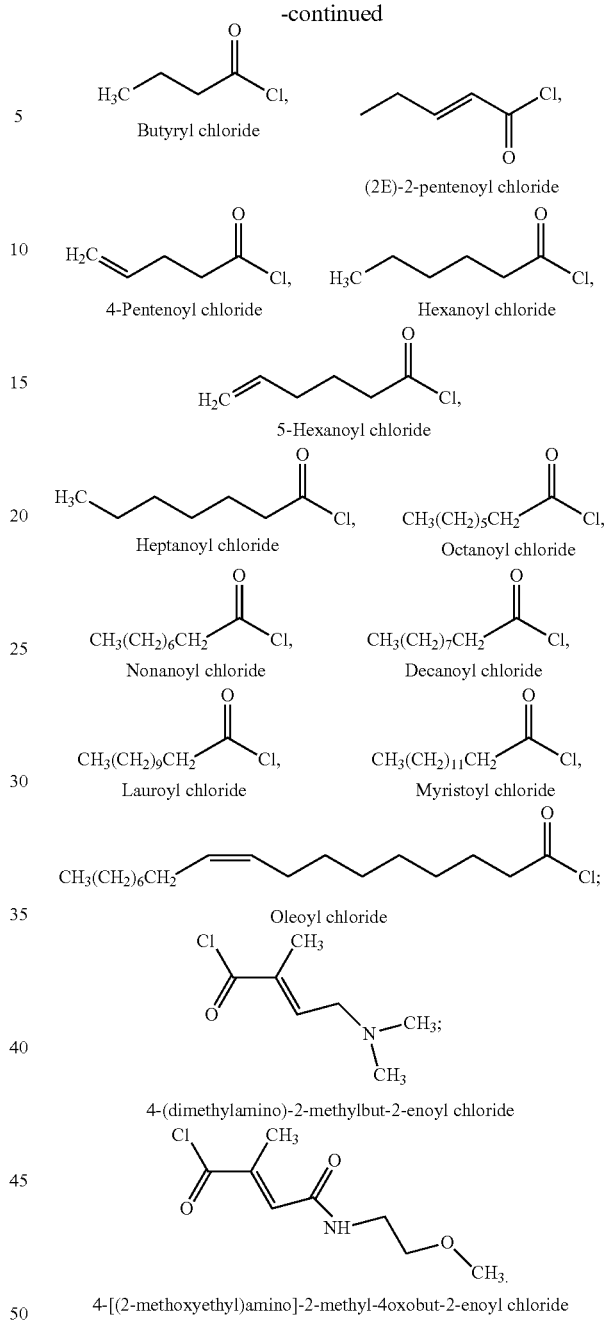

Acryloyl chloride [Synonym: 2-propenoly chloride]; Propionyl chloride [Synonym: methylpropanoyl chloride]; Crotonoyl chloride [Synonym: 2-butenoyl chloride]; Isobutyryl chloride [Synonym: 2-methylpropanoyl chloride]; 2-Ethylbutyryl chloride [Synonym: 2-Ethylbutanoyl chloride]; Butyryl chloride (Synonym: n-Butyryl chloride, butanoyl chloride, or C-4 Acyl halide); trans-2-Methyl-2-butenoyl chloride [Synonym: (E)-2,3-Dimethylacryloyl chloride, (E)-2-Methylcrotonoyl chloride, 3-cis-Methyl-methacryloyl chloride, Tigloyl chloride]; 3,3-Dimethylacryloyl chloride [Synonym: 3-Methyl-2-butenoyl chloride, 3-Methylcrotonoyl chloride, Senecioyl chloride]; Hexanoyl chloride [Synonym: Caproyl chloride]; Heptanoyl chloride [Synonym: Enanthic chloride, Oenanthic chloride] Octanoyl chloride [Synonym: Capryloyl chloride].

In the presented experiments, concentrations of drug that inhibit 15% cell-growth or less (i.e. 85% of control or above) as compared to the no-drug control (DMSO) are considered non-cytotoxic concentrations. In an embodiment, the concentrations of drug that inhibit 10% cell-growth or less (i.e. 90% of control or above) as compared to the no-drug control (DMSO) are considered non-cytotoxic concentrations. In an embodiment, the concentrations of drug that inhibit 5% cell-growth or less (i.e. 95% of control or above) as compared to the no-drug control (DMSO) are considered non-cytotoxic concentrations. In an embodiment, the concentrations of drug that inhibit 20% cell-growth or less (i.e. 80% of control or above) as compared to the no-drug control (DMSO) are considered non-cytotoxic concentrations. In an embodiment, the concentrations of drug that inhibit 25% cell-growth or less (i.e. 75% of control or above) as compared to the no-drug control (DMSO) are considered non-cytotoxic concentrations. In an embodiment, the concentrations of drug that inhibit 30% cell-growth or less as compared to the no-drug control (DMSO) are considered non-cytotoxic concentrations. In an embodiment, the concentrations of drug that inhibit 45% cell-growth or less as compared to the no-drug control (DMSO) are considered non-cytotoxic concentrations.

The triterpene compound or compounds selected from this invention can be administered to a subject in need thereof, treating the subject, wherein including preventing cancer, or providing an adjuvant effect to the subject, or inhibiting the initation or promotion of cancer, or killing the cancer/tumor cells, or inhibiting cancer cell invasion. In an embodiment the compounds inhibit the activation of Nuclear Factor-kB, wherein inhibiting the localization or wherein binding the DNA. In an embodiment the compounds block the DNA synthesis. In an embodiment the compounds induce apoptosis in cancer cells.

Determination of gene expression by Real-time PCR method (Brilliant QPCR, Agilent Technologies): The real-time polymerase chain reactions further confirm the results obtained from microarray analysis. The Real-time PCR results (shown below) confirmed that Compound Y3 and YM increase the expression of the genes: ANGPT2, DDIT3, LIF and NFKB1Z, wherein the results in Table 19-21 disclosed in PCT/US09/34115, filed Feb. 13, 2009.

The saponins are partially hydrolyzed into a mixture of products which can be separated by HPLC. Specific partial hydrolysis of saponins can also be achieved with enzymes. The glycosidases catalyze the hydrolysis of the glycosidic linkage. Galactosidase is an enzyme which catalyzes the hydrolysis of galactosides. Glucosidase is an enzyme which breaks glucose from saponin. Other enzyme examples are xylanases, lactase, amylase, chitinase, sucrase, maltase, and neuraminidase.

The sugar moiety of the triterpenoid saponin (example Xanifolia Y) can be removed by acid hydrolysis. The synthetic compound of ACH-Y is obtained. ACH-Y is a triterpene with acyl groups but no sugar moiety. The acyl group of the saponin (example Xanifolia Y) can be removed by alkaline hydrolysis. The synthetic compound AKOH-Y can be obtained. AKOH-Y is a pentacyclic triterpene with sugar moieties. A pentacyclic triterpene can be obtained by acid and alkaline hydroysis of saponins from natural sources. A pentacyclic triterpene can be obtained by synthetic methods (Reference: Surendra et al., Rapid and Enantioselective Synthetic Approches to Germanicol and Other Pentacyclic Triterpenes, Journal of the American Chemical Society, 2008, 130(27), 8865-8869). Pentacyclic triterpenes with sugar moieties can also be obtained by synthesis (Reference: Pie et al., Synthesis of L-arabinopyranose containing hederagenin saponins, Tetrahedron 61 (2005) 4347-4362). Acylation is the process of adding an acyl group to a compound. The Friedel-Crafts reaction is an example of this process. An active compound can be obtained by acylating a pentacyclic triterpenes, or hydroxylated triterpenes. In an embodiment, acylating C24, C28, C21 and C22 of a pentacyclic triterpenes, or hydroxylated triterpenes produce compounds for inhibiting cancer growth, cancer invasion, cell invasion, cancer cell invasion, molecular cell invasion, cell attachment adhesion, or cell circulation. In an embodiment, the acyl group(s) may be at C3. In an embodiment, a sugar moiety is at C21, 22, or 28, wherein the sugar moiety is attached with 2 acyl groups. In an embodiment, acylating the compounds of (A), (B), (C), (D1), (D2), (F), (G), (H), produce the compounds for inhibiting cancer invasion, cells invasion or cancer cell invasion; cancer metastasis; or cancer growth. The building blocks in the present application are used to synthesise active saponins. In enbodiment, the sugar moiety(ies) is/are included but not limited to a group of glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivatives or combinations thereof;

Acylating the compound (G) with angeloyl or tigloyl group gives the following compounds

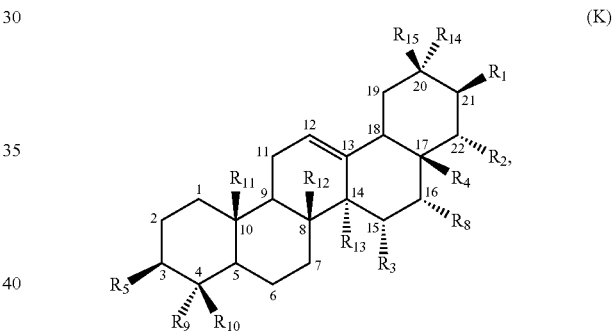

(K)

wherein R1, R2, R5, R8 represent OH or O-angeloyl; R3 represents OH, H or O-angeloyl; R4, R10 represent CH3, CH2OH or CH2Oangeloyl; R3 represents OH, H or O-angeloyl; R9, R11, R12, R13, R14, R15 represent CH3; or wherein R1, R2, R5, R8 represent OH or O-tigloyl; R3 represents OH, H or O-tigloyl; R4, R10 represent CH3, CH2OH or CH2O tigloyl; R9, R11, R12, R13, R14, R15 represent CH3; wherein the compounds inhibit cancer growth, cancer invasion, cells invasion or cancer cell invasion.

Acylating the compound (G) with angeloyl, tigloyl, senecioyl, acetyl, Crotonoyl, 3,3-Dimethylartyloyl, Cinnamoyl, Pentenoyl, Hexanoyl, benzoyl, Ethylbutyryl, alkyl, dibenzoyl, benzoyl, alkanoyl, alkenoyl, benzoyl alkyl substituted O-alkanoyl, alkanoyl substituted phenyl, alkenoyl substituted phenyl, aryl, acyl, heterocylic, heteroraryl, CH2O-alkenylcarbonyl, alkane, alkene give the compound (K) wherein R1, R2, R5, R8 represent OH, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; R4, R10 represent CH3, CH2OH, CH2O-angeloyl, CH2O-tigloyl, CH2O-senecioyl, CH2O-acetyl, CH2O-Crotonoyl, CH2O-3,3-Dimethylartyloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, alkane, alkene; R3 is absent of represents OH, H, O-angeloyl, O-tigloyl, O-senecioyl, O-acetyl, O-Crotonoyl, O-3,3-Dimethylartyloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl; wherein R9, R11, R12, R13, R14, R15 represent CH3; wherein the compounds inhibit cancer growth, cancer invasion, cells invasion or cancer cell invasion; wherein the compound for use as mediator or inhibitor of adhesion protein or angiopoietin; wherein the compounds use as mediator modulating the secretion, expression, or synthesis of adhesion protein comprises reducing the fibronectin for inhibiting cell attachment, cell adhesion or cell circulation; wherein the adhesion proteins comprise fibronectin, integrins family, myosin, vitronectin, collagen, laminin, polyglycans, cadherin, heparin, tenascin, $CD_{54}$, and CAM; the compounds use for anti adhesion therapy and targeting adhesion molecules for therapy.

Applicant further states that anti-adhesion therapy and targeting adhesion molecules for therapy is a new direction for development of drugs. Some examples of anti-adhesion drugs in clinical trials are Efalizumab, Odulimomab, Alicaforsen, Aselizumab etc, which target varies adhesion proteins. Please see TEXT BOOK, Adhesion Molecules: Function and Inhibition, (Reference 2), edited by Klaus Ley page 289-291, 297.

Adhesion molecules in inflammatory disease, (Reference 4), Abstract, line 7-8 "Blockade of the function of expression of CAM has emerged as a new therapeutic target in inflammatory diseases". Applicants' invention is an anti-adhesion therapy which is a new use of the compound as a mediator or inhibitor of adhesion proteins and angiopoietins. It inhibits excess adhesion and inhibits cell attachment.

In the present application, Applicants have used compounds selected from structure (2A) for anti adhesion therapy, as a mediator or inhibitor of adhesion proteins and angiopoietins, and modulation of the cell attachment, and cell adhesion.

This invention provide a synthetic method to obtain semi-natural compounds by chemically removing functional groups of complex natural products to the basic core structure before de-novo chemically adding on active groups directly or sequentially by reaction with the active group donating chemical under different reaction temperature and time to produce series of different active group modified core structure compounds that can be fractionated and easily structurally determined as well as screening for different bio-active efficacies and toxicities as potential new drug candidates.

The activities of compounds are tested with cancer of leukemia (CCRF-CEM, HL60(TB), K-562, MOLT-4, RPMI8226, SR), lung (A549/ATCC, HOP-62, HOP92, NCI-H226, NCI-H322M, NCI-H460, colon (COL0205, HCC-2998, HCT-116, HCT-15, HT29, KM12, SW-620), CNS(SF-268, SF295, SF539, SNB-19, SNB-75, US51), melanoma (LOX IMVI, MALME-3M, M14, MDA-MB-3M, M14, MDA-MB-435, SK-MEL-2, SK-MEL-28, SK-MEL-5, UACC-257, UACC-62), ovary (ICTOV1, OVCAR-3, OVCAR-4, OVCAR-5, OVCAR-8, NCIADR-RES, SKOV3), renal (786-0, A498, ACHN, CAKI-1, SN12 C, TK-10, UO-31), prostate (PC-3, DU-145), breast (MCF7, MDA-MB-231, HS578T, T47D, MDA-MB-468). The room temperature is 25 C in the present application.

Experimental Details

Experiment details of herb extraction, analysis of extract components by HPLC, determination of the cell-growth activity effected by Xanifolia Y with cells derived from different human organs using MTT Assay, purification of the bioactive components from plant extract, fractionation of plant extracts with FPLC, isolation of component Ys with preparative HPLC, determination of the chemical structure, cell experiments and animal studying are disclosed in PCT/US05/31900, U.S. Ser. No. 11/289,142, U.S. Ser. No. 10/906,303, U.S. Ser. No. 11/131,551 and U.S. Ser. No. 11/683,198, filed on Mar. 7, 2007, PCT/US2007/077273, filed Aug. 30, 2007, U.S. Ser. No. 60/890,380, filed on Feb. 16, 2007, U.S. Nos. 60/947,705, filed on Jul. 3, 2007, PCT/US2008/002086, 1188-ALA-PCT, filed Feb. 15, 2008, App'l No. PCT/US09/34115, filed Feb. 13, 2009, Experiments 1-23 of PCT/US2008/002086, 1188-ALA-PCT, filed Feb. 15, 2008 are incorporated in this application.

Experiment 1: Removal of the Sugar Moiety from Saponin by Acid Hydrolysis 15 mg saponin was dissolved in 1 ml of Methanol. 1 ml of 2N HCl was then added. The mixture was refluxed in 80 C water bath for 5 hours. The solution was then neutralized by adding 2 ml of 1N NaOH (to final pH 4-6). The aglycone was then extracted with ethylacetate 3 ml×2. The extracts were collected and pooled. Further isolation of aglycone (sugar-removed saponin) was achieved by HPLC with isocratic elution of 80-100% acetonitrile.

Experiment 2: Removal of the Acyl Group by Alkaline Hydrolysis

Methods: 20 mg of saponin was dissolved in 0.5 ml of 1N NaOH. The solution was incubated in 80 C water bath for 4 hours. It was cooled to room temperature before neutralized with 0.5 ml 1N HCl (adjust pH to about 3). The mixture was extracted with 2 ml 1-butanol 3 times. The butanol fractions were collected and lyophilized. The hydrolyzed saponin with further purified with HPLC in a C-18 column eluted with 25% acetonitrile.

Experiment 3: Adding the Acyl Group to Triterpene by Esterification

Method: 40 mg of triterpene core (fraction IV) was dissolved in 1 ml pyridine in a 50 ml tube. Reaction is started by adding 0.2 ml of acyl chloride (Tigloyl chloride, angeloyl chloride, Acetyl chloride, Crotonoyl chloride, 3,3-Dimethylartyloyl chloride (senecioyl chloride), Cinnamoyl chloride, Pentenoyl chloride, Hexanoyl chloride, benzoyl chloride or Ethylbutyryl chloride). The mixture is stirred for 5 sec, 1 min, 2 min, 5 min, 10 min, 30 min, 1 hr, 2 hr, 18 hr, 2 days or 3 days at 0 C, 25 C or 75 C temperature. At the end of reaction, 5 ml of 2N HCl or 1M NaHCO3 is added to the reaction mixture. The solution is then extracted 3 times with 10 ml of ethyl acetate which is then evaporated under vacuum and at 45 C and lyophilization. The reaction product is dissolved in 80% acetonitrile—0.005% Trifluoroacetic acid or DMSO; and was separated with HPLC. Selecting the HPLC fractions for isolation is according to the cytotoxic activity of the reaction product obtained at a specific reaction time. The active esterification products are purified with HPLC. The reaction product of mixtures and individual compounds are tested with MTT cytotoxic assay. Structures are determined with NMR. See examples FIGS. 1-12 (U.S. Ser. No. 14/313,080)

Experiment 4: Preparation of E4A

1. Beta-Escin dissolved in 1M NaOH (20 mg/ml) was incubated at 70 C for 5 hours.
2. The hydrolyzed solution was neutralized with HCl and the water was evaporated by lyophilization.
3. The product was dissolved in 50% methanol and 1N HCl. The mixture was incubated at 70 C for 5 hours.
4. The solution was neutralized with NaOH.
5. The hydrolyzed product was extracted with ethylacetate, which was subsequently removed by evaporation.
6. Further purification of the hydrolyzed product (E4A) was archived with FPLC chromatography in a C18 column equilibrated with 70% acetonitrile/TFA at the flow rate of 1 ml/min.

Experiment 5: Esterification of E4A with Tigloyl Chloride 1. 50 mg of E4A in 1 ml pyridine, stir gently in a 50 ml tube. Esterification was carried out at 25 C by adding 200 ul Tigloyl chloride.
2. Stir for 1 minute; then immediately add 5 ml of 2N HCl.
3. Stir for 1 hour and sit at room-Temp over night.
4. Extract the esterification products with 10 ml ethylacetate.
5. Evaporate the ethylacetate.
6. Dissolve the sample with 1 ml DMSO.
7. Fractionate the reaction products with HPLC.
8. Collect samples.

Experiment 6: Isolation of E4A-Tig Active Compounds with HPLC

1. Column: ZORBAX ODS 9.4×250 mm, 5 um
2. Solvents: A: 45% AN/TFA; B: 100% AN/TFA
3. Chromatography conditions: a) Elution: Solvent A to B in 80 min; then with solvent B for 40 min; b) flow rate: 1 ml/mim. c) Monitor OD: at 207 nm;

Experiment 7: MTT Experiment

Cells. HTB-9 (bladder), HeLa-S3 (cervix), DU145 (prostate), H460 (lung), MCF-7 (breast), K562 (leukemia), HCT116 (colon), HepG2 (liver), U2OS (bone), T98G (brain), SK-MEL-5 (Skin) and OVCAR 3, ES2 (ovary), Pancreas (Capan), Mouth (KB), Kidney (A498).

MTT Assay. The procedure for MTT assay followed the method described by Carmichael et al. (1987) with modifications. The cells were seeded into a 96-well plate at for 24 hours before drug-treatment. The cells were then exposed to the drugs for 48, 72, or 96 hours. After the drug-treatment, MTT (0.5 mg/mL) was added to cultures and incubated for an hour. The formazan (product of the reduction of tetrazolium by viable cells) formed and was dissolved with DMSO and the O.D. at 490 nm, and was measured by an ELISA reader. The MTT level of the cells before drug-treatment was also measured (T0). The % cell-growth (% G) is calculated as: % G=(TD−T0/TC−T0)×100(1), where TC or TD represents O.D. readings of control or drug-treated cells. When T0>TD, then the cytotoxicity (LC) expressed as % of the control is calculated as: % LC=(TD−T0/T0)×100(2).

MTT Assay is performed to intermediate and final products from experiments.

Experiment 8: Chemical Synthesis, Isolation and Characterization of E4A-Tig-R

Chemical synthesis of E4A-Tig-R: 1. Preparation of E4A;
2. Esterification of E4A with
Tigloyl Chloride; 3. Isolation of E4A-Tig-R with HPLC
Cytotoxic activity determination: 1. MTT assay
Chemical structure determination: 1. NMR analysis; 2. Mass Spectrum analysis
Compound E4A-Tig-R: 24,28-O-Tigloyl-3β,16α, 21β, 22α, 24β, 28-hexahydroxyolean-12-ene

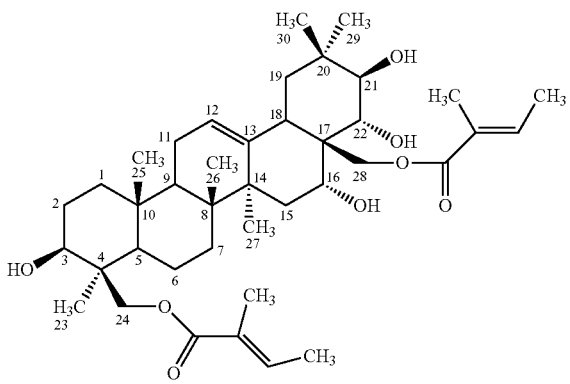

Experiment 9: Chemical Synthesis, Isolation and Characterization of E4A-Tig-N

Chemical synthesis of E4A-Tig-N: 1. Preparation of E4A;
2. Esterification of E4A with Tigloyl Chloride; 3. Isolation of E4A-Tig-N with HPLC
Cytotoxic activity determination: 1. MTT assay
Chemical structure determination: 1. NMR analysis; 2. Mass Spectrum analysis

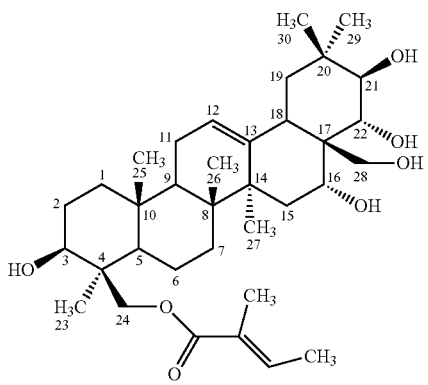

Experiment 10: Chemical Synthesis, Isolation and Characterization of E4A-Tig-Q

Chemical synthesis of E4A-Tig-Q: 1. Preparation of E4A; 2. Esterification of E4A with Tigloyl Chloride; 3. Isolation of E4A-Tig-Q with HPLC
Cytotoxic activity determination: 1. MTT assay
Chemical structure determination: 1. NMR analysis; 2. Mass Spectrum analysis

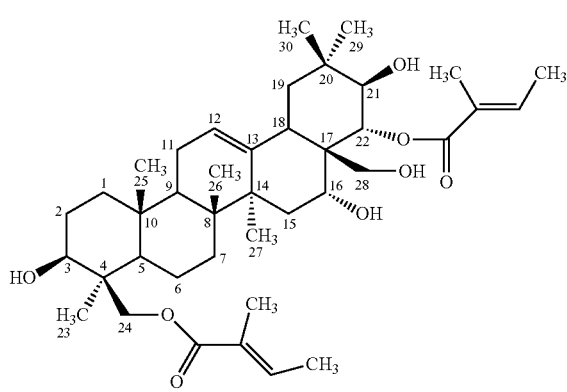

Experiment 11: Chemical Synthesis, Isolation and Characterization of E4A-Tig-V

Chemical synthesis of E4A-Tig-V: 1. Preparation of E4A; 2. Esterification of E4A with Tigloyl Chloride; 3. Isolation of E4A-Tig-V with HPLC
Cytotoxic activity determination: 1. MTT assay
Chemical structure determination: 1. NMR analysis; 2. Mass Spectrum analysis

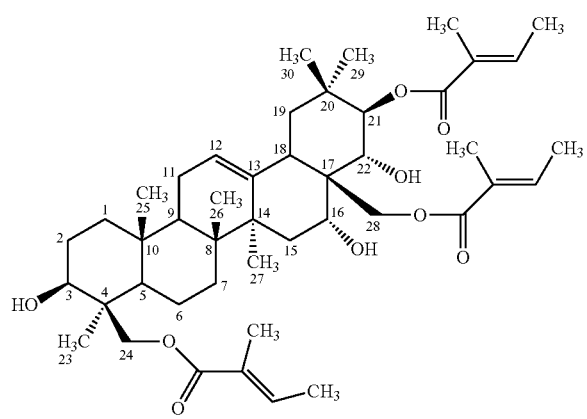

Experiment 12

Chemical Synthesis, Isolation and Characterization of E4A-Tig-T
Chemical synthesis of E4A-Tig-T: 1. Preparation of E4A; 2. Esterification of E4A with Tigloyl Chloride; 3. Isolation of E4A-Tig-T with HPLC Cytotoxic activity determination: 1. MTT assay
Chemical structure determination: 1. NMR analysis; 2. Mass Spectrum analysis

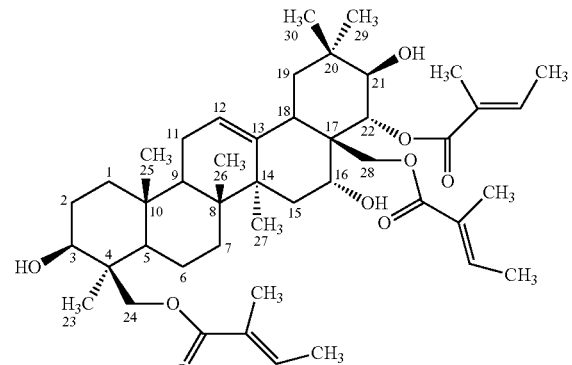

Experiment 13: Chemical Synthesis, Isolation and Characterization of E4A-Tig-U

Chemical synthesis of E4A-Tig-U: 1. Preparation of E4A; 2. Esterification of E4A with Tigloyl Chloride; 3. Isolation of E4A-Tig-U with HPLC
Cytotoxic activity determination: 1. MTT assay
Chemical structure determination: 1. NMR analysis; 2. Mass Spectrum analysis

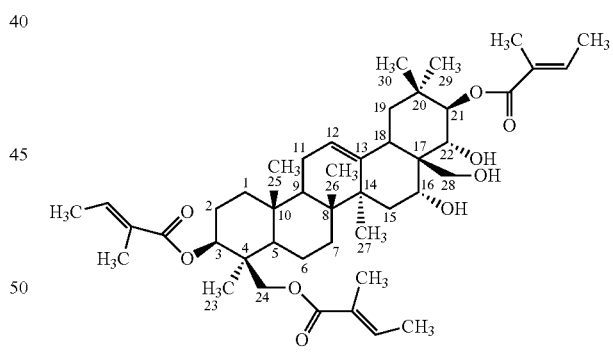

Experiment 14: Chemical Synthesis, Isolation and Characterization of E4A-Tig-S

Chemical synthesis of E4A-Tig-S: 1. Preparation of E4A; 2. Esterification of E4A with Tigloyl Chloride; 3. Isolation of E4A-Tig-S with HPLC
Cytotoxic activity determination: 1. MTT assay
Chemical structure determination: 1. NMR analysis; 2. Mass Spectrum analysis

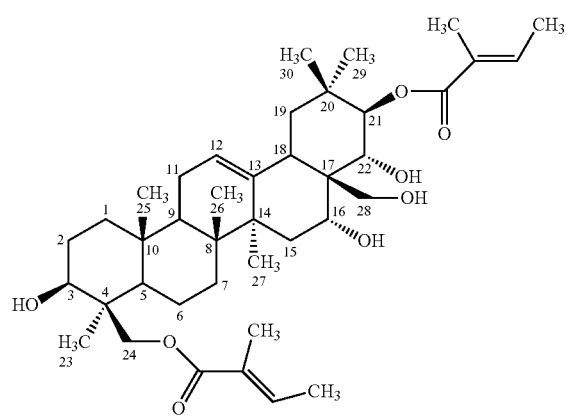
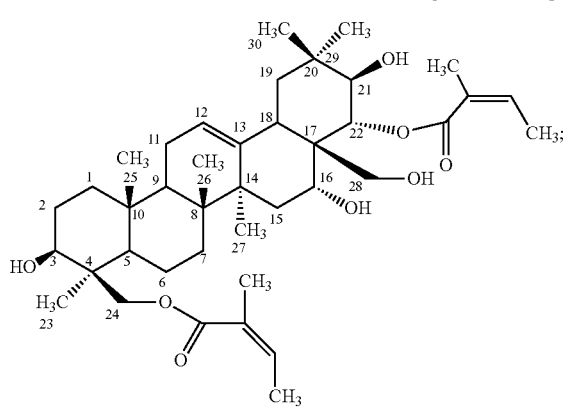
Compound E4A-Ang-Q
Experiment 15
Using Method in Experiment 3, Esterification of E4A with Acetyl, angeloyl, tigloyl, senecioyl, Crotonoyl, Cinnamoyl, Pentenoyl gave the following compounds:
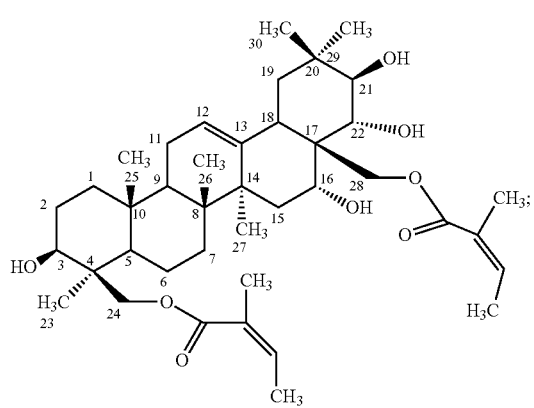
Compound E4A-Ang-N
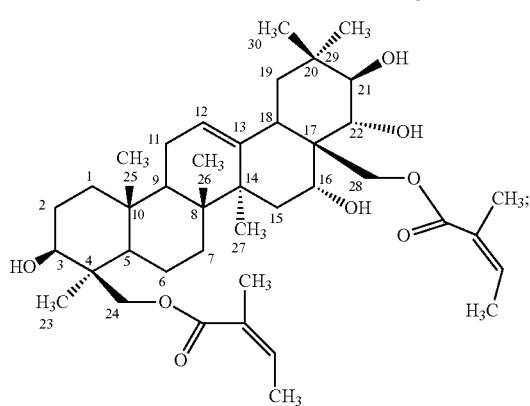
Compound E4A-Ang-R
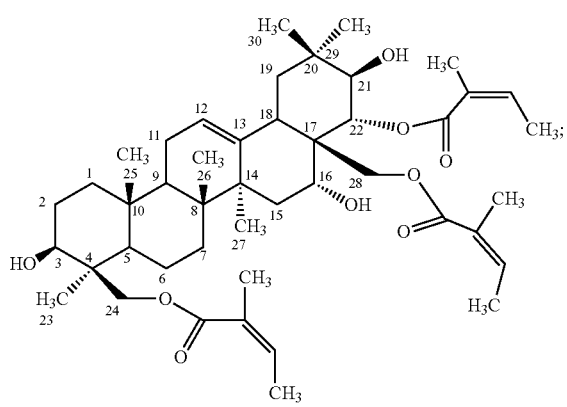
Compound E4A-Ang-T
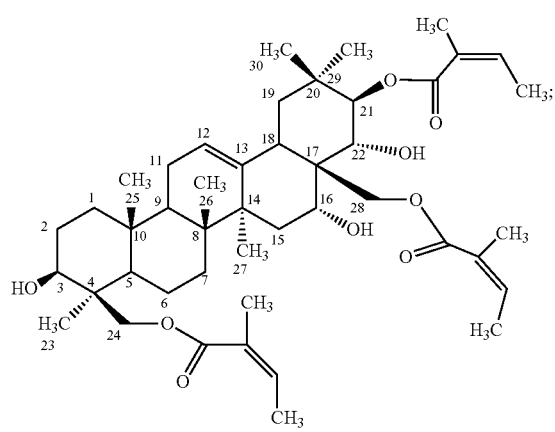
Compound E4A-Ang-V
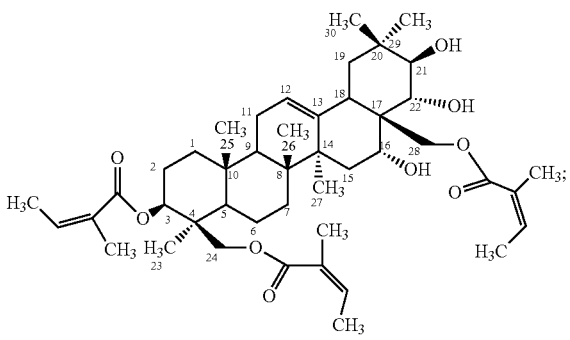
Compound E4A-Ang-U Compound E4A-Ang-S
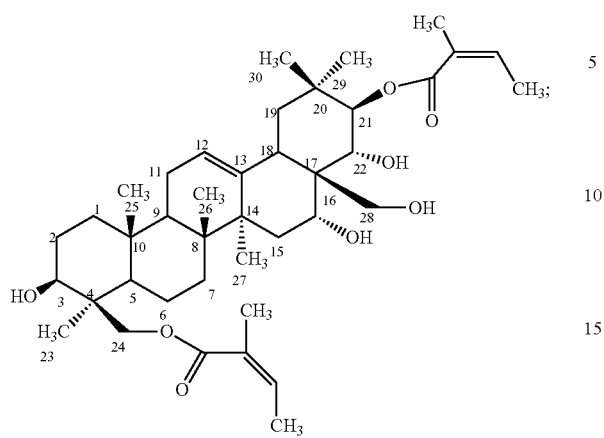
Compound E4A-Sen-N
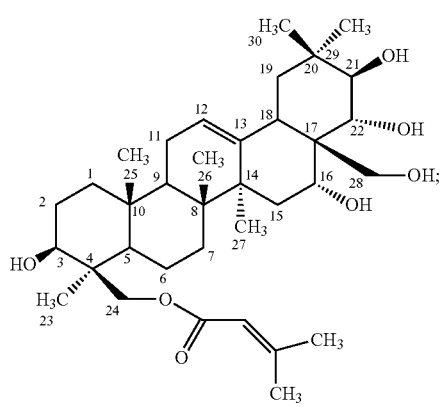
Compound E4A-Sen-R
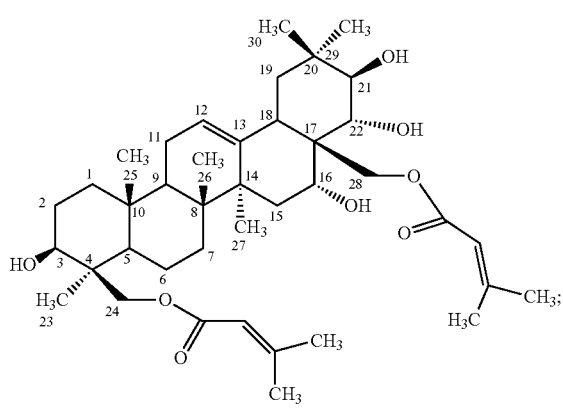
Compound E4A-Sen-Q
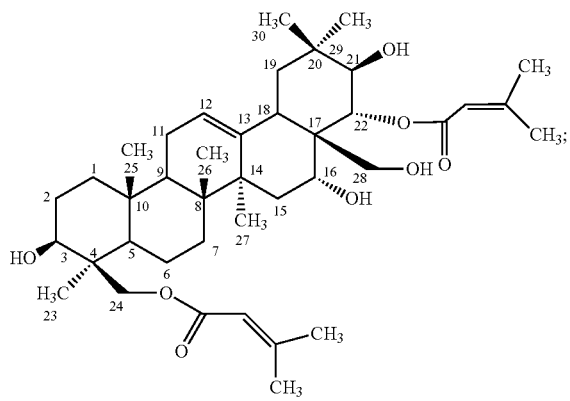
Compound E4A-Sen-V
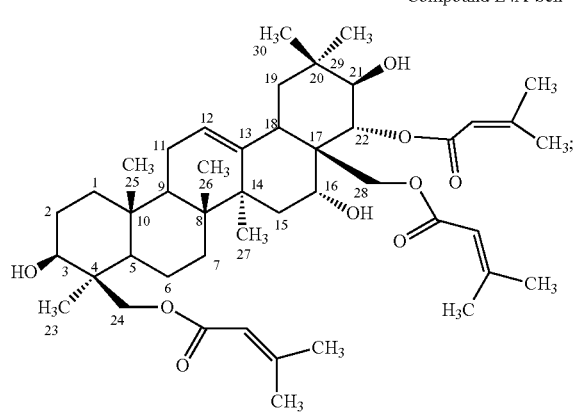
Compound E4A-Sen-S
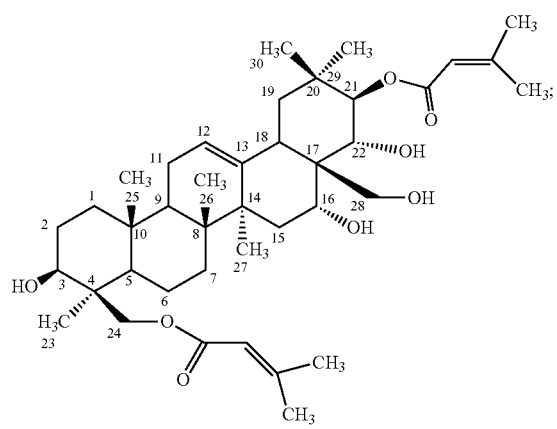

Compound E4A-Sen-T
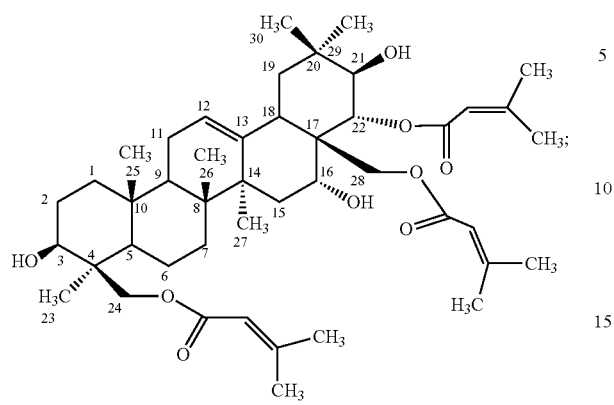
Compound E4A-Cro-N
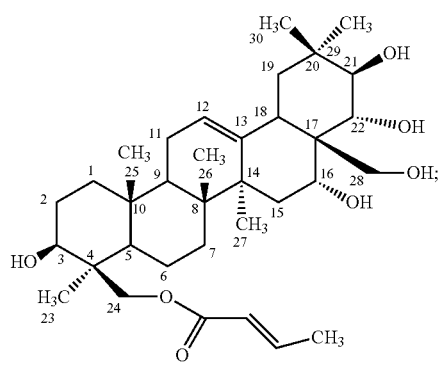
Compound E4A-Sen-U
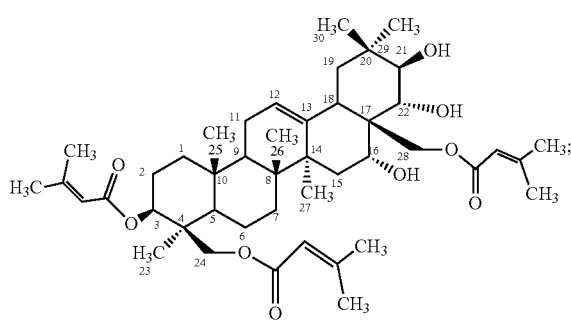
Compound E4A-Cro-Q
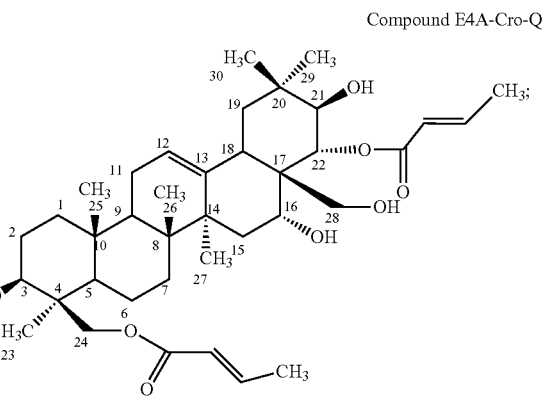
Compound E4A-Cro-R
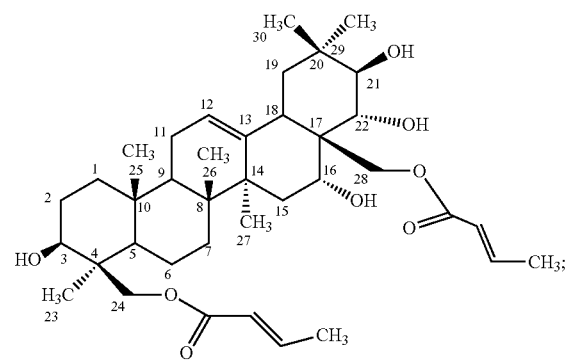
Compound E4A-Cro-S
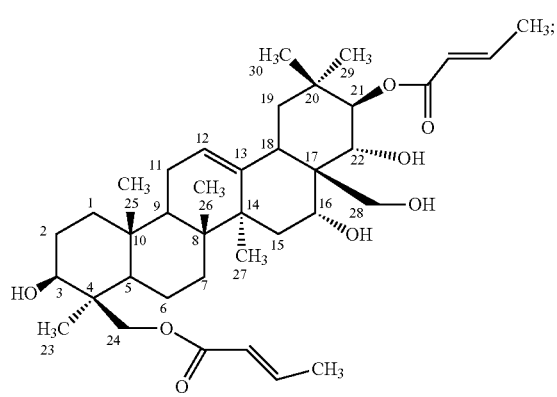
Compound E4A-Cro-V
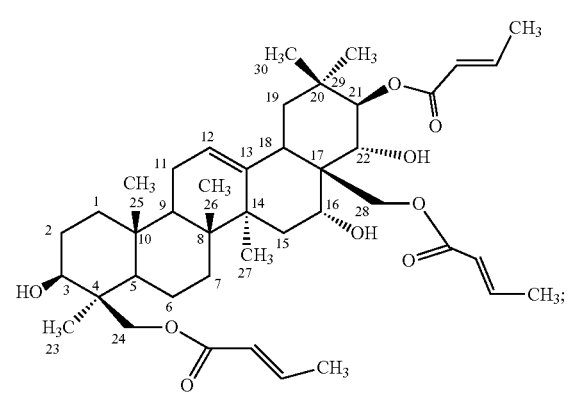
Compound E4A-Cro-T
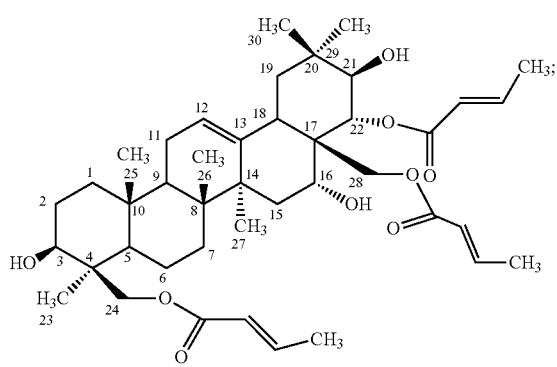

123
-continued
Compound E4A-Cro-U
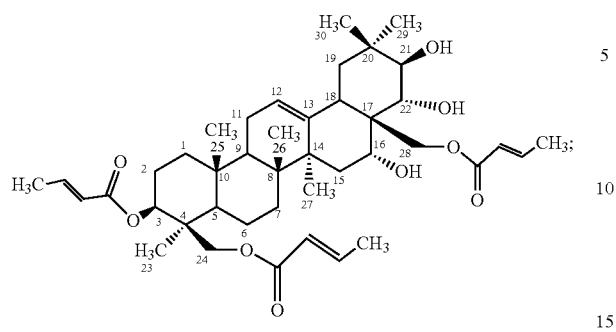
Compound E4A-Acy-R
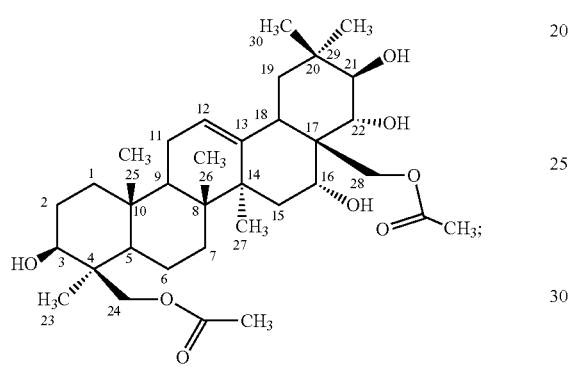
Compound E4A-Acy-V
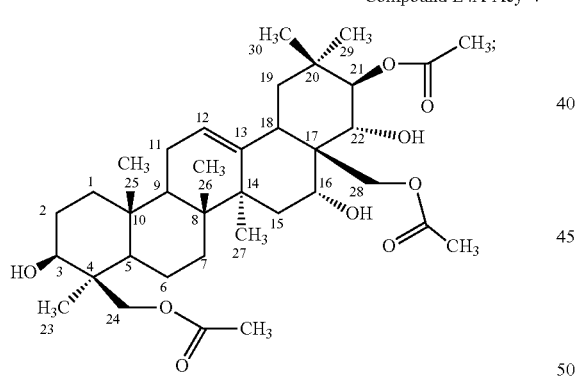
Compound E4A-Acy-N
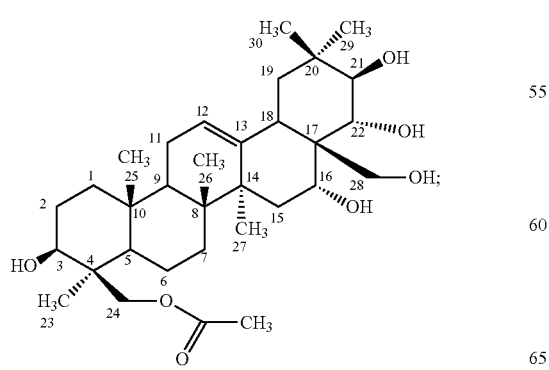
124
-continued
Compound E4A-Acy-Q
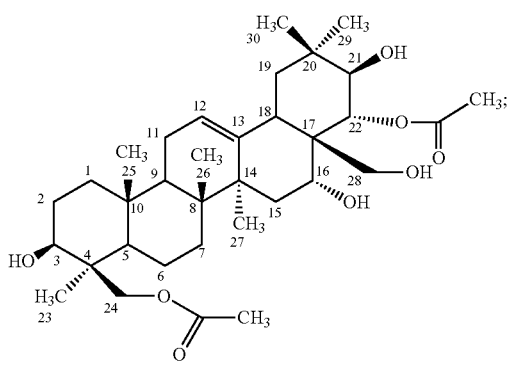
Compound E4A-Acy-S
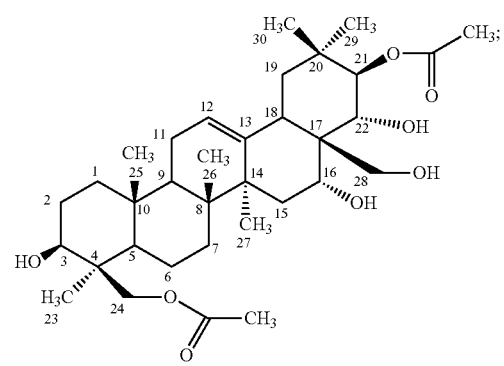
Compound E4A-Acy-T
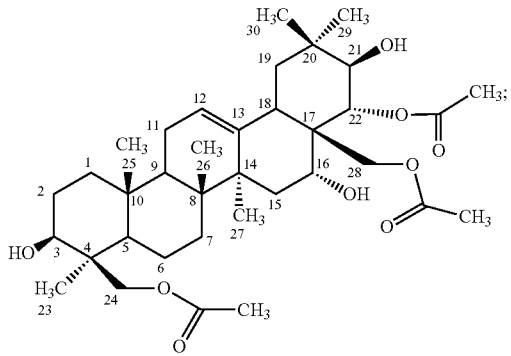
Compound E4A-Acy-U
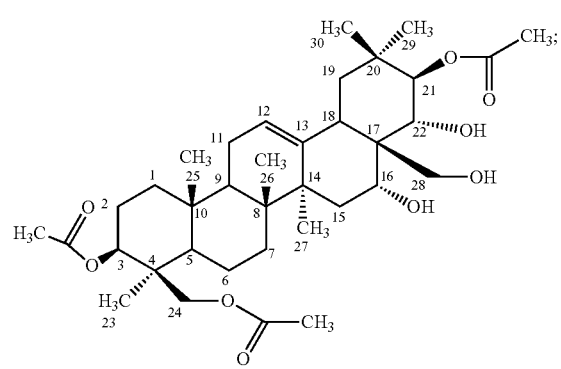

Compound E4A-Pen-R
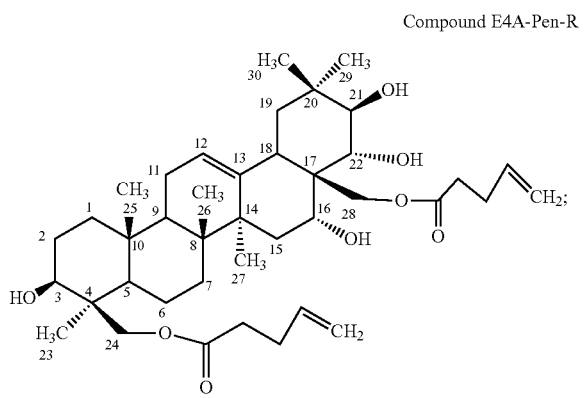
Compound E4A-Pen-S
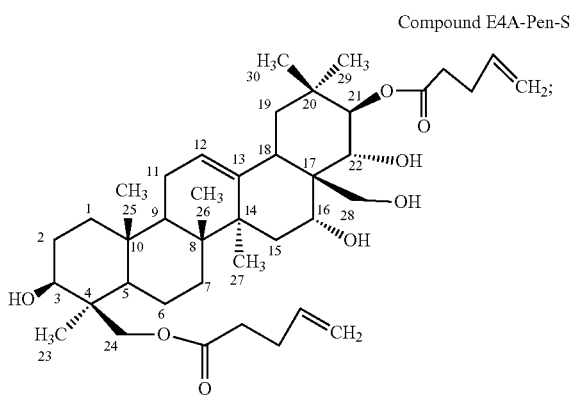
Compound E4A-Pen-V
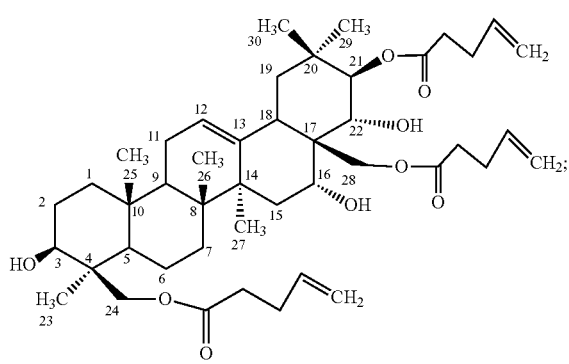
Compound E4A-Pen-T
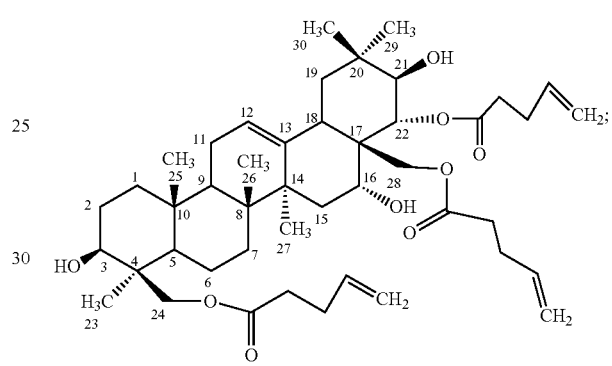
Compound E4A-Pen-N
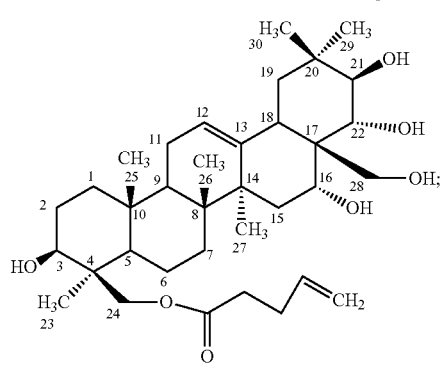
Compound E4A-Pen-U
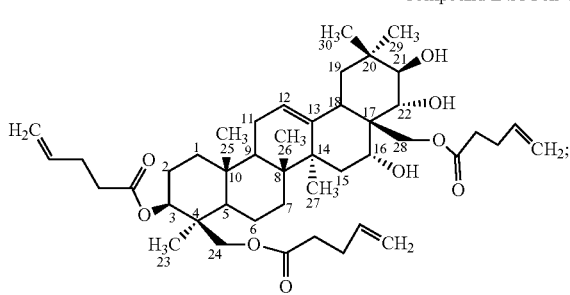
Compound E4A-Pen-Q
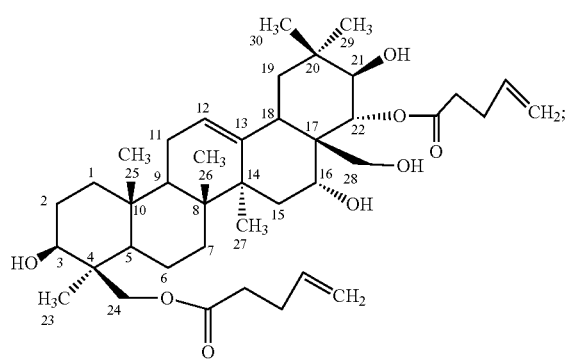
Compound E4A-Pen-R
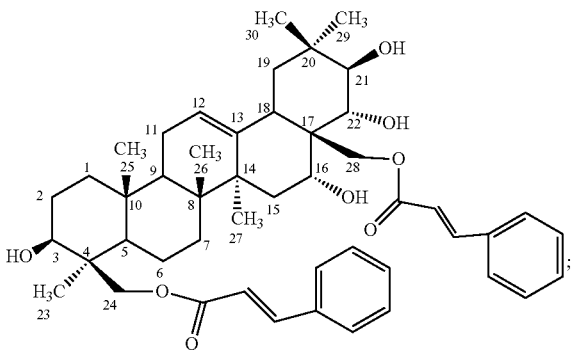

-continued

Compound E4A-Pen-V

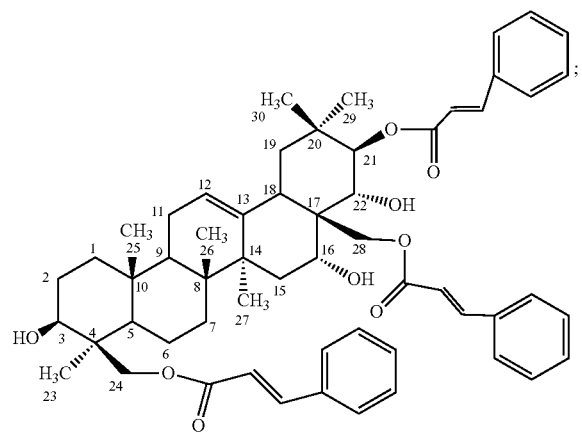

Compound E4A-Cin-N

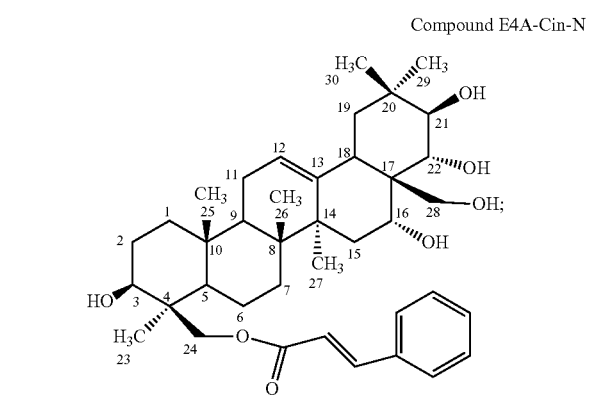

Compound E4A-Cin-Q

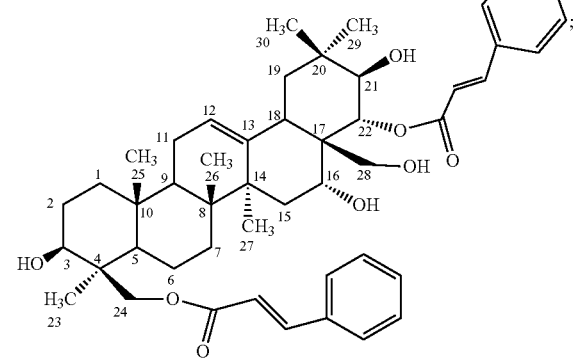

-continued

Compound E4A-Cin-S

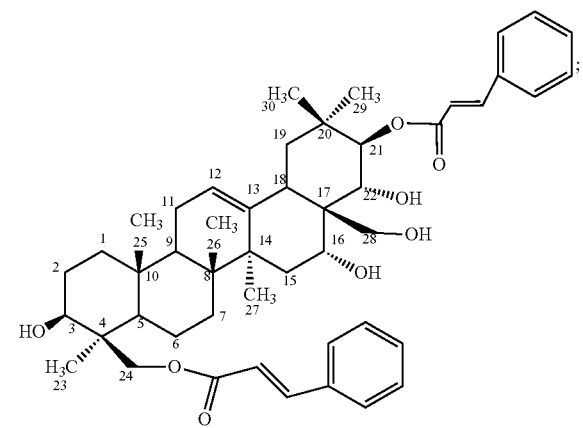

Compound E4A-Cin-T

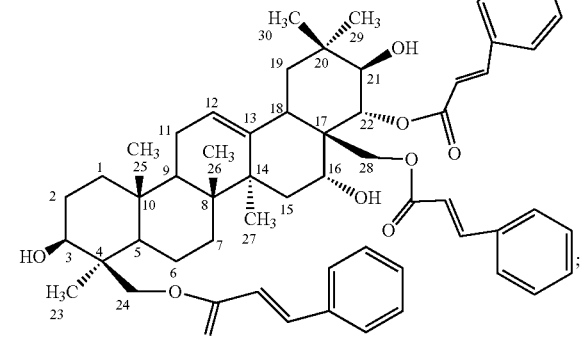

Compound E4A-Cin-U

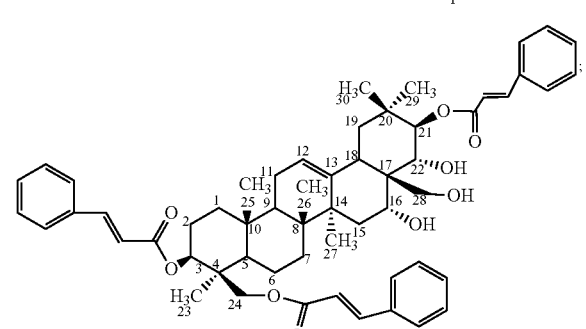

Experiment 16: Esterification of E4A-Tig-N with Senecioyl Chloride

Chemical synthesis of E4A-Tig-Sen-1: 1. Esterification of E4A-Tig-N with Senecioyl Chloride; 3. Isolation of E4A-Tig-Sen-1 with HPLC Cytotoxic activity determination: 1. MTT assay Chemical structure determination: 1. NMR analysis; 2. Mass Spectrum analysis

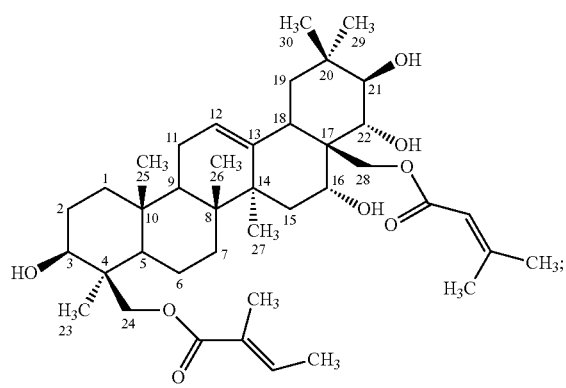

Experiment 17

Esterification of E4A-Tig-N with Angeloyl Chloride, Acetyl Chloride, Crotonoyl chloride, 3,3-Dimethylartyloyl chloride, senecioyl chloride, Cinnamoyl chloride, Pentenoyl chloride, Hexanoyl chloride, benzoyl chloride or Ethylbutyryl chloride; Isolation with HPLC; Cytotoxic activity determination; Chemical structure determination with the method of Experiment 8, gave the following compounds:

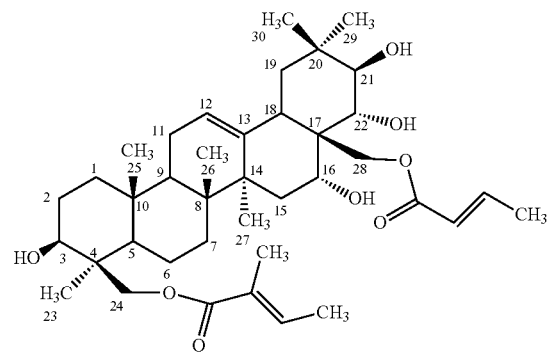

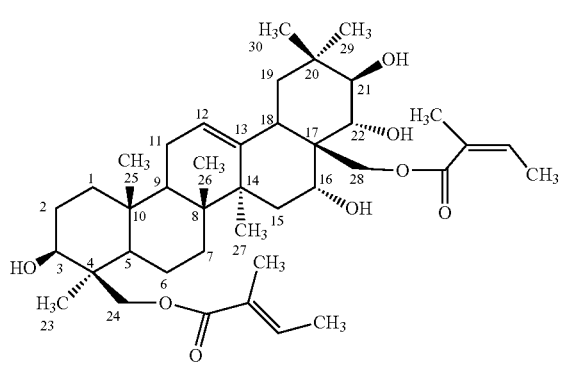

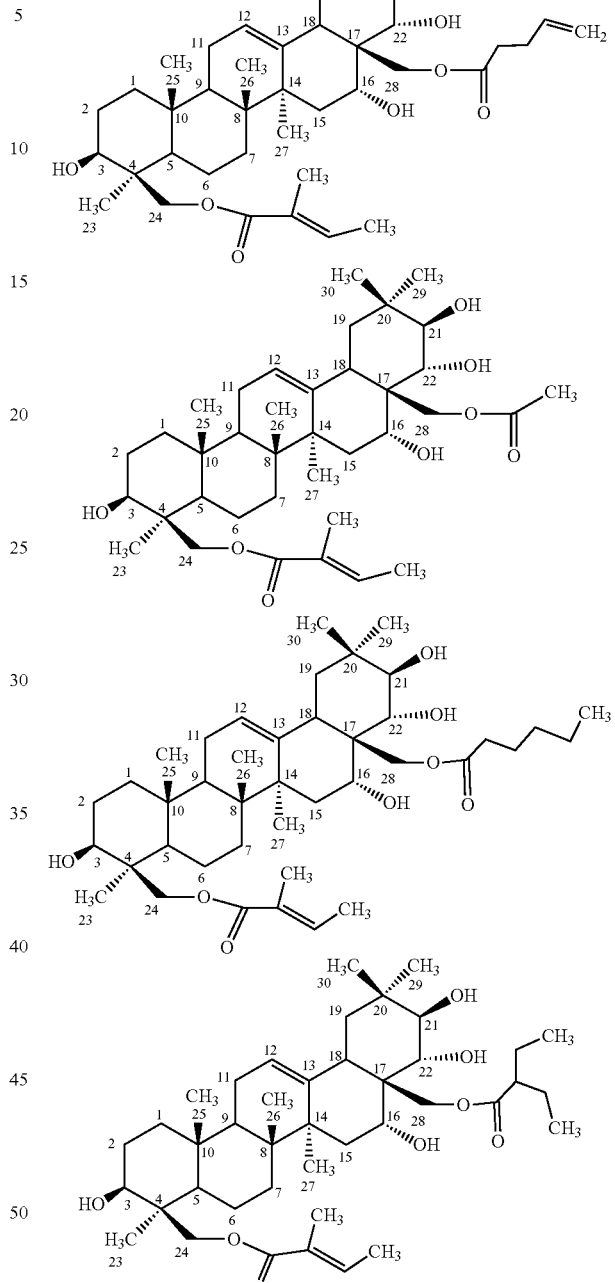

Experiment 18: Inhibition of Cell Adhesion

Methods and Results. ES2 or Hey8A cells were plated in T25 flasks with medium containing 5 ug/ml of compounds selected from structure (2A) including E4A-Tig-R, E4A-Tig-V, E4A-Tig-S, E4A-Tig-N, E4A-Tig-Q, E4A-Tig-T. Cultures were incubated for 5 hours. Attached cells were removed from flasks by trypsinization and the numbers/amounts were counted. Compare to no drug controls, 80 b 4% of ES2 cells and 60±4% of Hey8A cells were found attached to flasks under this condition. At 5 ug/ml of above compounds, over 90% of unattached cells are alive as determined by the trypan Blue exclusion assay and by their ability to re-attach to flasks when plating in medium without tested compounds. However, with 10 ug/ml tested compounds, less than 40% of cells attached to flasks and many of them are dead cells. This experiment shows that tested compounds inhibit cells adhesion process.

Experiment 19: Fibronectin Secretion Experiment

Western blot is applied in this invention as a method to detect the specific proteins in treated and untreated cells with compounds in this invention, wherein the cells are bladder, cervix, prostate, lung, breast, leukemia, colon, liver, bone, brain, Skin, ovary, Pancreas (Capan), Mouth (KB), Kidney.

Cells: targeted cells were grown in RPMI 1640 medium. 1.5 million cells were seeded in a T25 flask and grown for 24 hours before drug-treatment.

Drug-treatment: Cells cultures were replaced with fresh RPMI medium containing either 2.5 ul of DMSO (as control) [D]; or 10, 20, 30, 40, 80 ug/ml of tested compounds.

After 24 hours, aliquot of culture medium was taken out for Fibronectin determination (Western blot method).

Cell viability at 24 hours was determined by MTT assay. Cultures were replaced with RPMI medium (5 ml) with MTT and incubated for an hour. The formation of formazan was dissolved in 10 ml of DMSO and OD at 570 nm was measured (MTT units).

Western Blot: Spent culture medium was mixed with SDS sample buffer, boiled for 3 minutes before loading to SDS gel. Samples were applied to a 6-10% SDS gel and electrophoresis was conducted with 100 volts for 2 hours. Protein was transferred to a nitrocellulose membrane electrophoretically. The nitrocellulose blot was incubated with the first antibody and second antibody (AP conjugated, Promega S3721). The immuno-bands were developed with BCIP/NBT color development system.

Determination of Western blot band intensity: The band-images of Western blot were captured with a digital camera and the intensity of bands was determined using "Image J" software.

Results show that compounds of E4A-Tig-R, E4A-Tig-V, E4A-Tig-S, E4A-Tig-N, E4A-Tig-Q, E4A-Tig-T inhibit fibronectin secretion from 20-40%. in bladder, cervix, prostate, lung, breast, leukemia, colon, liver, bone, brain, Skin, ovary, Pancreas (Capan), Mouth (KB), Kidney.

Experiment 20: Esterification of E4A with Propionyl Chloride

Methods: 50 mg of E4A in 1 ml pyridine, stir gently in a 50 ml tube. Esterification was carried out at 25 C by adding 200 ul Propionyl chloride, and immediately withdrawn 200 ul from the mixture and added to 1 ml of 2N HCl. (ASAP sample). At 1, 2, 5, 10 and 60 minutes afterward; 200 ul of reaction mixture was similarly withdrawn and add to 1 ml of 2N HCl. Mixtures were sit at room-Temp over night. Extract the esterification products with 2 ml ethylacetate. Evaporate the ethylacetate. Dissolve the sample with DMSO (final concentration of 40 mg/ml). Fractionate the reaction products with HPLC (C18 column, 1 ml/min).

HPLC condition: Column: C18 (9.4×250 mm, 5 um); Solvents: 80% Acetonitrile—0.005% TFA; Gradient: isocratic; Flow-rate: 1 ml/min; O.D.: 207 nm, AT=1024; Chart speed: 0.1 cm/min; Run time: 120 min). MTT assay (Cytotoxicity determination) condition: Cells: ES2 (ovarian cancer). Cell density: plate10K cells per well over night before addition of drug. Drug incubation time: 2 days.

Experiment 21: Esterification of E4A with Isobutyryl Chloride

Methods: 52 mg of E4A in 1 ml pyridine, stir gently in a 50 ml tube. Esterification was carried out at 25° C. by adding 200 ul of isobutyryl chloride. 2 minute later, 4 ml 2N HCl was added to the reaction mixture. Mixtures were kept at room-Temp over night. Extract the esterification products with 5 ml ethyl acetate. Evaporate the ethyl acetate. Dissolve the sample with DMSO (final concentration of 40 mg/ml). Fractionate the reaction products with HPLC (C18 column).

HPLC condition: Column: C18 (9.4×250 mm, 5 um); Solvents: 80% Acetonitrile—0.005% TFA; Gradient: isocratic; Flow-rate: 1 ml/min; O.D.: 207 nm, AT=1024; Chart speed: 0.1 cm/min; Run time: 200 min.

MTT assay (Cytotoxicity determination) condition: Cells: ES2 (ovarian cancer); Cell density: plate1 OK cells per well over night before addition of drug; Drug incubation time: 2 days.

Experiment 22

Esterification of E4A with 3,3-Dimethylacryloly Chloride from Different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature and 0 C. Fractionate the reaction products with HPLC (C18 column). Cytotoxic activity is determined with MTT. Chemical structure determined with NMR.

Experiment 23

Esterification of E4A with Pentenoyl chloride—from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at Room temperature. Fractionate the reaction products with HPLC (C18 column). Cytotoxic activity is determined with MTT. Chemical structure determined with NMR.

Experiment 24

Esterification of E4A with Hexanoly chloride from different times of esterification reaction. Reaction products obtained from each time of reaction (5 sec, 1 min, 2 min, 5 min, and 10 min) were fractionated by HPLC. The profile is plotted according to HPLC elution time and optical density of fractions. Reaction was performed at 0 C. Fractionate the reaction products with HPLC (C18 column). Cytotoxic activity is determined with MTT. Chemical structure determined with NMR.

Experiment 25

Esterification of E4A with Acetyl chloride (H) from different times of esterification reaction. Reaction products obtained from each time of reaction (1 min, 2 min, 5 min and 10 min) were fractionated by HPLC. The profile is plotted according to HPLC elution time and optical density of fractions. Reaction was performed at Room temperature.

Fractionate the reaction products with HPLC (C18 column). Cytotoxic activity is determined with MTT. Chemical structure determined with NMR.

Experiment 26

Esterification products of E4A with Crotonoyl chloride (I) from different times of esterification reaction. Reaction products obtained from each time of reaction (5 sec, 1 min, 2 min, 5 min and 10 min) were fractionated by HPLC. The profile is plotted according to HPLC elution time and optical density of fractions. Reaction was performed at Room temperature. Fractionate the reaction products with HPLC (C18 column). Cytotoxic activity is determined with MTT. Chemical structure determined with NMR.

Experiment 27

Esterification products of E4A with Cinnamoyl chloride (J) from different times of esterification reaction. Reaction products obtained from each time of reaction (1 min, 1 hour, 2 hours, 18 hours, 18 hours (heat)) were fractionated by HPLC. The profile is plotted according to HPLC elution time and optical density of fractions. Reaction was performed at Room temperature and 75 C. Fractionate the reaction products with HPLC (C18 column). Cytotoxic activity is determined with MTT. Chemical structure determined with NMR.

Experiment 28

Esterification products of E4A with pentenoyl, hexanoyl, benzoyl, ethylbutyryl, propionyl, 2-propenoyl, isobutyryl, butyryl, (2E)-2-pentenoyl, 4-Pentenoyl, 5-hexenoyl, heptanoyl, octanoyl, nonanoyl, decanoyl, Lauroyl, myristoyl, from different times of esterification reaction. Reaction products obtained from each time of reaction were fractionated by HPLC. The profile is plotted according to HPLC elution time and optical density of fractions. Fractionate the reaction products with HPLC (C18 column). Cytotoxic activity is determined with MTT. Chemical structure determined with NMR.

Experiment 29

Esterification products of E4A with propanoyl, propenoyl, butanoyl, butenoyl, pentanoyl, hexenoyl, heptanoyl, heptenoyl, octanoyl, octenoyl, nonanoyl, nonenoyl, decanoyl, decenoyl, propionyl, 2-propenoyl, 2-butenoyl, Isobutyryl, 2-methylpropanoyl, 2-ethylbutyryl, ethylbutanoyl, 2-ethylbutanoyl, butyryl, (E)-2,3-Dimethylacryloyl, (E)-2-Methylcrotonoyl, 3-cis-Methyl-methacryloyl, 3-Methyl-2-butenoyl, 3-Methylcrotonoyl, 4-Pentenoyl, (2E)-2-pentenoyl, Caproyl, 5-Hexenoyl, Capryloyl, Lauroyl, Dodecanoyl, Myristoyl, Tetradecanoyl, Oleoyl from different times of esterification reaction. Reaction products obtained from each time of reaction were fractionated by HPLC. The profile is plotted according to HPLC elution time and optical density of fractions. Fractionate the reaction products with HPLC (C18 column). Cytotoxic activity is determined with MTT. Chemical structure determined with NMR.

Experiment 30

A comparison of non-cancerous with cancer cells:
Method: A. Cells
  W138 is a Normal Lung fibroblast. Cells were grew in MEM medium supplemented with 10% FCS, antibiotics and glutamine. 20K cells were seeded per well (96-welled plate) for one day before drug-treatment
  ES2 is a Ovary Clear cells carcinoma. Cells were grew in RPMI-1640 medium supplemented with 10% FCS, antibiotics and glutamine. 1 OK cells were seeded per well (96-welled plate) for one day before drug-treatment.
B. Drug treatment:
  Drug: Tig-S. stored as 1000× stock solution in DMSO.
  Drug concentration used: from 0.15-20 ug/ml.
  Drug-treatment was carried out for 2 days (ES2) or 6 days (W138). For the 6 days incubation, cells were fed with fresh medium (with drug) on day 3 and 5.
C. At the end of the drug-treatment, cytotoxic test was performed with MTT assay.
Conclusion:
  For comparison between cancer cells (ES2) and non-cancerous cells (W138), it is found that:
  1. the $IC_{50}$ for ES2 cells (0.3 ug/ml) is lower than those of W138 cells (1.5 ug/ml), and
  2. The $IC_{100}$ for ES2 cells (0.15-0.3 ug/ml) is lower than those of W138 cells (10 ug/ml)
  3. With 10 ug/ml of Tig-S, about 90% of ES2 cells died while only 10% of W138 cells died after the drug-treatment.
  Based on these studies, it is concluded that the fast growing tumor cells (ES2) are more sensitive to Tig-S than the slow growing normal cells (W138).

Experiment 31: Inhibition of Cell Cycling

1. Method: Cells: Human leukemia cells K562 cultured in RPM11640 medium.
2. Drug: compound from present application or Tig-S (1000× stock solution in DMSO).
3. Start cells concentration: 500000/ml.
4. Cells were cultured with drug (O-20 ug/ml) for total of three days.
5. Cells were harvested by centrifugation (136×g, 6 minutes); fixed with 70% ethanol and kept in −20 C before staining.
6. Staining: Fixed cells were stained with Propidium iodide/RNase A/0.1% Triton X-100 in PBS.
7. Flow Cytometry Analysis was performed in Baylor Core Facility with a LSRII instrument.
8. Analysis: Single cell was gated and cell count—FL2-Area histogram were plotted.
9. Cell distribution in different cell-cycle phases (G0/G1, S, G2/M) was analyzed.

Reseults: Cells with no drug, or with 0.15 ug/ml and 0.3 ug/ml of Tig-S, have a similar (same) cell distribution in the G0/G1, S and G2/M phases of cell-cycle. With higher Tig-S concentrations, starting from 0.6 ug/ml, the cells in G2/M phase decrease. The decrease of G2/M cells correlated with higher drug concentrations (up to 20 ug/ml). These results indicate that drug-treated cells were arrested in the S-phase and unable to enter into the G2/M phase of the cell cycle.

Conclusion: The drug-effect of Tig-S on human leukemia K562 cells is arresting cells in the S-phase and blocking their entering into the G2/M phase of cell cycle. The Compound Tig-S block the DNA synthesis of cancer cell.

Experiment 32: Inhibition of H460 Cells Growth with Tig-S

Methods:

A. Cells

H460 cells are derived from a Human Lung large cell carcinoma. Cells were grew in RPMI 1640 medium supplemented with 10% FCS, antibiotics and glutamine. 5000 cells were seeded in a well (96-welled plate) for one day before drug-treatment B. Drug treatment:

Drug: Tig-S (stored as a 1000× stock solution in DMSO) was used.

Drug concentration used: from 0.15-20 ug/ml.

Drug-treatment was carried out for 1, 2 and 4 days. For the 4 days incubation, cells were fed with fresh medium (with drug) on day 2.

C. At the end of the drug-treatment, cytotoxic test was performed with MTT assay.

Results:

1. Tig-S inhibits H460 cells' growth with the IC50 of drug 3 ug/ml.
2. Minimum cells growth inhibition was observed beyond drug 5 ug/ml.
3. No dead cell was found at drug concentration in 20 ug/ml.

The results indicate that Tig-S inhibits the H460 cell's growth, but is not killing cells at high concentrations. Therefore, Tig-S is an effective drug for inhibition of cancer growth but has low toxicity.

Experiment 33: Inhibition of Human Leukemia K562 Cells by Tig-S

Method:

1. Cells: Human leukemia cells K562 in RPM11640 medium.
2. Drug: Tig-S (1000× stock solution in DMSO).
3. Start cells concentration: 50×10K per ml (500000/ml).
4. Cells were cultured with or without drug for total of four days.
5. Cell number is doubled after 2 days of incubation. Fresh medium (equal volume, with or without drug) was then added to culture.
6. Cells were counted every day.

Conclusion:

Tig-S inhibits Leukemia K562 cells growth with IC50 about 0.6 ug/ml.

No grow (IC100) was observed beginning on day 2 at 2.5 ug/ml or higher.

Experiment 34: Apoptosis in K562 Cells Induced by Tig-S

Figure 19:
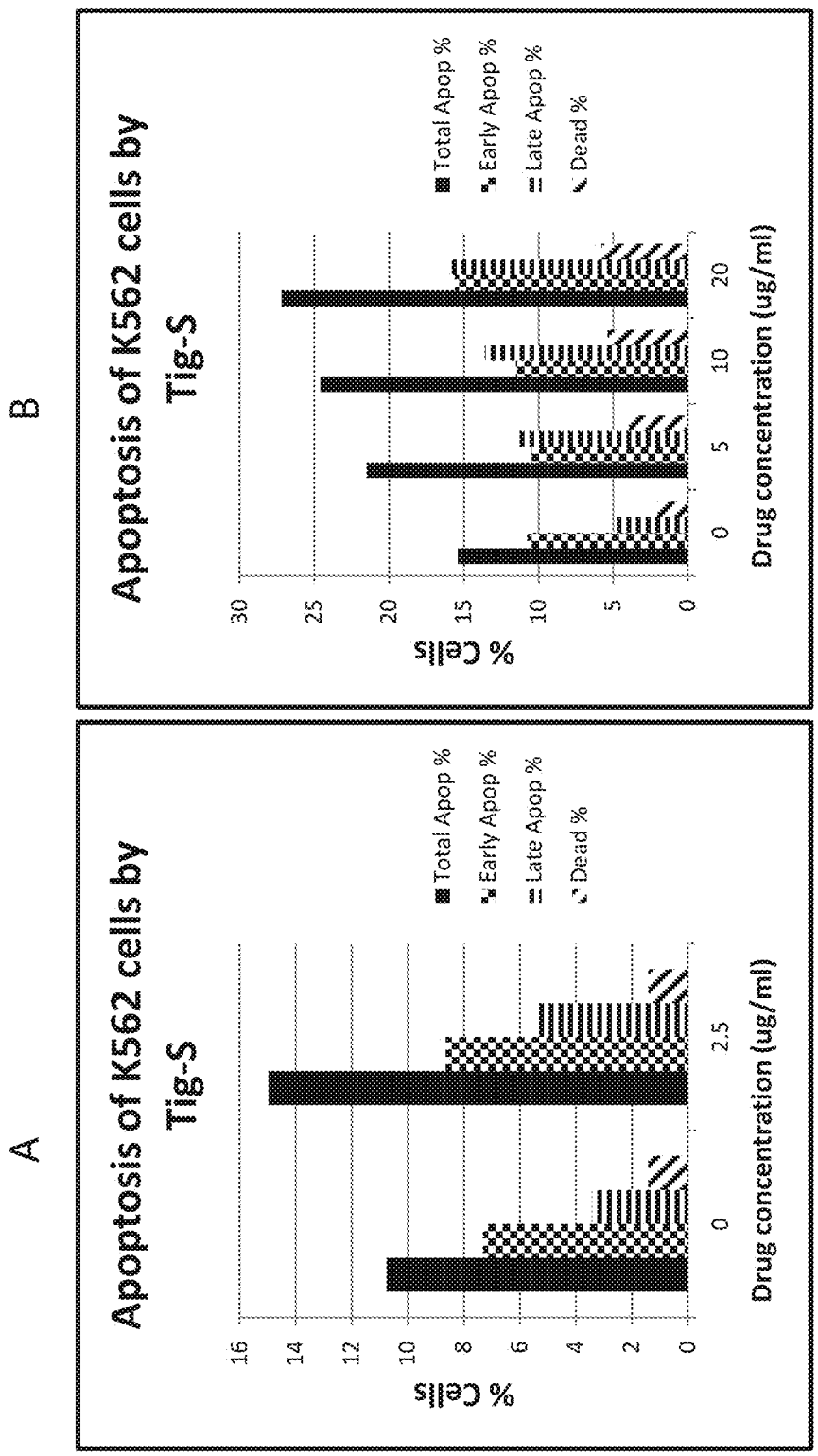
FIG. 19. Tig-S induces cell-death by the apoptosis mechanism.
Figure 20:
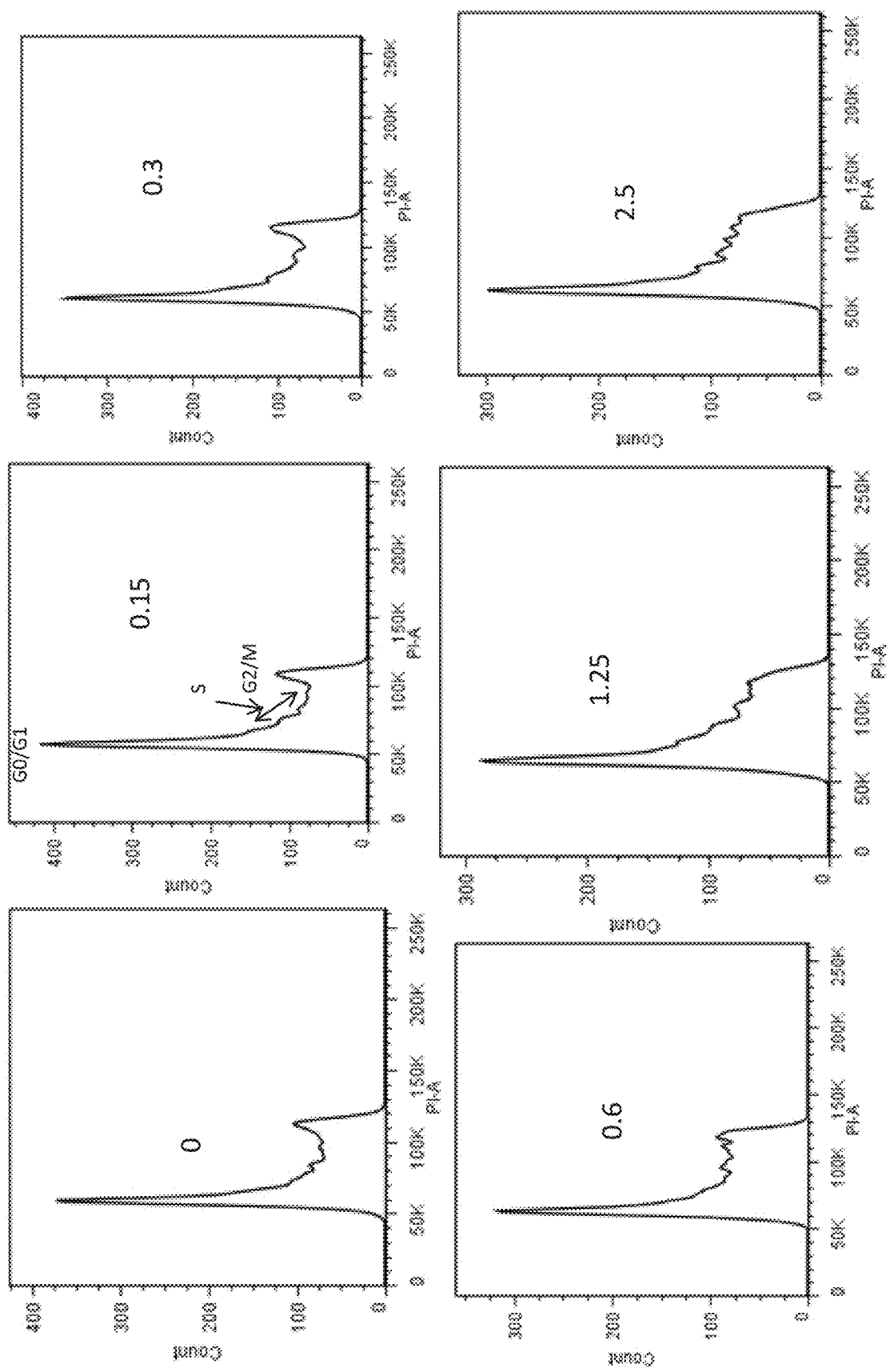
FIG. 20-21. Leukemia K562 cells were treated with Tig-S for three days; The number inside charts is the Tig-S concentration in ug/ml; The first peak is the intensity of G0/G1 cells. The last peak is the G2/M cells. Between these two peaks represents the intensity of S-phase cells.
Figure 21:
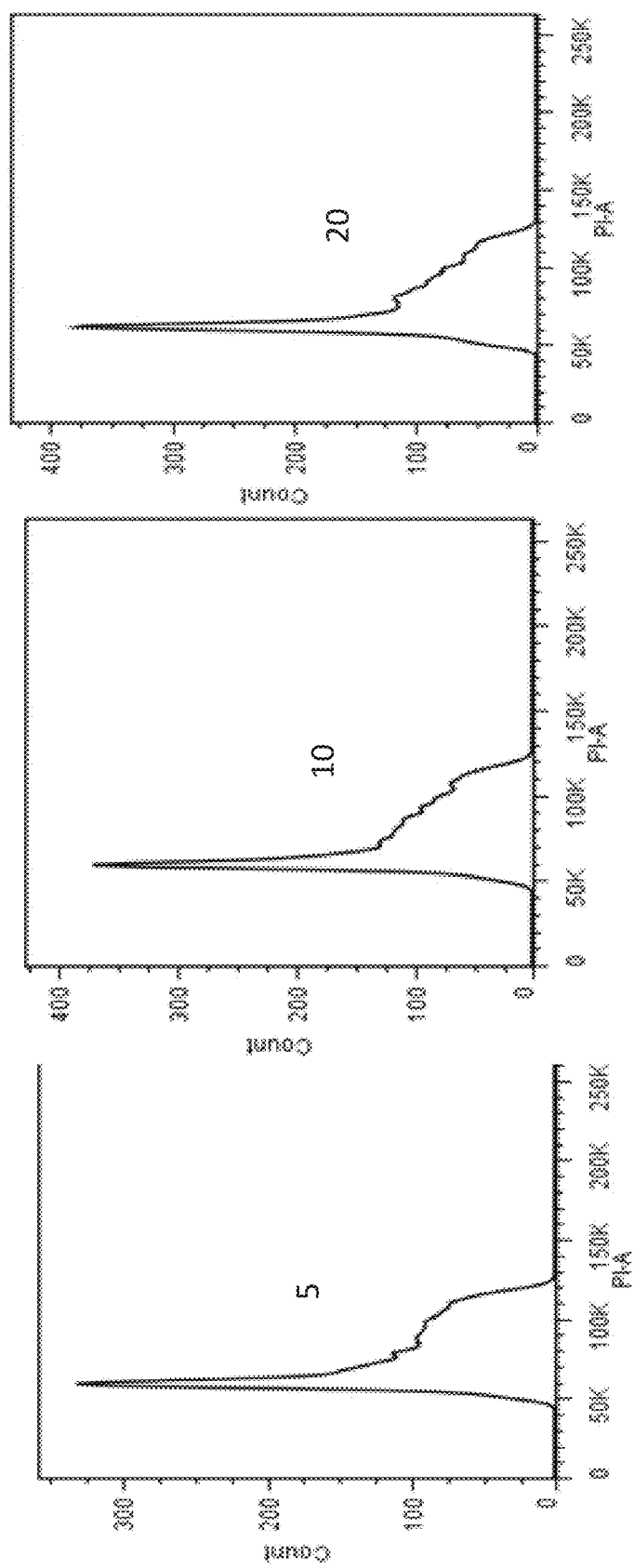

1. Cells: Human leukemia cells K562 cultured in RPM11640 medium.
2. Drug: Tig-S (1000× stock solution in DMSO).
3. Start cells concentration: 500000/ml.
4. Cells were cultured with drug (0-20 ug/ml) for Two days.
5. Collect cells from culture (1-4 million) by centrifugation (136×g for 5 min. remove supernatant).
6. Wash cells with 1 ml of cold PBS, collect cells by centrifugation (136×g, 5 min, remove supernatant).
7. Re-suspend cells in 200 ul Binding buffer (10 mM HEPES, 140 mM NaCl, 2.5 mM CaCl2, pH 7.4).
8. Stained cells by adding 10 ul Annexin V (Alexa Fluor 488, Invitrogen cat # A13201), and 2 ul Propidium iodide (1 mg/ml in water) to cell suspension. Mix.
9. Sit at Room temperature for 15 min.
10. Wash cells with 1 ml binding buffer. Collect cells by centrifugation.
11. Re-suspend cells with in 1 ml of binding buffer for analysis by flow cytometry.
12. Flow Cytometry analysis was performed in Baylor Core Facility with a LSRII instrument.
13. Analysis: Control cells stained with PI or Annexin V-488 (Annexin V-FITC) alone were served as references. About 50000 cells were analyzed for each sample.
14. Cell distribution in following groups: live, early apoptosis, late-apoptosis, total apoptosis and dead cells were determined.
15. The percentage of cells in these groups is presented in the FIG. 19.

Results:

The background apoptosis level of K562 cells (no-drug control) is about 10-15%.

After drug-treatment with Tig-S, the apoptotic cells population increased (from 15% to 27%) with increased drug concentration (from 2.5 ug/ml to 20 ug/ml).

Similarly, the dead cell population was also increase with the drug concentration.

Conclusion:

Tig-S induces cell-death by the apoptosis mechanism (not necrosis mechanism).

Experiment 35: The Haemolytic Assay

Erythrocytes (RBC) were isolated from human blood (EDTA whole blood, collected randomly). 50 ul of the 10% RBC suspension (in PBS) was added to 2 ml of sample solutions (concentration range from 0.1 ug/ml to 400 ug/ml) in PBS. The mixture was vortexed briefly and sat for 60 min at room temperature. The mixture was spun at 3K for 10 min and the relative amounts of lysed hemoglobin in the supernatant were measured at 540 nm. The synthetic compounds of present application were tested with this method.

Experiment 36: Animals Experiments

Methods

Athymic Nu/Nu mice are divided into two groups (A, and B).

On day 0, mice of group A and B were transplanted intra-peritoneally (i.p.) with ES2 (human ovarian cancer) cells.

On day 1 to 5, mice from A group received daily administration of 127 solvent by i.p. route.

On days 1 to 5, mice from B group received daily drug administration (tested drug Tig-S in 127 solvent) by i.p. route at dose of 100 mg/kg, twice daily.

Figure 22:
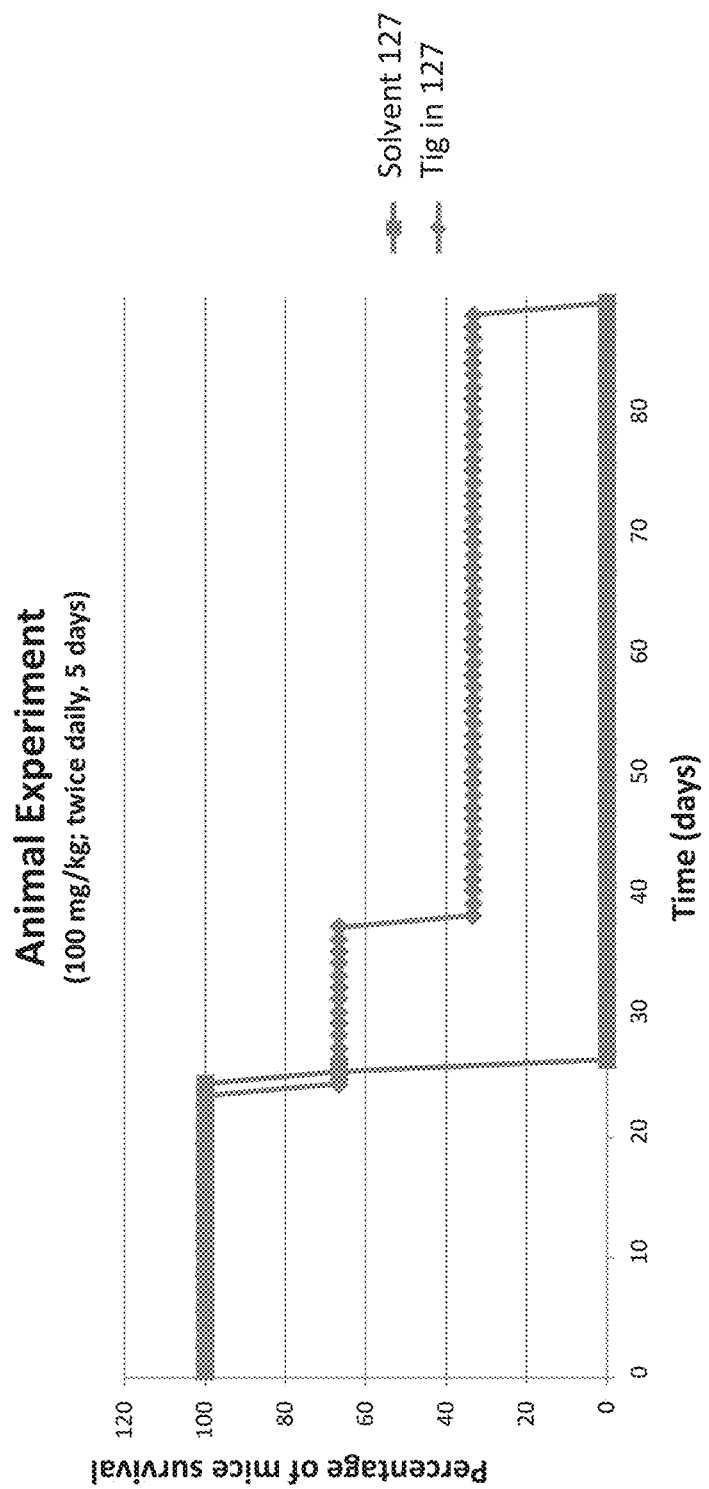
FIG. 22. Animal study result shows Group A Mice—Implanted tumor and no drug, Died on day 27; Group B Mice—Implanted tumor and with (Tig-S) drug 100 mg/kg, twice daily, 5 days.

Result in FIG. 22

Experiment 37: Animals Experiments

Methods

Athymic Nu/Nu mice are divided into two groups (A, and B).

On day 0, mice of group A and B were transplanted intra-peritoneally (i.p.) with ES2 (human ovarian cancer) cells.

On day 1 to 5, mice from A group received daily administration of 127 solvent by i.p. route.

On days 1 to 5, mice from B group received daily drug administration (tested drug Tig-R in 127 solvent) by i.p. route at dose of 100 mg/kg, twice daily.

Figure 23:
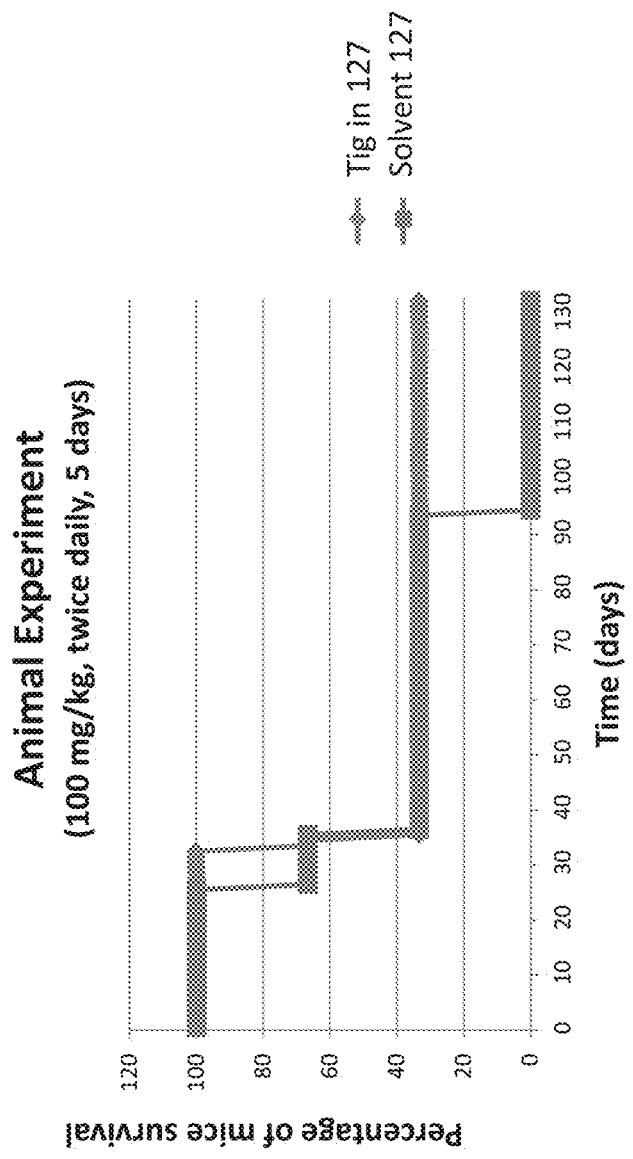
FIG. 23. Animal study result shows Group A Mice—Implanted tumor and no drug; Group B Mice—Implanted tumor and with (Tig-R) drug 100 mg/kg, twice daily, 5 days.

Result in FIG. 23

Experiment 38: Animals Experiments

Methods

Athymic Nu/Nu mice are divided into two groups (A, and B).

On day 0, mice of group A and B were transplanted intra-peritoneally (i.p.) with ES2 (human ovarian cancer) cells.

On day 1 to 5, mice from A group received daily administration of 127 solvent by i.p. route.

On days 1 to 10, mice from B group received daily drug administration (tested drug Tig-V in 127 solvent) by i.p. route at dose of 50 mg/kg, twice daily.

Figure 24:
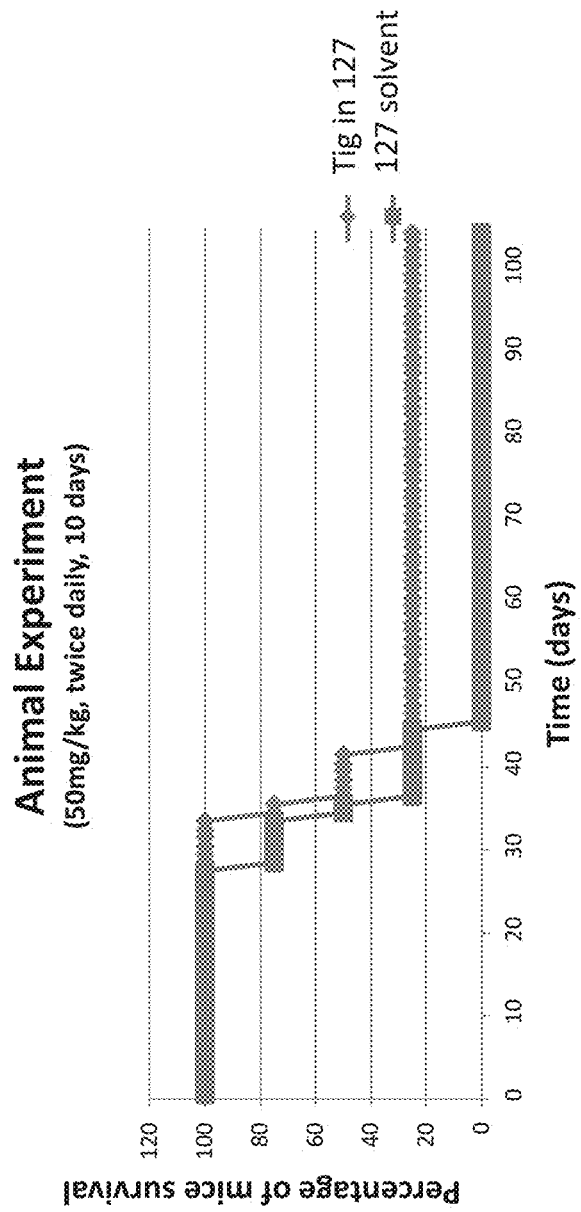
FIG. 24. Animal study result shows Group A Mice—Implanted tumor and no drug; Group B Mice—Implanted tumor and with (Tig-V) drug 50 mg/kg, twice daily, 10 days.
Figure 25:
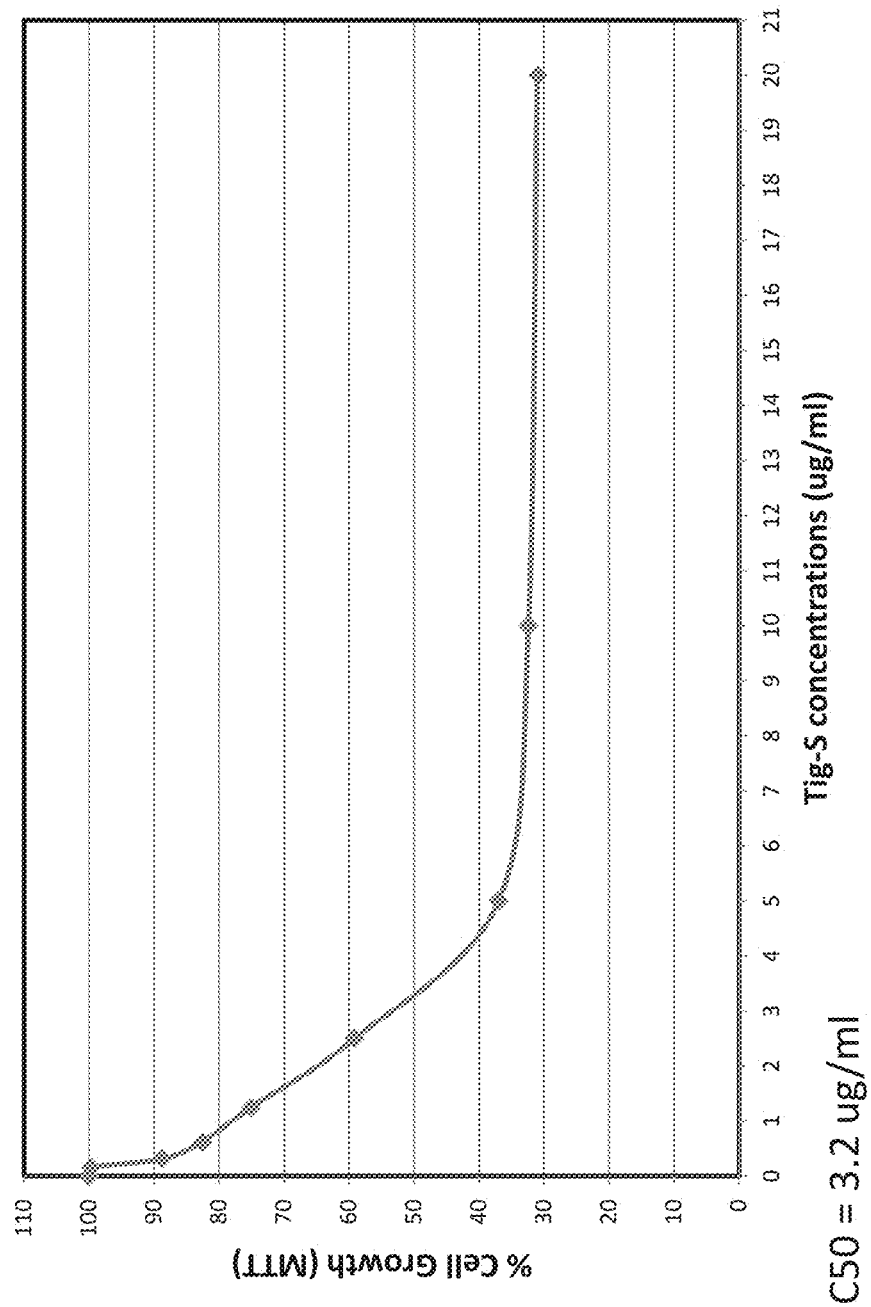
FIG. 25. Inhibition of lung H460 cells growth with Tig-S for one day. IC50=3.4 ug/ml FIG. 26. Inhibition of lung H460 cells growth with Tig-S for 4 days. IC50=3 ug/ml FIG. 27. Inhibition of Leukemia K562 cells by Tig-S: Tig-S inhibits Leukemia K562 cells growth with IC50 about 0.6 ug/ml. No grow (IC100) was observed beginning on day 2 at 2.5 ug/ml or higher.
Figure 26:
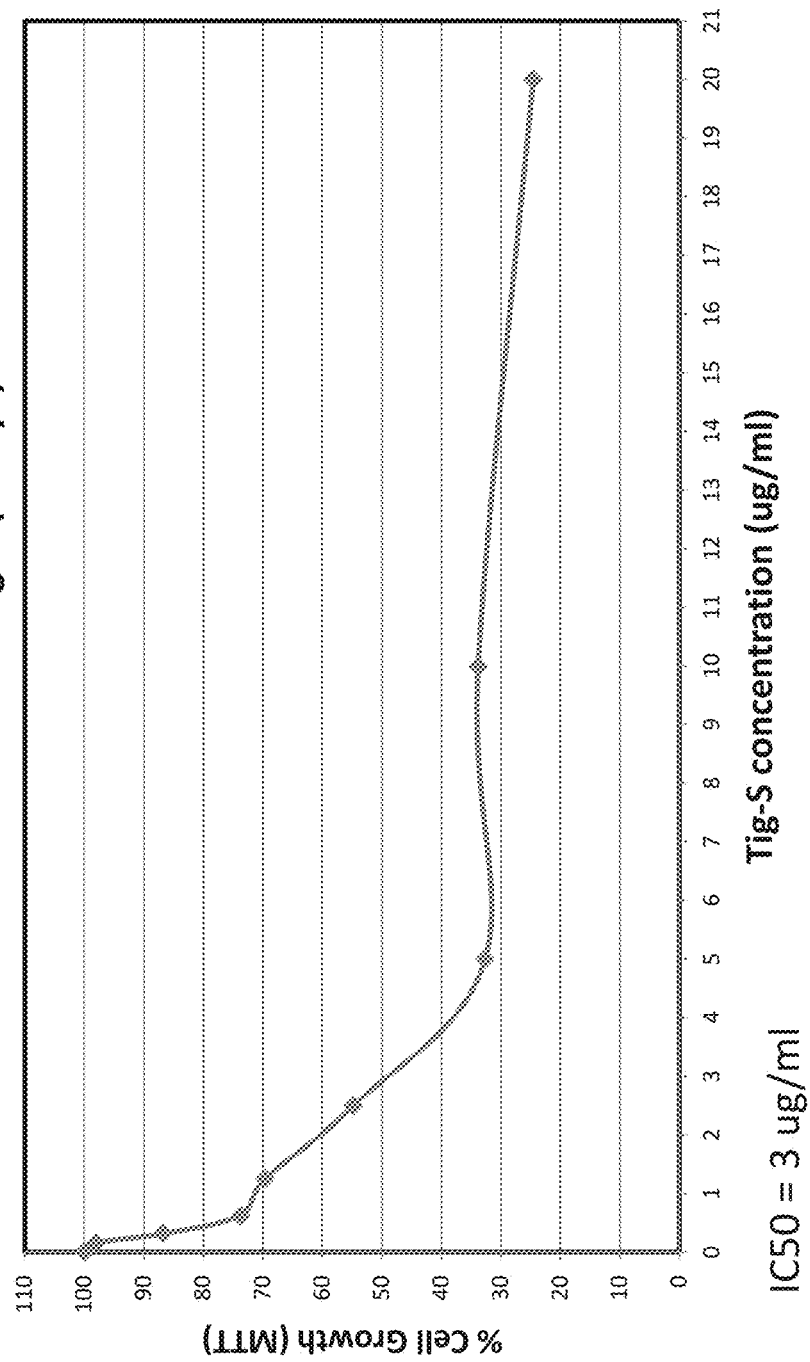
Figure 27:
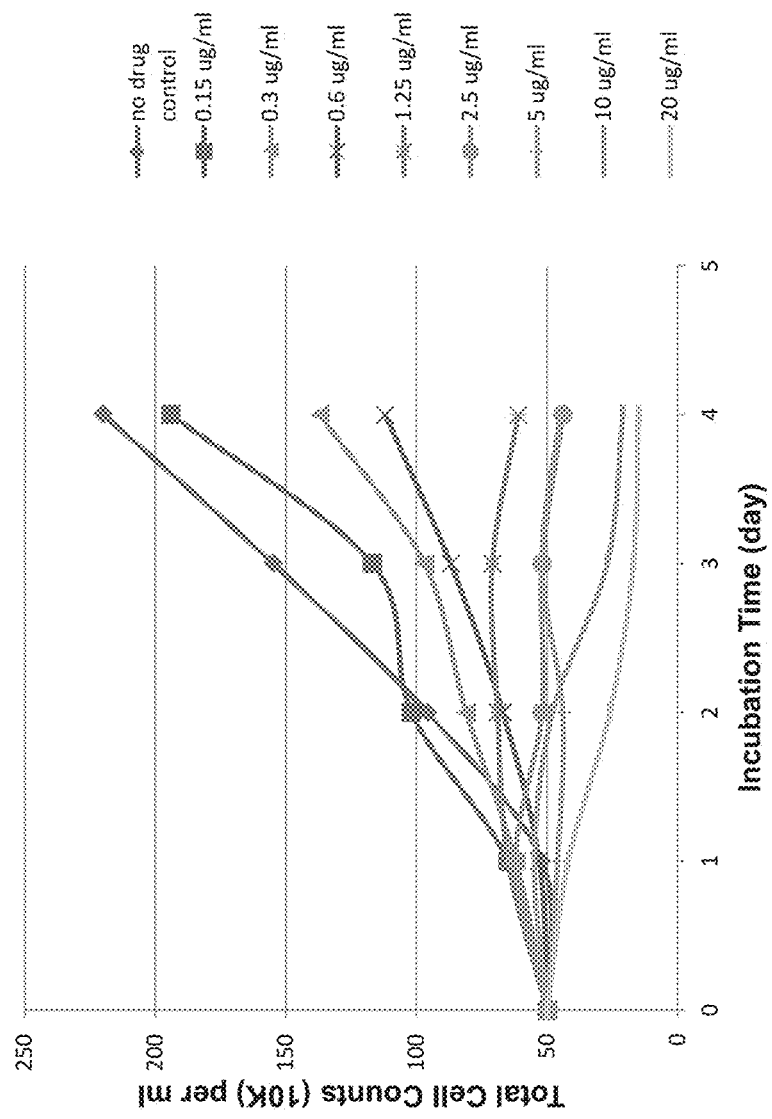
Figure 28:
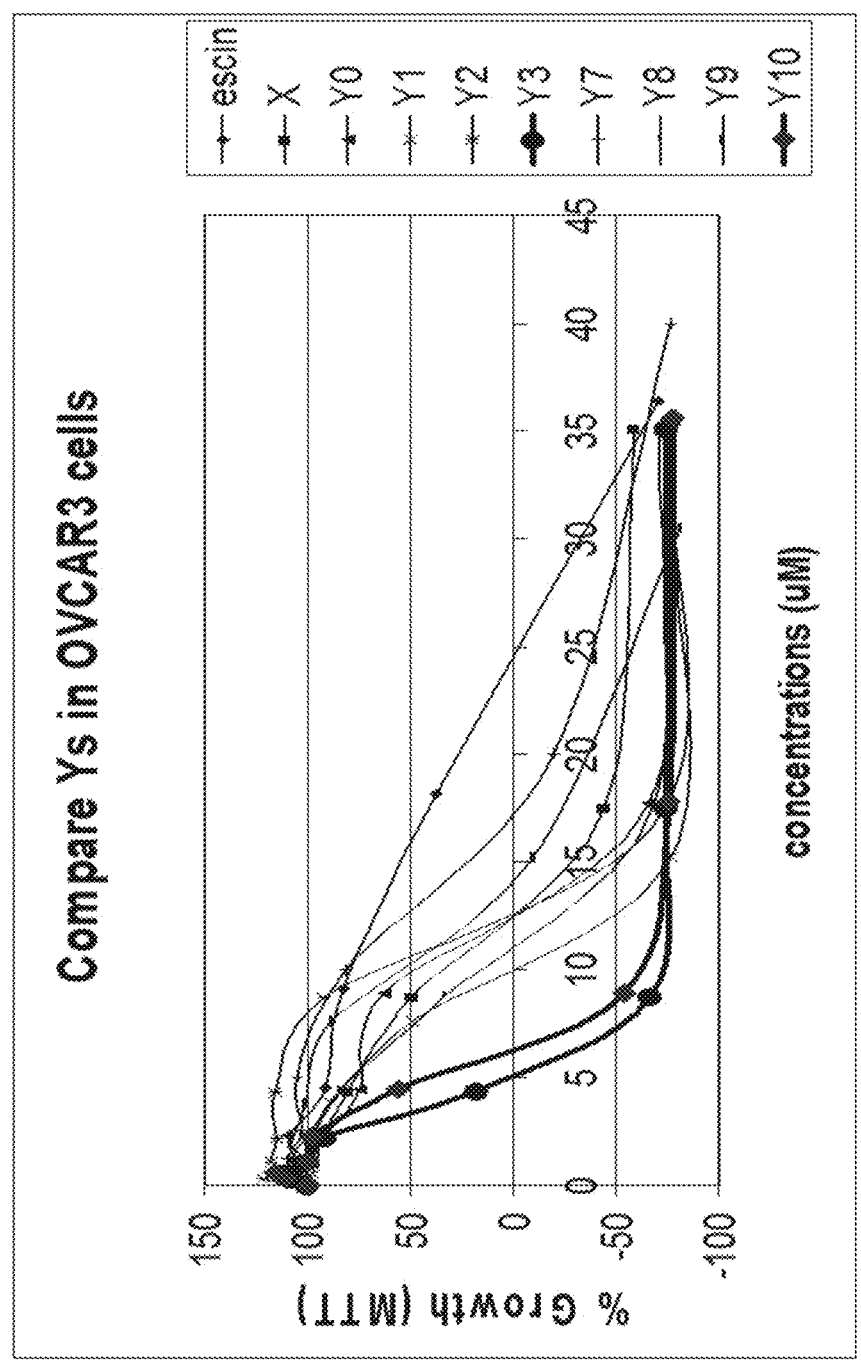
FIG. 28. Inhibition of cancer OVCAR3 cells by natural compounds escin, X, Y0, Y1, Y2, Y3, Y7, Y8, Y9, Y10
Figure 29:
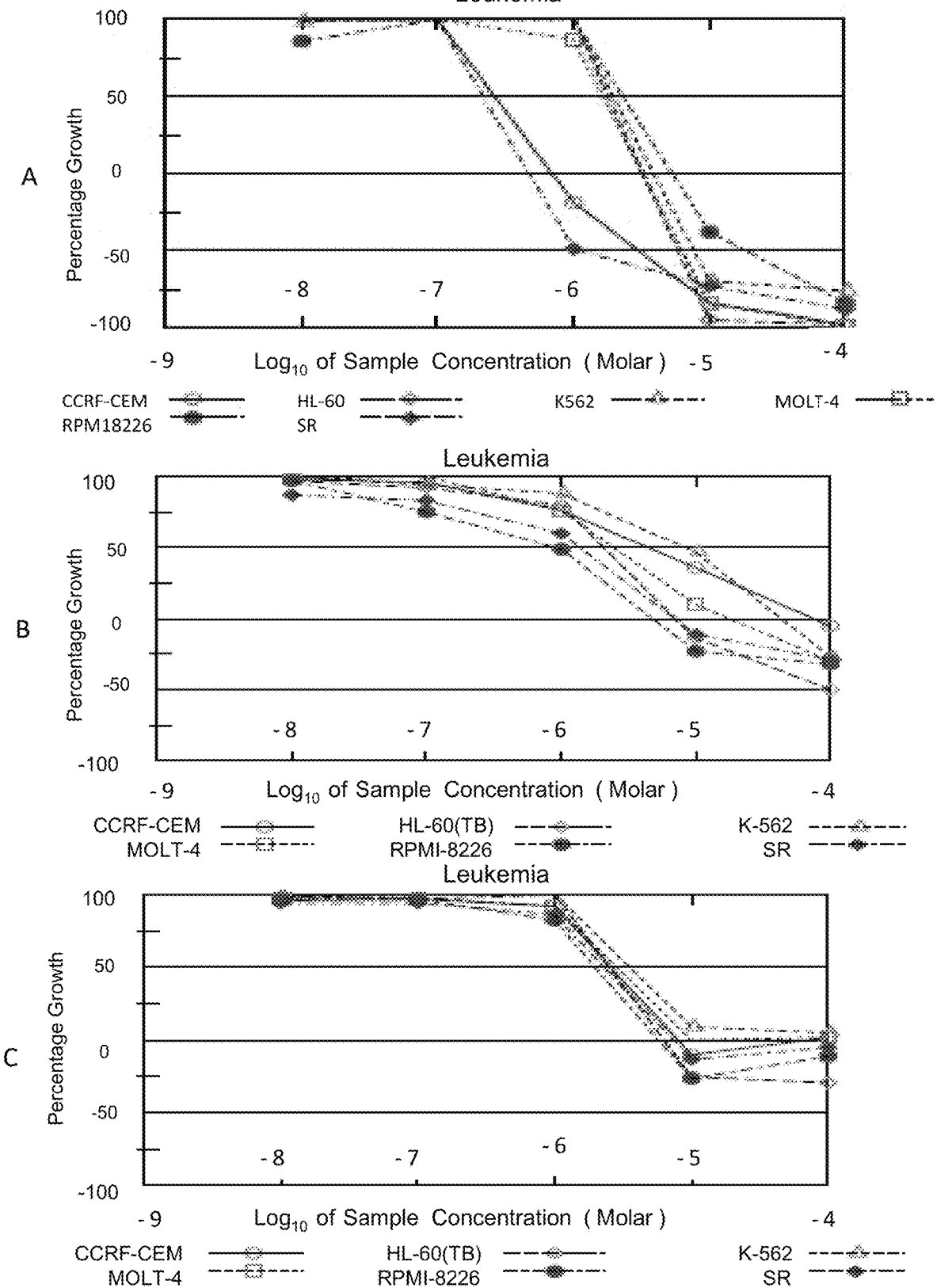
FIG. 29. Compare the activities of natural compound Y and synthetic compound Tig-S and Tig-R with leukemia cancer. The synthetic compounds increase the potency and decrease the toxicity. A: Natural compound; B: synthetic compound Tig-S; C: synthetic compound Tig-R.
Figure 31:
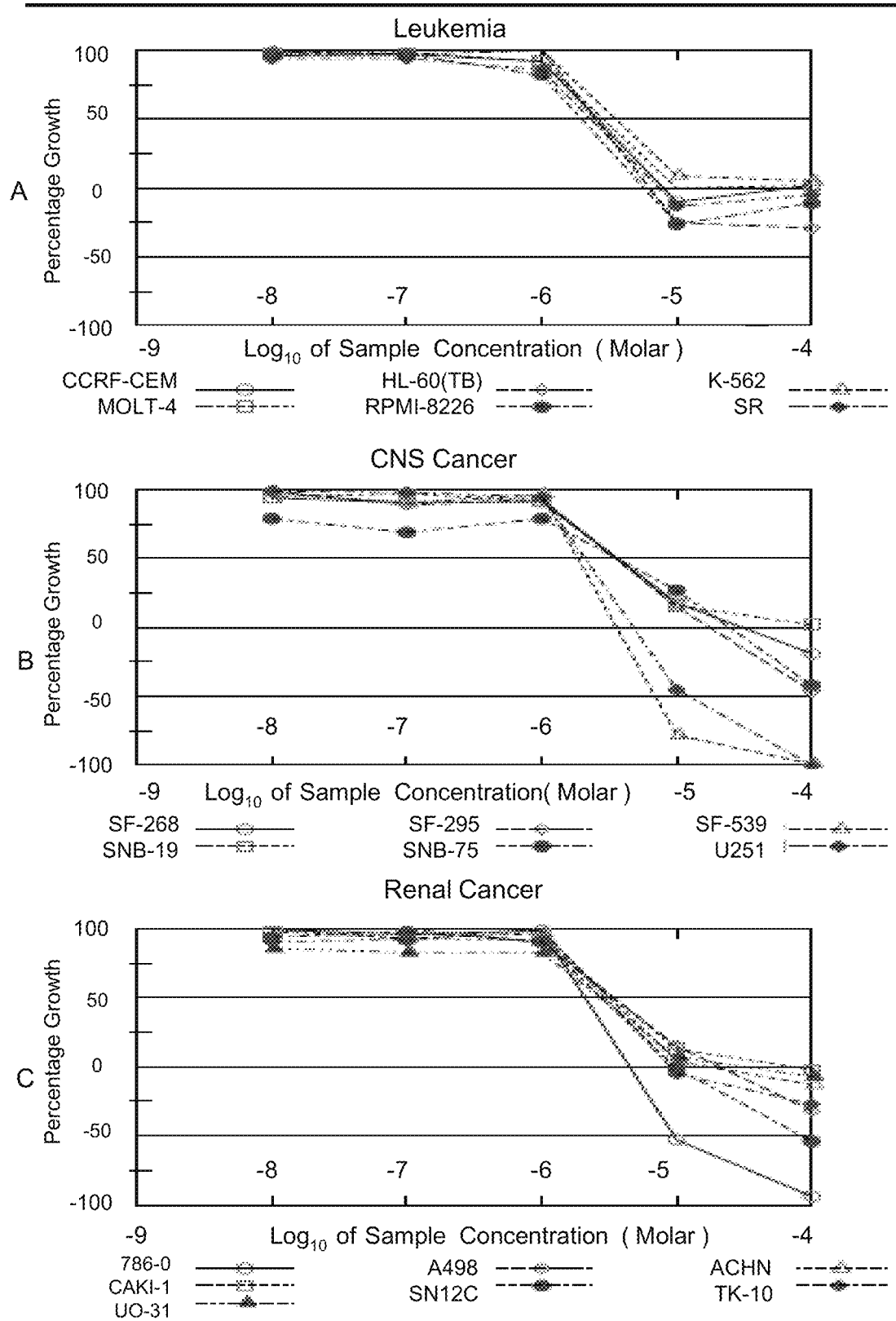
Figure 33:
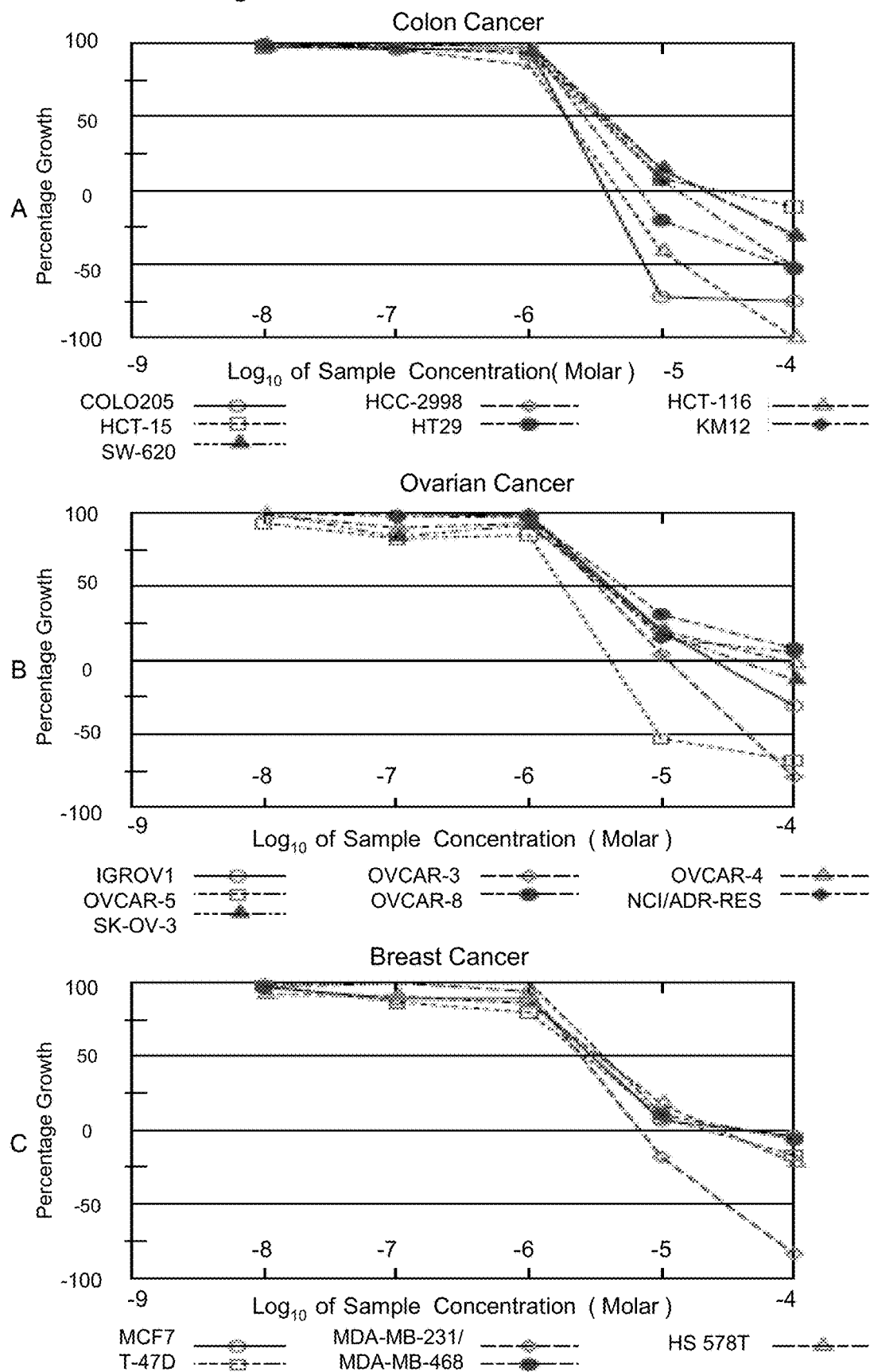
Figure 34:
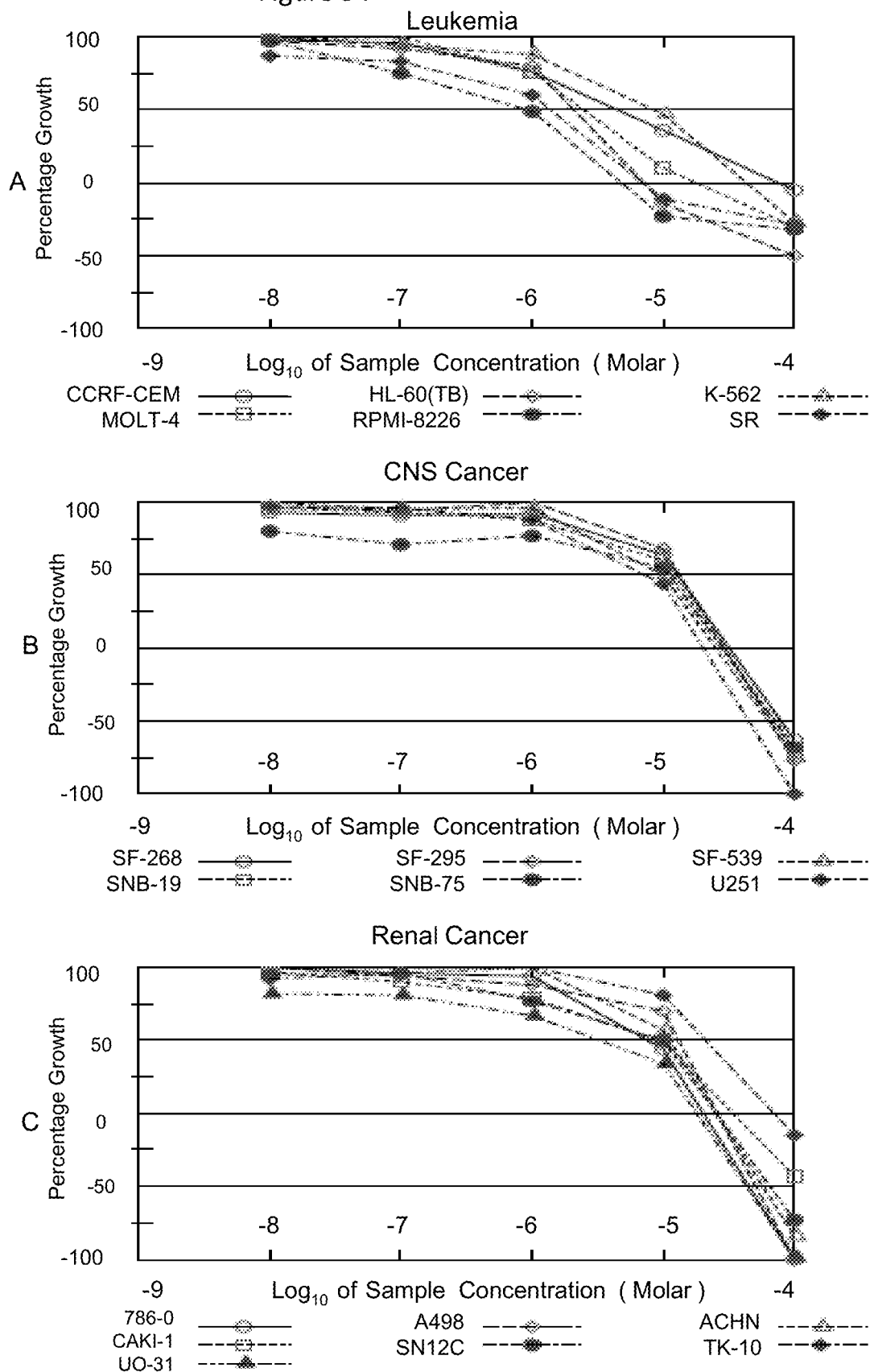
FIG. 34-36. Drug-effects of Tig-S
Figure 35:
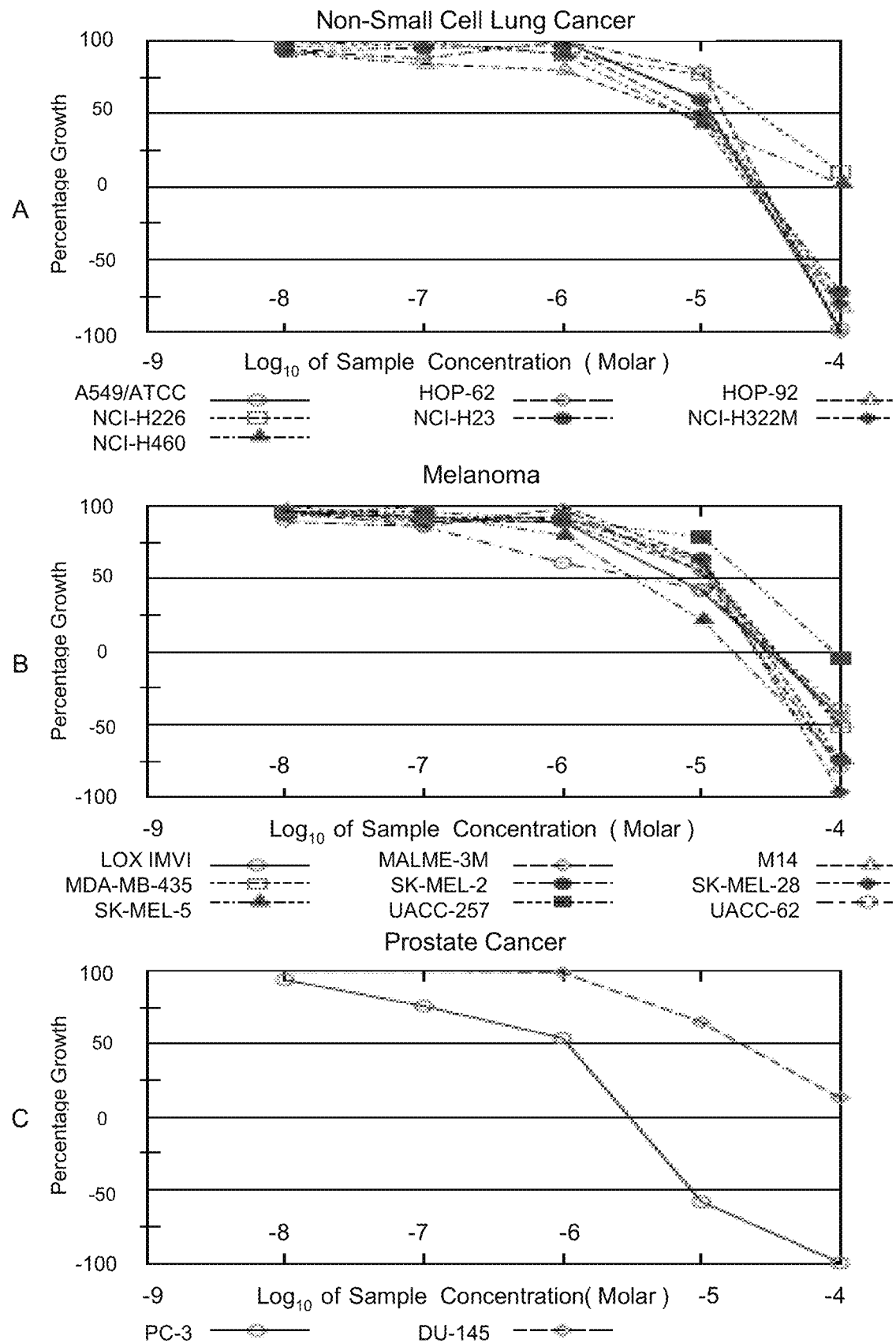
Figure 36:
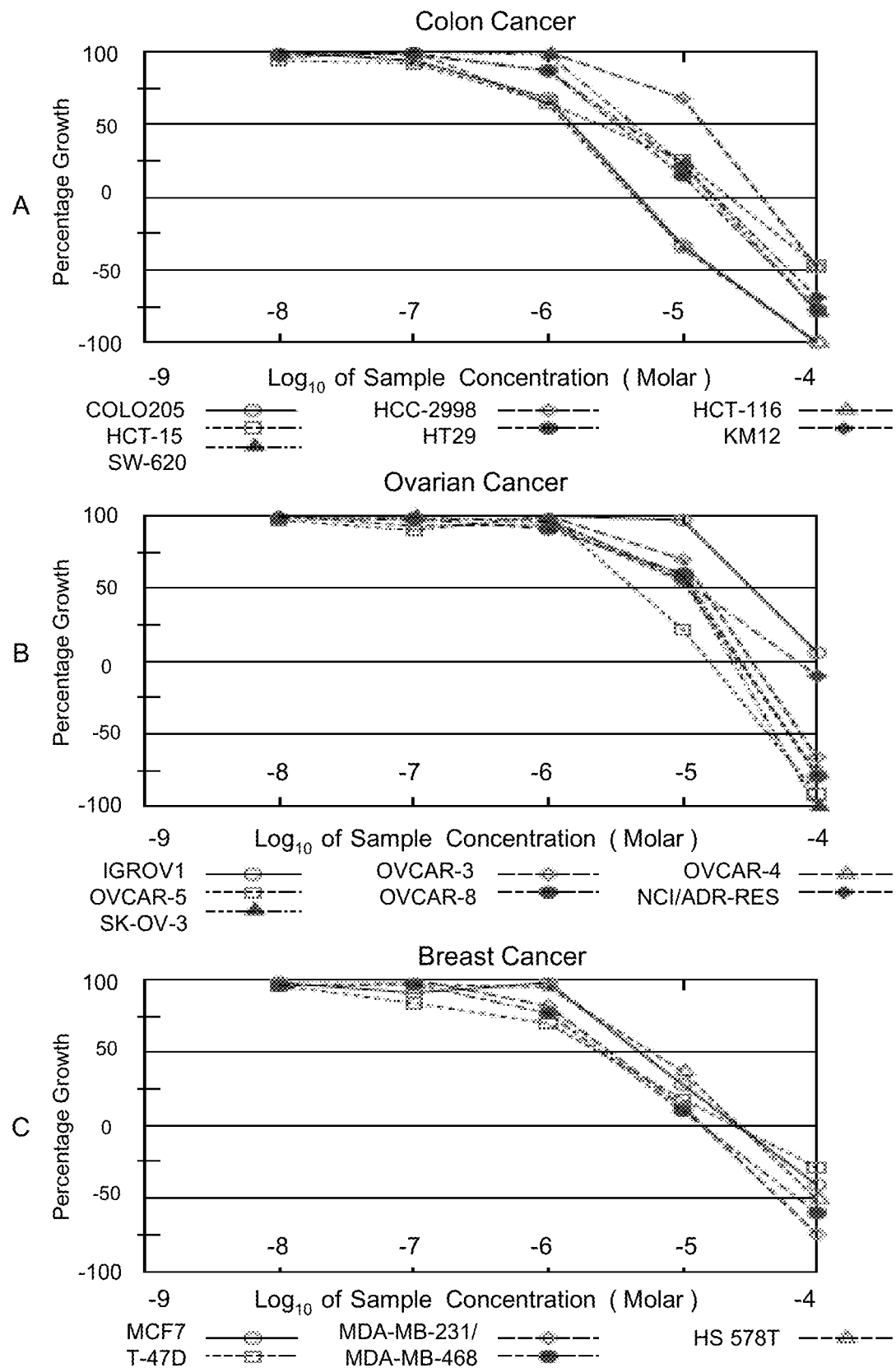

Result in FIG. 24(U.S. Ser. No. 14/313,080)

Experiment 39: Inhibition of Capan Cells Growth by Tig-S

A. Cells: Capan cells are derived from Human pancreas carcinoma (pancreas). Cells were grew in RPMI 1640 medium supplemented with 10% FCS, antibiotics and glutamine. 10000 cells were seeded in a well (96-welled plate) for one day before drug-treatment B. Drug treatment:

Drug: Tig-S (stored as a 1000× stock solution in DMSO) was used.

Drug concentration used: from 0.15-20 ug/ml.

Drug-treatment was carried out for 3 days.

C. At the end of the drug-treatment, cytotoxic test was performed with MTT assay. The percentage of drug-treated cells' growth as compared to those of the no drug control is determined. See FIG. 37.

Experiment 40

Using method in Experiment 3, esterification of E4A2Y with acetyl, angeloyl, tigloyl, senecioyl, Crotonoyl, Cinnamoyl, Pentenoyl, 4-(dimethylamino)-2-methylbut-2-enoyl, and 4-[(2-methoxyethyl)amino]-2-methyl-4oxobut-2-enoyl gave the following compounds:

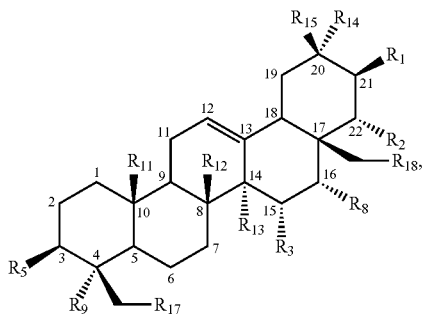

wherein:
1) R1, R2, R3, R5, R8 are OH; R17, R18 are O-acetyl;
2) R1, R2, R3, R5, R8 are OH; R17, R18 are O-angeloyl
3) R1, R2, R3, R5, R8 are OH; R17, R18 are O-tigloyl
4) R1, R2, R3, R5, R8 are OH; R17, R18 are O-senecioyl
5) R1, R2, R3, R5, R8 are OH; R17, R18 are O-Crotonoyl
6) R18, R2, R3, R5, R8 are OH; R17, R18 are O-Cinnamoyl
7) R18, R2, R3, R5, R8 are OH; R17, R18 are O-Pentenoyl
8) R18, R2, R3, R5, R8 are OH; R17, R18 are O-4-(dimethylamino)-2-methylbut-2-enoyl
9) R18, R2, R3, R5, R8 are OH; R17, R18 are O-4-[(2-methoxyethyl)amino]-2-methyl-4oxobut-2-enoyl
10) R18, R2, R3, R5, R8 are OH; R17, R1 are O-acetyl;
11) R18, R2, R3, R5, R8 are OH; R17, R1 are O-angeloyl
12) R18, R2, R3, R5, R8 are OH; R17, R1 are O-tigloyl
13) R18, R2, R3, R5, R8 are OH; R17, R1 are O-senecioyl
14) R18, R2, R3, R5, R8 are OH; R17, R1 are O-Crotonoyl
15) R18, R2, R3, R5, R8 are OH; R17, R1 are O-Cinnamoyl
16) R18, R2, R3, R5, R8 are OH; R17, R1 are O-Pentenoyl
17) R18, R2, R3, R5, R8 are OH; R17, R1 are O-4-(dimethylamino)-2-methylbut-2-enoyl
18) R18, R2, R3, R5, R8 are OH; R17, R1 are O-4-[(2-methoxyethyl)amino]-2-methyl-4oxobut-2-enoyl
19) R2, R3, R5, R8 are OH; R1, R17, R18 are O-acetyl;
20) R2, R3, R5, R8 are OH; R1, R17, R18 are O-angeloyl
21) R2, R3, R5, R8 are OH; R1, R17, R18 are O-tigloyl
22) R2, R3, R5, R8 are OH; R1, R17, R18 are O-senecioyl
23) R2, R3, R5, R8 are OH; R1, R17, R18 are O-Crotonoyl
24) R2, R3, R5, R8 are OH; R1, R17, R18 are O-Cinnamoyl
25) R2, R3, R5, R8 are OH; R1, R17, R18 are O-Pentenoyl
26) R2, R3, R5, R8 are OH; R1, R17, R18 are O-4-(dimethylamino)-2-methylbut-2-enoyl
27) R2, R3, R5, R8 are OH; R1, R17, R18 are O-4-[(2-methoxyethyl)amino]-2-methyl-4oxobut-2-enoyl.

What is claimed is:

1. A synthetic compound selected from the structure:

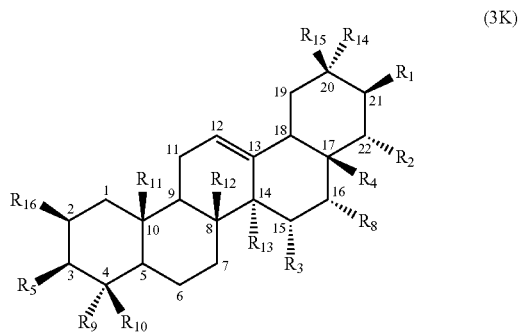

(3K)

R1, R2, R3, R4, R5, R8, R9, R11, R12, R13, R14, R15, R16 are independently selected from the group of H, OH, CH3, CH2OH, COOH, hydrogen, hydroxyl, methyl, O-angeloyl, O-tigloyl, O-senecioyl, O-acetyl, O-Crotonoyl, O-3,3-Dimethylacryloyl, O-Cinnamoyl, O-Pentenoyl, O-Hexanoyl, O-benzoyl, O-Ethylbutyryl, O-alkyl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-aryl, O-acyl, O-heterocylic, O-heteroraryl, O-alkenylcarbonyl, O-alkane, O-alkene, O-acid moiety, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O-C(2-18) Acyl, O-4-(dimethylamino)-2-methylbut-2-enoyl, O-4-[(2-methoxyethyl)amino]-2-methyl-4oxobut-2-enoyl, CH2O-angeloyl, CH2O-tigloyl, CH2O-senecioyl, CH2O-acetyl, CH2O-Crotonoyl, CH2O-3,3-Dimethylacryloyl, CH2O-Cinnamoyl, CH2O-Pentenoyl, CH2O-Hexanoyl, CH2O-benzoyl, CH2O-Ethylbutyryl, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-alkane, CH2O-alkene, CH2O-angeloyl, CH2O-tigloyl, CH2O-senecioyl, CH2O-acetyl, CH2O-Crotonoyl, CH2O-3,3-Dimethylacryloyl, CH2O-Cinnamoyl, CH2O-Pentenoyl, CH2O-Hexanoyl, CH2O-benzoyl, CH2O-Ethylbutyryl, CH3, CH2OH, CH2O-alkyl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-aryl, CH2O-acyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O-C(2-18) Acyl, CH2O-4-(dimethylamino)-2-methylbut-2-enoyl, CH2O-4-[(2-methoxyethyl)amino]-2-methyl-4oxobut-2-enoyl; wherein R10 is attached an O-angeloyl, O-tigloyl, O-senecioyl, O-, O-Crotonoyl, O-3,3-Dimethylacryloyl, O-Cinnamoyl, O-Pentenoyl, O-Hexanoyl, O-benzoyl, O-Ethylbutyryl, O-dibenzoyl, O-benzoyl, O-alkanoyl, O-alkenoyl, O-benzoyl alkyl substituted O-alkanoyl, O-alkanoyl substituted phenyl, O-alkenoyl substituted phenyl, O-heterocylic, O-heteroraryl, O-alkenylcarbonyl, O-ethanoyl, O-propanoyl, O-propenoyl, O-butanoyl, O-butenoyl, O-pentanoyl, O-hexenoyl, O-heptanoyl, O-heptenoyl, O-octanoyl, O-octenoyl, O-nonanoyl, O-nonenoyl, O-decanoyl, O-decenoyl, O-propionyl, O-2-propenoyl, O-2-butenoyl, O-Isobutyryl, O-2-methylpropanoyl, O-2-ethylbutyryl, O-ethylbutanoyl, O-2-ethylbutanoyl, O-butyryl, O-(E)-2,3-Dimethylacryloyl, O-(E)-2-Methylcrotonoyl, O-3-cis-Methyl-methacryloyl, O-3-Methyl-2-butenoyl, O-3-Methylcrotonoyl, O-4-Pentenoyl, O-(2E)-2-pentenoyl, O-Caproyl, O-5-Hexenoyl, O-Capryloyl, O-Lauroyl, O-Dodecanoyl, O-Myristoyl, O-Tetradecanoyl, O-Oleoyl, O-4-(dimethylamino)-2-methylbut-2-enoyl, O-4-[(2-methoxyethyl)amino]-2-methyl-4oxobut-2-enoyl, CH2O-angeloyl, CH2O-tigloyl, CH2O-senecioyl, CH2O-acetyl, CH2O-Crotonoyl, CH2O-3,3-Dimethylacryloyl, CH2O-Cinnamoyl, CH2O-Pentenoyl, CH2O-Hexanoyl, CH2O-benzoyl, CH2O-Ethylbutyryl, CH2O-dibenzoyl, CH2O-benzoyl, CH2O-alkanoyl, CH2O-alkenoyl, CH2O-benzoyl alkyl substituted O-alkanoyl, CH2O-alkanoyl substituted phenyl, CH2O-alkenoyl substituted phenyl, CH2O-heterocylic, CH2O-heteroraryl, CH2O-alkenylcarbonyl, CH2O-ethanoyl, CH2O-propanoyl, CH2O-propenoyl, CH2O-butanoyl, CH2O-butenoyl, CH2O-pentanoyl, CH2O-hexenoyl, CH2O-heptanoyl, CH2O-heptenoyl, CH2O-octanoyl, CH2O-octenoyl, CH2O-nonanoyl, CH2O-nonenoyl, CH2O-decanoyl, CH2O-decenoyl, CH2O-propionyl, CH2O-2-propenoyl, CH2O-2-butenoyl, CH2O-Isobutyryl, CH2O-2-methylpropanoyl, CH2O-2-ethylbutyryl, CH2O-ethylbutanoyl, CH2O-2-ethylbutanoyl, CH2O-butyryl, CH2O-(E)-2,3-Dimethylacryloyl, CH2O-(E)-2-Methylcrotonoyl, CH2O-3-cis-Methyl-methacryloyl, CH2O-3-Methyl-2-butenoyl, CH2O-3-Methylcrotonoyl, CH2O-4-Pentenoyl, CH2O-(2E)-2-pentenoyl, CH2O-Caproyl, CH2O-5-Hexenoyl, CH2O-Capryloyl, CH2O-Lauroyl, CH2O-Dodecanoyl, CH2O-Myristoyl, CH2O-Tetradecanoyl, CH2O-Oleoyl, CH2O-4-(dimethylamino)-2-methylbut-2-enoyl, CH2O-4-[(2-methoxyethyl)amino]-2-methyl-4oxobut-2-enoyl.

2. A synthetic compound having the structure:

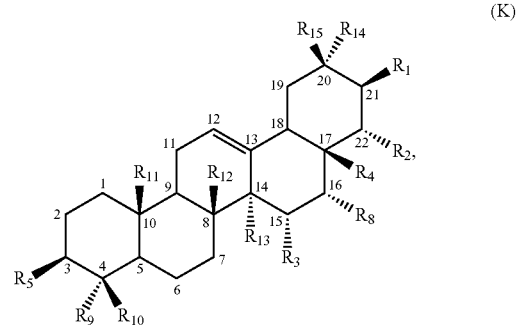

(K)

wherein R10 is selected from the group of CH2O-angeloyl, CH2O-tigloyl, CH2O-senecioyl, CH2O-crotonoyl, CH2O-3,3-Dimethylacryloyl, CH2O-cinnamoyl, CH2O-pentenoyl, CH2O-hexanoyl, CH2O-benzoyl, CH2O-Ethylbutyryl, CH2O-4-(dimethylamino)-2-methylbut-2-enoyl, and CH2O-4-[(2-methoxyethyl)amino]-2-methyl-4oxobut-2-enoyl, wherein R1, R2, R4, R5, and R8 are independently selected from the group of CH2OH, hydroxyl, O-angeloyl, O-tigloyl, O-senecioyl, O-acetyl, O-crotonoyl, O-3,3-Dimethylacryloyl, O-cinnamoyl, O-pentenoyl, O-hexanoyl, O-benzoyl, O-ethylbutyryl, O-4-(dimethylamino)-2-methylbut-2-enoyl, O-4-[(2-methoxyethyl)amino]-2-methyl-4oxobut-2-enoyl, CH2O-angeloyl, CH2O-tigloyl, CH2O-senecioyl, CH2O-acetyl, CH2O-crotonoyl, CH2O-3,3-Dimethylacryloyl, CH2O-cinnamoyl, CH2O-pentenoyl, CH2O-hexanoyl, CH2O-benzoyl, and CH2O-ethylbutyryl CH2O-4-(dimethylamino)-2-methylbut-2-enoyl, CH2O-4-[(2-methoxyethyl)amino]-2-methyl-4oxobut-2-enoyl, wherein R3 is OH or H; wherein R9, R11, R12, R13, R14, and R15 are CH3.

3. The compound of claim 2, wherein R10 is CH2O-angeloyl, CH2O-tigloyl, CH2O-senecioyl, CH2O-crotonoyl, CH2O-3,3-Dimethylacryloyl, CH2O-cinnamoyl, CH2O-Pentenoyl, CH2O-Hexanoyl, CH2O-benzoyl, or CH2O-Ethylbutyryl CH2O-4-(dimethylamino)-2-methylbut-2-enoyl, CH2O-4-[(2-methoxyethyl)amino]-2-methyl-4oxobut-2-enoyl, and at least of R1, R2, R4, R5, R8, are O-angeloyl, O-tigloyl, O-senecioyl, O-acetyl, O-crotonoyl, O-3,3-Dimethylacryloyl, O-cinnamoyl, O-pentenoyl, O-hexanoyl, O-benzoyl, O-ethylbutyryl, O-4-(dimethylamino)-2-methylbut-2-enoyl, O-4-[(2-methoxyethyl)amino]-2-methyl-4oxobut-2-enoyl, —CH2O-angeloyl, CH2O-tigloyl, CH2O-senecioyl, CH2O-crotonoyl, CH2O-3,3-Dimethylacryloyl, CH2O-cinnamoyl, CH2O-Pentenoyl, CH2O-Hexanoyl, CH2O-benzoyl, or CH2O-Ethylbutyryl or O-4-(dimethylamino)-2-methylbut-2-enoyl, O-4-[(2-methoxyethyl)amino]-2-methyl-4oxobut-2-enoyl.

4. The compound of claim 2, wherein R1 is O-angeloyl, O-tigloyl, O-senecioyl, O-acetyl, O-crotonoyl, O-3,3-Dimethylacryloyl, O-cinnamoyl, O-pentenoyl, O-hexanoyl, O-benzoyl, or O-ethylbutyryl, O-4-(dimethylamino)-2-methylbut-2-enoyl, O-4-[(2-methoxyethyl)amino]-2-methyl-4oxobut-2-enoyl, and R10 is CH2O-angeloyl, CH2O-tigloyl, CH2O-senecioyl, CH2O-crotonoyl, CH2O-3,3-Dimethylacryloyl, CH2O-cinnamoyl, CH2O-pentenoyl, CH2O-hexanoyl, CH2O-benzoyl, CH2O-ethylbutyryl, CH2O-4-(dimethylamino)-2-methylbut-2-enoyl, CH4O-4-[(2-methoxyethyl)amino]-2-methyl-4oxobut-2-enoyl.

5. The compound of claim 2, wherein R10 is CH2O-angeloyl, CH2O-tigloyl, CH2O-senecioyl, CH2O-crotonoyl, CH2O-3,3-Dimethylacryloyl, CH2O-cinnamoyl, CH2O-Pentenoyl, CH2O-Hexanoyl, CH2O-benzoyl, CH2O-Ethylbutyryl CH2O-4-(dimethylamino)-2-methylbut-2-enoyl, CH2O-4-[(2-methoxyethyl)amino]-2-methyl-4oxobut-2-enoyl.

6. The compound of claim 2, wherein R4 and R10 are independently CH2O-angeloyl, CH2O-tigloyl, CH2O-senecioyl, CH2O-crotonoyl, CH2O-3,3-Dimethylacryloyl, CH2O-cinnamoyl, CH2O-pentenoyl, CH2O-hexanoyl, CH2O-benzoyl, or CH2O-ethylbutyryl O-4-(dimethylamino)-2-methylbut-2-enoyl, O-4-[(2-methoxyethyl)amino]-2-methyl-4oxobut-2-enoyl.

7. The compound of claim 2, wherein the compound is selected from the following:

a) A compound having structure:

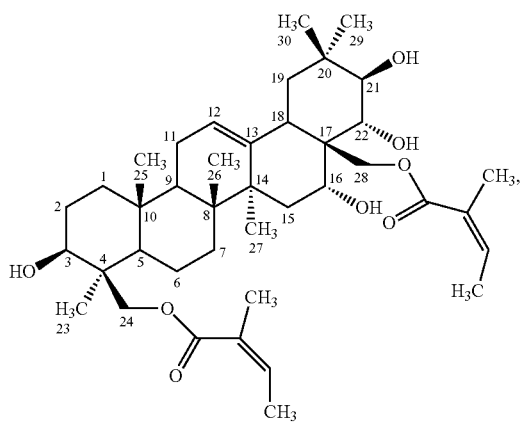

b) A compound having structure:

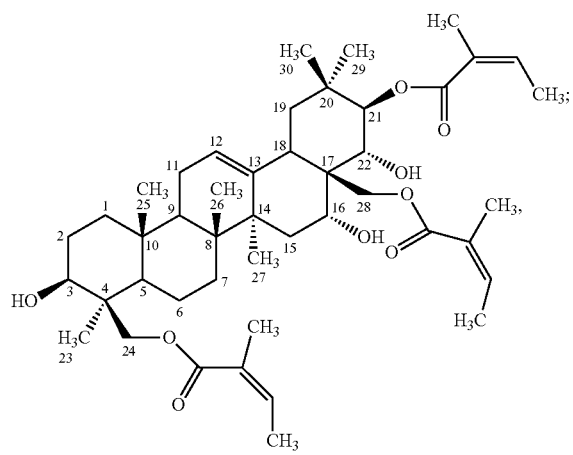

c) A compound having structure:

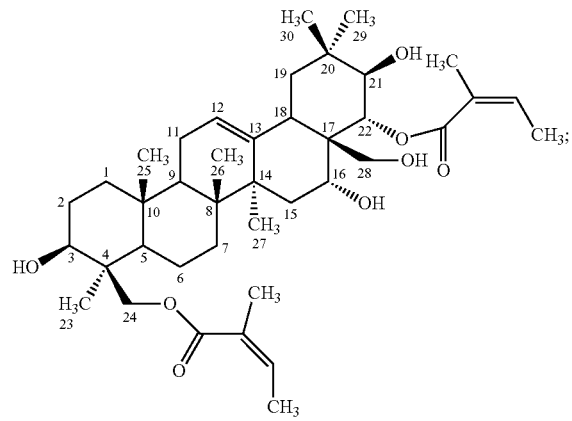

d) A compound having structure:

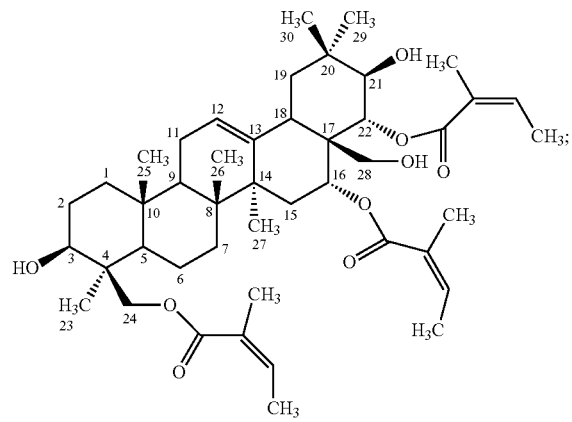

e) A compound having structure:
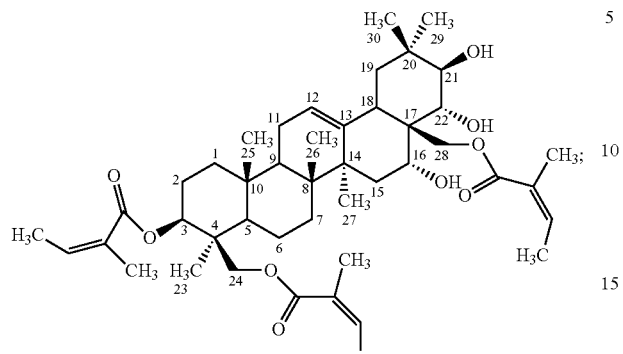
f) A compound having structure:
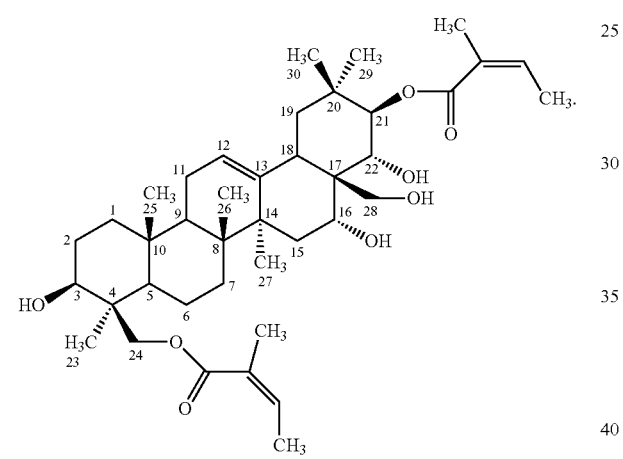
8. The compound of claim 2, wherein the compound is selected from the following:
a) A compound having structure:
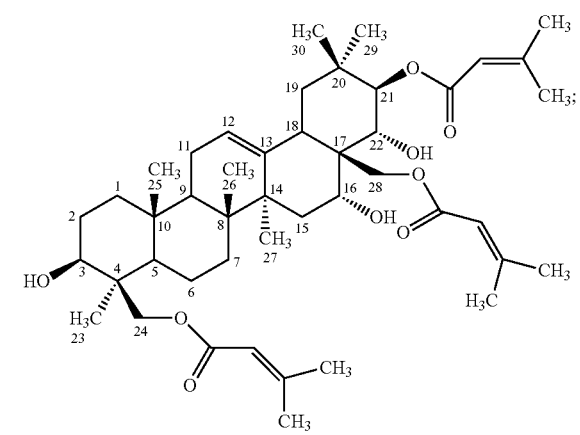
b) A compound having structure:
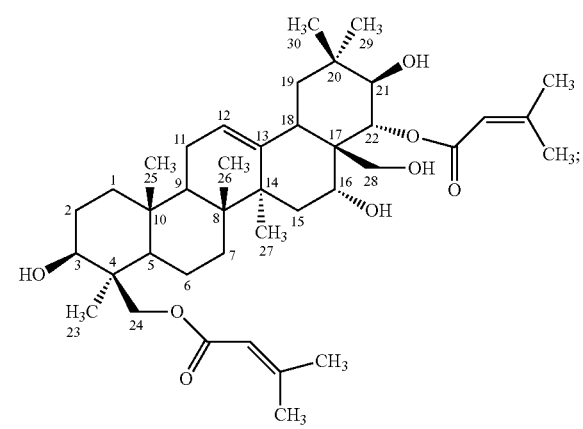
c) A compound having structure:
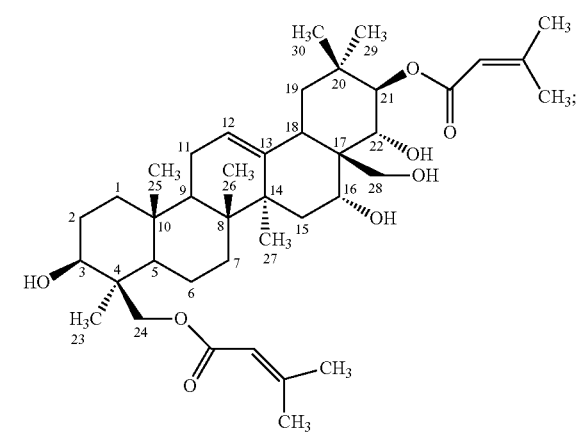
d) A compound having structure:

e) A compound having structure:
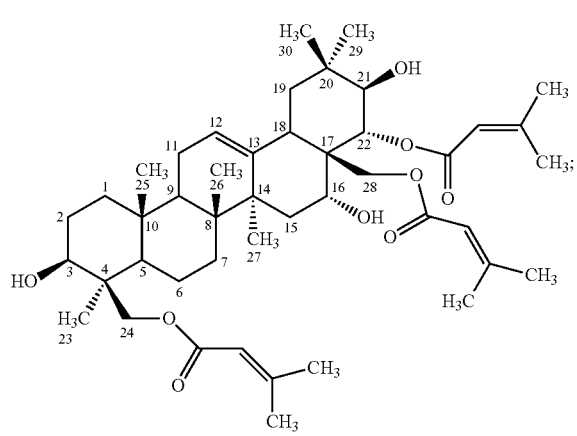
f) A compound having structure:
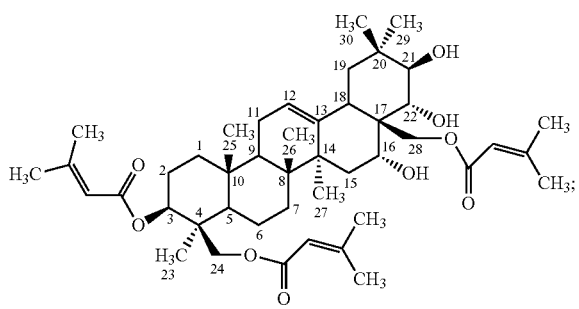
9. The compound of claim 2, wherein the compound is selected from the following:
a) A compound having structure:
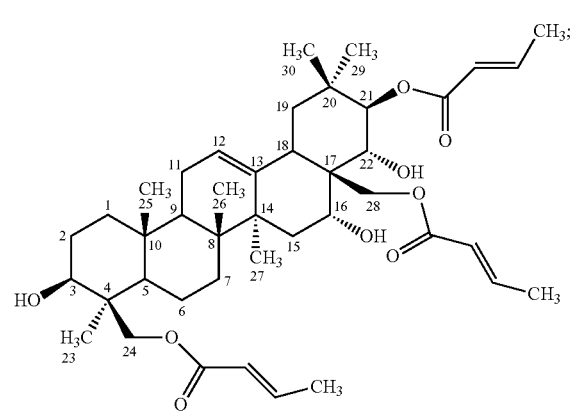
b) A compound having structure:
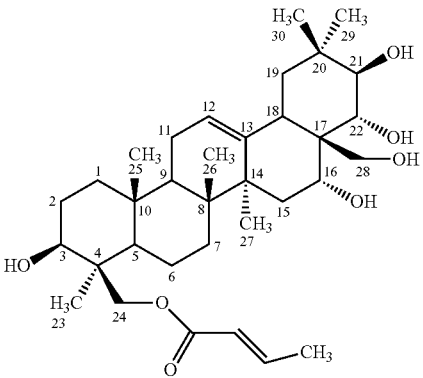
c) A compound having structure:
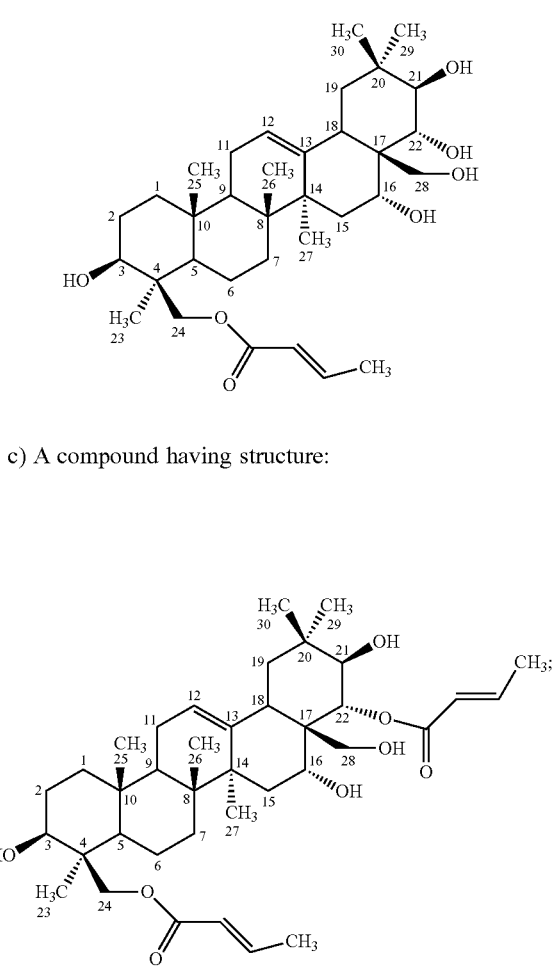
d) A compound having structure:
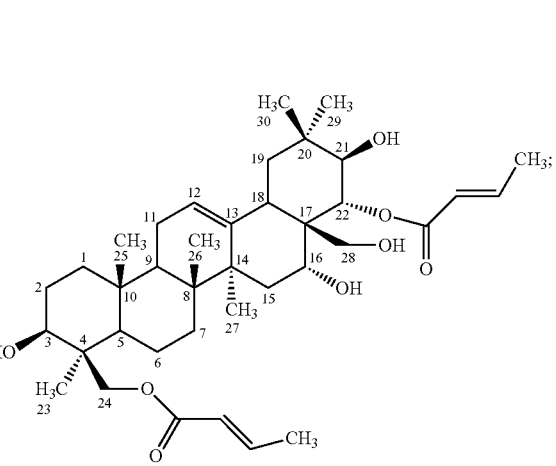

e) A compound having structure:
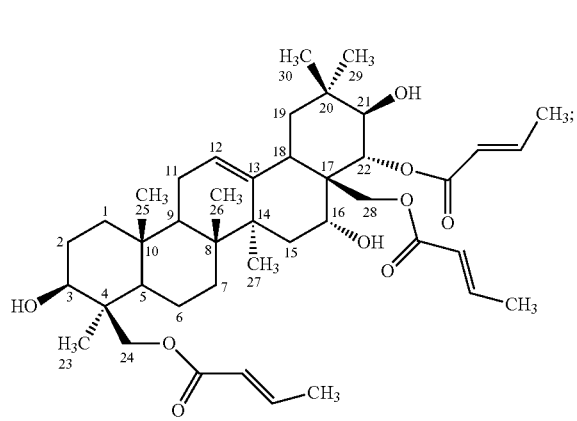
f) A compound having structure:
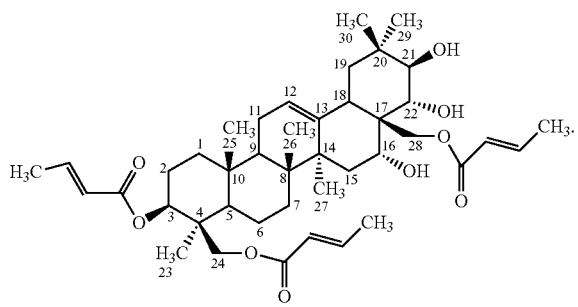
10. The compound of claim 2, wherein the compound is selected from the following:
a) A compound having structure:
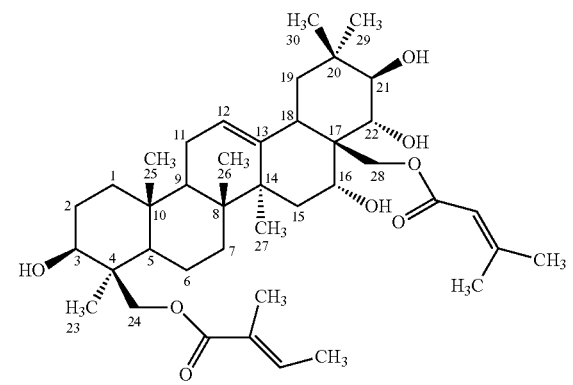
b) A compound having structure:
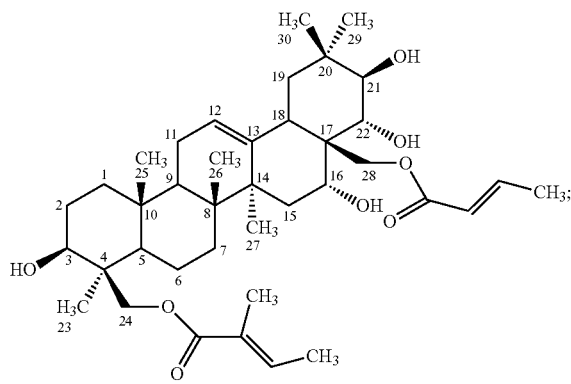
c) A compound having structure:
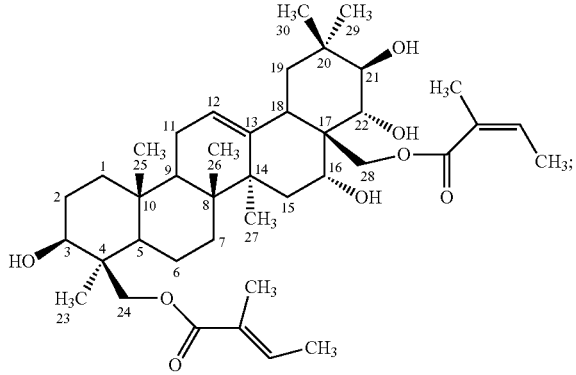
d) A compound having structure:
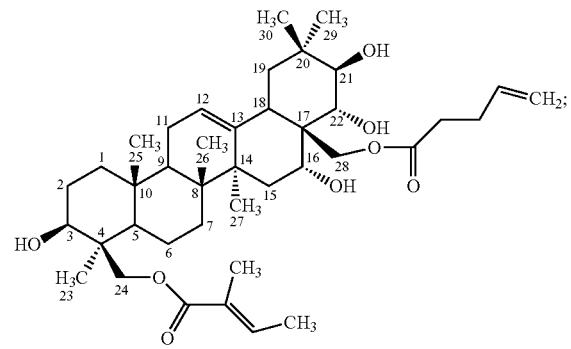

e) A compound having structure:

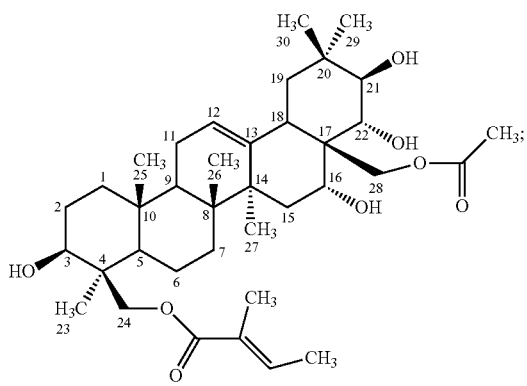

f) A compound having structure:

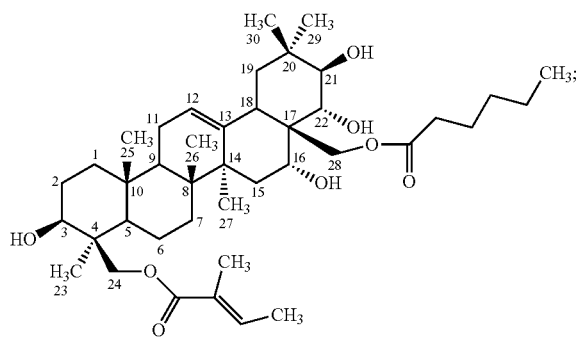

g) A compound having structure:

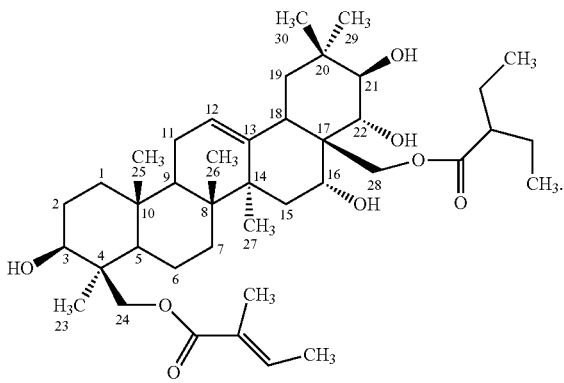

11. The compound of claim 2, wherein the compound is attached one or more of the functional groups selected from the group consisting of angeloyl, tigloyl, senecioyl, acetyl, crotonoyl, Dimethylacryloyl, cinnamoyl, pentenoyl, hexanoyl, benzoyl, ethylbutyryl, alkyl, phenyl 4-(dimethylamino)-2-methylbut-2-enoyl, 4-[(2-methoxyethyl)amino]-2-methyl-4oxobut-2-enoyl; wherein the compound can be obtained by a method comprising the following steps:

1. Dissolving core compound, triterpenes, hydroxylated triterpenes core in pyridine;
2. Adding the functional group or acyl chloride;
3. Stirring the mixture for a length of time including 5 sec, 1 min, 2 min, 5 min, 10 min, 30 min, 1 hr, 2 hr, 18 hr, 2 days or 3 days at different temperature;
4. At the end of reaction, adding an aqueous solution of acid or base, or water to the reaction mixture;
5. Extracting the solution with ethyl acetate followed by lyophilization;
6. Dissolving the reaction product in acetonitrile with Trifluoroacetic acid or DMSO;
7. Testing the reaction product of mixtures and individual fractions with MTT cytotoxic assay;
8. Selecting the HPLC fractions for isolation according to the cytotoxic activity of the reaction product obtained at a specific reaction time;
9. Purifying the active esterification products with HPLC;
10. Collecting the products; and
11. Testing the products.

12. The compound of claim 2, for treating cancer, inhibiting cancer growth, inhibiting cancer invasion, inhibiting cancer metastasis, modulating cell adhesion, modulating cell attachment, wherein the cancer is selected from the group of breast cancer, leukocytic cancer, liver cancer, ovarian cancer, bladder cancer, prostatic cancer, skin cancer, bone cancer, brain cancer, leukemia cancer, lung cancer, colon cancer, CNS cancer, melanoma cancer, renal cancer, cervical cancer, esophageal cancer, testicular cancer, spleenic cancer, kidney cancer, lymphhatic cancer, pancreatic cancer, stomach cancer and thyroid cancer; wherein the cells is selected from the group of breast cell, leukocytic cell, liver cell, ovarian cell, bladder cell, prostatic cell, skin cell, bone cell, brain cell, leukemia cell, lung cell, colon cell, CNS cell, melanoma cell, renal cell, cervical cell, esophageal cell, testicular cell, spleenic cell, kidney cell, lymphhatic cell, pancreatic cell, stomach cell and thyroid cell.

13. The compound of any of claim 1, wherein the compound for treating cancers, inhibition of cancer growth, cancer invasion, cells invasion, cancer cell invasion; cell adhesion, cell attachment, cell circulating; for inhibiting viruses; for preventing cerebral aging; for improving memory; improving cerebral functions; for curing enuresis, frequent micturition, urinary incontinence; dementia, Alzheimer's disease, autism, brain trauma, Parkinson's disease or other neurodegenerative diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-kappa B activation; for treating brain edema, severe acute respiratory syndrome, respiratory viral diseases, chronic venous insufficiency, hypertension, chronic venous disease, oedema, inflammation, hemorrhoids, peripheral edema formation, varicose vein disease, flu, post traumatic edema and postoperative swelling; for inhibiting blood clots, for inhibiting ethanol absorption; for lowering blood sugar; for regulating adrenocorticotropin and corticosterone levels; for Anti-MS, anti-aneurysm, anti-asthmatic, anti-oedematous, anti-inflammatory, anti-bradykinic, anti-capillarihemorrhagic, anti-cephalagic, anti-cervicobrachialgic, anti-ec-lamptic, anti-edemic, anti-encaphalitic, anti-epiglottitic, anti-exudative, anti-flu, anti-fracture, anti-gingivitis, anti-hematomic, anti-herpetic, anti-histaminic, anti-hydrathritic, anti-meningitic, antioxidant, anti-periodontic, anti-phlebitic, anti-pleuritic, anti-raucedo, anti-rhinitic, anti-tonsilitic, anti-ulcer, anti-varicose, anti-vertiginous, cancerostatic, corticosterogenic, diuretic, fungicide, hemolytic, hyaluronidase inhibitor, lymphagogue, natriuretic, pesticide, pituitary stimulant, thymolytic, vasoprotective, inhibiting leishmaniases, modulating adhesion or angiogenesis of cells, antiparasitic; increase the expression of the genes: ANGPT2, DDIT3, LIF and NFKB1Z, and manufacturing an adjuvant composition and venotonic treatment.

14. The compound is selected from claim 2 as a medicament.

15. A composition comprising an effective amount of compound of any of claim 2 as a medicament.

16. The composition comprises compound of any of claim 2, further comprising a pharmaceutically acceptable carrier or diluent.

17. The compound is selected from claim 7 as a medicament.

18. The compound is selected from claim 8 as a medicament.

19. The compound is selected from claim 9 as a medicament.

20. The compound is selected from claim 10 as a medicament.

* * * * *